United States Patent [19]

Gotoh et al.

[11] Patent Number: 4,772,487
[45] Date of Patent: Sep. 20, 1988

[54] METHOD AND APPARATUS OF FORMING SOLID PHASE REAGENT IN MICRO-MODULE

[75] Inventors: Yutaka Gotoh, Hachiohji; Masao Agawa, Inagi; Kazutomo Takahashi; Kiyoshi Takao, both of Hachiohji; Katsuaki Takano, Tachikawa, all of Japan

[73] Assignee: Olympus Optical Company Limited, Tokyo, Japan

[21] Appl. No.: 100,341

[22] Filed: Sep. 23, 1987

[30] Foreign Application Priority Data

Oct. 1, 1986 [JP] Japan .................. 61-233424
Oct. 1, 1986 [JP] Japan .................. 61-233425
Oct. 2, 1986 [JP] Japan .................. 61-235193

[51] Int. Cl.$^4$ .................. A01N 1/02; B05C 11/00
[52] U.S. Cl. .................. 427/2; 118/712; 435/809
[58] Field of Search .................. 118/712; 427/2; 435/809

[56] References Cited

U.S. PATENT DOCUMENTS 4,584,275  4/1986  Okano et al. .................. 435/809 X
4,666,853  5/1987  Meserol et al. .................. 435/809 X Primary Examiner—Michael R. Lusignan
Attorney, Agent, or Firm—Bruce L. Adams; Van C. Wilks

[57] ABSTRACT

Solid reagent film is formed in a micro-well for diagnosis of e.g. AIDS. The process is formed fully automatically without any manual operation. The process includes dispensing reagent solution in micro-wells of one or two rows simultaneously on sequentially feeding microplate, measuring the liquid level in the wells, incubating the wells to form solid film in the well surface, cleaning the dispense nozzles and measuring electrodes by cleaning fluid, dispensing protect cover forming liquid in the wells, measuring the liquid level in the wells, incubating the wells to form protect cover, cleaning the dispense nozzles and electrodes by cleaning fluid, and drying the wells. Also, storing and discharge the microplate relative to magazine, and transferring the microplate through the process are performed automatically.

4 Claims, 116 Drawing Sheets

FIG. 1
PROCESS DIAGRAM

| | | | |
|---|---|---|---|
| reagent solution dispense stage | 1 | dispense | 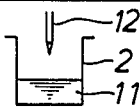 |
| | 2 | level monitor | 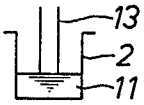 |
| incubation stage | 3 | incubation | 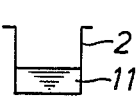 |
| cleaning stage | 4 | cleaning | 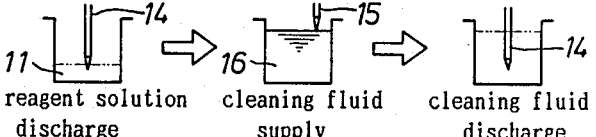<br>reagent solution discharge    cleaning fluid supply    cleaning fluid discharge |
| | 5 | level monitor | 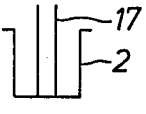 |
| blocking solution dispense stage | 6 | dispense | 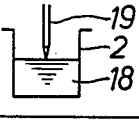 |
| | 7 | level monitor | 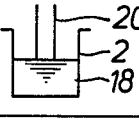 |
| incubation stage | 8 | incubation | 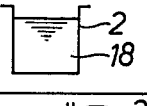 |
| cleaning stage | 9 | cleaning | 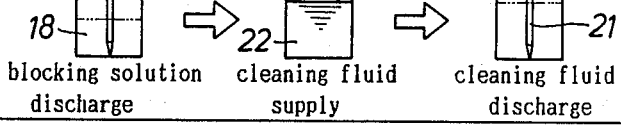<br>blocking solution discharge    cleaning fluid supply    cleaning fluid discharge |
| | 10 | level monitor | 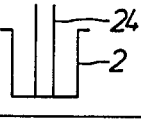 |
| drying stage | 11 | drying | 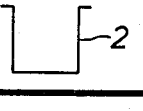 |

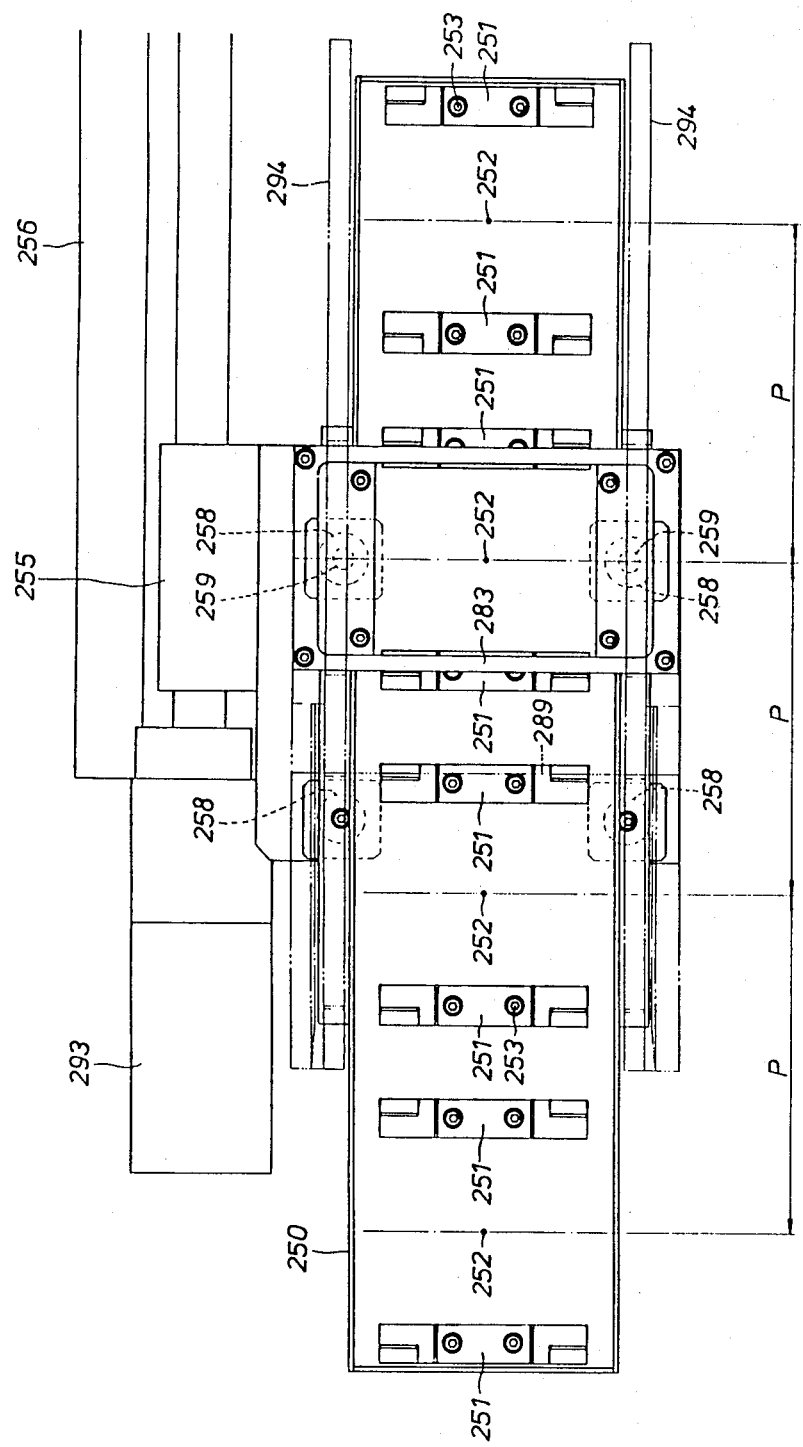

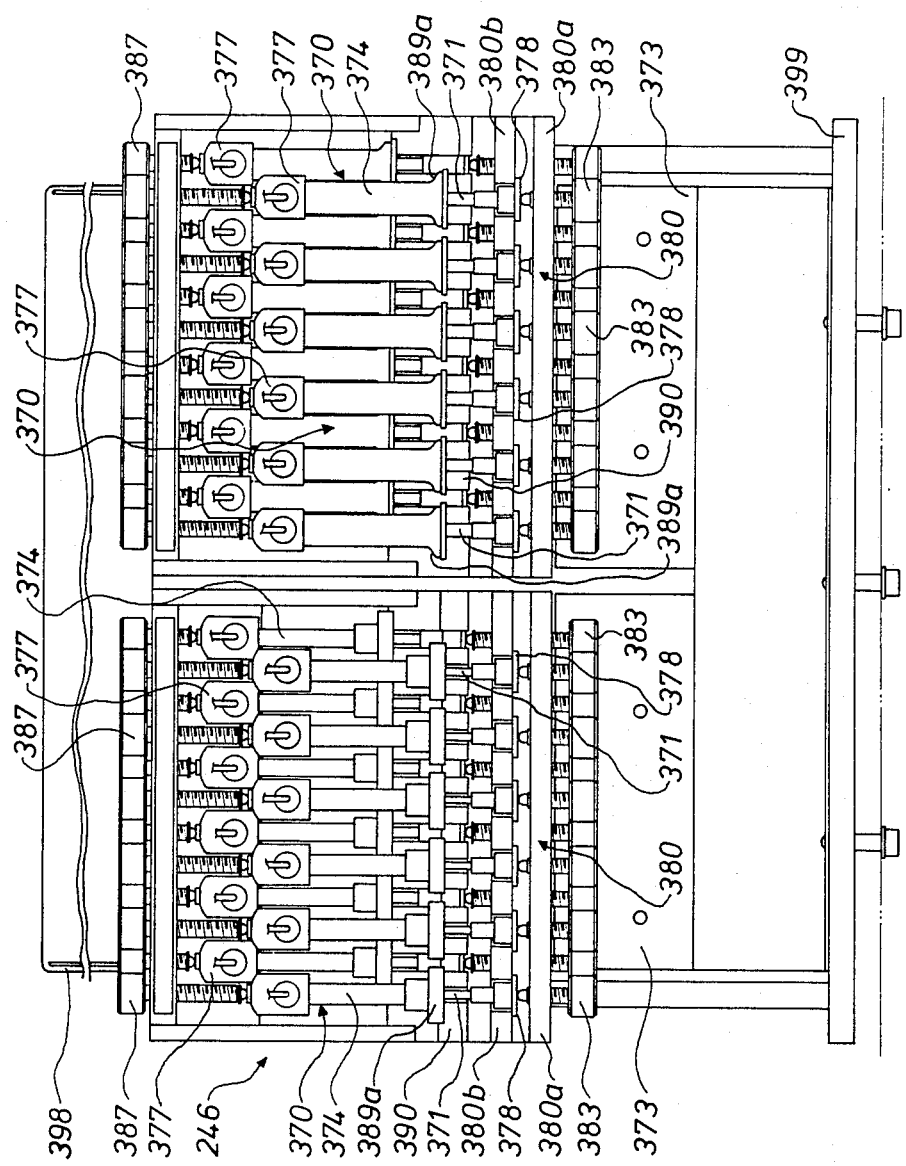

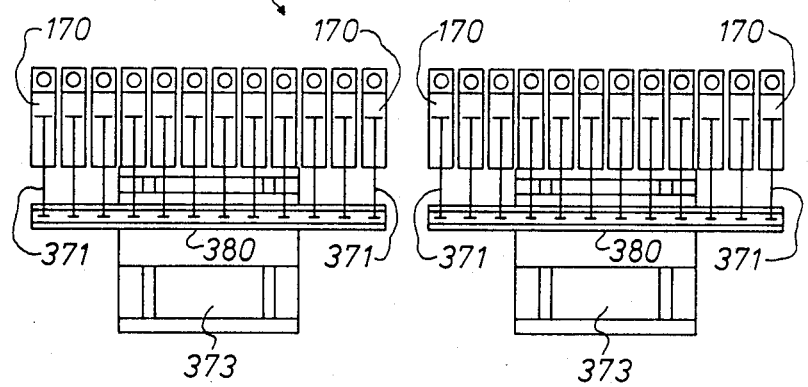
FIG. 12 (d)
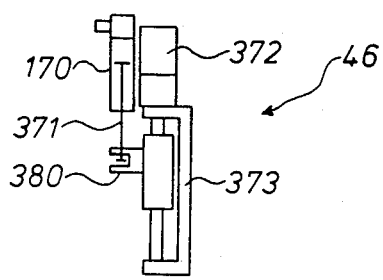
FIG. 12 (e)
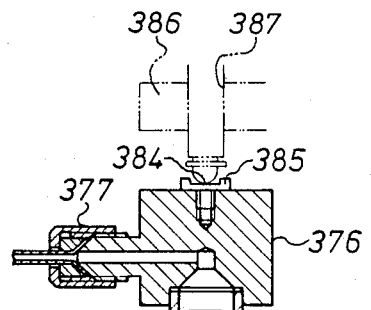
FIG. 12 (f)
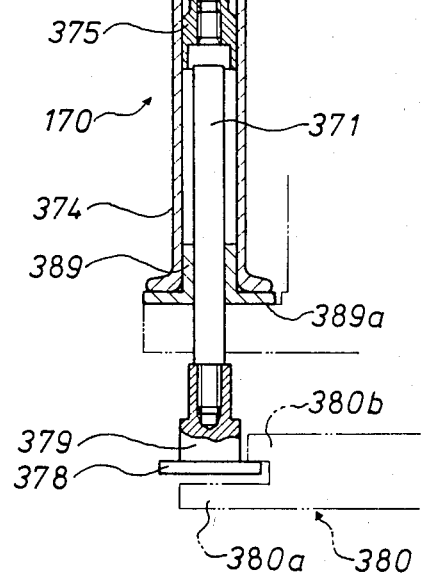

F I G. 12 (g)
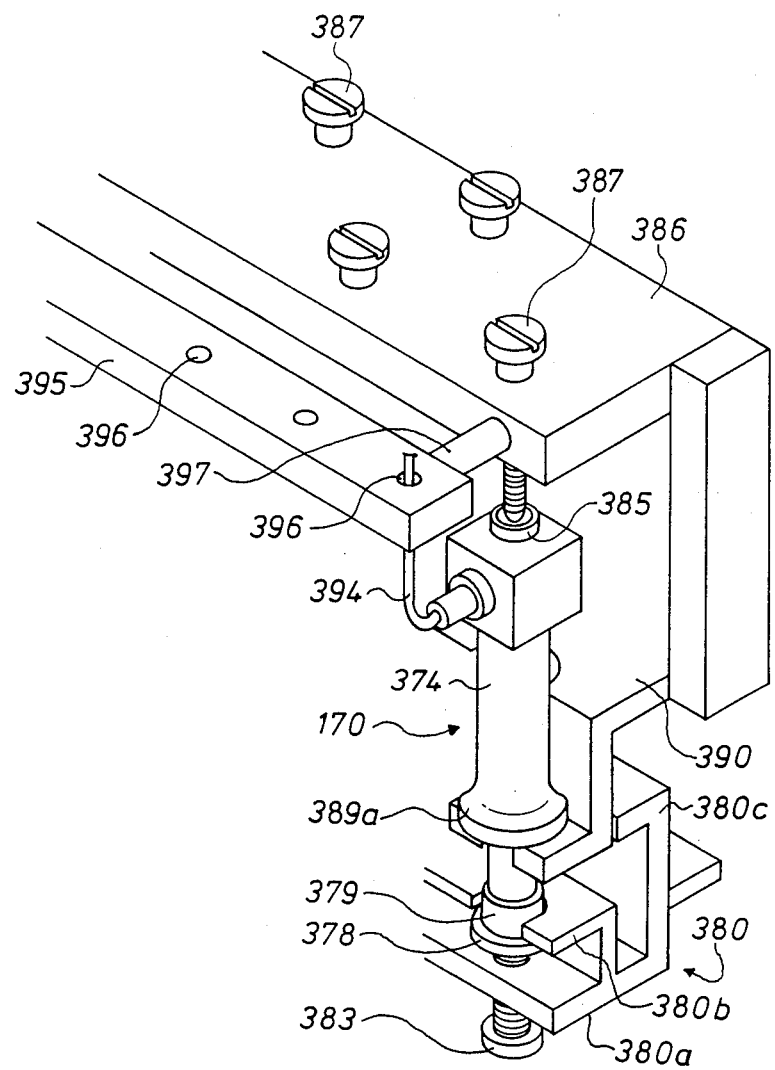

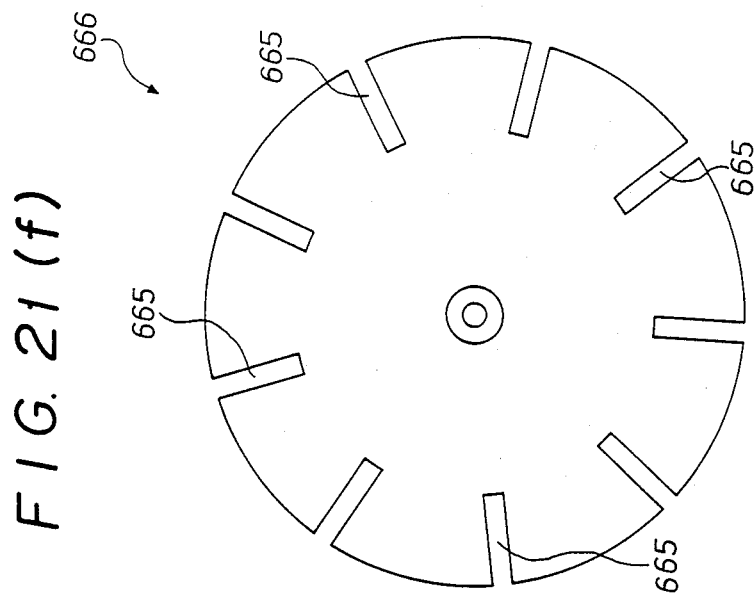
F I G. 21(f)
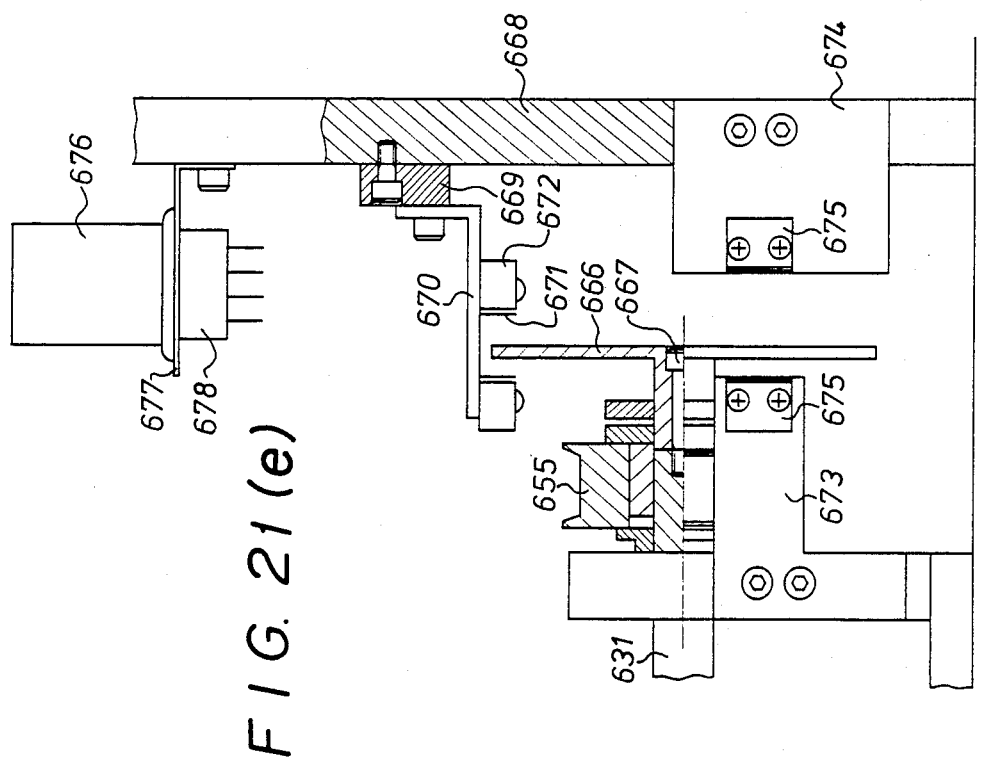
F I G. 21(e)

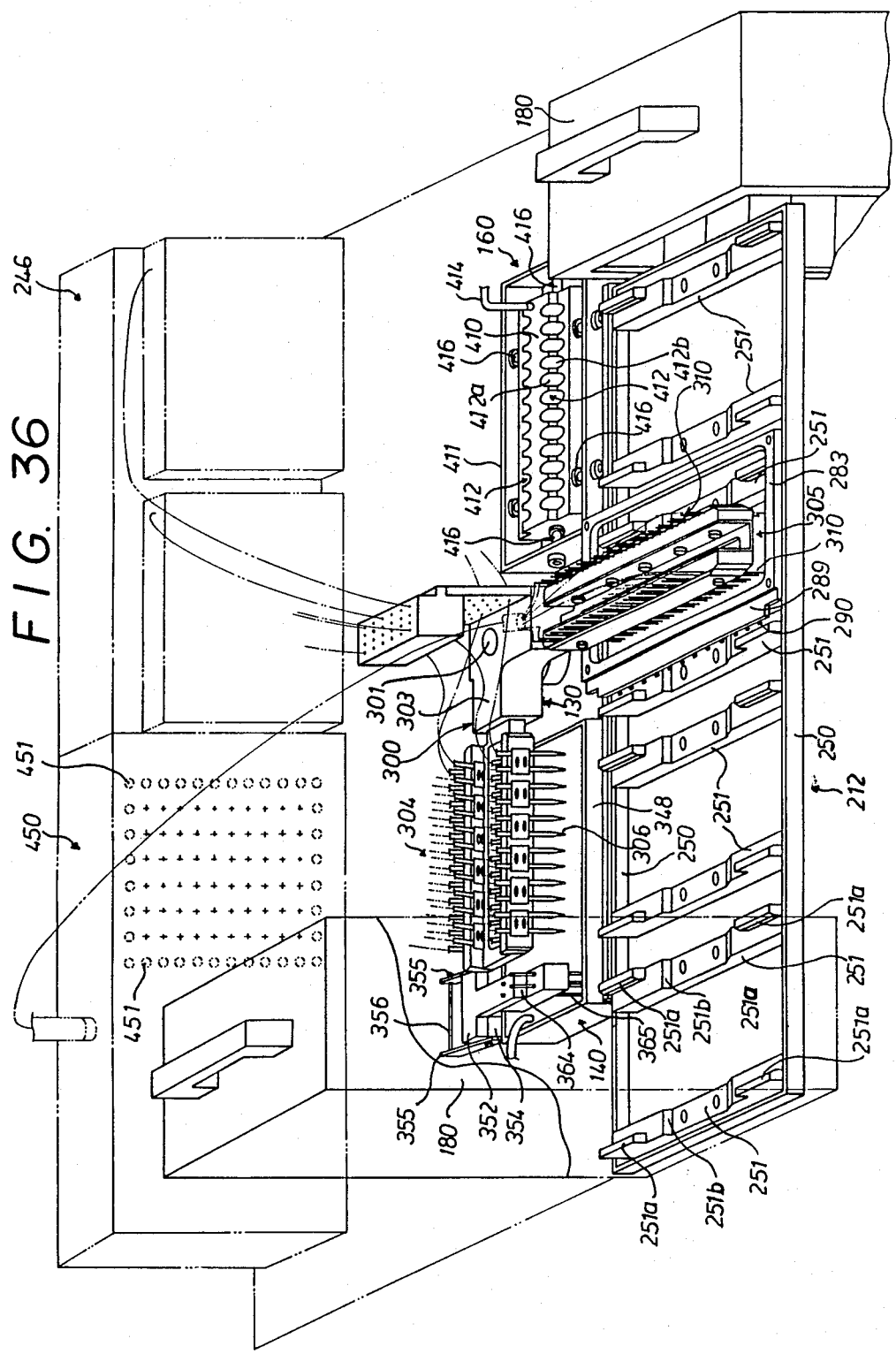

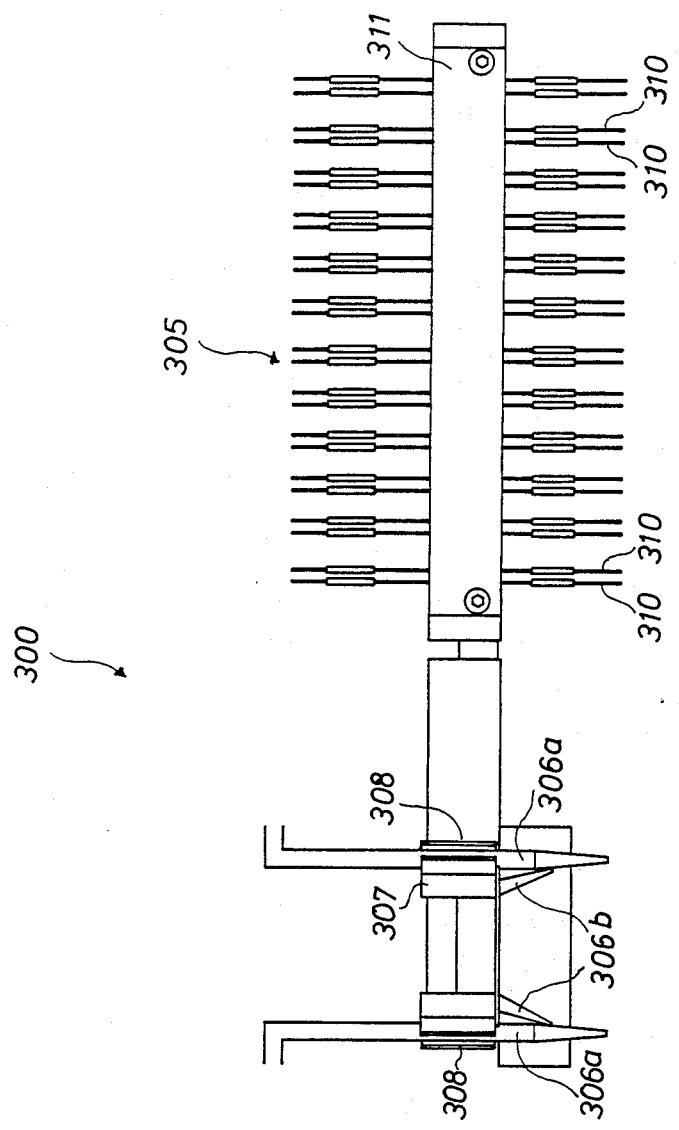

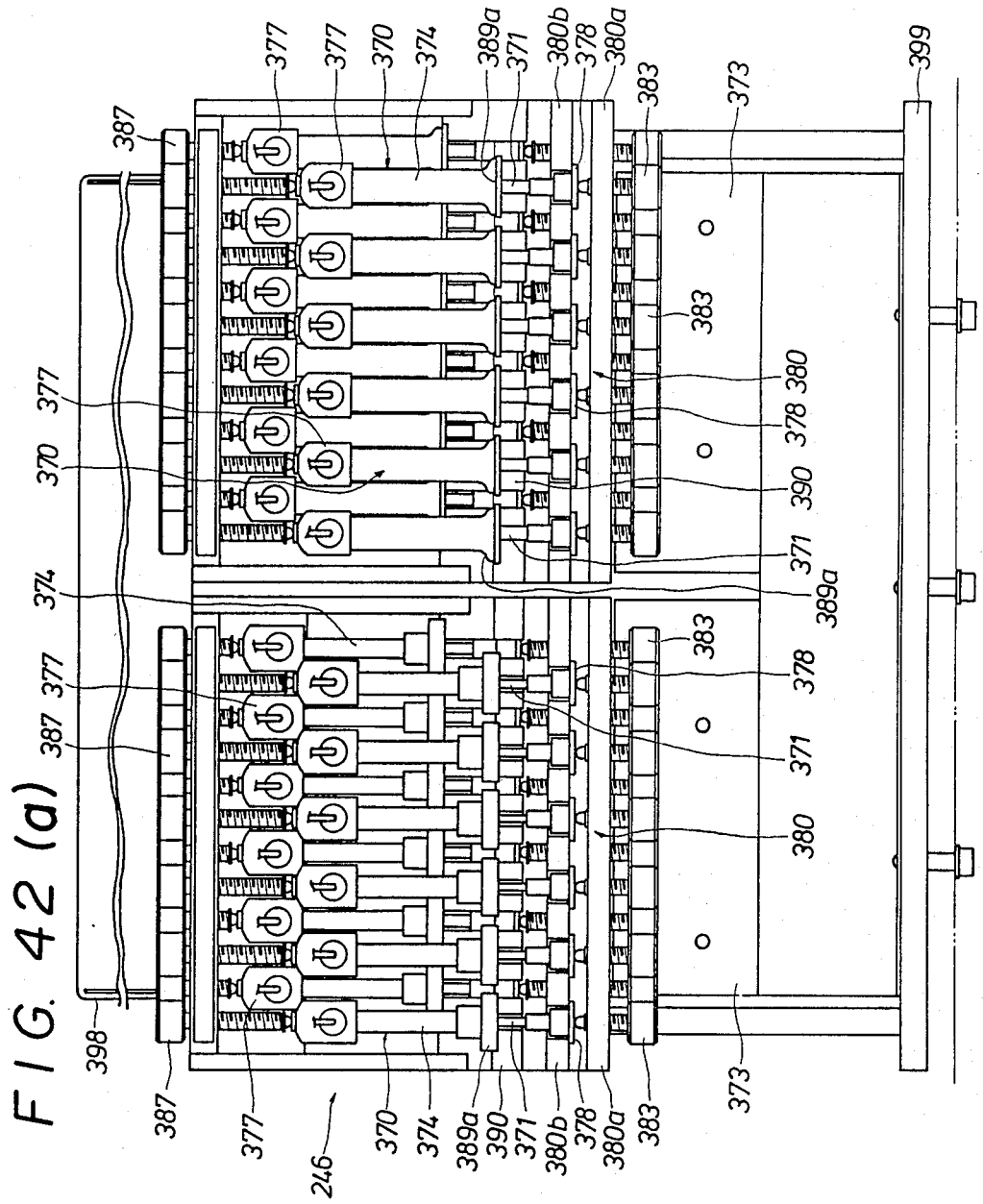

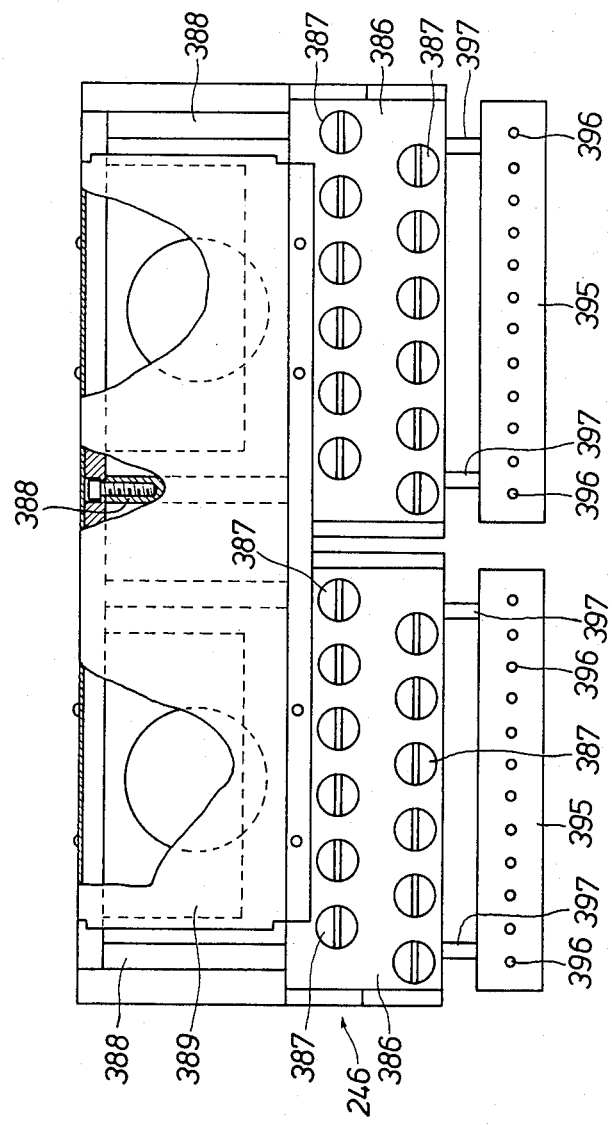

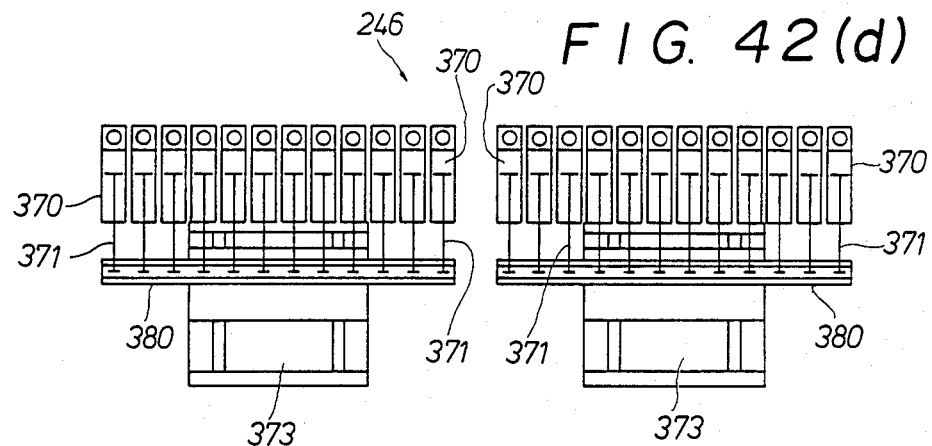
FIG. 42(d)
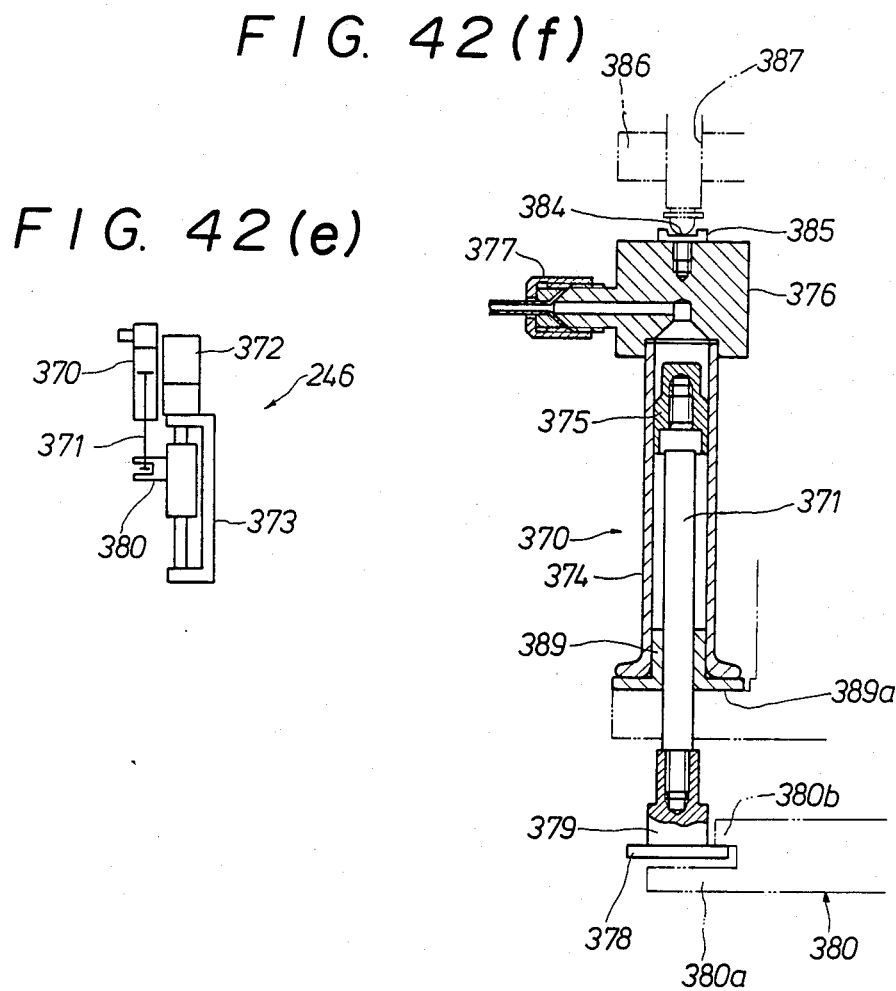
FIG. 42(e)
FIG. 42(f)

METHOD AND APPARATUS OF FORMING SOLID PHASE REAGENT IN MICRO-MODULE

BACKGROUND OF THE INVENTION

The present invention relates to method and apparatus of forming solid phase reagent in micro-module, and more particularly forming solid phase reagent for use in hematology and bacteriology.

Recently, also in Japan, patients of acquired immunity deficiency symptoms (AIDS) are reported. Especially, as AIDS is considered as infection of virus through blood, and as Japan depends 90% of blood for transfuse for hemopheliac from import, that is important problem.

As the diagnosis of AIDS, indirect method to measure immunity function in body, and direct method to determine whether antibody against AIDS virus is producing in body are utilised. As to the latter method, U.S. Pat. No. 4,520,113 discloses method of detecting antibody in serum of AIDS and pre-AIDS patients, utilising reagent H9/HTLV-3.

To utilise the H9/HTLV-3 as reagent, diagnosis kit utilising incubated H9/HTLV-3 is developed by NCI Co. USA and sold by Abbott Lab. USA. Effective method is desired to develope manufacturing such diagnosis kit.

To produce the above mensioned diagnosis kit utilising the incubated H9/HTLV-3 developed as AIDS diagnosis method should be very carefully performed to use the HTLV-3 as reagent to prevent healthy operator from immunity by HTLV-3 infection. The HTLV antigen can be inactive by treatment by surface-active agent or super-sonic wave. The HTLV-3 antigen positive human blood-plasma which is used as positive control can be inactive by super-heat treatment at 60° C., 3 hours.

Whether the inactivated virus is used, contact with virus may cause antibody production in healthy operator body. If antibody is produced, mistake diagnosis as AIDS, ARC or pre-AIDS might accompany.

Further, presence of inner celler substance of *E. Coli* or H9 cell in the agent, may cause mistaken result in the HTLV-3 screening test from person who has antigen to the *E. Coli* and H9 cell.

The mistaken positive reaction may cause severe trouble to the healthy person and his family.

SUMMARY OF THE INVENTION

The primary object of the present invention is to eliminate known manual operation to produce solid phase reagent in micro-module to be used in hematology and bacteriology e.g. diagnosis of AIDS, and to provide method and apparatus to produce solid phase reagent in micro-module by fully automatic operation with high productivity and high uniformity.

According to a feature of the present invention, a method of forming solid phase reagent in micro-module comprising preparing a module plate receiving a plurality of wells to be coated with reagent film, dispensing reagent in each well of the module plate from a plurality of dispensing nozzles corresponding to the number of wells of at least one row on the module plate, incubating the reagent dispensed in the wells to form reagent film in each well while transferring the module plate in predetermined temperature atmosphere, cleaning the wells on the module plate comprising (a) discharging remaining reagent from the wells by means of discharge nozzles corresponding to the number of the dispensing nozzles, (b) dispensing cleaning fluid into the wells by means of cleaning nozzles corresponding to the number of the discharge nozzles, (c) discharging the cleaning fluid from the wells by means of said discharge nozzles, dispensing protect film forming solution into the wells by means of another dispense nozzles corresponding to the number of the first mensioned dispense nozzles, incubating the protect film forming solution in the wells while transferring the module plate in predetermined temperature atmosphere, cleaning the wells on the module plate comprising (a) discharging remaining protect film for ming solution from the wells by means of discharge nozzles corresponding to the number of the dispensing nozzles, (b) dispensing cleaning fluid into the wells by means of cleaning nozzles corresponding to the number of the discharge nozzles, (c) discharging the cleaning fluid from the wells by means of said discharge nozzles, and, drying the wells on the module plate in predetermined temperature atmosphere to form coated solid phase reagent film in each well.

According to another feature of the present inventoin, a reagent coating apparatus in a solid phase reagent producing apparatus comprises magazine means storing a plurality of microplates each having a plurality of microwells to be coated, microplate transfer means transferring the microplate one by one from the magazine means to working station and from the working station to next station, and, reagent coating means dispensing reagent in each well on the microplate which is stopped in the working station.

According to further feature of the present invention, a reagent incubation apparatus comprises means to supply microplates each having a plurality of reagent coated wells one by one into incubation atmosphere, supply side transfer means transferring the microplate supplied from the supply means in the incubation atmosphere at predetermined transfer speed, means to deliver the microplate from said supply means to said transfer means, discharge side transfer means transferring the micro-plate transferred from the supply side transfer means in the incubation atmosphere at predetermined transfer speed, means to transfer the microplate from the supply side transfer means to the discharge side transfer means, means to discharge the microplate from the incubation atmosphere, and, means to deliver the microplate from the discharge side transfer means to the discharge means.

The solid phase reagent in micro-module is produced, according to the present invention, such that to the wells on the module plate, dispense of reagent, discharge of remained reagent, dispense and discharge of cleaning fluid after automatic incubation, dispense of protect film forming solution, and cleaning by cleaning fluid are all performed automatically without any manual operation. Thus, the process is performed uniformly to form solid phase reagent film covered by protect film in each micro-well on the microplate so that any danger of infection to the operator can be eliminated.

BRIEF DESCRIPTION OF THE DRAWING

FIG. 1 is a diagramamtic illustration of the micro-module solid phase forming method, according to the present invention, FIG. 2b is a sectional view along line A—A in FIG. 2a.

FIG. 36 is a perspective view of a portion of the cleaning apparatus.

DESCRIPTION OF THE PREFERRED EMBODIMENTS

Referring to FIG. 1 and FIGS. 2a, 2b and 2c, a method of forming solid phase reagent film for diagnosis of AIDS in each well of microplate will be described.

Figure 2A:
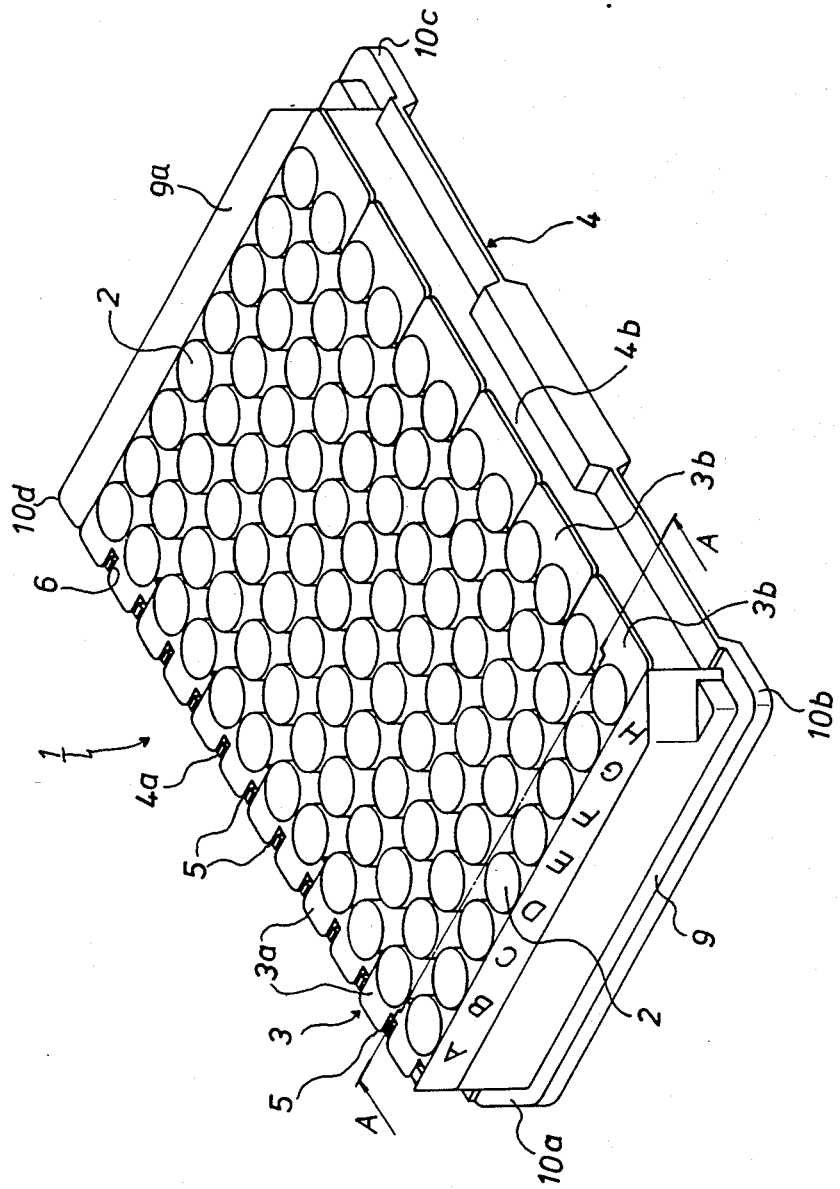
FIG. 2a is a perspective view of a microplate used in the apparatus, according to the present invention.
Figure 2B:
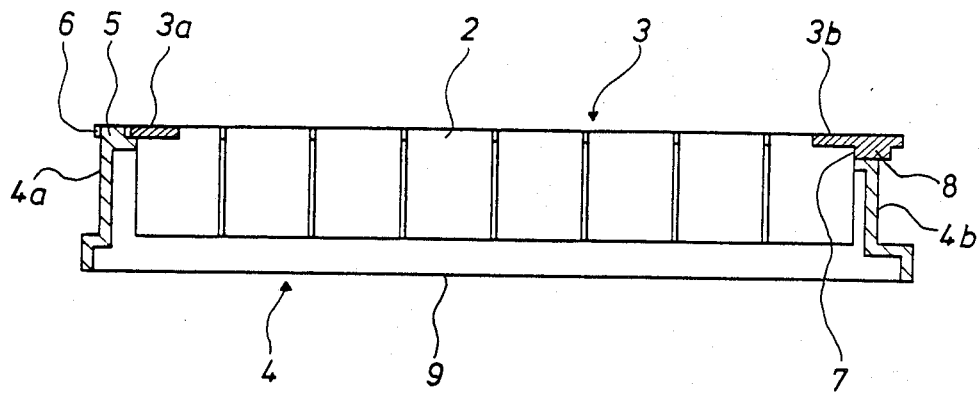
Figure 2C:
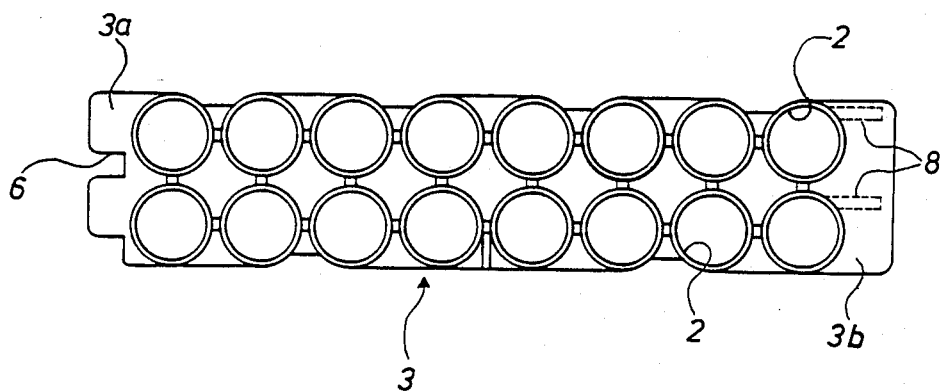
FIG. 2c is a plan view of a module having a plurality of wells and removably mounted in the microplate.

At first, the microplate 1 will be described. As shown in FIGS. 2a, 2b and 2c, the microplate 1 comprises a module-plate 4 which removably mounts six modules 3 each of which in turn mounts flat bottom wells 2 which are arranged 8×2. Thus, 96 wells 2 are arranged on the module plate 4.

To maintain mounting direction of the module 3 relative to the module plate 4, one end surface 3a of the module 3 forms engage recess 6 which engages one of engage projections 5 projected along one mounting edge 4a of the module plate 4. Along the opposite end surface 3b of the module 3, engage projections 8 are formed to engage with coresponding recesses 7 formed along opposite end surface 4b of the module plate 4.

Also, one of the four corners formed by frames 9 of the module plate 4 forms a diagonal cut portion 10a, and the other corners form round portions 10b, 10c and 10d.

FIG. 1 shows a procedure of the method of forming the solid phase film of the reagent in the above mentioned wells 2 on the microplate 1.

In reagent solution dispensing stage, eight dispense nozzles 12 which are arranged on a nozzle arm; not shown, dispense predetermined amount of reagent solution 11 in the eight wells 2 on each module 3 of the microplate 1 simultaneously in first stage. Then in second stage, the dispensed quantity, i.e. 100 micro liter plus minus 10%, of the reagent solution 11 in each well 2 is checked by inserting a pair of electrode 13 in the well 2, and the data is processed.

The dispensing of reagent solution 11 through the dispensing nozzles 12 is performed by dispensing from eight nozzles simultaneously in the above mentioned embodiment. However, two rows of eight nozzles corresponding to two rows of the wells 2 may be arranged on one dispensing unit so that sixteen wells 2 may be simultaneously dispensed.

The next dispense quantity check stage also may be performed by two rows of eight pairs of electrodes 13 which check the quantity of reagent solution 11 in sixteen wells 2 simultaneously.

The first and second stage, i.e. dispense and dispense quantity check may be performed interchangeably for each one or two rows of the wells by transferring the microplate 1 by suitable tranfer means, not shown, which moves the microplate intermittently by a pitch corresponding to the pitch of the rows of the wells 2.

Although not shown in FIG. 1, a well check stage detects absence of the module 3 on the module plate 4. If absence of the module 3 is detected, alarm signal e.g. buzzer is produced and the dispensing stage is interrupted.

When the data process means detects one or more wells 2 which are under dispensed, corresponding module 3 including such well 2 is exchanged by other module 3 including properly dispensed wells 2 before next stage.

The reagent solution 11 to be dispensed is stored in vessels, not shown, at predetermined low temperature, and the dispense nozzles 12 such the reagent solution from the vessels for predetermined quantity.

The dispense stage and the dispense quantity check stage are performed such that after each dispense and quantity check stage, the dispense nozzles 12 and the electrode 13 are cleaned. As described, the dispense and dispense quantity check stages are performed alternately so that the dispense nozzles 12 are cleaned while the electrodes 13 are checking the dispense quantity to prepare reagent solution dispensing to next pairs of wells. When the dispense quantity check by the electrodes 13 in the wells 2 is completed, suction of reagent solution 11 and the dispensing stage is initiated by the dispense nozzles 12, and the electrodes 13 are cleaned meanwhile.

The wells 2 each of which are dispensed predetermined quantity of reagent solution are supported on the module 3 which is attached on the module plate 4 of the microplate 1. The microplate 1 is sequentially discharged from the first and second stages and is received in a magazine, not shown, which receives a plurality of plates. When the magazine receives predetermined number of such plates, the magazine is transferred to next incubation chamber. In the incubation chamber which is temperature controlled at 37°±2° C., the reagent solution in the wells are incubated by keeping the microplates for one hour. Thus, reagent film is formed and attached inside wall and the bottom surface of each well.

The microplates sequentially discharged from the incubation chamber is stored in the magazine placed at discharge side, and is transferred to next cleaning stage. The cleaning stage is performed by cleaning shown as 4-th stage and cleaning fluid discharge check stage shown as 5-th stage in FIG. 1.

The 4-th stage or cleaning stage is performed as follows: after the incubation, the microplate 1 is transported by transfer means from the magazine to the cleaning stage. At first, remaining reagent solution 11 in the wells on the microplate is discharged by discharge nozzles 14 which correspond to the number of wells of one or two rows on the microplate 1. Then, the wells 2 are dispensed by cleaning fluid 16 from cleaning nozzles 15 which also correspond to the number of wells 2 of one or two rows on the module 3. The dispense of cleaning fluid 16 from the cleaning nozzles 15 and the discharge by the discharge nozzles 14 are performed in three times.

The cleaning of the wells is performed by the discharge nozzles 14 and cleaning nozzles 15 which are equal to the number of wells of one row on the module, and are arranged on a nozzle arm, not shown. However, two sets of such cleaning nozzles 15 and discharge nozzles 14 may be attached on opposite side of the nozzle arm to clean twice number of wells simultaneously.

The 5-th stage or discharge check of the cleaning fluid is performed by a pair of the electrodes used to check the dispense quantity check and the number of the pairs of the electrodes corresponds to the number of the wells in one or two rows on the module. The electrodes 17 are inserted in the well 2 and the result is processes by data process procedure.

The 4-th and 5-th stages or cleaning and discharge check stages are performed alternately while the microplate is transferred for every one pitch corresponding to the pitch of the wells, by the transfer means which take out the microplate from the magazine. Between the stages, cleaning of the discharge nozzles 14 and the electrodes 17 are performed same as the dispense stage and quantity check stages of the first and second stages.

After the cleaning stage, blocking solution dispense proces is performed by the 6-th stage or dispense of blocking solution 18, and the 7-th stage or blocking solution dispense quantity check and data processing stage.

Dispense nozzles 19 perform the blocking solution dispense of 6-th stage, and pairs of electrodes 20 perform the dispense quantity check and data process of blocking solution 18 of 7-th stage, to the wells 2 on the microplate 1. Both stages are similar with the above mentioned reagent solution 11 dispense stage and dispense quantity check and data process stage so that detailed description will not be necessary.

The reagent solution 11 to be used in the reagent dispense stage is stored in predetermined low temperature. However, as to the blocking solution 18 to be used in the blocking solution dispense stage, normally no warming or cooling process is necessary.

As to the incubation stage of the blocking solution 18 of the 8-th stage, the stage is similar with the third stage or reagent incubation stage so that detailed description will not be necessary.

The cleaning process after the blocking solution incubation stage is performed by cleaning stage of 9-th stage and cleaning fluid discharge check stge of 10-th stage. discharge nozzles 21 perform discharge of the blocking solution 18 remaining in the wells 2, and discharge of the cleaning fluid after cleaning, and cleaning nozzles 23 perform supply of cleaning fluid 22. The cleaning fluid discharge check is performed by inserting a pair of electrodes 24 in each well 2. The 9-th and 10-th stages are similar with the 4-th and 5-th stages respectively so that detailed description will not be necessary.

After the incubation and cleaning of the blocking solution, the microplates 1 are dried in a drier chamber, not shown, at predetermined temperature and time so that solid phase film covered by protect film is formed inside wall and bottom surface of each well uniformly.

SECOND EMBODIMENT

Now, an embodiment of solid phase forming apparatus to use in the above mentioned solid phase forming method will be described.

Figure 3:
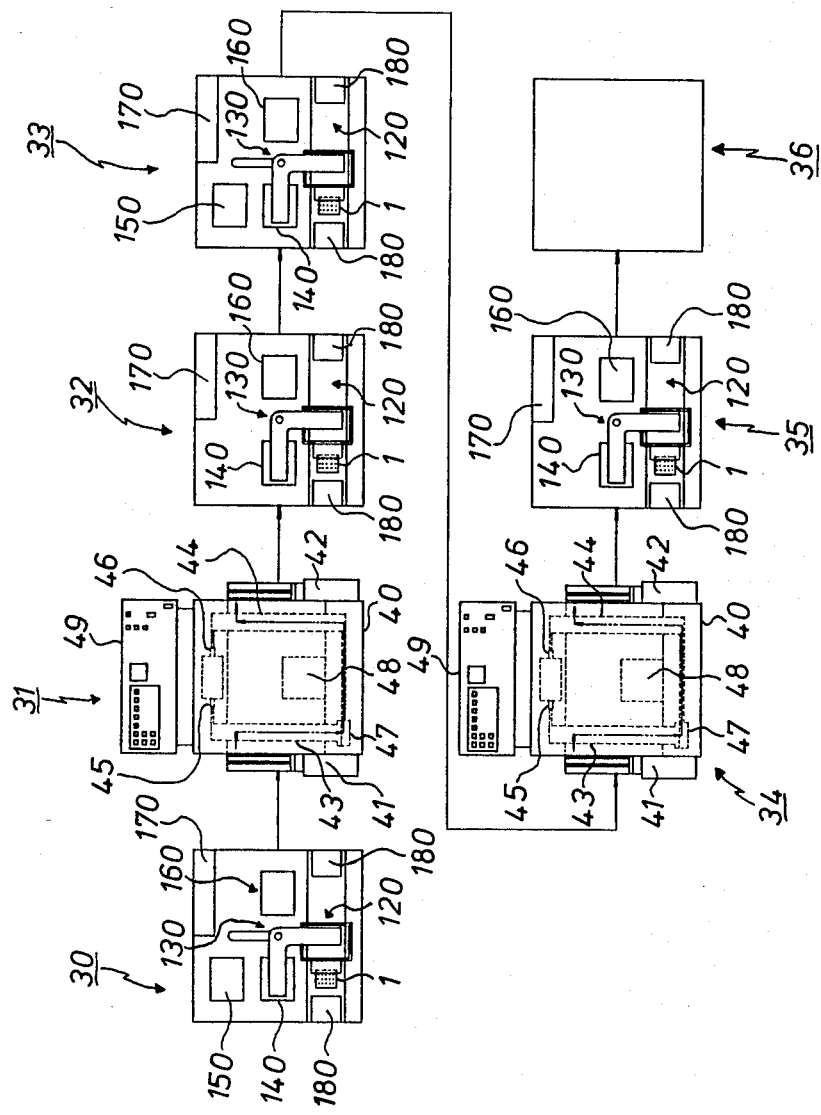
FIG. 3 is a diagrammatic arrangement of the solid phase forming apparatus.

FIG. 3 shows general construction of the micromodule solid phase forming apparatus of reagent according to the present invention and comprises a reagent dispense and coating apparatus 30, a reagent incubation apparatus 31, a reagent cleaning apparatus 32, a blocking solution dispense and coating apparatus 33, a blocking solution incubation apparatus 34, a blocking solution cleaning apparatus 35 and a drier apparatus 36.

The apparatus forming the solid phase forming apparatus will be described following to the order of the process.

The reagent dispense and coating apparatus 30 will be described in detail referring to FIGS. 4 to 17.

Figure 4A:
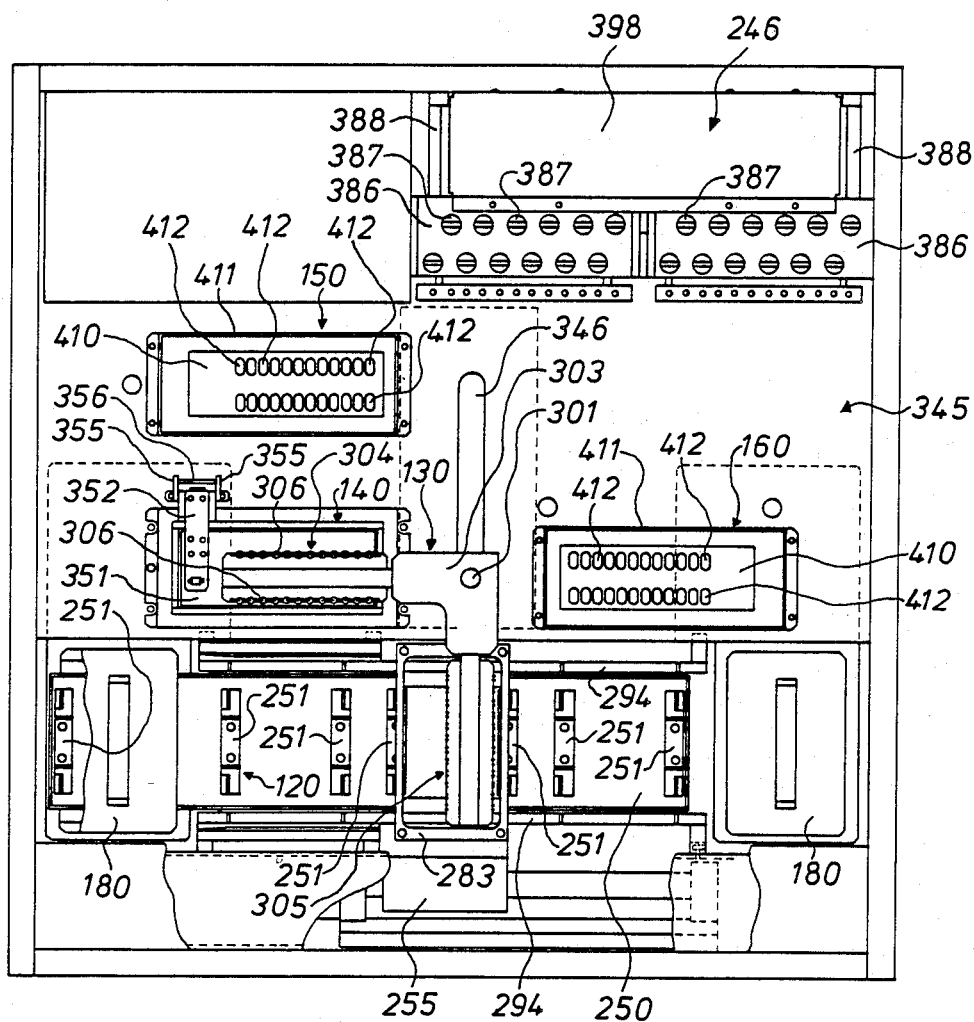
FIGS. 4a, 4b and 4c are plan view, front view and side view, respectively of the dispense and coating apparatus.
Figure 4B:
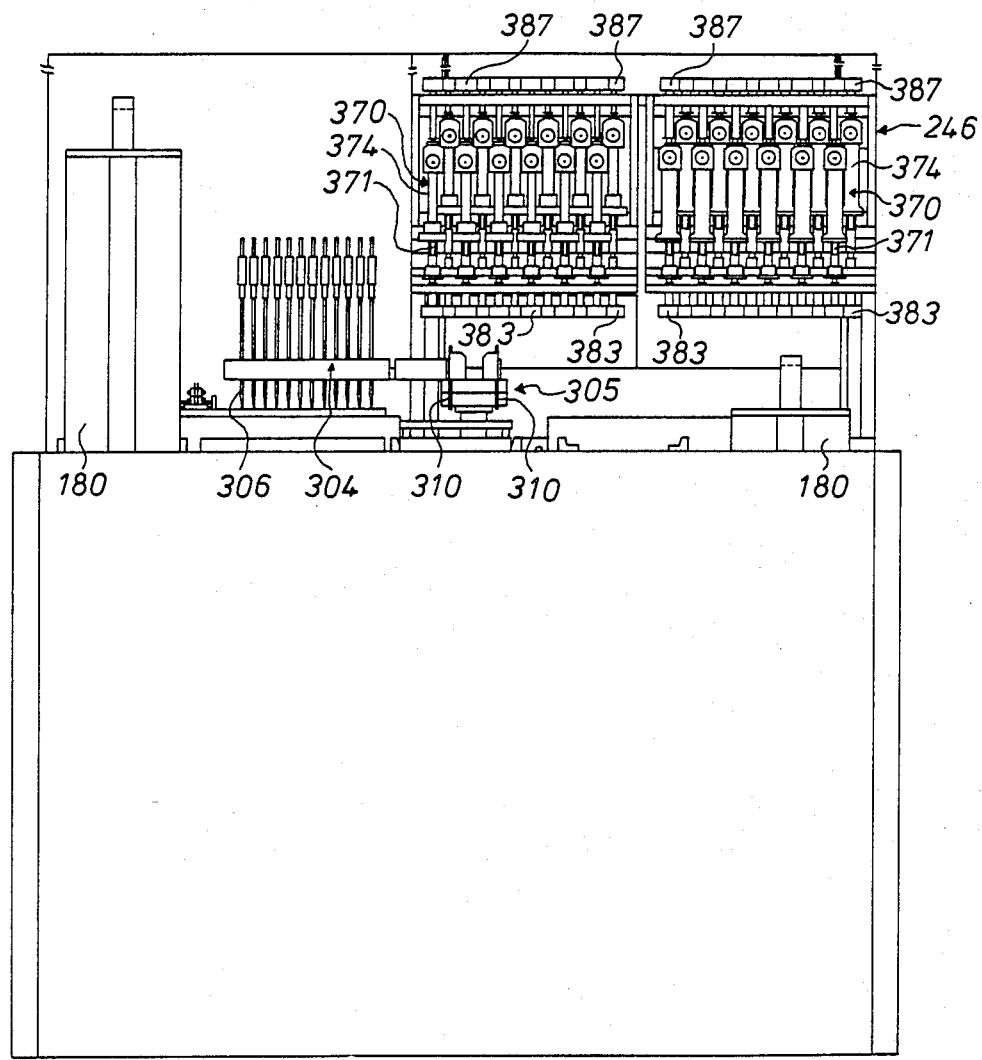
Figure 4C:
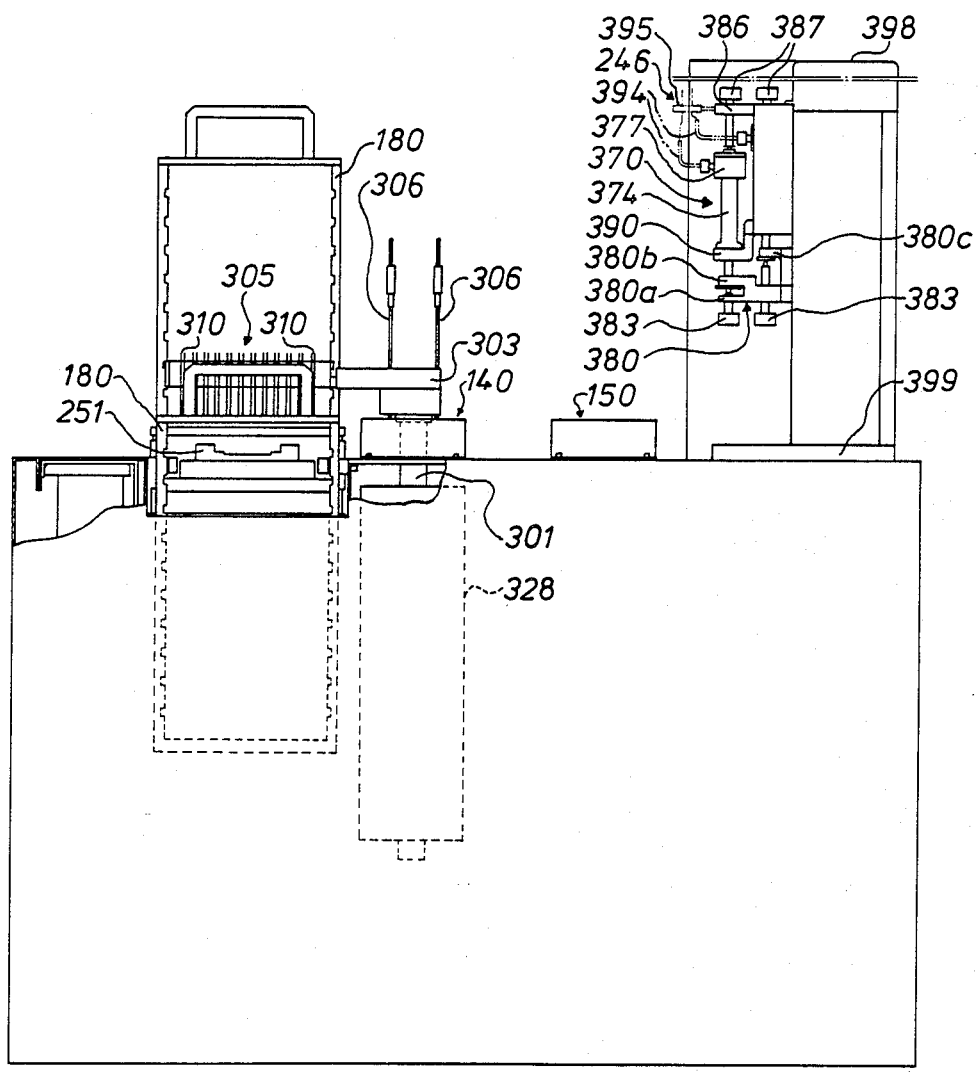
Figure 5A:
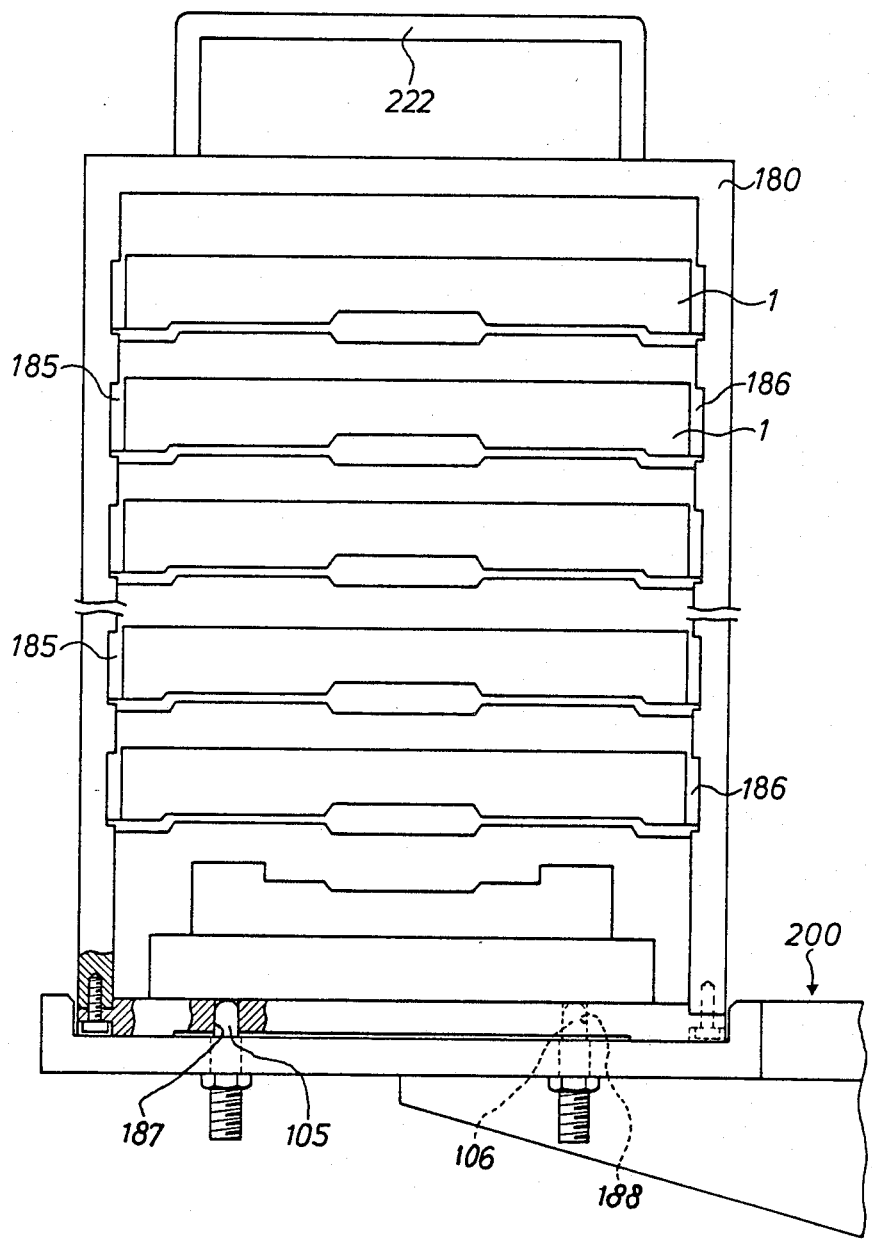
FIG. 5a to 5j are illustrations of a magazine to store the microplates.
Figure 5B:
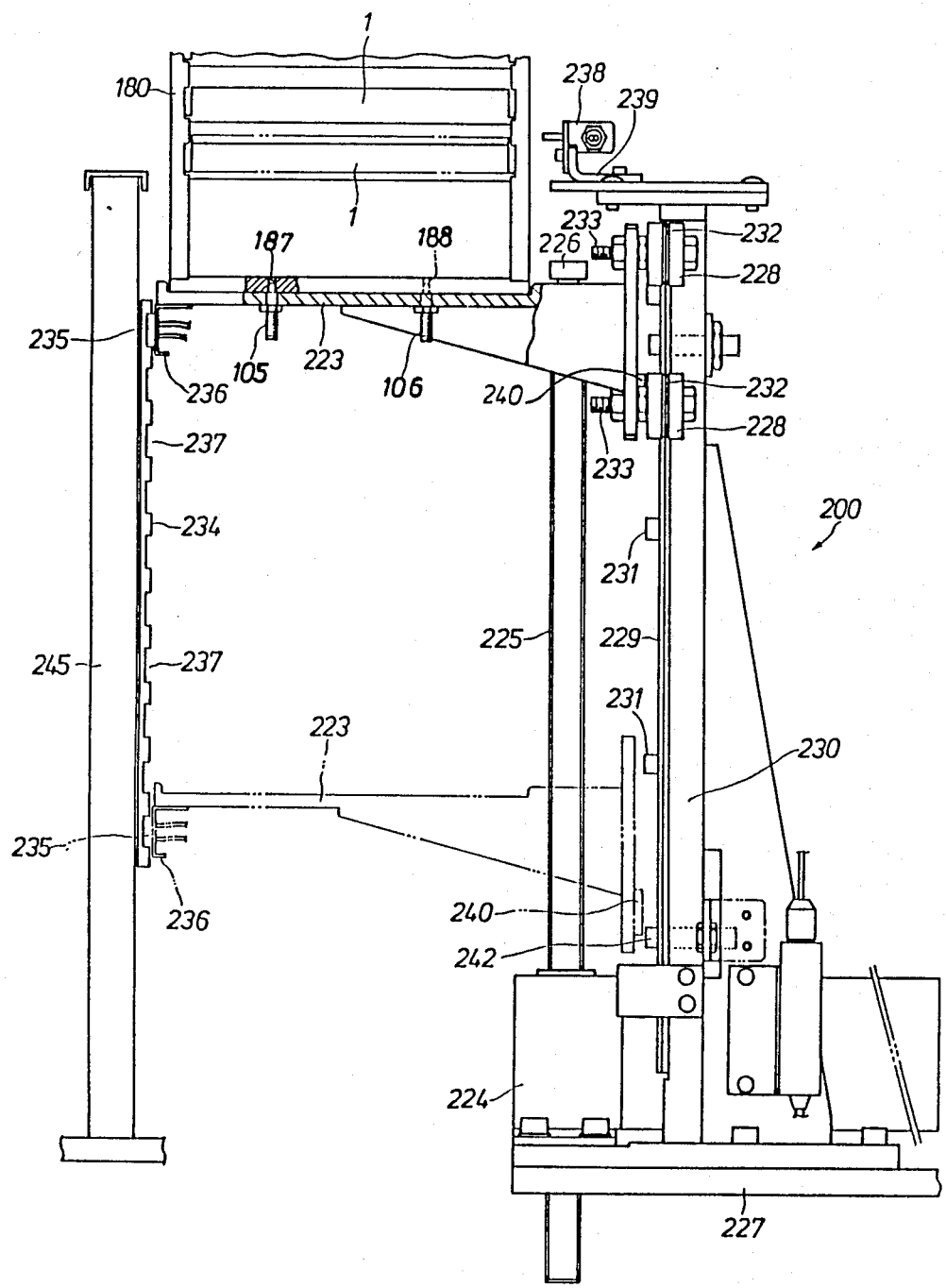
Figure 5C:
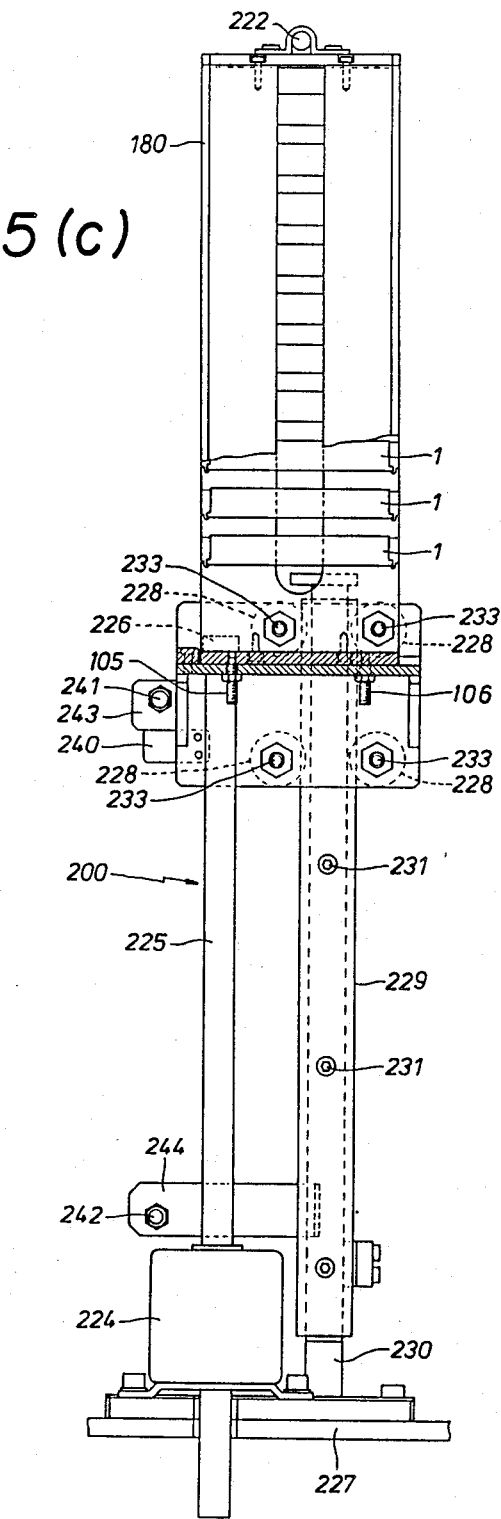
Figure 5:
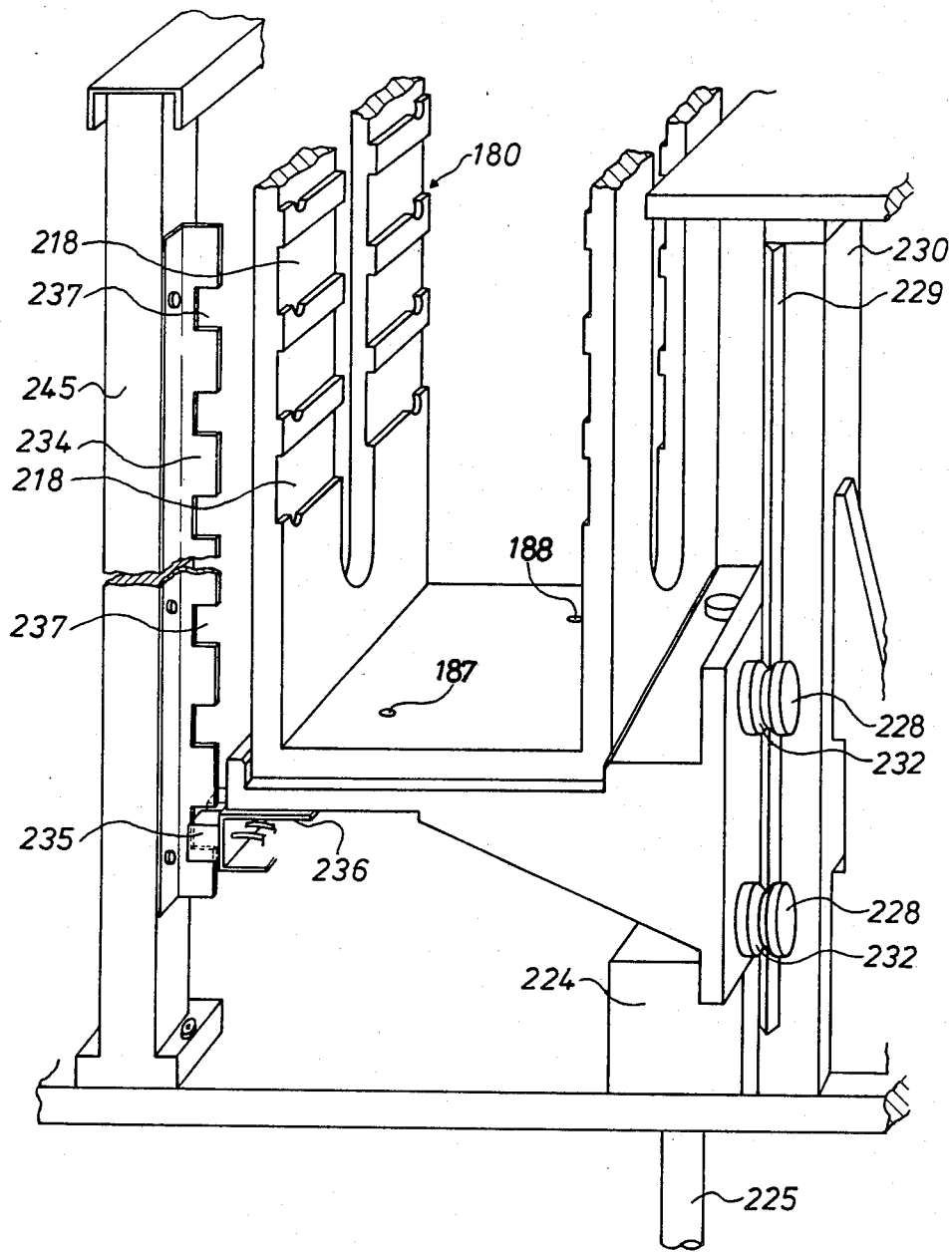
Figure 5E:
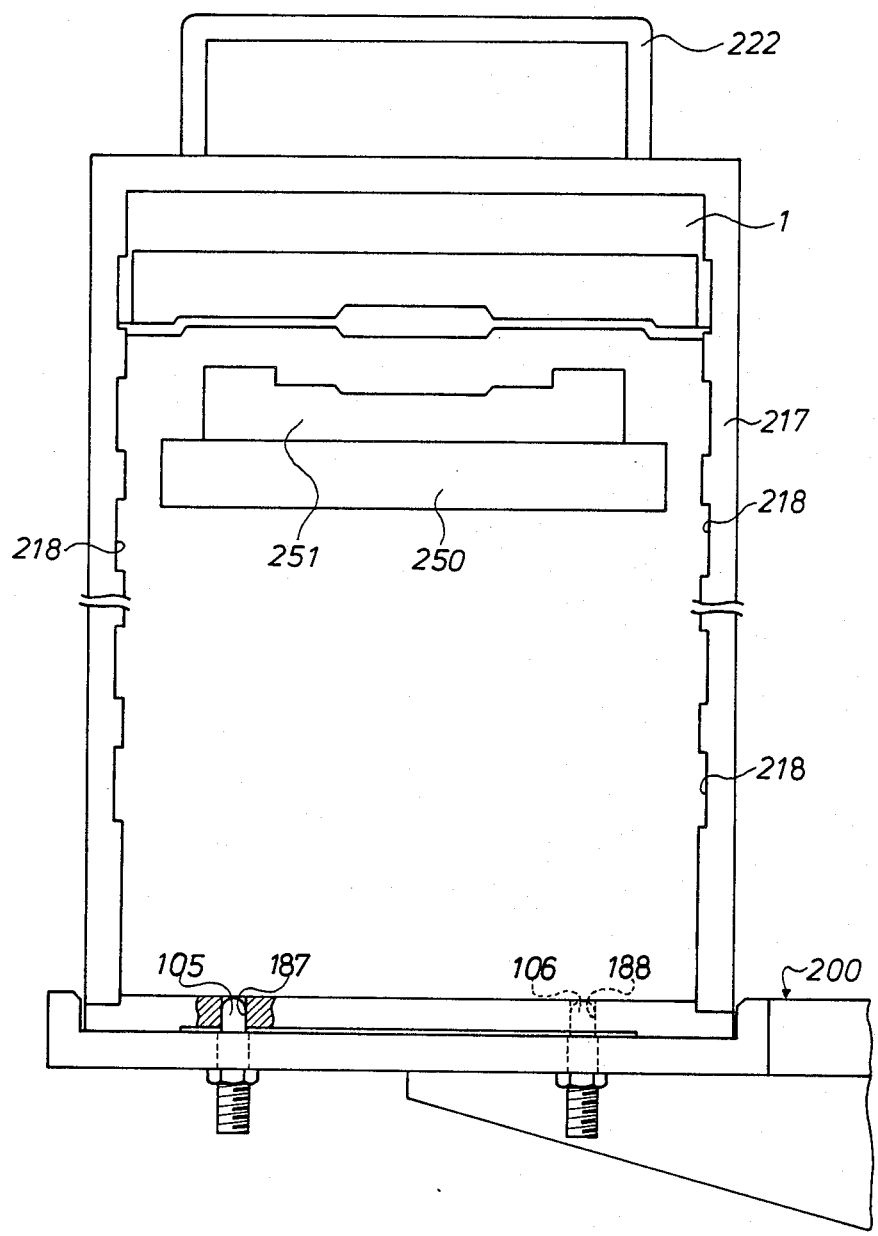
Figure 5:
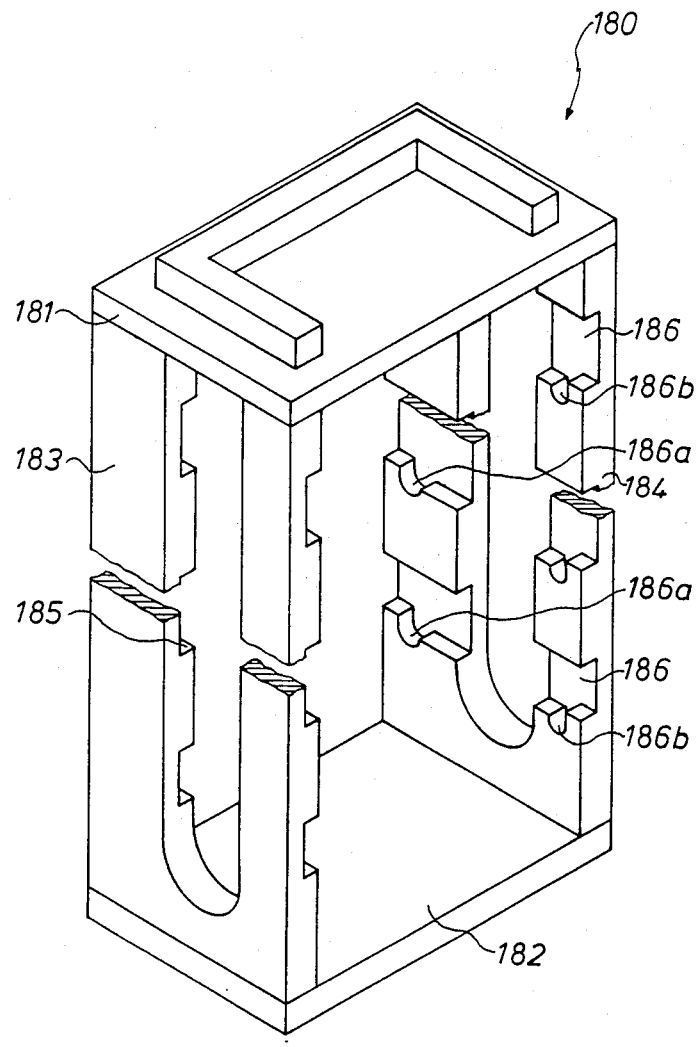
Figure 5G:
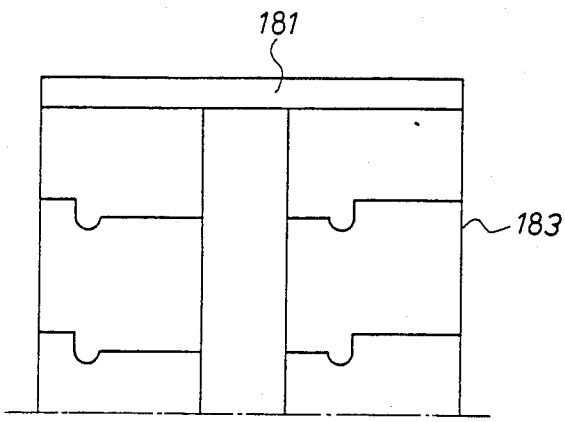
Figure 5H:
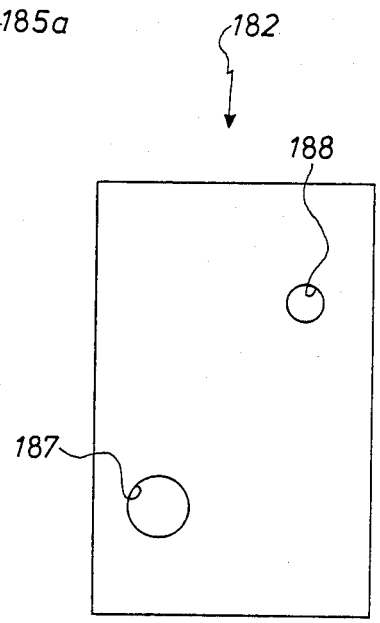
Figure 5:
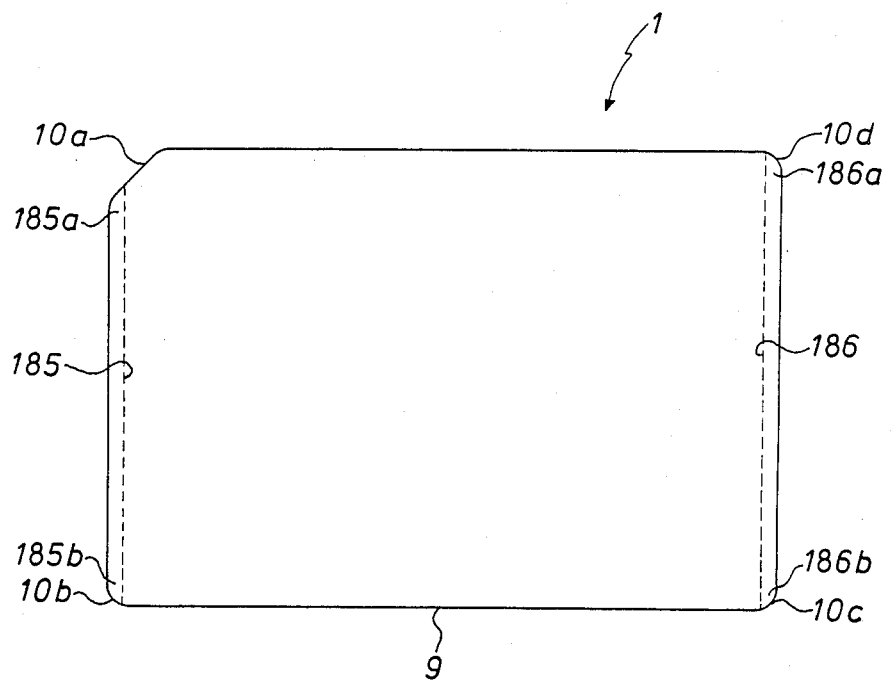
Figure 5:
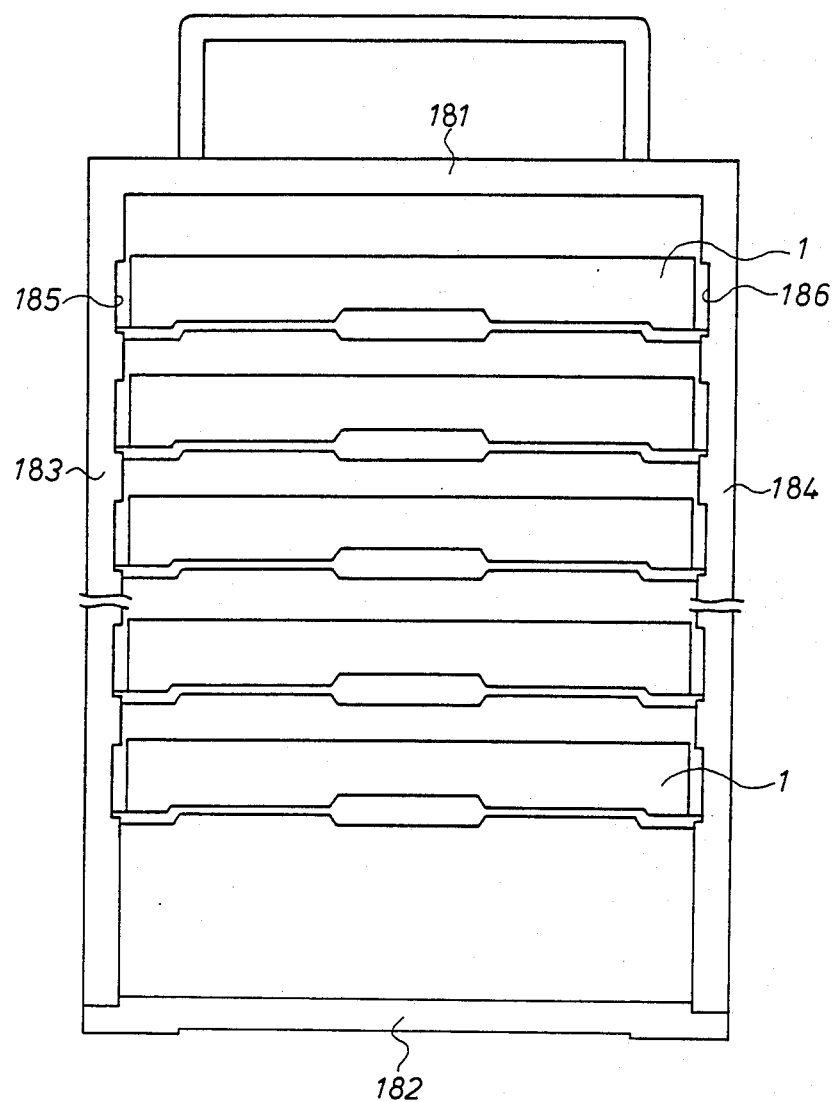
Figure 6:
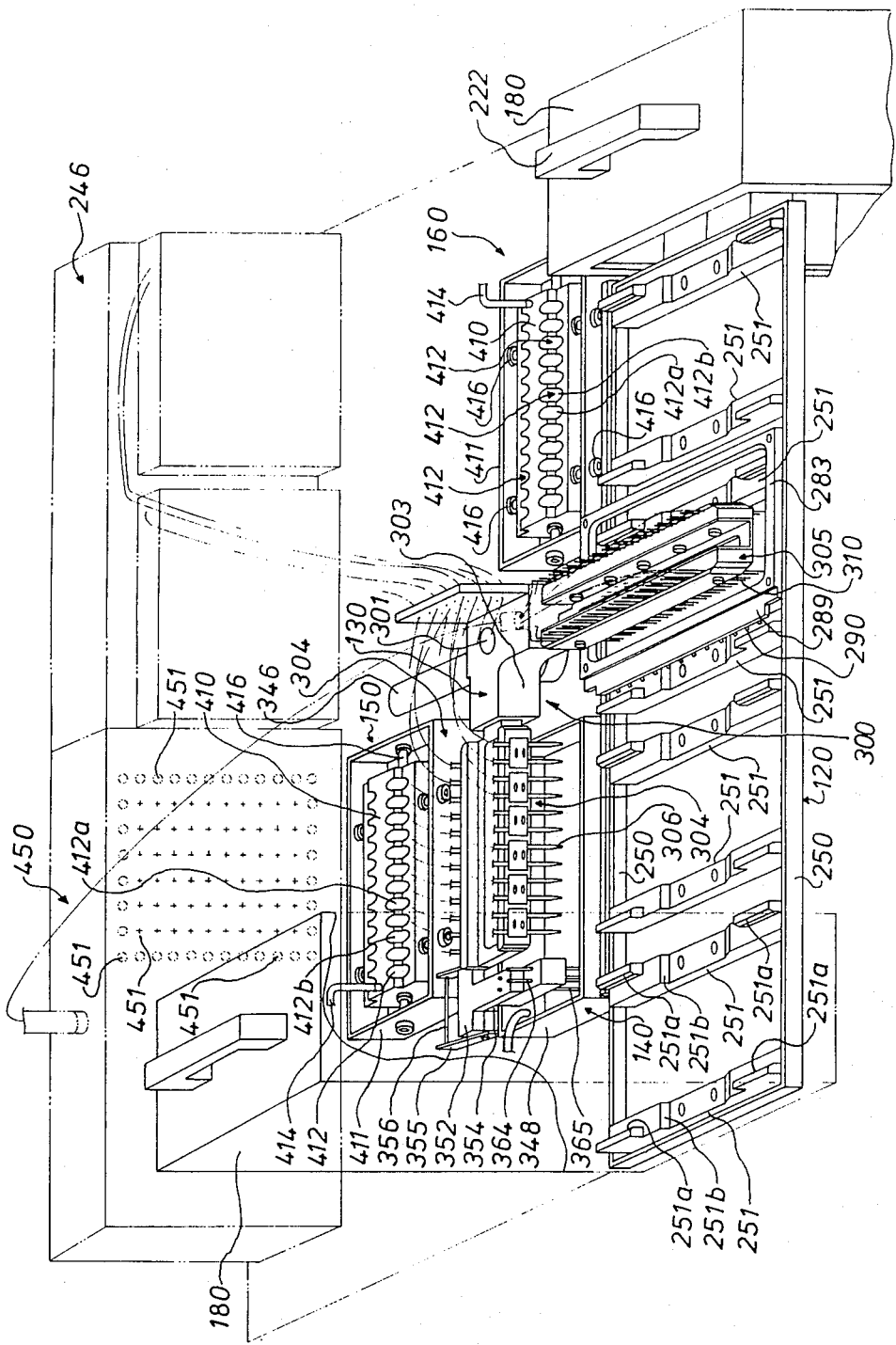
FIG. 6 is a perspective view of a portion of the dispense and coating apparatus.
Figure 7A:
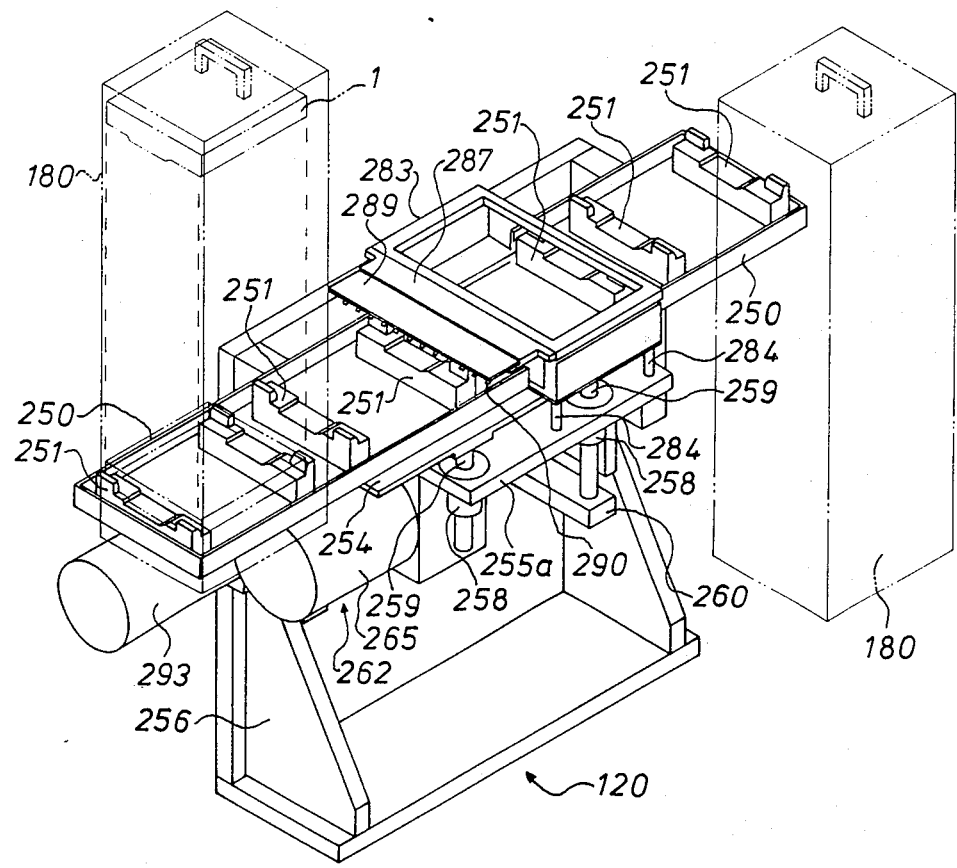
FIGS. 7a to 7c are illustrations of the plate transfer mechanism of the apparatus shown in FIG. 6, FIGS. 8a to 8c are illustrations of the microplate transfer unit of the apparatus shown in FIG. 6, FIGS. 9a to 9g are illustrations of the nozzle unit and electrode unit of the apparatus shown in FIG. 6, FIGS. 10a to 10c are illustrations of the arm drive unit shown in FIG. 6, FIGS. 11a and 11b are illustrations of the reagent solution store device shown in FIG. 6, FIGS. 12a to 12i are illustrations of the dispense unit shown in FIG. 6.
Figure 7B:
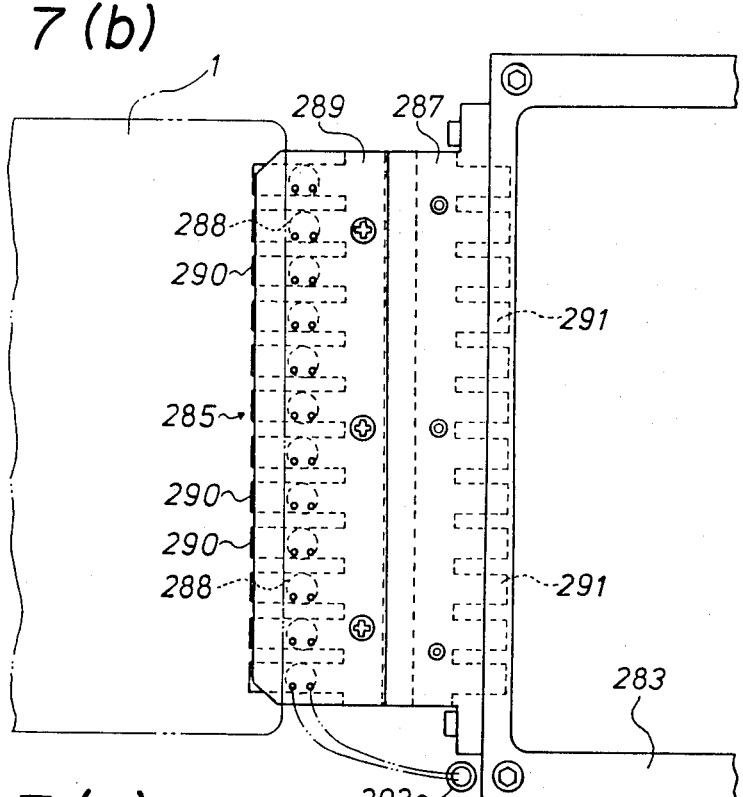
Figure 7C:
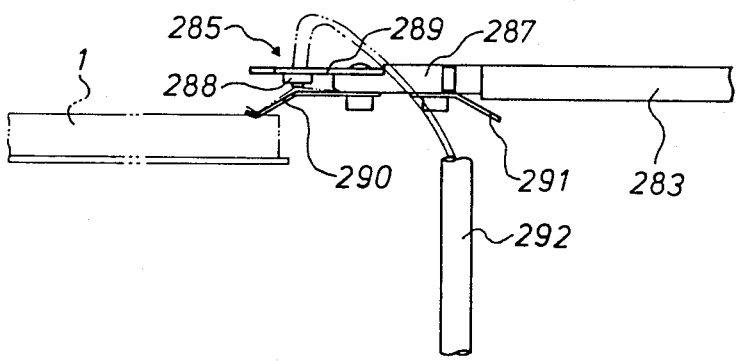
Figure 8B:
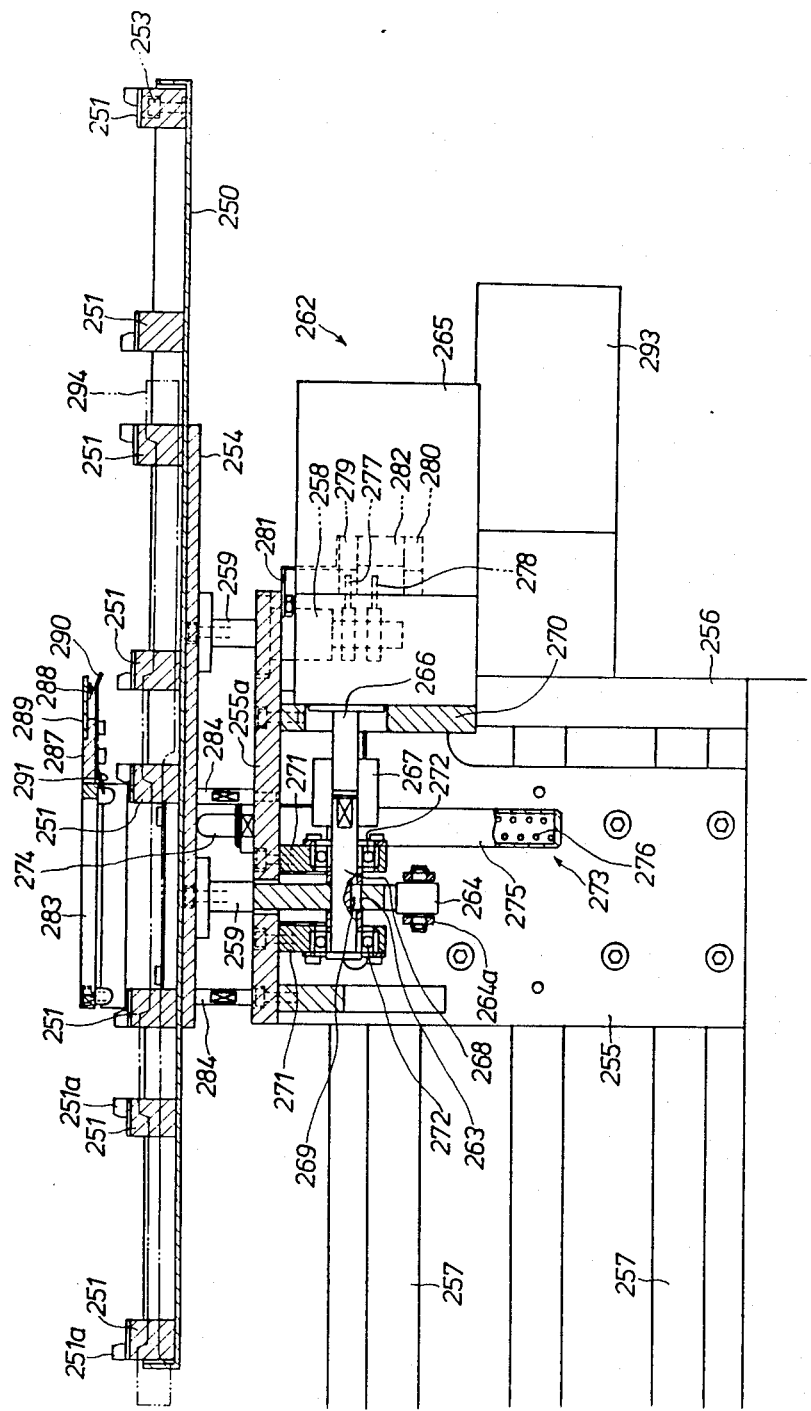
Figure 8C:
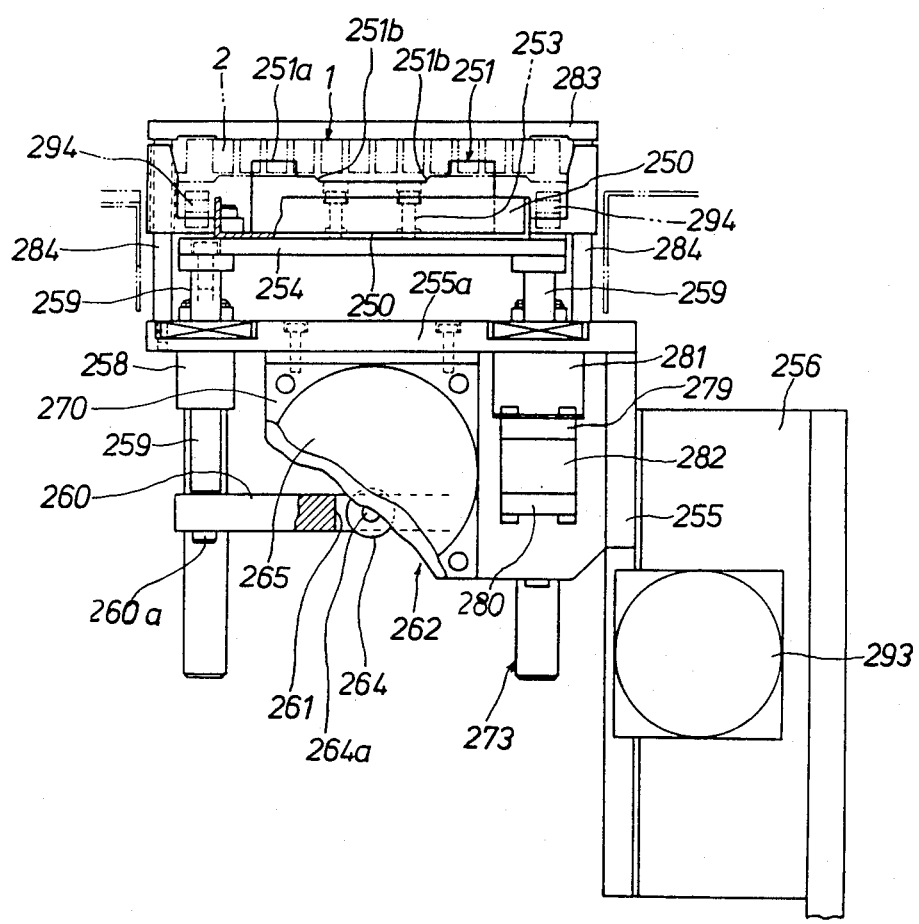
Figure 9:
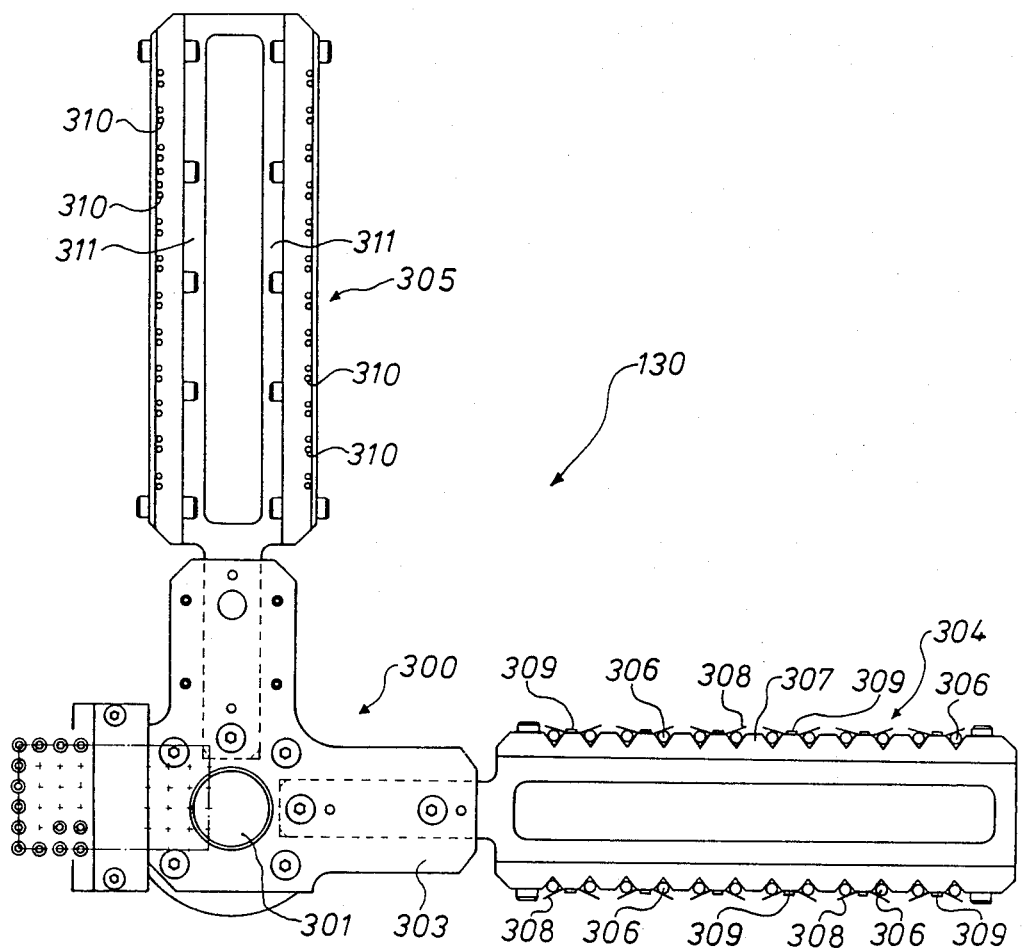
Figure 9B:
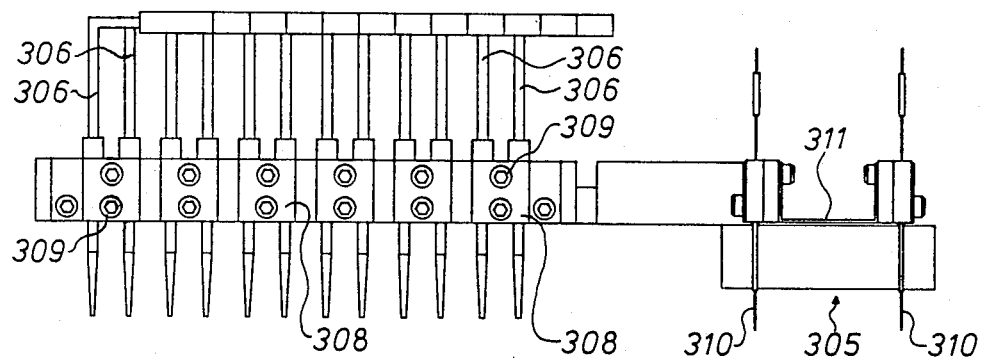
Figure 9C:
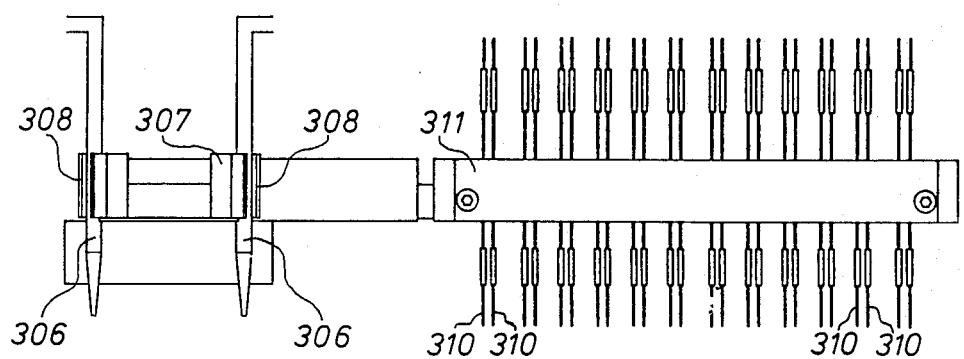
Figure 9:
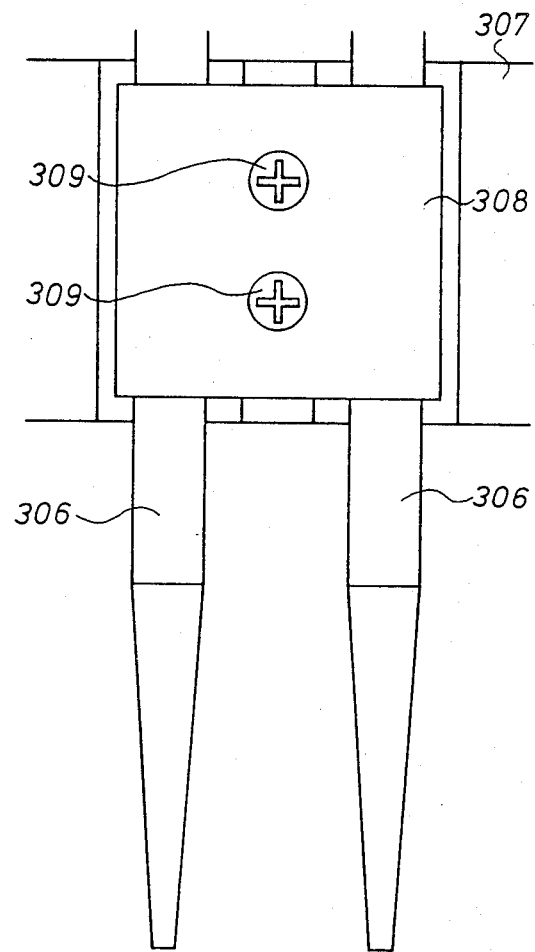
Figure 9E:
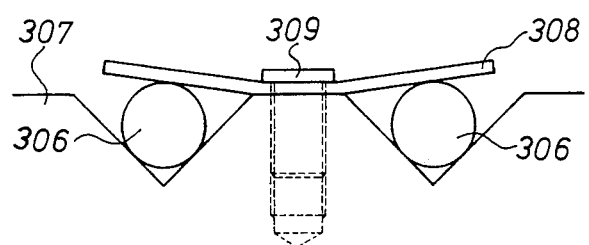
Figure 9F:
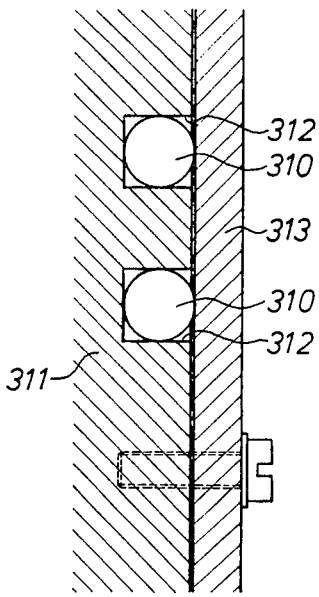
Figure 9G:
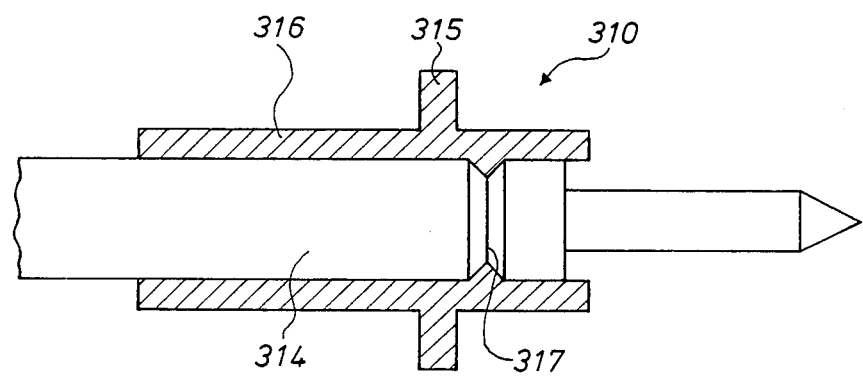
Figure 10:
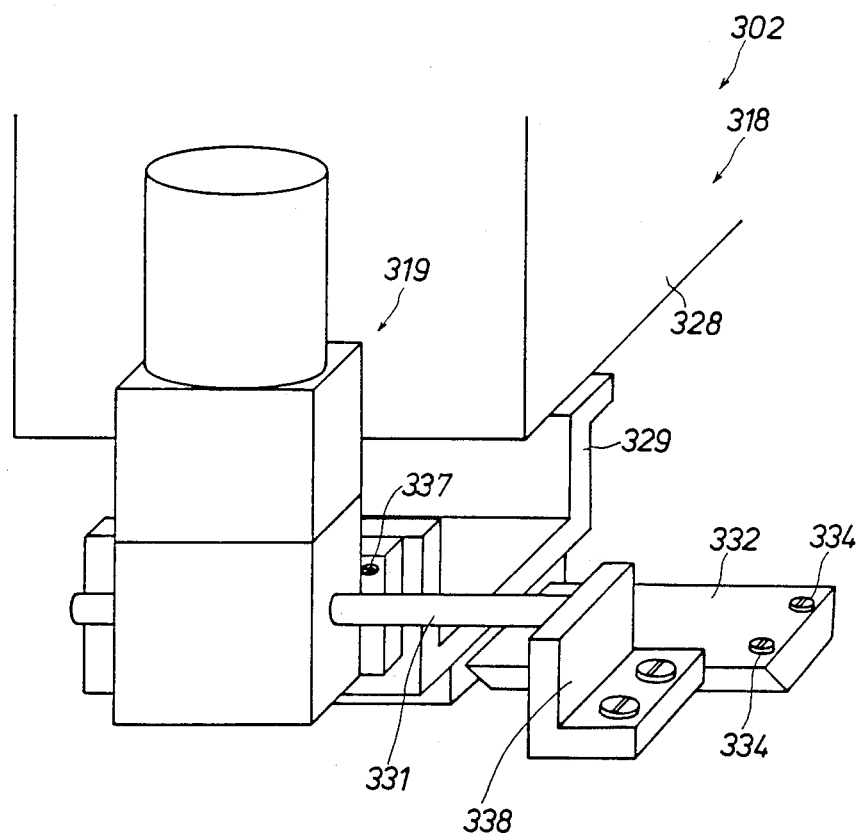
Figure 10:
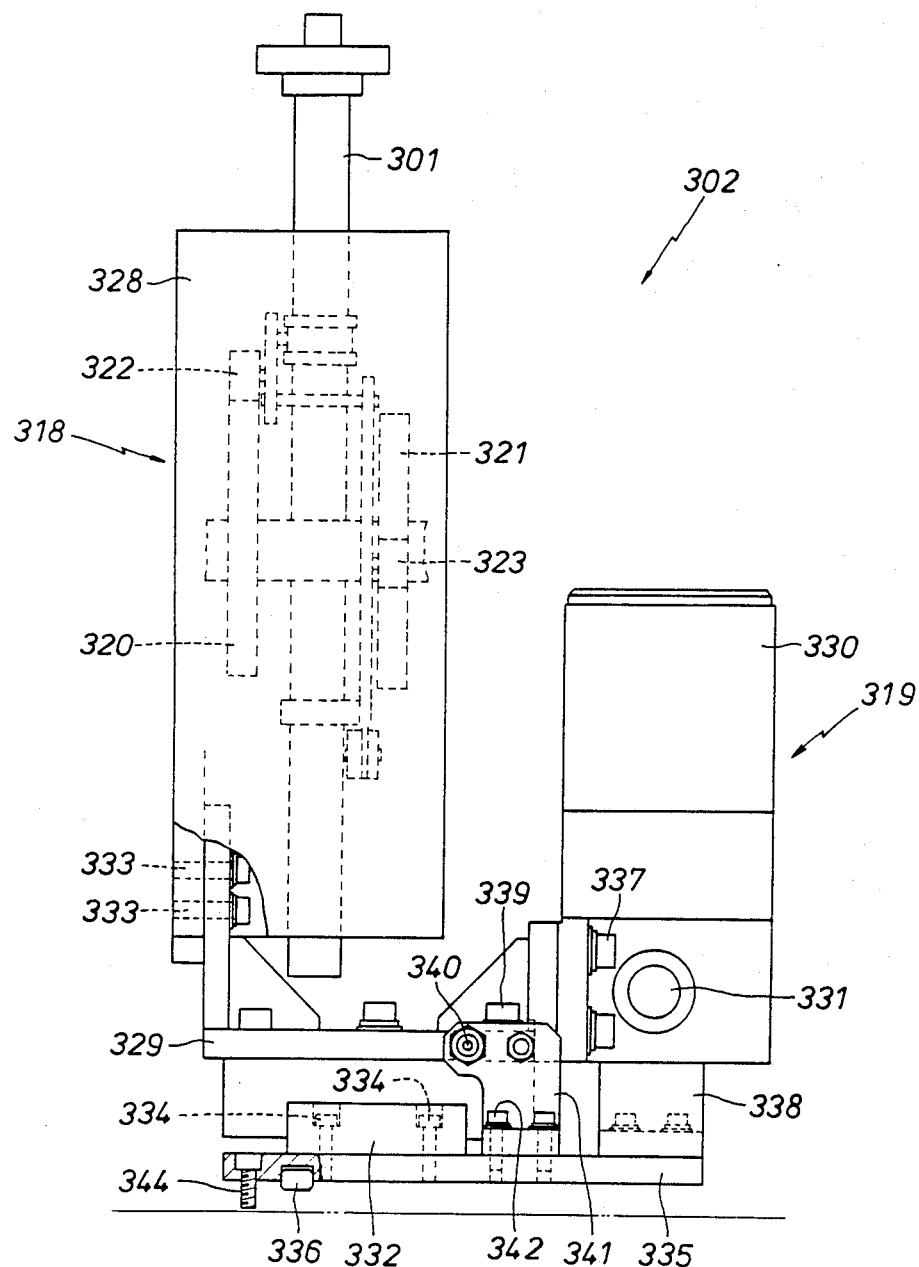
Figure 10C:
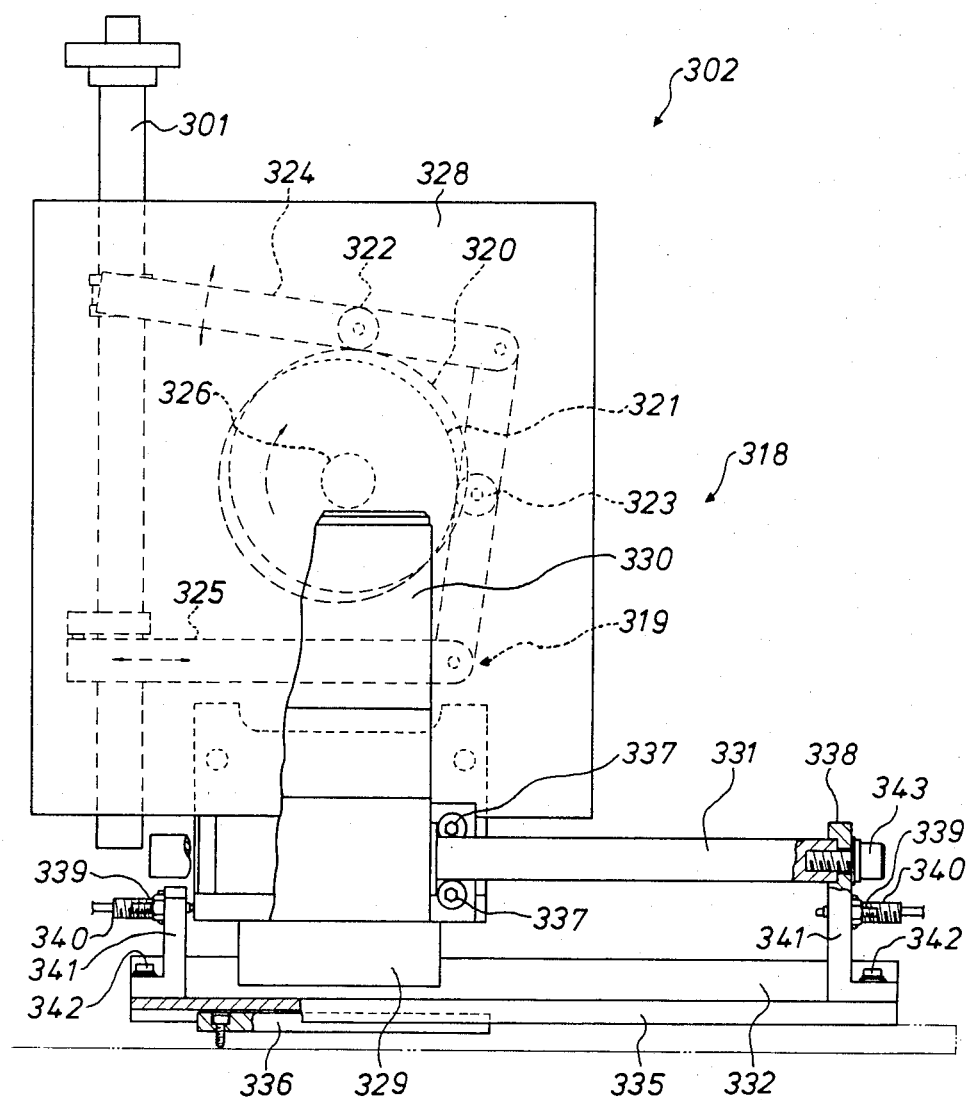
Figure 11A:
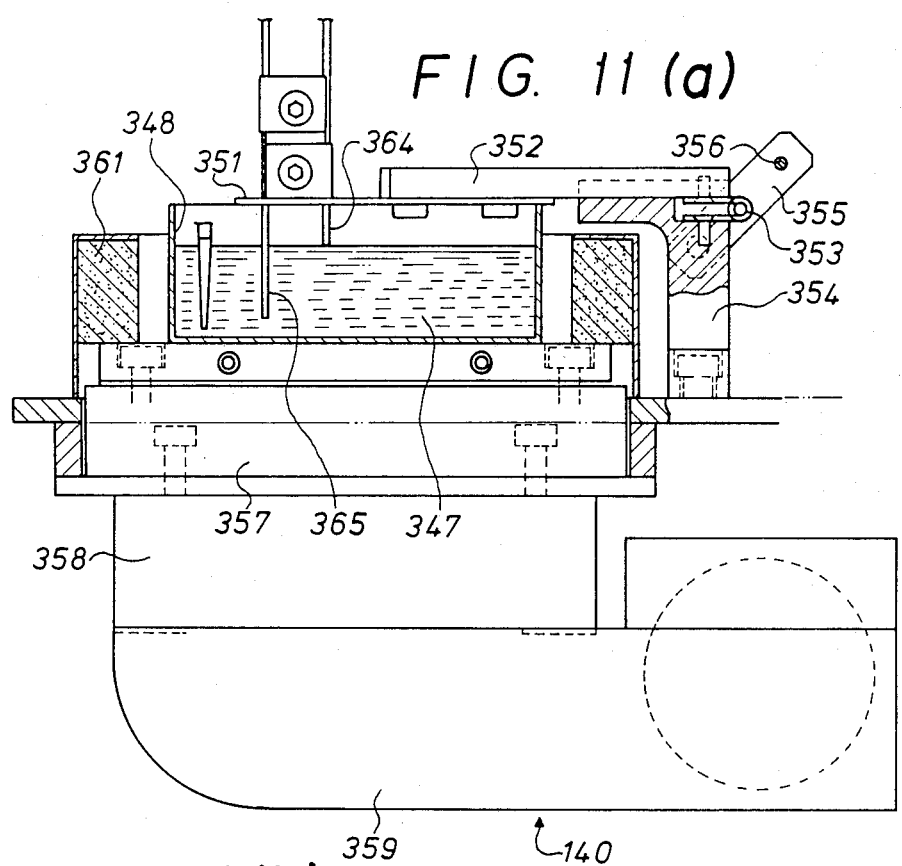
Figure 11B:
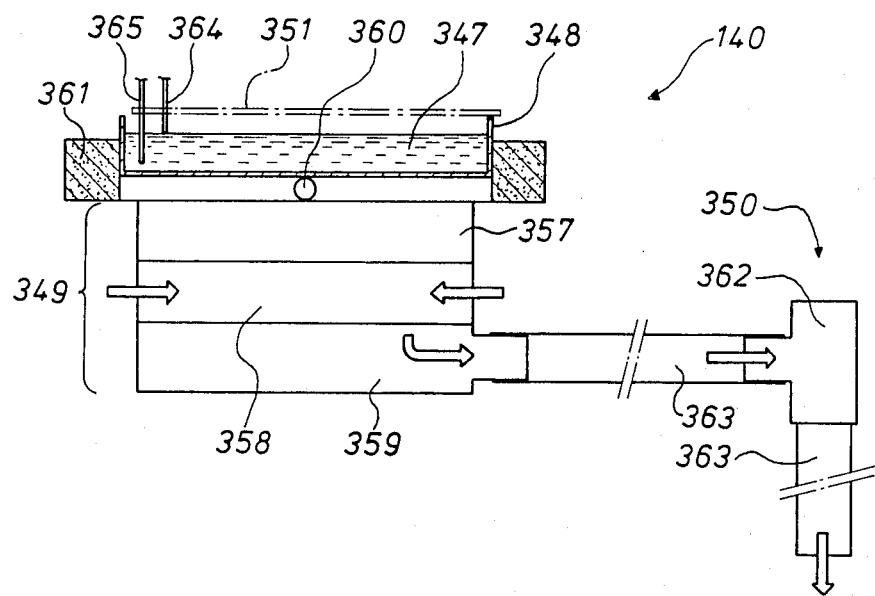
Figure 12:
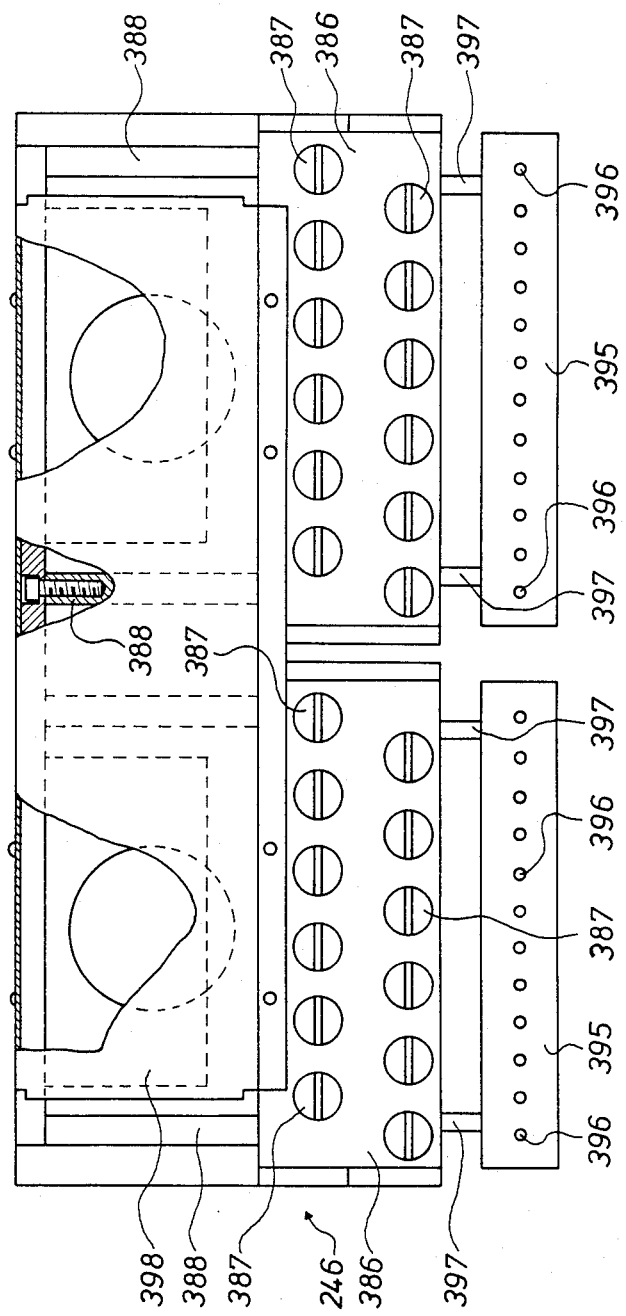
Figure 12:
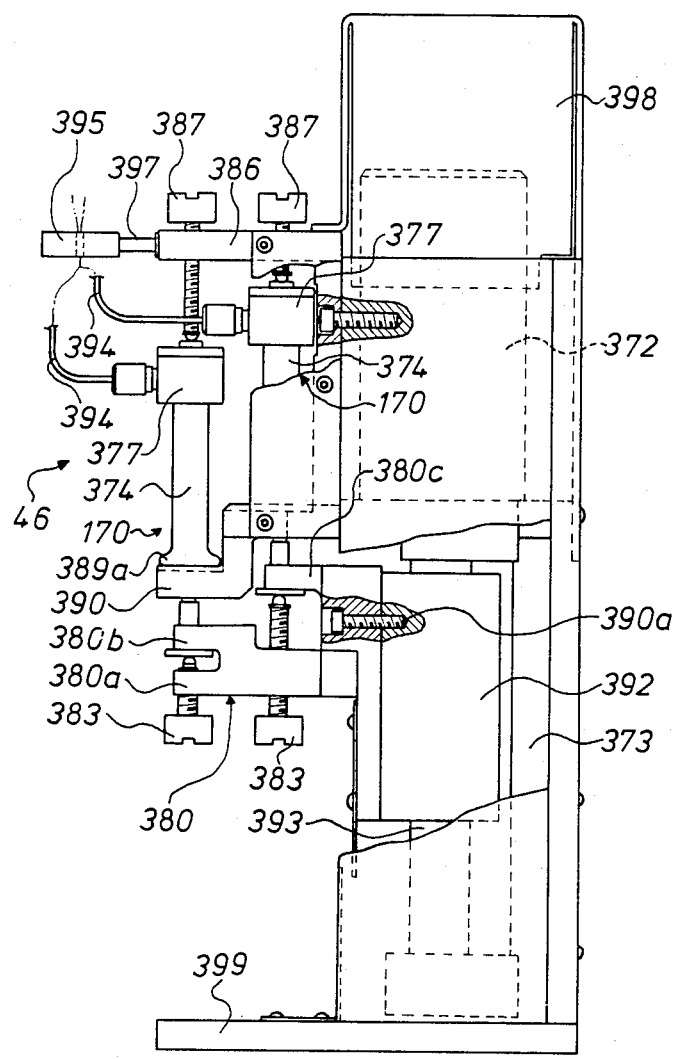
Figure 12:
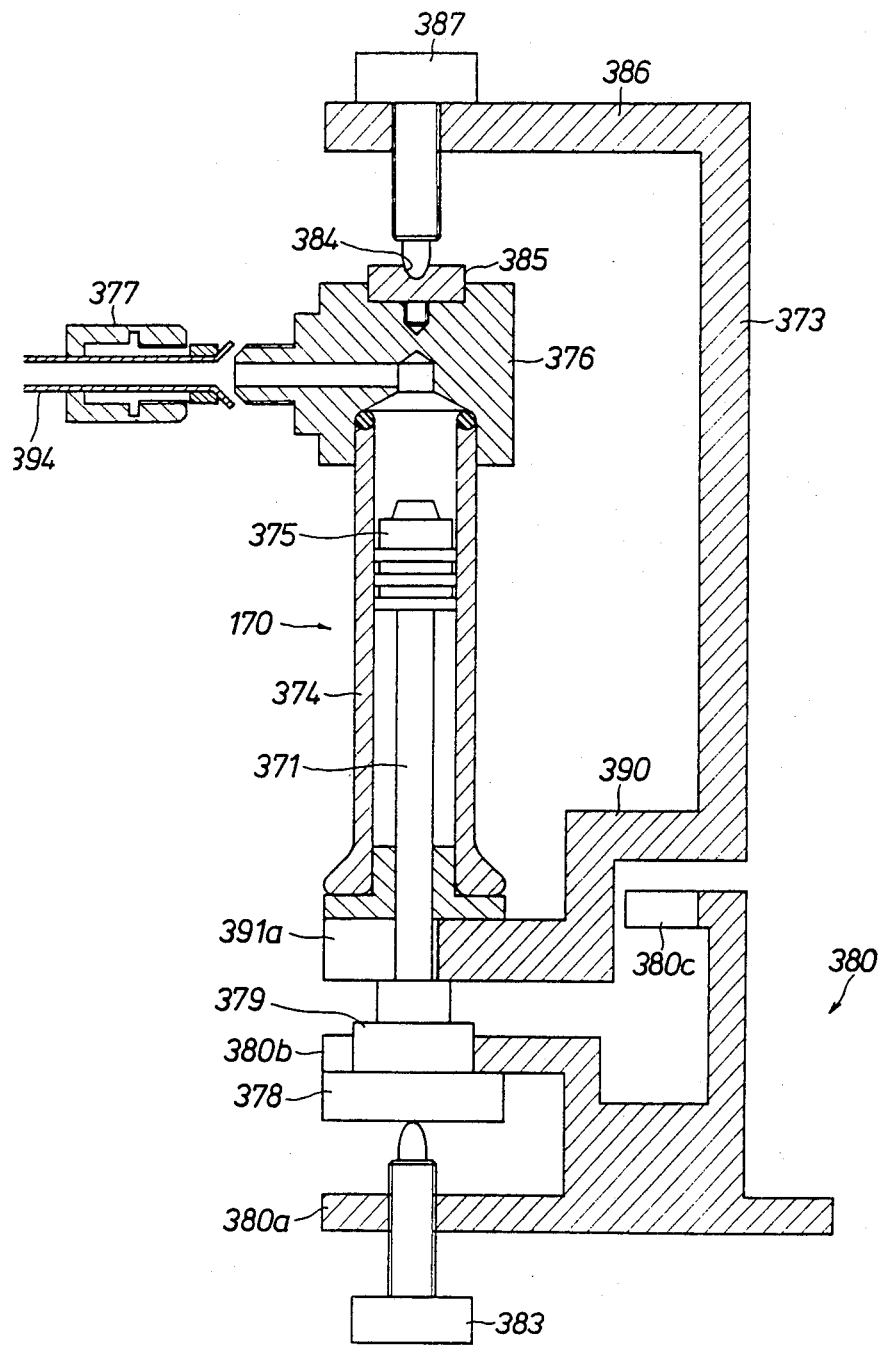
Figure 12I:
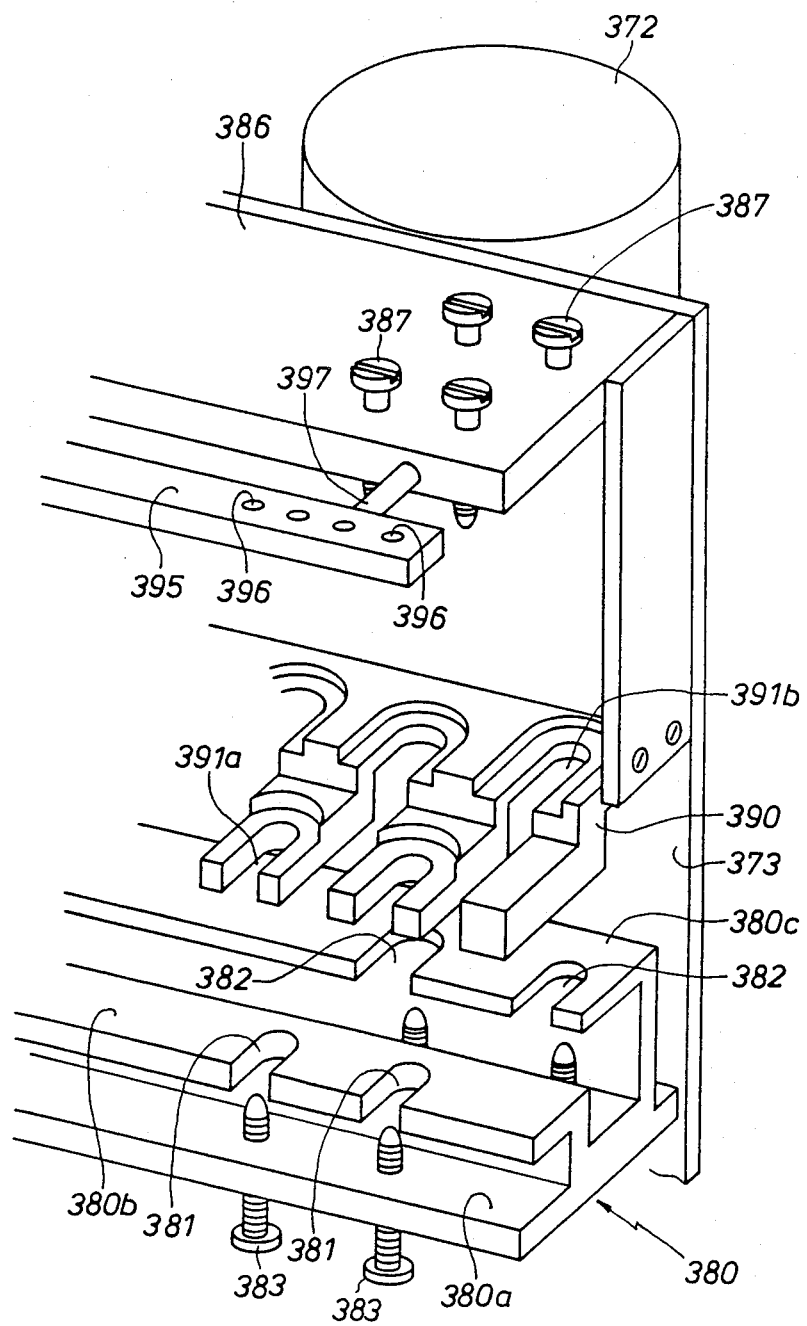
Figure 13:
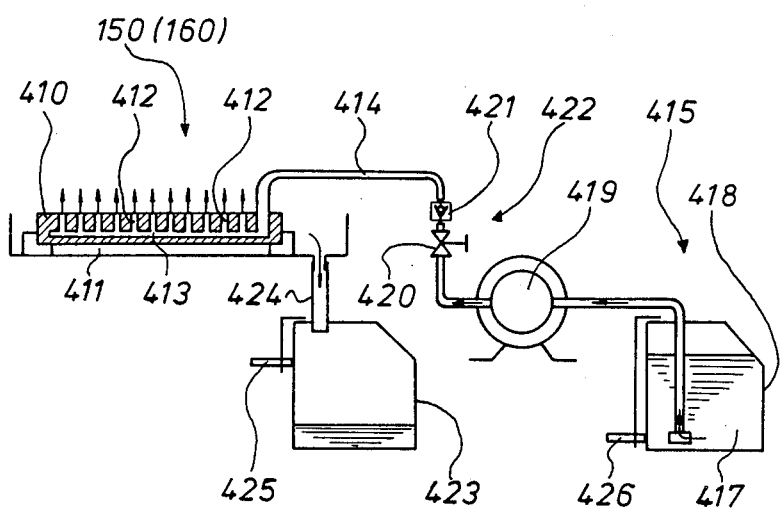
FIGS. 13 is an illustration of the cleaning unit shown in FIG. 6, FIGS. 14a to 14f, FIG. 15 and FIGS. 16a and 16b are illustrations of the process, according to the present invention.

FIGS. 4a, 4b and 4c show general views of the reagent dispense and coating apparatus 30, FIGS. 5a, 5b, 5c, 5d, 5e, 5f, 5g, 5h, 5i and 5j show microplates receiving magazine and elevator thereof, FIG. 6 shows general construction of coating apparatus, FIGS. 7a, 7b and 7c show details of the coating apparatus, FIGS. 8a, 8b and 8c show a microplate transfer apparatus, FIGS. 9a, 9b, 9c, 9d, 9e, 9f and 9g show a nozzle unit and an electrode unit, FIGS. 10a, 10b and 10c show an arm drive unit, FIGS. 11a and 11b show reagent solution store, FIGS. 12a, 12b, 12c, 12d, 12e, 12f, 12g, 12h and 12i show a dispense unit, FIG. 13 shows a cleaning unit, FIGS. 14a, 14b, 14c, 14d, 14e and 14f, FIGS. 15 and 16 show detail of a coating apparatus, and FIGS. 17a and 17b show coating of the wells on the microplate.

As shown in FIG. 3, the reagent dispense and coating apparatus 30 comprises a supply magazine 180 which receives the microplate 1 arranging wells 2 shown in FIG. 2, to which reagent will be coated, a plate transfer mechanism 120 to transfer the microplates at constant pitch, solution nozzle arm unit 130 dispensing reagent solution into each well on the microplate 1 and detecting the liquid level of the reagent, a reagent shelf 140 to store reagent at constant low temperature, a nozzle cleaning shelf 150 to clean the reagent solution dispense nozzles at the solution nozzle arm unit 130, an electrode cleaning shelf 160 to clean the liquid level detecting electrode in the solution nozzle arm unit 130, a reagent dispense unit 170 to dispense reagent in each well on the microplate, and a discharge magazine 180 to receive microplates which completed dispense and coating of reagent solution.

The supply side and discharge side magazine 180 are same and the detail is shown in FIGS. 5a to 5j, and is adapted to receive ten microplates sequentially from top to bottom.

As shown in FIGS. 5f to 5j, the magazine 180 comprises a top plate 181 and a bottom plate 182, and left and right side plates 183 and 184 to form open sided container. The inner side surfaces of the side plates 183 and 184 form opposed steps 185 and 186 of constant pitch to engage and retain ten microplates 1. The front and rear end portions of the steps 185 and 186 form engage recesses 185a, 185b, 186a and 186b. As shown in FIG. 5g, the engage recesses 185a and 185b of each step 185 of one side plate 183 are formed assymmetry to the center line of the left side plate 183 to orient the microplates 1. The engage recess 185a is formed to engage the diagonal corner 10a of the microplate 1, and the other engage recesses 185b, 186a and 186b are formed to engage with the round corners 10b, 10c and 10d. Thus, the orientation of the microplates 1 is determined by the engage recesses 185a, 185b, 186a and 186b of the steps 185 and 186 in the magazine 180 relative to the microplate 1. One side surface of the side plate 183 may be painted to show the diagonal recess 10a side of the microplate 1 to easily receive the microplates 1.

As shown in FIG. 5h, the bottom plate 182 forms positioning openings 187 and 188 corresponding to positioning pins 105 and 106 shown in FIG. 5e. One of the opening 187 has larger diameter than that of the opening 188 so that misalignment of the magazine 180 can not occur. The positioning pin 105 and 106 also have different diameters.

The side plates 183 and 184 have different colors so that the magazine can be easily set relative to the supply side and discharge side elevation units.

The magazine 180 can be moved up and down by a magazine elevator apparatus 200 shown in FIGS. 5b to 5d. The magazine elevator apparatus 200 comprises a support base 223 which is secured through mounting screws 226 with upper end of an elevator rod 225 which is driven by a motor 224. The motor 224 has means to transfer rotary motion to linear motion. The motor 224 is mounted on an intermediate base 227 about the middle portion of the body of the apparatus 30. On the intermediate base 227, a guide rail plate 229 is secured to guide guide rollers 228 which is rotatably supported on the support base 223. The guide rail plate 229 is secured with the intermediate base 227 through support posts 230, and is secured by screws 231. The guide roller 228 is shown in FIG. 5c. The guide rollers 228 are adapted to support upper and lower guide surfaces of the guide rail plate 229. Two pairs of guide rollers 228 stably support the guide plate 229. Each guide roller 228 forms V-shaped guide groove 232 to engage with corresponding V-shaped edge on the guide plate 229. The guide roller 228 is mounted by a support bolt 233. A sensor plate 234 cooperates with a sensor 235 which is secured with the support base 223 and controls displacement of the support base 223 i.e. elevation of the supply magazine 180, and is parallel with the elevator rod 225. The sensor 235 is a sensor having light transmitter and receiver and is secured with the support base 223 through a support plate 236. The sensor plate 234 forms constant pitch recesses 237 so that when the support base 223 is lowered and the sensor 235 reaches to a position aligning the recess 237, the light receiver of the sensor 235 receives light from the transmitter to stop the lower displacement of the support base 223. The recesses 237 are same as the number of the microplates 1 to be stored, i.e. ten in the embodiment. A sensor 238 detects presence of the microplates 1 stored in the supply magazine 180, and is secured with upper end of the support post 230 through a bracket 239. A sensor plate 240 cooperates with sensors 241 and 242 to control upper and lower limit of the support base 223, and is secured with the support base 223. The sensors 241 and 142 are supported by support plates 243 and 244, and the sensors plate 234 is secured with a support post 245. The supply magazine 180 loaded with ten empty microplates 1 is set to elevated position through the magazine elevator apparatus 200 as shown in FIGS. 4b and 4c.

The discharge magazine 180 is same as above mentioned supply magazine 180 and is only difference is initial set position. The empty magazine 180 is set to lowered position by magazine elevator apparatus 200 as shown in FIG. 5d. The microplate 1 completed with coating of solid phase reagent is stored in the magazine 180 sequentially from uppermost shelf.

The plate transfer mechanism 120 takes out the microplate 1 one by one from the supply magazine 180 and transfers the same at constant pitch to the solution nozzle arm apparatus 130, and further stores the microplate 1 which is coated with reagent into the discharge side magazine 180. The mechanism of the plate transfer mechanism 120 will be described referring to FIGS. 6, 7 and 8.

FIG. 6 shows the plate tranfer mechanism 120 and the adjacent apparatus, FIG. 7a shows the plate tranfer mechanism 120. FIGS. 7b and 7c show detail thereof, FIGS. 8a, 8b and 8c are details of FIG. 7a. In the drawing, a receive member support frame 250 secures receive members 251 for the microplate 1 to transfer the microplate 1 at a constant pitch. The receive members 251 are arranged as four pairs of two, and the center distance of the pairs is constant. The members 251 are secured by screws 253. The bottom surface of the frame 250 contacts with a base plate 254 which is secured with the support frame 250 through screws 253. An inverted L-shaped slide base 255 is slidably mounted under the plate 254 by a slide rod 257 which is mounted on a fixed frame 256 of the apparatus body, so as to slidable horizontal direction in FIG. 8. A horizontal part 255a of the slide base 255 mounts four ball bushes 258 on lower surface, and a slide shaft 259 passes through the ball bush 258 vertically slidably. Thus, the plate 254 and the receive member support frame 250 are vertically movable relative to the horizontal part 255a of the slide base 255 through the ball bush 258. Among the four slide shafts 259 which pass through the four ball bushes 258, right side slide shaft 259 in FIG. 8 is connected through connecting plate 260 at lower end by screws 260. Center portion of the connecting plate 260 has an elongated opening 261 in which a cam follower 264 is rotatably supported by a support shaft 264a to engage with a cam 263 of a cam drive apparatus 262. The cam drive apparatus 262 drives the cam 263 which engages with the cam follower 264, and has a motor 265 having a gear head, a cam shaft 268 connected with an output shaft 266 of the motor 265 through a coupling 267, and a cam 263 secured with the cam shaft 268 through a key 269.

The motor 265 is secured with a motor base 270 which is integrally secured under the horizontal part 255a of the slide base 255. The cam shaft 268 is rotatably supported through bearings 272 which are inserted in cam shaft support plates 271 and 271 depending from the horizontal part 255a of the slide base 255. On the horizontal part 255a of the slide base 255, a support frame upward urging means 273 is mounted to urge upwards the receive member support frame 250 normally. The support frame upward urging means 273 is formed from an urging pin 274 engaging with lower surface of the plate 254, a pin store 275 receiving the urging pin 274, and a coil spring urging the pin 274 upwards, to urge the receive member support table 250 by the urging pin 274 which is urged by the spring 276. The cam 263 is an eccentric cam, and when the cam 263 is driven by the cam drive apparatus 262, the cam 263 cooperates with the cam follower 264 to urge the cam follower 264 downwards to move the receive member support frame 250 downwards against the upwards urging force of the support frame upward urging means 273.

The lower side of the slide shaft 259 mounts vertically spaced two detect members 277 and 278. On the horizontal part 255a of the slide base 255, two sensors 279 and 280 are mounted through a support plate 281 to detect the detect members 277 and 278. By cooperation between the detect members 277 and 278 and the sensors 279 and 280, vertical movement of the receive member support frame 250 is detected. A spacer 282 is shown.

A stopper plate 283 is upward from the horizontal part 255a of the slide base 255 to engage with upper surface of the well 2 on the microplate placed on the receive member 251 when the receive member support frame moves upwards to position the microplate 1. The stopper plate 283 is secured on the horizontal part 255a of the slide base 255 through support posts 284. One side surface of the stopper plate 283 mounts a microwell module detect device 285 to detect module on the microplate 1. On the microplate 1, as shown in FIGS. 2a, 2b and 2c, a plurality of modules 3 are placed, and the microwell module detect device 285 dtects presence or absence of the module 3. The microwell module detect device 285 is shown in FIGS. 7b and 7c and includes a switch base 287, a switch plate 289 mounting a plurality of detect switches 288, and plate springs 290 to actuate the detect switches 288. The plate springs 290 is adapted to operate the switches 288 individually. The plate spring 290 engages with the edge 3a of the module 3 on the microplate 1. When the microplate 1 moves upwards on the receive member 251, the mounting edge 3a of the module 3 engages with the plate spring 290 to operate the switch 288. Thus, when the all switches 288 are not ON, ther is no microplate 1, and when a portion of the switches 288 are not ON, some module 3 are not placed on the microplate 1. A plate spring 291 to separate the microplate 1, and duct means 292 to pass lead wires of the switches 288 are shown.

A pulse motor 293 is mounted on the fixed frame 256 of the apparatus body to displace and control the slide base 255 along the slide rod 257. The receive member support frame 250 displace a pitch P which is center distance between the center line 252 of the pair of receive members 251 by the pulse motor 293. That is, the microplate 1 placed on the pair of the receive members 251 moves one pitch P through the receive member support frame 250 which is controlled by the pulse motor 293. Also, the microplate 1 on the pair of the receive members 251 is adapted to move constant minor pitch by the pulse motor 293 so that each row of the wells 2 on the microplate 1 can receive reagent from the solution nozzle arm 130 shown in FIG. 3.

A fixed receive member 294 temporary supports the microplate 1 which is transferred from the supply magazine 180. That is, the receive member support frame 250 moves leftward at lowered state through the cam 263 to one pitch P shown in FIG. 8a to penetrate into the supply magazine 180 shown in FIG. 3. In this state, when the cam 263 is rotated releasing the frame 250 to move upwards, one microplate 1 is placed on the left end pair of the receive member 251. In this case, the microplate 1 moves upwards from the fixed receive member 294, and at the upward position, the frame 250 moves to the left by the pulse motor 293 at one pitch P. After the one pitch movement, the receive member support frame 250 moves downwards by the cam 263 lower than the fixed receive member 294 so that the microplate 1 which is on the receive member 251 is temporary received on the fixed receive member 294. In this state, the support frame 250 penetrates into the supply magazine 180, to carry out the microplate 1 in the magazine 180 as before sequentially one by one.

The receive member 251 forms tapered engage surfaces 251a and 251b to engage with corresponding engage portions of the microplate 1 so that the microplate 1 can be suitably positioned.

The solution nozzle arm apparatus 130 dispenses reagent in each well 2 on the microplate 1 and to detect liquid level dispensed in the well 2, and as shown in FIGS. 9 and 10, includes an arm body unit 300, and arm shaft 301 supporting the arm body unit 300, and an arm drive unit 302 to vertically move and to swirl the arm body unit 300.

The arm body unit 300 is shown in FIG. 9a and comprises an arm base 303 secured with an arm shaft 302 and a reagent suction arm 304 and a liquid level detecting arm 305 extending from the arm base 303. The reagent suction arm 304 and the liquid level detecting arm 305 are perpendicular each other, and the both arms 304 and 305 are adapted to rotate 90 degree by the arm drive unit 302. The reagent suction arm 304 includes nozzles 306 (corresponding to the nozzles 12 shown in FIG. 1) which suck reagent from the reagent shelf 140 shown in FIG. 3 and dispense into one or two rows of wells 2 in the microplate 1, a nozzle support base 307 supporting the nozzles 306, and nozzle retainers 308. As shown in FIGS. 9d and 9e, adjacent two nozzles 306 are retained by one retainer 308 and a screw 309. The liquid level detecting arm 305 includes liquid level detecting electrodes 310 (corresponding to the electrodes 13 shown in FIG. 1) and electrode bases 311 supporting the electrodes 310. The electrodes 310 are received in recesses 312 formed on the electrode base 311 as shown in FIG. 9f and are retained in place by electrode retainers 313. The electrode 310 is shown in FIGS. 9f and 9g and includes an electrode needle 314 and an outer sleeve 316 having a flange 315. The electrode needle 314 and the sleeve 316 are connected each other by V-shaped clamp portion 317. The electrode needle 314 is adapted to absorb needle tip displacement when the tip is urged. The number of nozzles 306 are 24, i.e. two rows of twelve, and the number of electrodes 310 are 24 sets i.e. 2 rows of 12 sets in the embodiment shown.

The arm drive unit 302 is shown in FIGS. 10a, 10b and 10c, and includes a drive unit 318 to swirl and vertical movement of the arm shaft 301 and a drive unit 319 to displace the arm body unit 300 normal to the direction of the microplate transfer, shown by arrow in FIG. 3.

The drive unit 318 to swirl and vertical movement of the arm shaft 301 is shown in FIGS. 10b and 10c and includes two rotary driven cams 320 and 321, cam followers 322 and 323 engaging the cams 320 and 321, a vertical movement arm 324 and a swirl movement arm 325 operated through the cams 320 and 321 and the cam followers 322 and 323. The cams 320 and 321 are secured with a cam shaft 326, and the cam shaft 326 is rotary driven by a motor, not shown. By rotating the cams 320 and 321, the arm shaft 301 moves vertically or rotates 90 degrees through the vertical movement arn 324 and the swirl movement arm 325. A cover 328 is shown.

The drive unit 319 to drive the arm body unit 300 normal to the direction of microplate 1 transfer is shown in FIGS. 10b and 10c and includes a transfer base 329 secured with the swirl movement drive unit 318, a motor 330 to drive the transfer base 329, and a guide rod 331 supporting the motor 330 displaceably. The transfer base 329 is supported displaceably through a guide member 332 which is normal to the direction of transfer of the microplate 1. Thus, as the vertical and swirl drive unit 318 is secured with the transfer base 329 by screws 333, the arm shaft 301 is also movable normal to the direction of the microplate transfer. The guide member is secured with the base 335 by screws 334 and a key 336. The motor 330 is secured with the transfer base 329 through screws 337 and is axially movable relative to the guide rod 331. That is, by rack and pinion mechanism, not shown, the motor 330 moves to the guide rod 331. The guide rod 331 is retained at one side edge to a support member 338 which is secured with the base 335. At each end of the transfer base 329 in transfer direction, a blaket 341 having a plunger 339 and a magnetic proximity switch 340 is mounted to limit the operation stroke of the tansfer base 329. Numerals 342, 343 and 344 are screws. The drive unit 319 operates to transfer the reagent suction arm 304 of the arm body unit 300 from the reagent shelf 140 to the nozzle cleaning shelf 150. Thus, as shown in FIG. 4a, the base 345 forms an elongated opening 346 to allow necessary movement of the arm shaft 301.

The reagent shelf unit 140 is shown in FIGS. 11a and 11b and includes a reagent container 348 to store reagent solution 347, (corresponding to reagent solution 11 shown in FIG. 1) a cooling unit 349 to cool the reagent 347 to a predetermined low temperature of about 4° C., and an exhaust unit 350. The reagent container 348 is covered by a cover 351 which is pivotably mounted to a support post 354 through a hinge plate 352 and a hinge 353. The support post 354 is secured with an arm 355 to which a stopper 356 is secured to limit the opening of the cover 351. The cooling unit 349 includes a thermo-module 357 or semiconductor cooling unit, an air inlet 358, an exhaust duct 359, and thermocouple 360 to cool and maintain the reagent 347 to predetermined low temperature. Heat insulator 361 is shown. The exhaust unit 350 includes a sirocco fan 362 and a flexible hose 363. Detecting members 364 and 365 detect upper and lower limit of the reagent 347 and adapted to operate such that when liquid level of the reagent solution exceeds lower limit, signal lamp is on and a buzzer operates.

The reagent solution 347 in the reagent container 348 is sucked by the nozzles 306 of the reagent arm unit 130 and is dispensed into each well 2 in the microplate 1. The process is performed by the reagent dispense unit 170.

The reagent dispense unit 170 is shown in FIGS. 11a to 11e and includes a shringe 370 to suck and dispense reagent solution 347, a pulse motor 372 for vertical drive of a movable shaft 371 of the shringe 370, and a support frame 373 to support the shringe 370 and the pulse motor 372. The shringe 370 is shown in FIG. 12f and includes a cylinder 374, a movable shaft 371 slidable in the cylinder 374, a piston 375 connected to inner end of the shaft 371, a cylinder head 376, and a tube connection 377. The cylinder 370 each corresponds to the nozzle 306 of the solution nozzle arm unit 130. As the number of nozzles 306 are 24, or 2 rows of 12, so that number of the cylinders 370 is also 24. The 24 cylinders 370 are shown in FIGS. 12b to 12d and are arranged on two support frames 373 as two sets of 12 cylinders 370. The 12 cylinders 370 on each support frame 373 are arranged as shown in FIG. 12b two rows of six, and arranged staggered as to the two rows. The lower end of the movable shaft 371 of each cylinder 370 mounts a boss 379 having a flange 378.

A movable shaft support member 380 is secured with a movable block 392 which moves vertically by the motor 372 and a guide rod 393. The movable shaft support member 380 has a plurality of steps 380a, 380b and 380c as shown in FIGS. 12g and 12h, and the steps 380b and 380c forms a plurality of engage recesses 381 and 382 corresponding to the number of cylinders to be moved. Each boss 379 of the movable shaft 371 of the cylinder 370 engages the recesses 381 and 382 and is retained by a screw 383 which is screwed in the support member 380. The upper portion of the cylinder-head 376 mounts a screw 385 having an engage recess 384, to which lower end of a screw 387 is engaged to retain the cylinder 374. The screw 387 is screwed in an upper base 386. The upper base 386 is secured with the support frame 373 through a connecting member 388. The lower end of the cylinder 374 includes a member 389 having a flange 389a which engages on a crank-like cylinder retainer 390 as shown in FIG. 12i. The retainer 390 forms as many engage recesses 391a and 391b to engage with each flange 389a of the cylinders 374.

Thus, the movable shaft 371 of the cylinder 370 moves up and down by the pulse motor 372 so that air in the cylinder 374 can be sucked and discharged. To the tube connecting member 377 a tube 394 for suction and exhaust is connected and the tube 394 of each cylinder 370 is connected with each nozzle 306 of the solution nozzle arm unit 130. A tube support member 395 having a plurality of tube insert opening 397 is mounted to the upper base 386 through support rod means 397.

The nozzle cleaning shelf unit 150 cleans the nozzles 306 of the solution nozzle arm unit 130. After the solution nozzle arm unit 130 moves sidewise along the elongated opening 346 upwards from the nozzle cleaning unit 150, cleaning fluid is supplied to the nozzles 306 to clean the nozzles 306.

The electrode cleaning shelf unit 160 cleans the liquid level detecting electrodes 310 of the solution nozzle arm unit 130. After the liquid level detecting arm 305 of the solution nozzle arm unit 130 rotates upwards from the electrode cleaning unit 160, i.e. every time when the liquid level detecting operation to the dispensed reagent solution in the wells 2 is completed, the electrodes 310 are cleaned by water flow. As the nozzle cleaning shelf unit 150 and the electrode cleaning unit 160 are similar construction, one shelf unit will be described in detail referring to FIGS. 6 and 13.

As shown in the drawing, the units 150 and 160 includes a vessel 411 in which a cleaning fluid supply member 410 is mounted. The cleaning fluid supply member 410 includes many cleaning fluid outlets 412 and a cleaning fluid passage 413 connecting with the cleaning fluid outlets 412. The fluid passage 413 is communicated through a supply hose 414 with a cleaning fluid tank 415. The fluid supply member 410 is secured and positioned relative to the vessel 411 to a predetermined position by four screws 416. The fluid outlets 412 are 24 i.e. two rows of 12, corresponding to the number and arrangement of the nozzles 306 and the electrodes 310, to clean each nozzle 306 and electrode 310 individually. As shown in FIG. 6, each fluid outlet 412 forms two stepped or inside high and outside low construction so that cleaning fluid injected upwards from upper openings 421a backs to the vessel 411 through the lower opening 421b. Thus, washed fluid does not touch or mix with the flesh fluid, and the nozzles 306 or the electrodes 310 are kept clean condition.

The cleaning fluid supply unit 415 includes a supply tank 418 to store cleaning fluid 417, (corresponding to the cleaning fluid 16 shown in FIG. 1) a magnetic gear pump 419 to suck the fluid from the tank 418 and automatically supply the fluid 417, and a flow rate regulator 422 having a flow rate regulating valve 420 and a check valve 421. The washed fluid passes through an exhaust pipe 424 under the vessel 411 to a waste tank 423 which has an upper limit detect sensor 425. Also the supply tank 418 has a lower limit detect sensor 426. The cleaning fluid flow simultaneously from the 24 outlets 412 and the flow rate is regulated by the flow rate regulating valve 420. The sensors 425 and 426 are electro-static capacity sensors and when the lower limit sensor 426 is OFF or the upper limit sensor 425 is ON, warning means, i.e. lamp and buzzar are operated.

As shown in FIG. 6, an indicating panel 450 indicates 96 lamps 451 corresponding to the number of wells 2 of one microplate 1 and is connected with each electrode 310 of the liquid level detecting arm 305 and the microwell module detecting apparatus 285. The liquid level detection result of the wells 2 by the electrodes 310 is indicated by each lamp 451.

Now, the reagent incubation apparatus 31 will be described referring to FIG. 3.

As shown in FIG. 3, the incubation apparatus 31 includes a support frame unit 40, a magazine supply side elevation unit 41 at left side of the support frame unit 40, a magazine discharge side elevator unit 42 opposed to the unit 41 and at right side of the support frame unit 40, microplate downward and upward conveyor units 43 and 44 adjacent inside of both elevator units 41 and 42, a loader unit 45 mounted on upside center portion of the frame unit 40 and adapted to receive the microplate 1 from a magazine held in the supply side elevation unit 41 and to feed to the downward conveyor unit 43, an unloader unit 46 adapted to receive the microplate 1 held in the upward conveyor unit 44 and to feed to a magazine held in the discharge side elevator unit 42, a carrier unit 47 monted on the lower side of the frame unit 40 between the lower ends of the downward and upward conveyor units 43 and 44 and adapted to receive the microplate 1 conveyed to lower end by the downward conveyor unit 43 and to feed the same to the lower end of the upward conveyor unit 44, a heater unit mounted on the center portion of the frame 40 and adapted to heat each convey passage of the carrier unit 47 connecting between the lower ends of the downward and upward conveyor units 43 and 44 to a predetermined temperature atmosphere by forced hot air circulation ventillation system, and a control unit 49 mounted upward from the frame unit 40 and to control the abovementioned units.

Figure 18A:
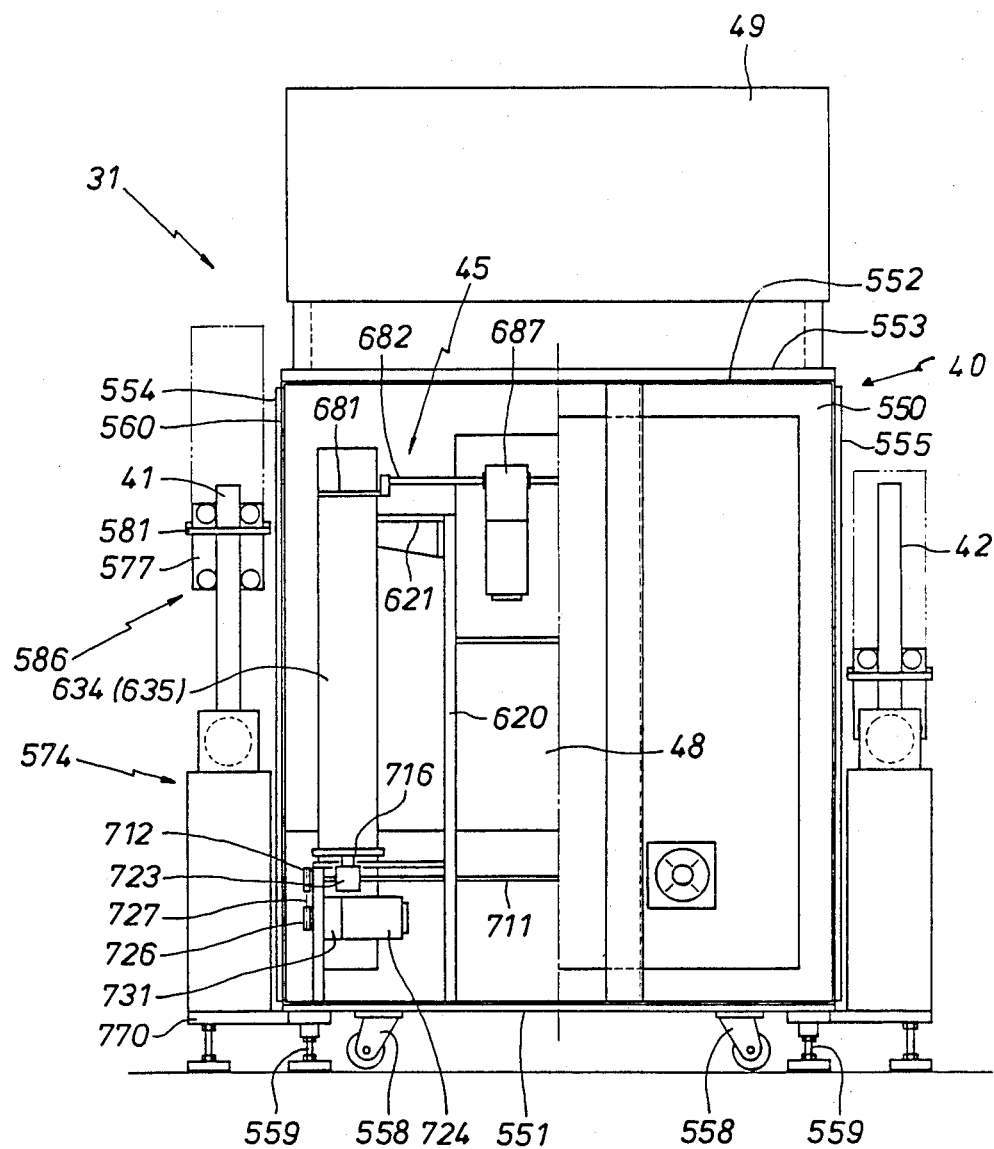
FIGS. 18a to 18c are front view, plan view and side view, respectively of the incubation apparatus, a portion of the frame unit being broken away, shown in FIG. 6, FIGS. 19a to 19c are side view, front view and plan view, respectively of the supply side elevator unit shown in FIG. 6, FIGS. 20a to 20c are side view, front view and plan view, respectively of the discharge side elevator unit shown in FIG. 6, FIGS. 21a to 21f are side view, front view and sectional views, respectively of the downward conveyor unit, a portion broken away, shown in FIG. 6, FIGS. 22a to 22c are front view, plan view and side view, respectively of the loader unit shown in FIG. 6, FIGS. 23a and 23b are front view and plan view of the unloader unit shown in FIG. 6, FIGS. 24a to 24d are front view, plan view and side views respectively of the carrier unit shown in FIG. 6, FIGS. 25a and 25b are front view and side view of the heater unit shown in FIG. 6.
Figure 18B:
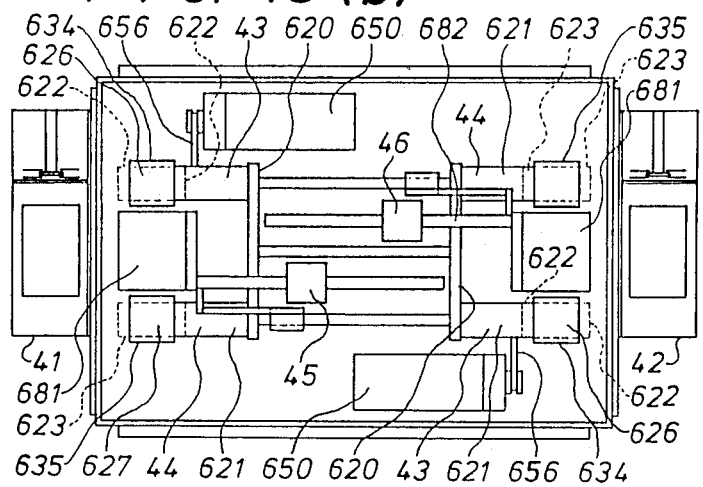
Figure 18C:
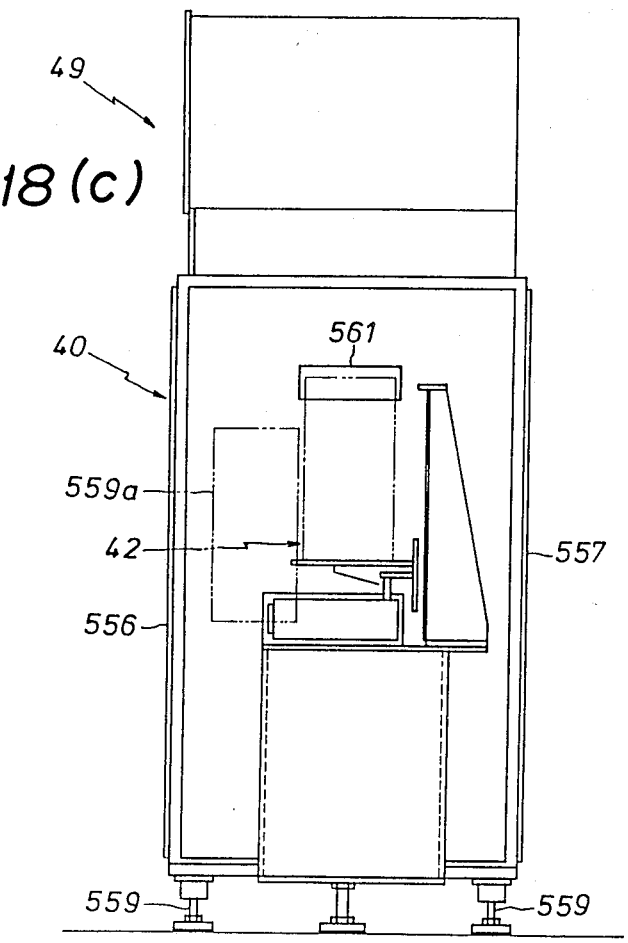

The frame unit 40 is shown in FIGS. 18a to 18c and includes a frame 550 having a base 551 and a top plate 552. On the top plate 552 a top cover 553 is mounted, and the frame 550 is removably covered by side covers 554 and 555, a front cover 556 and a rear cover 557 to maintain necessary temperature in the frame unit 40. Caster means 558 mounted under the base 551 allow movable, and adjuster foot means 559 allow height adjustment.

The side covers 554 and 555 each has transparent window 559a to observe presence or absence of the microplate 1 under incubation in the down- and upward conveyor unit 43 and 44. A feed port 560 to convey the microplate 1 from the magazine supply side elevation unit 41 through the loader unit 45 to the downward conveyor unit 43, and a discharge port 561 to convey the microplate 1 from the upward conveyor unit 44 through the unloader unit 46 to the magazine discharge side elevator unit 42 are formed.

Figure 19A:
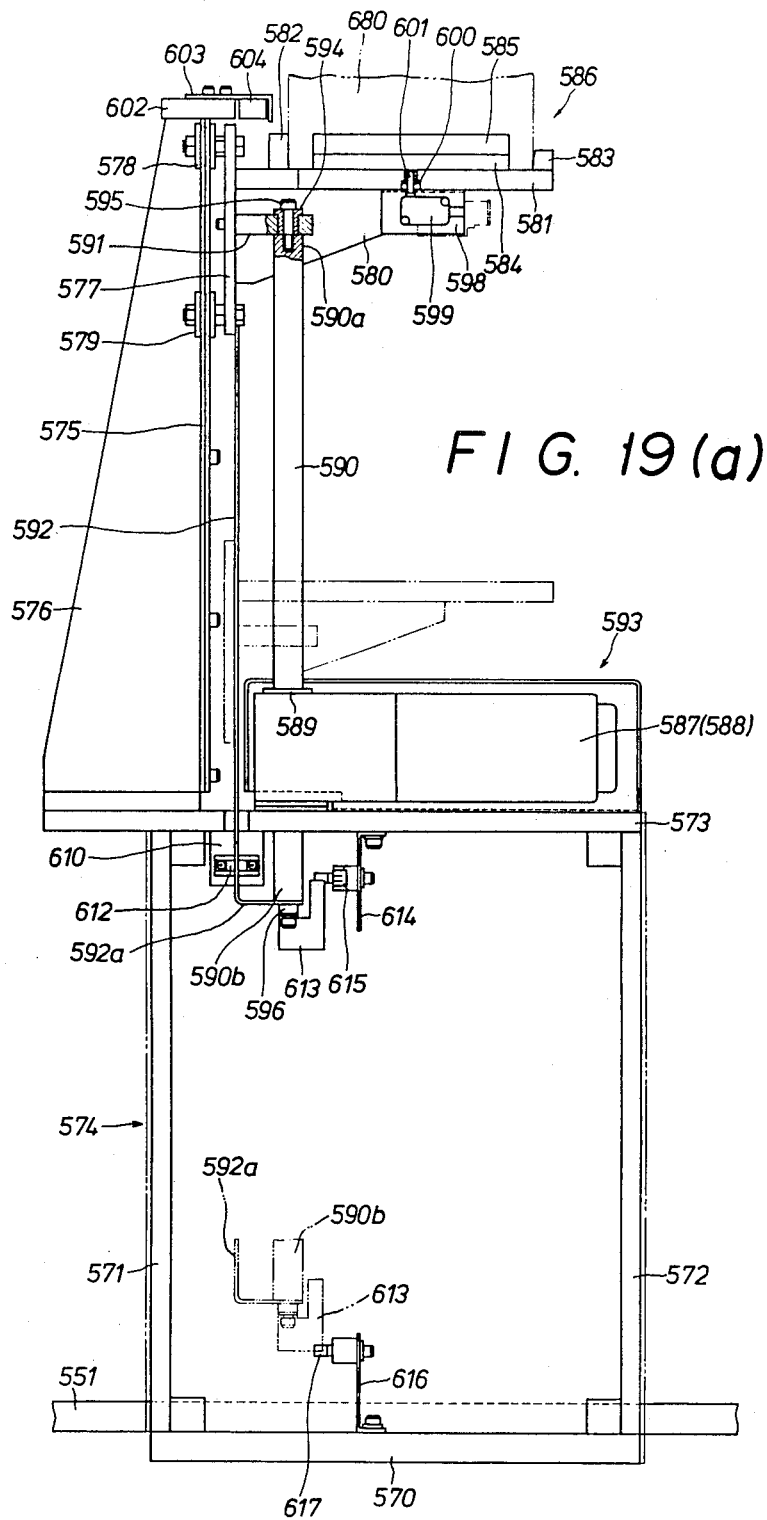
Figure 19B:
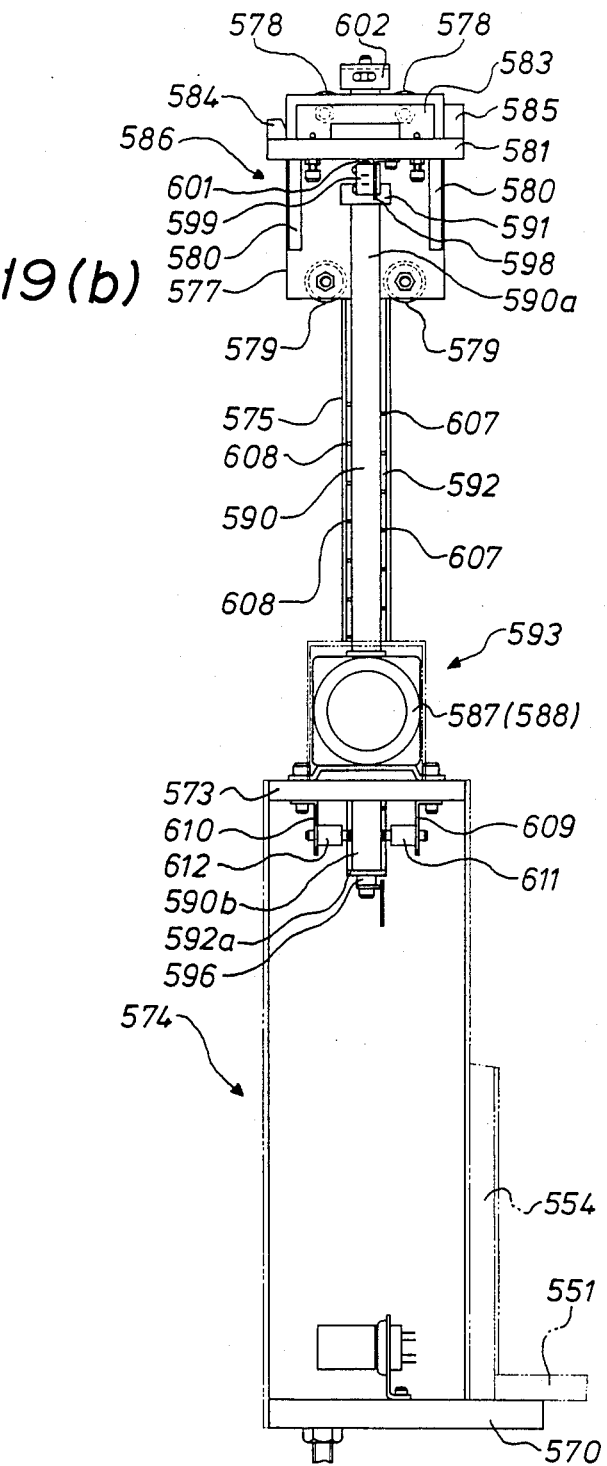
Figure 19:
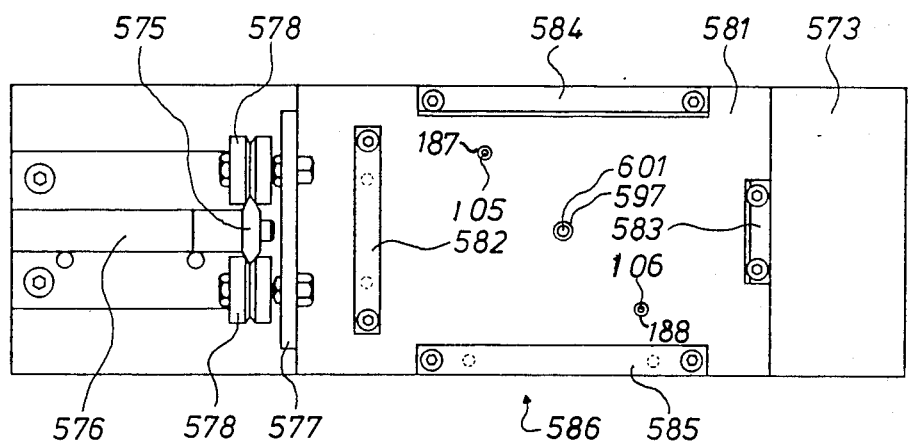

The magazine supply side elevation unit 41 will be described referring to FIGS. 19a and 19b. The unit 41 includes a base 570 which is mounted on the left side of the base 551 of the frame unit 40, support plates 571 and 572 vertically mounted on both sides of the base 571 and a base 573 mounted on the support plates 571 and 572, to form a frame 574 of the elevation unit 41. On the base 573 of the frame 574, a slider support frame 576 having a slide plate 575 is mounted. To the slide plate 575, a slider plate 577 is vertically slidably mounted through a pair of journal assemblies 578 and 579 which are rotatably mounted on both sides of the slide plate 575. To the slider plate 577, a lift plate 581 is mounted through a support plate 580, and on the lift plate 581, magazine guide plates 582, 583, 584 and 585 are secured to form a magazine lift 586.

On the base 573 of the frame 574, drive motors 587 and 588 drving the magazine lift 586 are mounted. To the motor 588, a lead screw 590 is connected through connecting gear means, not shown, and is held rotatably and vertically movably through bearing means 589. The top end 590a of the lead screw 590 is connected through a connecting member 591 to the slider plate 577 of the magazine lift 586, and the lower end 590b is connected with a lower end 592a of a shutter 592 mounted to the lower end of the slider plate 577 of the magazine lift 586 so that magazine lift drive means is formed. The lead screw 590 is connected with the connecting member 591 through a joint member 594 and a bolt 595, and is connected with the shutter 592 through a shutter collar 596.

At the center portion of the lift plate 581 of the magazine lift 586, a magazine detect hole 597 is formed, and a micro-switch 599 is attached on the center lower surface of the plate 581 through a mounting member 598. Lower end of a detect pin 601 which is mounted in the hole 597 through a bush 600 is engageable with the switch end of the microswitch 599 to detect presence of the magazine in the magazine lift 586.

At the upper end of the slider support frame 576, a stopper 602 is attached. A sensor 604 is attached through a sensor blaket 603 to the stopper 602 to detect microplate 1 in the magazine set in the magazine lift 586.

Figure 20A:
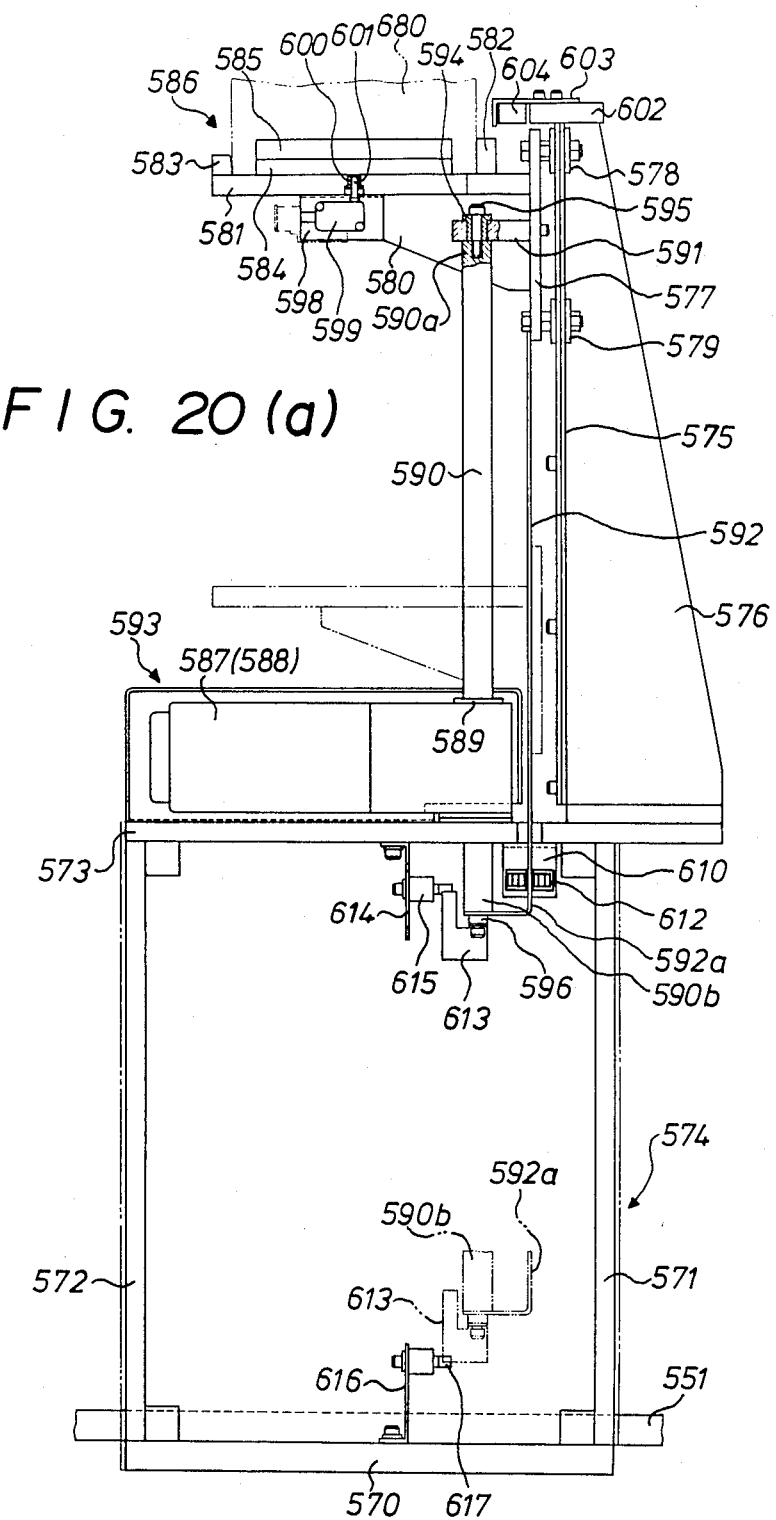
Figure 20B:
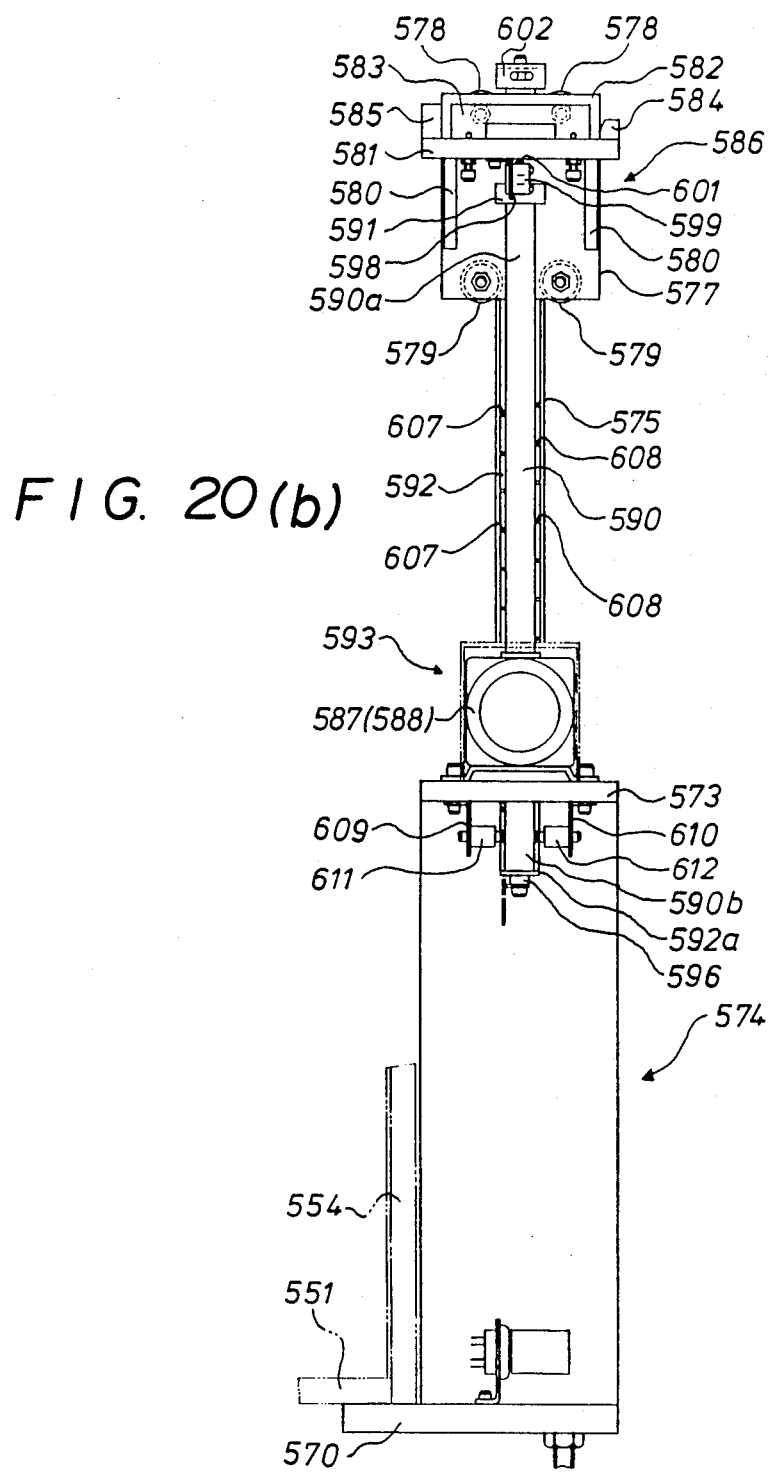
Figure 20C:
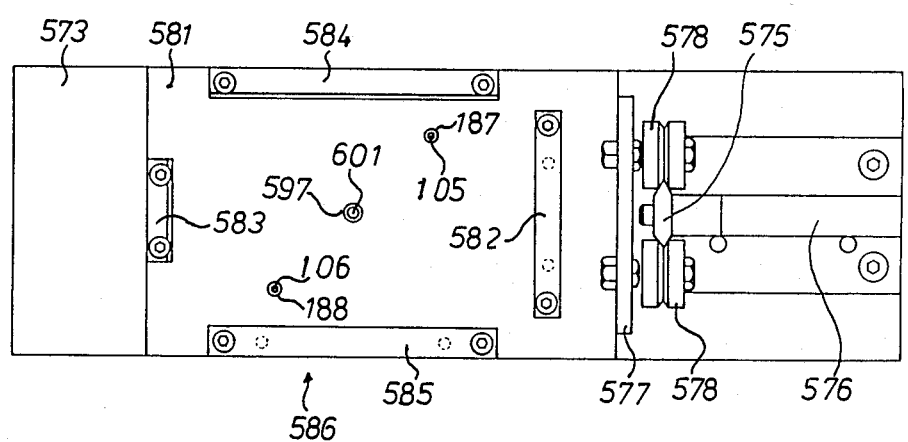

To the lift plate 581 of the magazine lift 586, magazine positioning pins 605 and 606 is mounted as shown in FIG. 20c to control set direction of the magazine which is set on the lift plate 581.

The shutter 592 forms slits 607 and 606 of predetermined space. On the lower side of the base 573 of the frame 574, a pair of photo-sensors 611 and 612 are attached through sensor angles 607 and 610. The sensors 601 and 602 includes light project and receive elements to detect the slits 607 and 608. The sensor 611 detects the slit 607 of the shutter 592 and the sensor 612 detects the slit 608 of the shutter 592, so that the sensor 611 acts as detect means of upward pitch of the magazine lift 586, and the sensor 612 acts as detect means feed pitch of the magazine lift 586 relative to the loader unit 45.

A shutter 613 is mounted on the lower end 590b of the lead screw 590, and a photo-sensor 615 having a pair of light project and receive elements is attached through a sensor angle 614 on the base 573 of the frame 574. Further, a photo-sensor 617 having a pair of light project and receive elements is attached through a sensor angle 616 on the base 570, to form detect means for upward and downward ends of the lead screw 590.

The magazine discharge side elevator unit 42 is shown in FIG. 20, and is mounted on right side of the frame unit 40. The magazine supply side elevator unit 41 is mounted on the left side of the frame unit. As the both elevator units are similar construction, same reference numeral shows same or similar part or portion, and detailed description will not be necessary.

The downward and upward conveyor units 43 and 44 will be described referring to FIGS. 21a to 21f.

The downward conveyor unit 43 is mounted on the left side of the frame unit 40 and adjacent to inner side of the supply side elevator unit 41.

On the support frame 620 on upper surface of the base 551 of the frame unit 40 shown in FIGS. 18a and 18b, a pair of right and left support plates 621 are mounted, and between the support plates 621, each a pair of bearing plates 622 and 623 shown in FIG. 18b is mounted. Further, between the bearing plates 622 and 623, rotary shafts 624 and 625 secured with timing pulleys 626 and 627 are supported.

On the base 551 of the frame unit 40, opposed to the timing pulleys 626 and 627, a pair of bearing plates 628 and 629 are mounted and between which rotary shafts 630 and 631 are supported. The shafts 630 and 631 support timing pulleys 632 and 633 each forming pairs with the timing pulleys 626 and 627 and between which conveyor belts 634 and 635 are engaged.

Figure 21A:
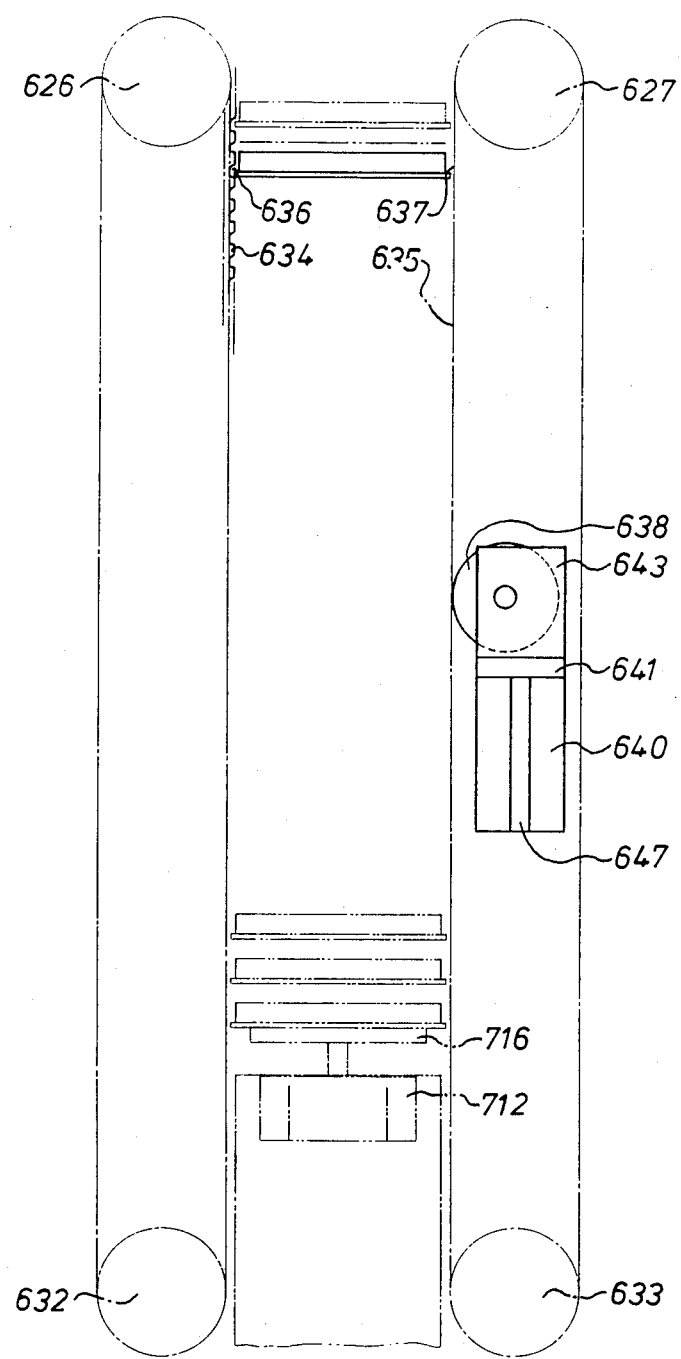
Figure 21B:
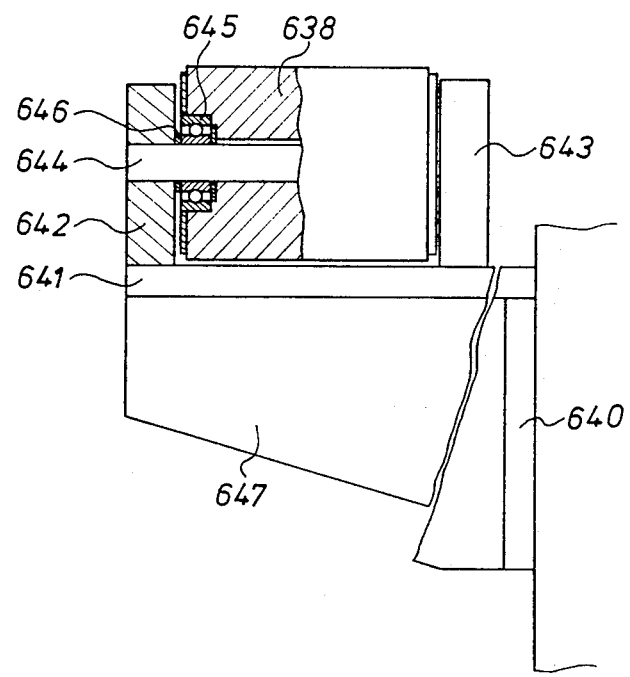
Figure 21C:
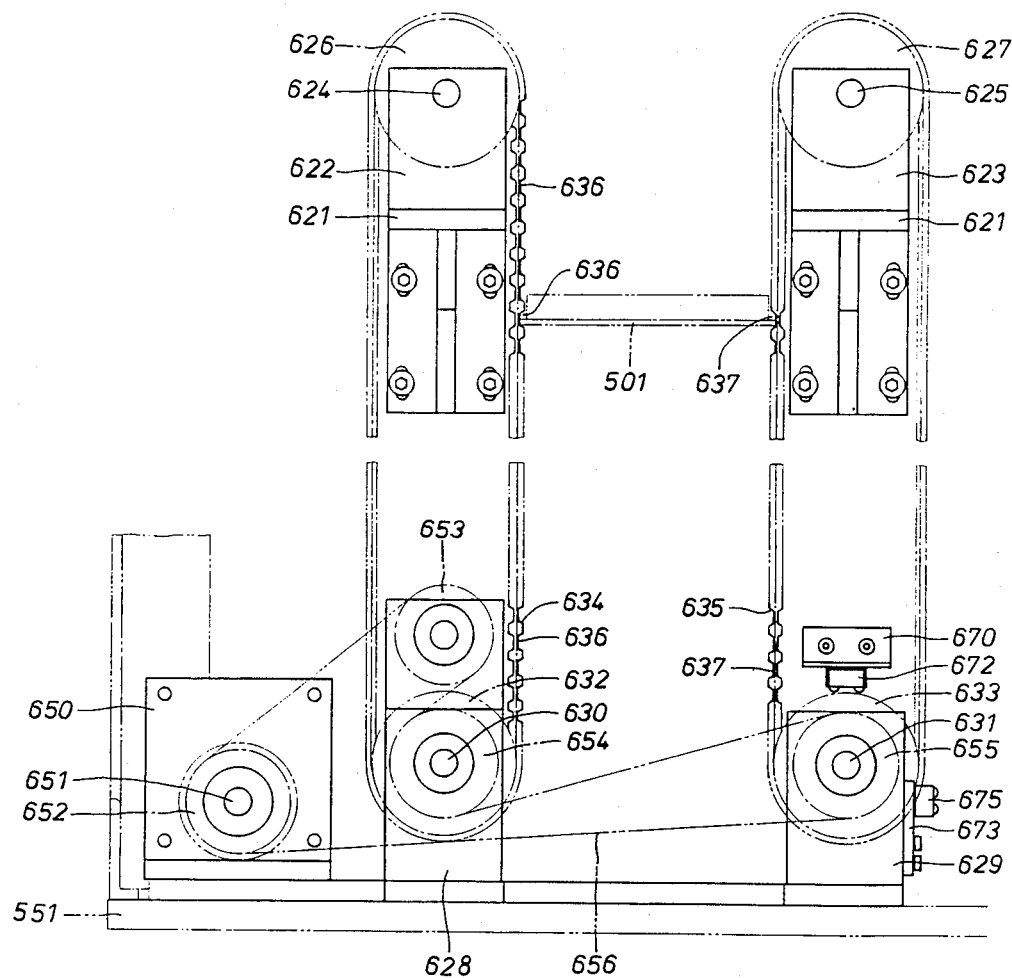

As shown in FIGS. 21a and 21c, the conveyor belts 634 and 635 are opposed each other, and the surface of the conveyor belts 634 and 635 form widthwise engage grooves 636 and 637 regularly spaced longitudinally to engage with left and right edges of the microplate 1. Thus, between the conveyor belts 634 and 635, a plurality of microplates 1 can be held as layers, and can be conveyed vertically according to the rotation of the timing pulleys 626, 627, 632 and 633.

To the conveyor belts 634 and 635, tension roller means 638 is engaged. A support plate 641 is secured through a plate 640 and a reinforce plate 647 with the support frame 620 of the frame unit 40. The tension roller 638 is supported by a shaft 644 which is supported by two bearing plates 642 and 643 mounted on the support plate 641. The roller 638 is supported by the shaft 644 through bearings 645 and collars 646, and can be adjusted as to the eccentricity to adjust tension of the belts.

Drive unit of the conveyor belts 634 and 635 will be described referring to FIGS. 21c to 21f. A drive motor 650 is mounted on the base 551 of the frame unit 40, and has a drive shaft 651 to which a drive timing pulley 652 is secured. A timing belt 656 is engaged from the timing pulley 652 throgh a intermediate pulley 653 to timing pulleys 654 and 655 which are secured with the rotary shafts 630 and 631 of the timing pulleys 632 and 633 of the conveyor belts 634 and 636. Thus, the timing pulleys 632 and 633 of the conveyor belts 634 and 635 are connected each other. By operation of the driven motor 650, both timing pulleys 632 and 633 are rotated to drive the conveyor belt vertically.

Figure 21D:
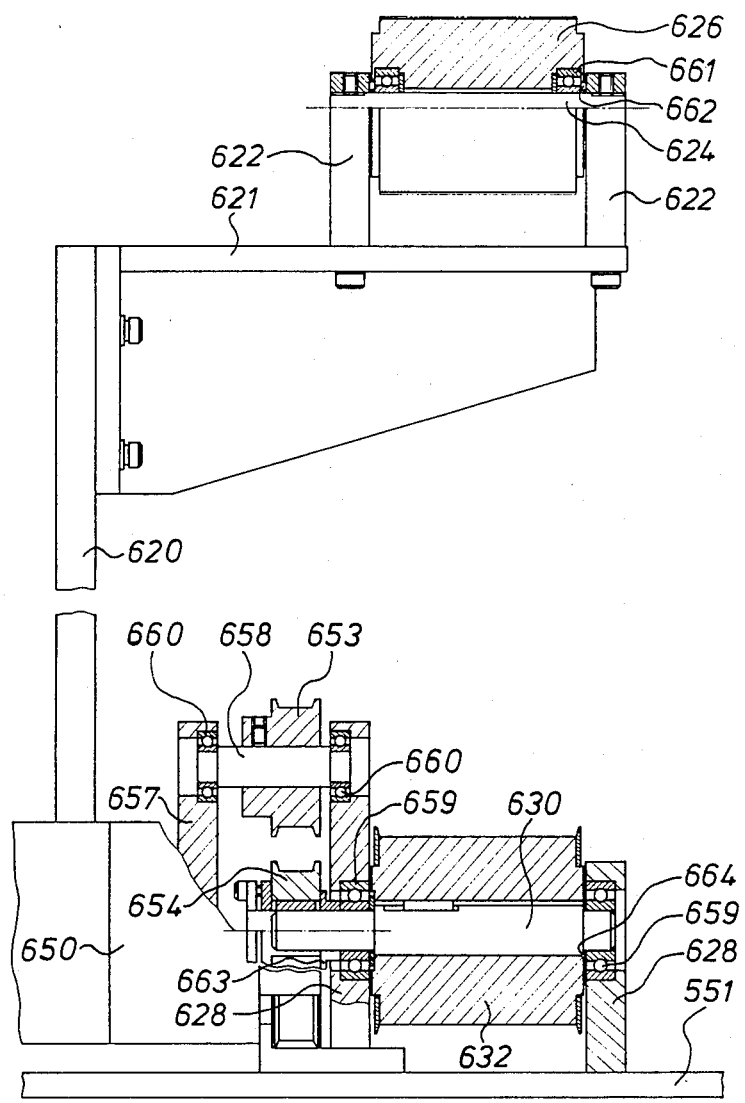

The intermediate timing pulley 653 is shown in FIG. 21d and includes a bearing plate 657 opposed to the bearing plate 628 of the timing pulley 632 of the conveyor belt 634 and on the base 551. Between the bearing plates 628 and 657 the timing pulley 653 is supported by a shaft 658.

In FIG. 21d, the rotary shafts 624, 630 and 658 are rotatably supported through bearings 661, 659 and 660. Collars 662, 663 and 664 hold the pulleys 626, 654 and 632 in place.

To the timing pulley 655 secured with the rotary shaft of the timing pulley 633 of the conveyor belt 635 has positive and reverse control apparatus for the motor 650.

As shown in FIGS. 21e and 21f, to the end of the rotary shaft 631 having the timing pulley 655 a shutter 666 is secured by a bolt 667. The shutter has peripherally regularly spaced slits 665 shown in FIG. 21f. A support frame 668 is mounted on the base 551, and a sensor block 669 and a sensor angle 670 extends upward from the shutter 666. Under the angle 670, a photo sensor 672 having light project and receive elements and having mask 671 is mounted. Beside the shutter 666, through sensor plates 673 and 674, a photo-sensor 675 having light project element and light receive element is mounted.

An amplifier 676 is mounted on the support frame 668 through amplifier mounting angle means 677.

The upward conveyor unit 44 is similar construction with the above mentioned downward conveyor unit 43, and the construction elements are shown schematically in FIG. 18b in which same reference numeral shows same or similar part or portion with that shown in the downward conveyor unit, and detailed description will not be necessary.

Figure 22A:
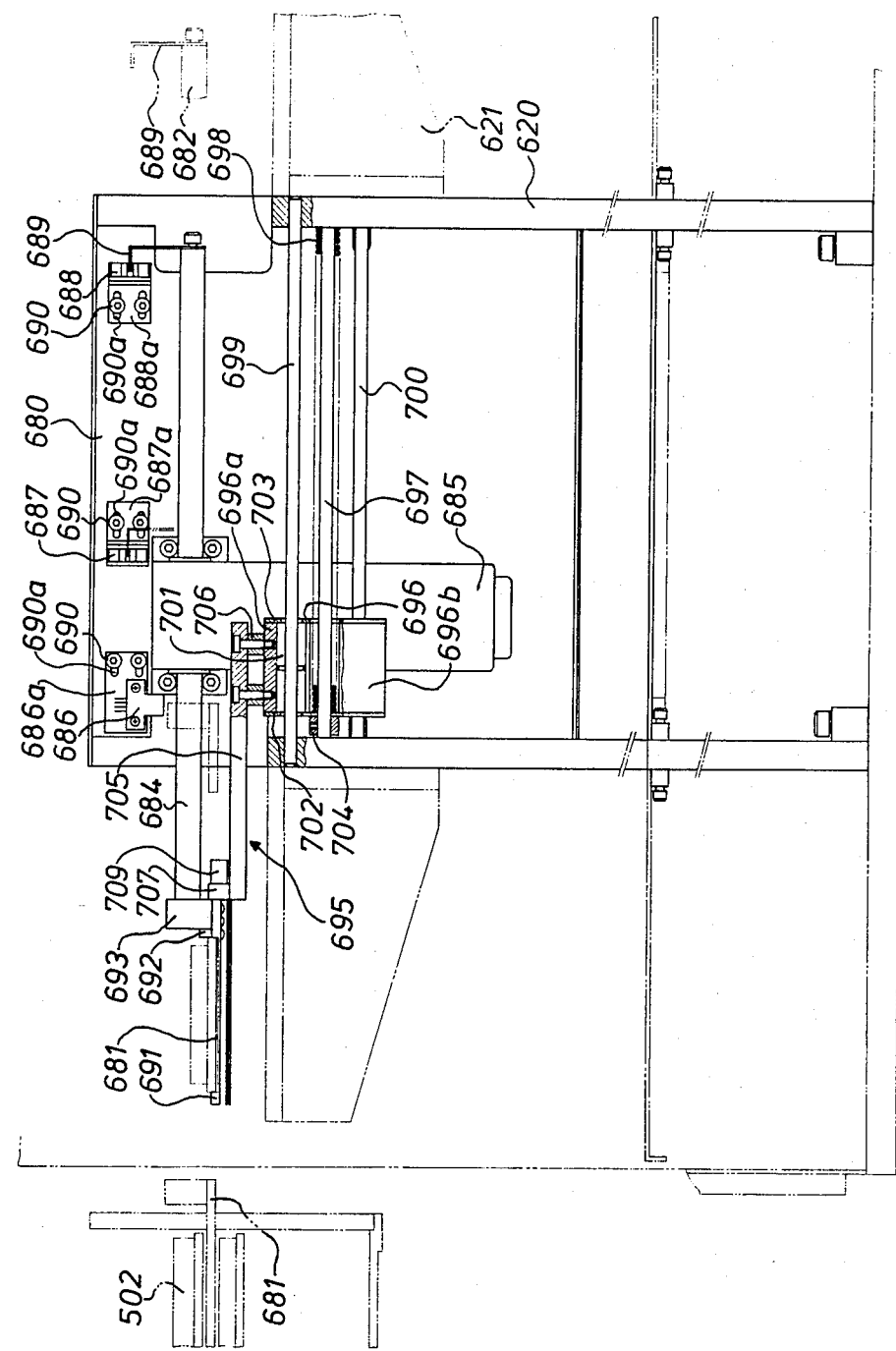
Figure 22:
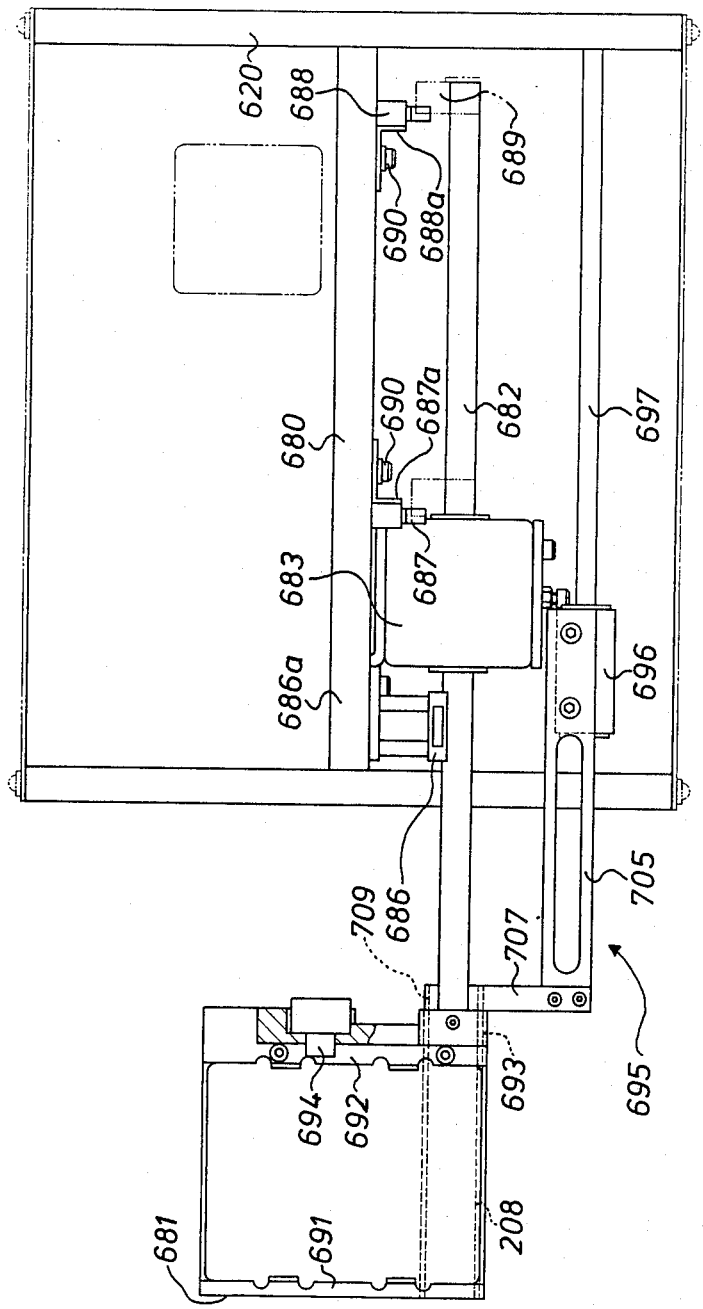
Figure 22C:
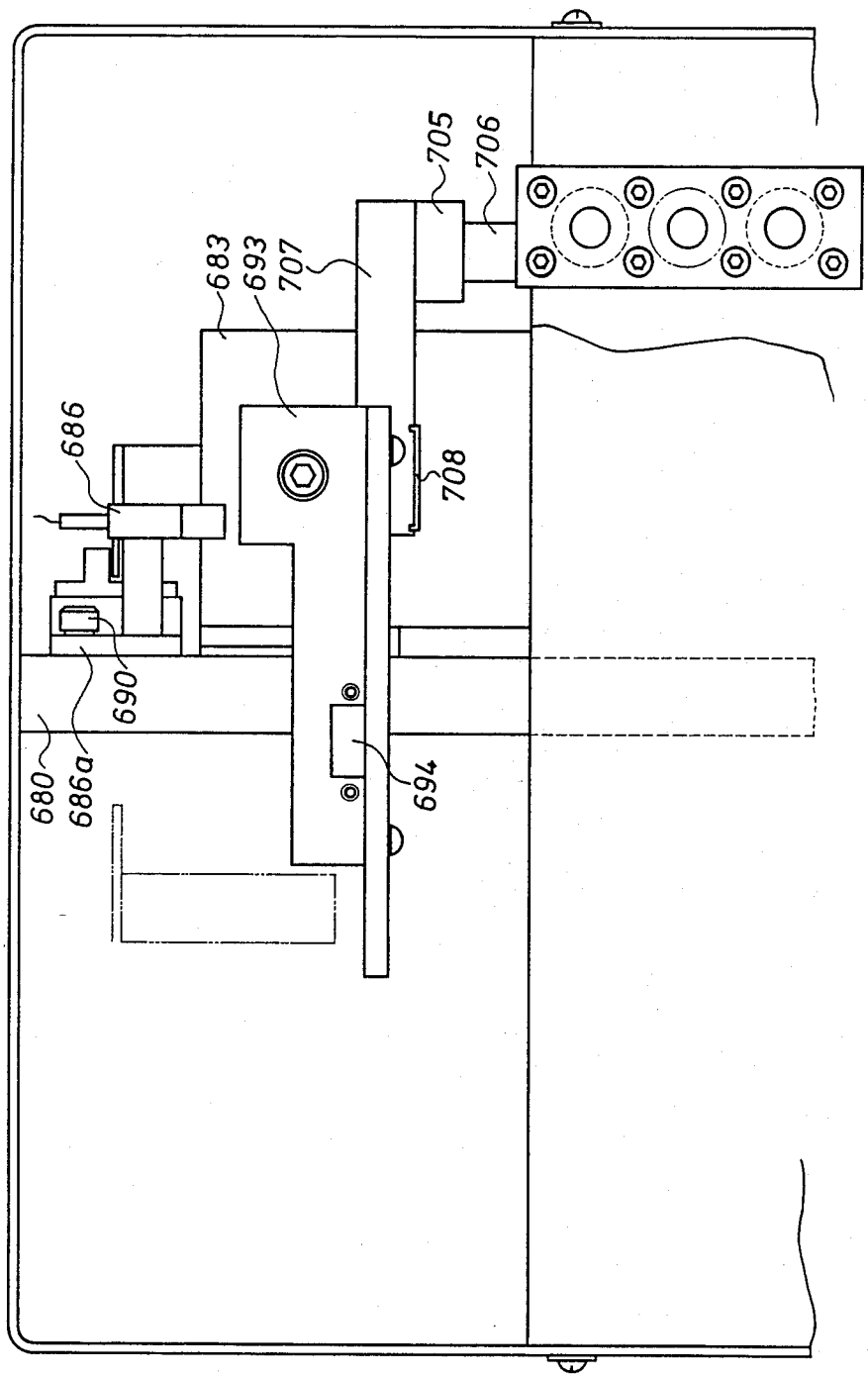

The loader unit 45 is shown in FIGS. 22a to 22c and is mounted on a support plate 680 between left and right support frames 621 on the base 551 of the frame unit 40.

An arm shaft 682 which mounts a transfer plate 681 for the microplate 1 at one end, forms a lead gear 684 for all periphery engaging drive gear means, not shown, in a gear box 683 mounted on the support plate 680. The lead gear 684 is adapted to reciprocate relative to the gear box 683.

The gear box 683 mounts a drive motor 685 to drive the drive gear means. The support plate 680 mounts at left portion, a photo sensor 686 detecting rearward limit of the arm shaft 682 of the transfer plate 681, and at middle portion, a photo snsor 667 detecting forward limit of the arm shaft 682, and also at right portion, a photo sensor 688 detecting center stop position of the arm shaft 682. At rear end of the arm shaft 682, a shutter 689 for the photo sensors 687 and 688 is attached.

To adjust the mounting position of the photo sensors 686, 687 and 688, receiving holes 690a of sensor plates 686a, 687a and 688a to receive bolts 690 are elongated holes.

The transfer plate 681 of the microplate 1 forms guides 691 and 692 to receive the microplates 1. The transfer plate 681 is secured with the arm shaft 682 through a block member 693 on which a photosensor 694 detecting the presence of the microplate 1 is attached.

In the loader unit 45, grease is applied on the lead gear 684 formed on the periphery of the arm shaft 682 to assist smooth transfer of the transfer plate 681 for the microplate 1. To prevent dripping of the grease into the wells 2 in the microplate 1, a grease receiver 695 is attached.

To form the grease receiver 695, a slide shaft 697 is mounted between the support frames 620 of the frame unit 40, and a movable block 696 is engaged slidably along the shaft 697 and is urged leftwards in FIG. 22a by a spring 698 which is coiled about the shaft 697.

The movable block 696 is guided by guide shafts 699 and 700 which are mounted between the support frames 620 at upper and lower positions to the slide shaft 697. Between the movable block 696 and the guide shafts 699 and 700, linear motion bearings 701 are inserted and are retained by end plates 702 and 703 mounted on front and rear ends of the movable block 696. A stopper 704 on the slide shaft 697 limits the stroke of the movable block 696.

A pusher bar 705 is attached to upper portion 696a of the movable block 696 through a spacer 706. At the end of the pusher bar 705, a grease receiver plate 708 is attached through a connecting block 707 having a stopper at one end so that grease dripping from the periphery of the arm shaft 682 is received.

Figure 23A:
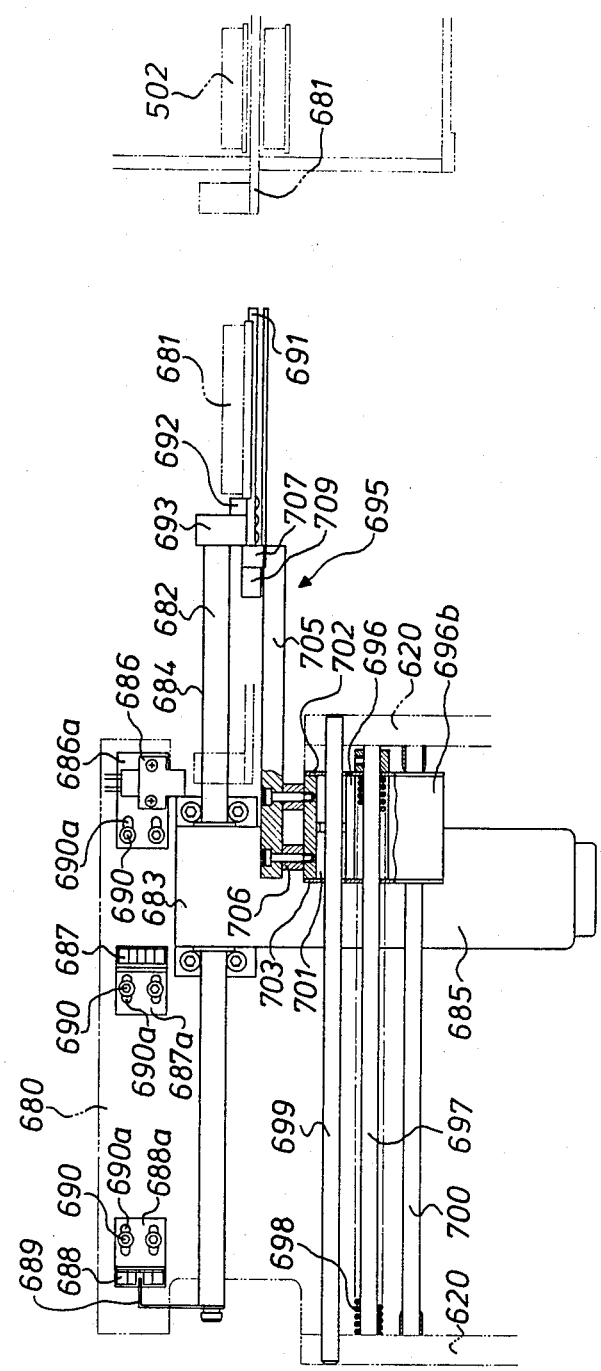
Figure 23B:
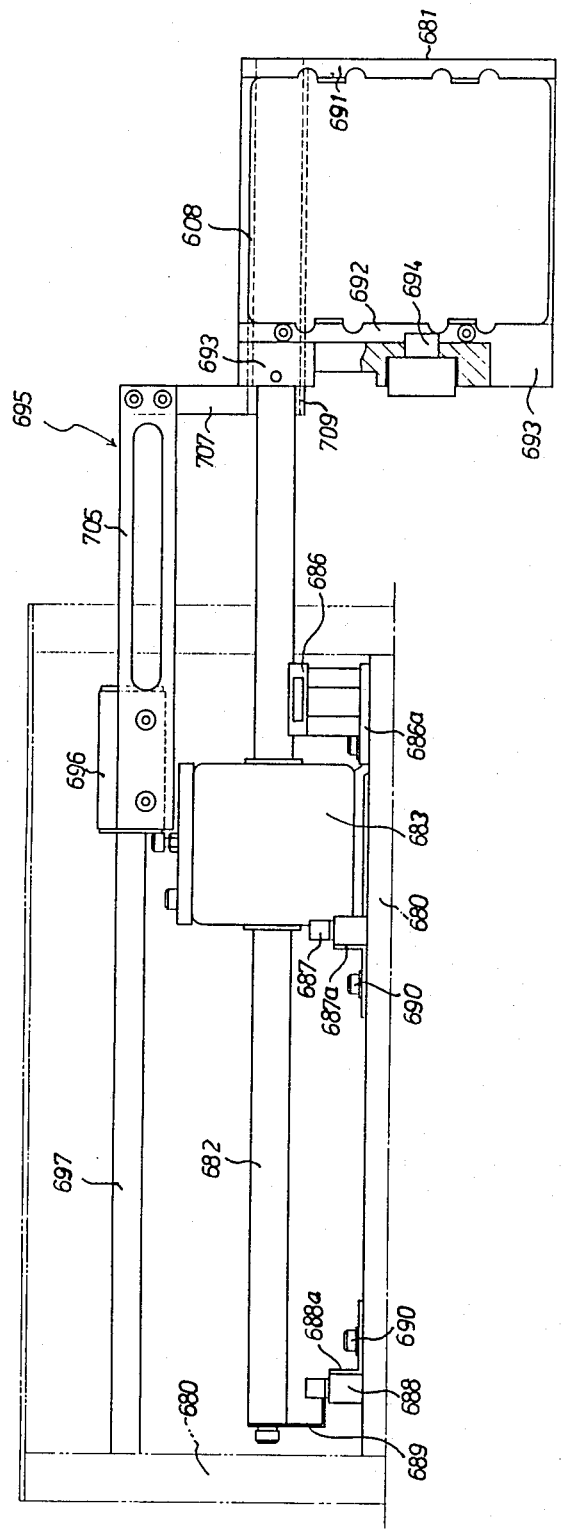
Figure 24A:
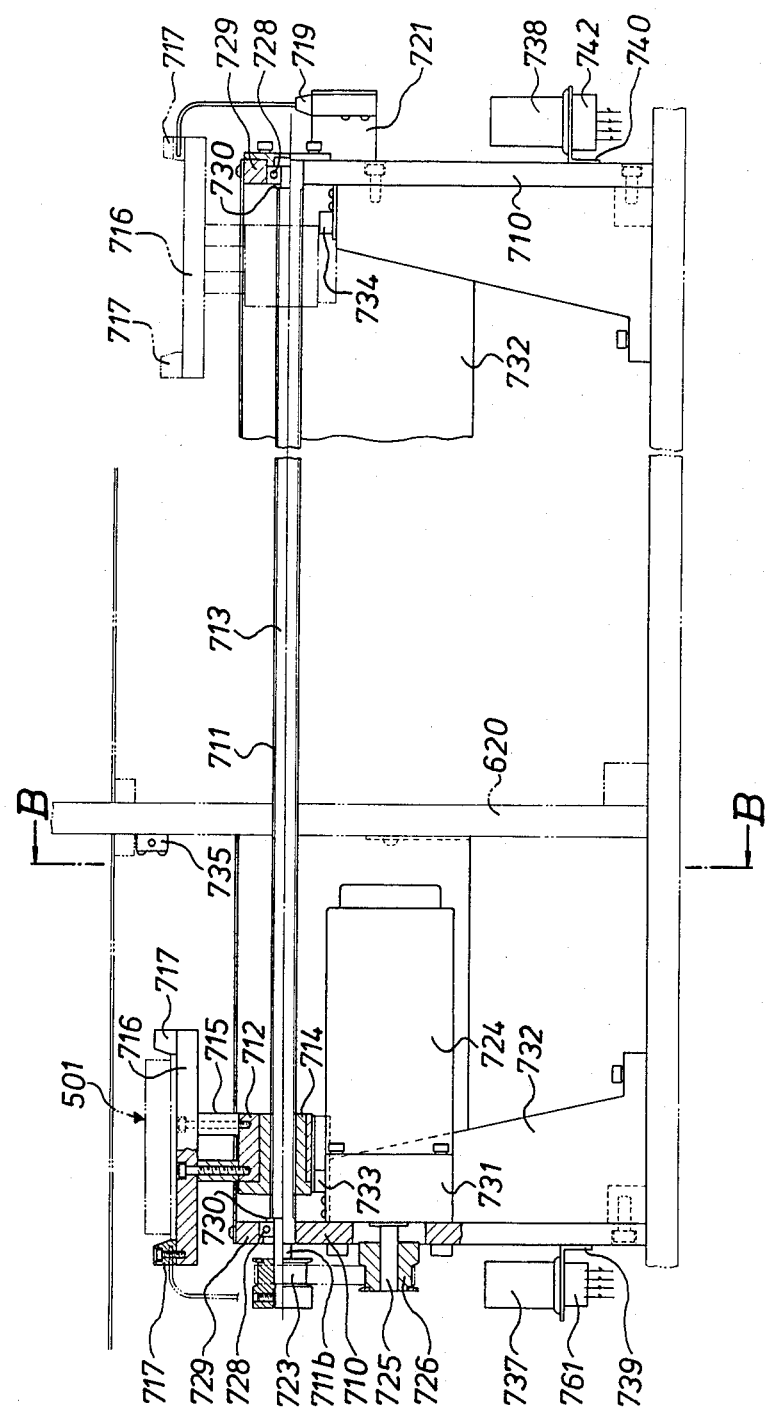
Figure 24:
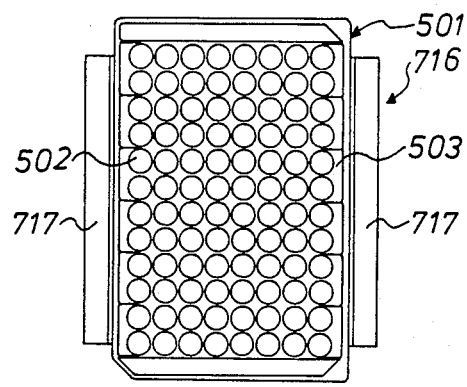
Figure 24:
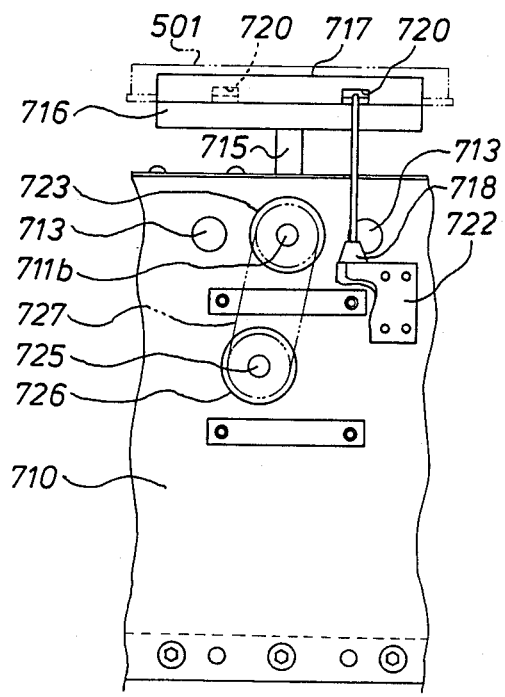
Figure 24:
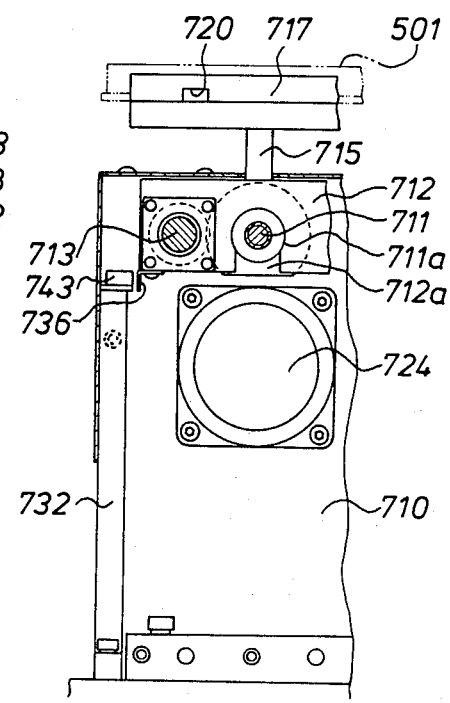

The unloader unit 46 which receives microplate 1 held on the upward conveyor unit 44 and stores the microplate 1 in the magazine held in the discharge side elebation unit 42, is shown in FIGS. 23a and 23b. The loader unit 45 is mounted on left side of the frame unit 40, whereas the unloader unit 46 is mounted on right side of the frame unit 40 and completely symmetry with the loader unit 45. Thus, same reference numerals are used, and detailed description will not be necessary.

Now, the carrier unit 47 which operates to receive the microplate 1 transferred by the downward conveyor unit 43 to lower end thereof, and to transfer the microplate to the lower end of the upward conveyor unit 44, will be described referring to FIGS. 24a to 24d.

The carrier unit 47 includes a pair of support frames 710 mounted on the base 551 at left and right ends of the frame unit 40, a ball screw 711 rotatably supported by the support frames 710, a movable block 712 having inside screw 711a engaging outside screw 711a of the ball screw 711 to be movable along the ball screw 711 when the ball screw 711 is rotated, and guide shafts 713 mounted between the support frame 710 at both sides of the ball screw 711 and slidably engaging with the movable block 712 through linear motion bearings 714 mounted on the movable block 712.

On the movable block 712, a carrier 716 is mounted through spacers 715 to carry the microplate 1.

At front and rear ends of the carrier 716, guide plates 717 for the microplate 1 are attached, and at symmetry positions of the guide plates 716, holes 720 are formed to insert supply and discharge sides fiber sensors 718 and 719. The fiber sensors 718 and 719 are mounted on the support frame 710 through sensor plates 721 and 722.

At one end of the ball screw 711, a timing pulley 723 is secured and is connected with a motor 724 through a timing pulley 726 connected to a drive shaft 725 of the motor 724 and a timing belt 727 engaging both pulleys 723 and 726. The motor 724 is mounted on the support frame 710 which has reinforcing plates 732. Between the ball screw 711 and the support frames 710, journal means 729 each having a bearing 728 and a collar 730 is inserted. The motor 724 has a gear box 731.

On both reinforce plates 732, photo sensors 733 and 734 are mounted to detect left and right ends of the carrier 716 and also on the support frame 620 a photo sensor 735 to detect the carrier 716 is mounted. On the movable block 712 a shutter 736 is attached for the photo sensors 733 and 734.

Amplifiers 737 and 738 including terminal boxes 741 and 742 are mounted on the support frame 710 through mounting angles 739 and 740.

Figure 25A:
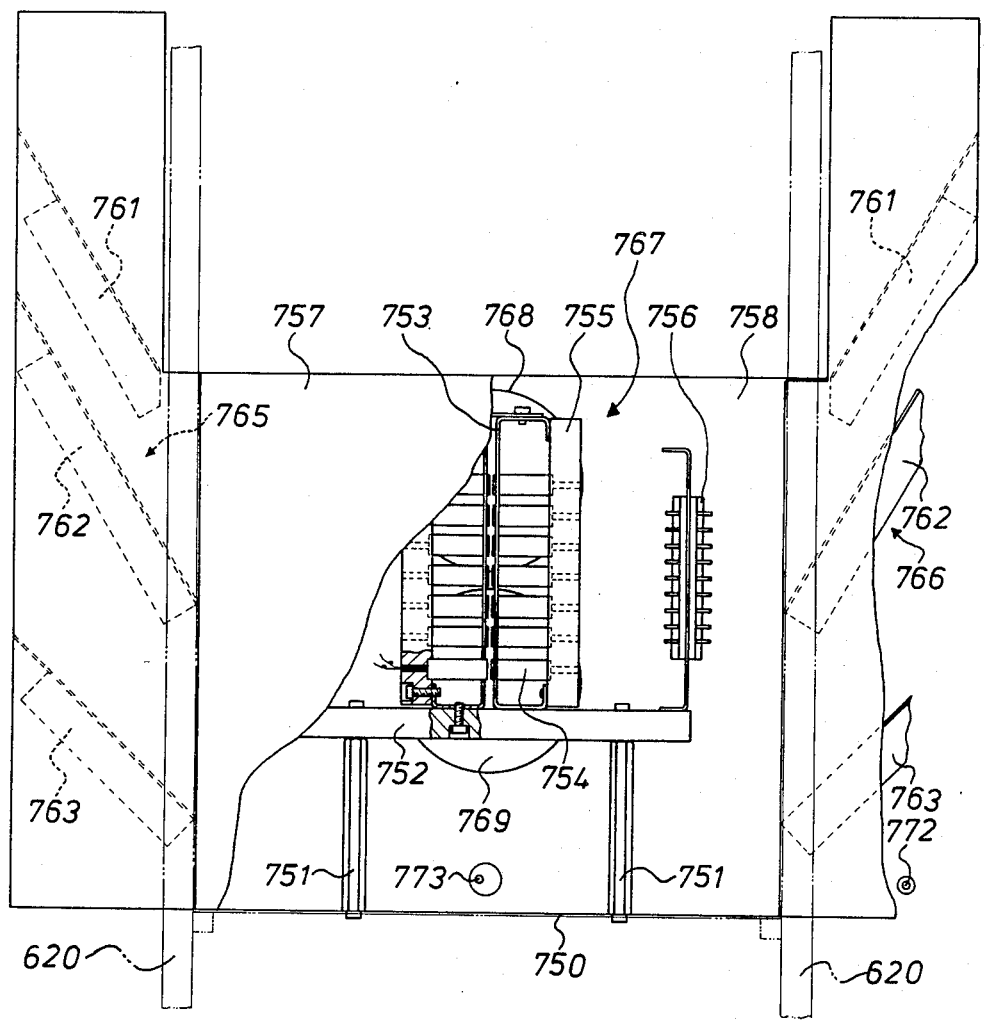
Figure 25:
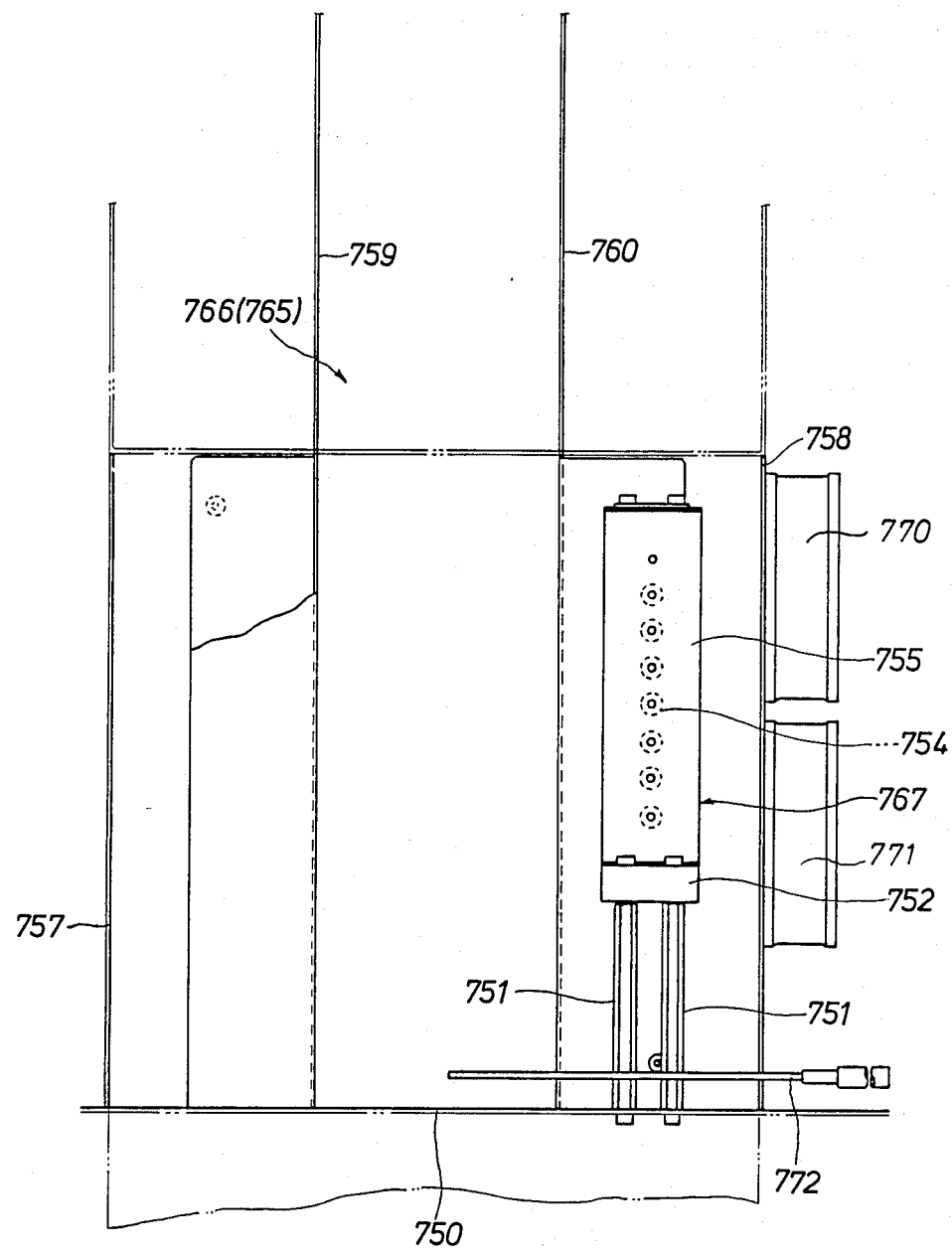

The heater unit 48 heating and maintaining predetermined temperature and atmosphere by forced draft hot air circulating system the space in the upward and downward conveyor units 43 and 44 and in the passages of the carrier unit 47 connecting the conveyor units 43 and 44 will be described referring to FIGS. 25a and 25b.

The heater unit 48 includes a support plate 750 between the support frame 620 of the frame unit 40, two support posts 751 mounted on the plate 751, a heater mounting table 752 attached on the posts 751, and a plurality of cartridge heaters 754 layered on the table 752 through a heater holder 753.

Insulating plates 755 are attached on both sides of the heater holder 753. The cartridge heaters 754 are connected electrically to electric sourse, not shown, through lead wires terminal plate 756 mounted on the mounting table 752.

Heater space 767 formed by the cartrige heaters 754 has front and rear covers 757 and 758. Also, duct covers 759 and 760 around the upward and downward conveyor units 43 and 44, form duct spaces 765 and 766. Upper, lower and intermediate flappers 761, 762, 763 on the duct covers 759 and 760 are attached. On the rear cover 758, fans 768 and 769 are mounted to perform forced circulation of hot air in the heater space heated by the cartridge heaters 754.

Heaters 770 and 771 supply heat to the fans 768 and 769. A temperature control sensor 772 controls temperature in the heater space 767, and an abnormal temperature detect sensor 773 detects abnormal heated condition in the heater space 767.

The cleaning apparatus 32 will be described referring to FIGS. 34a to 34c.

Figure 34A:
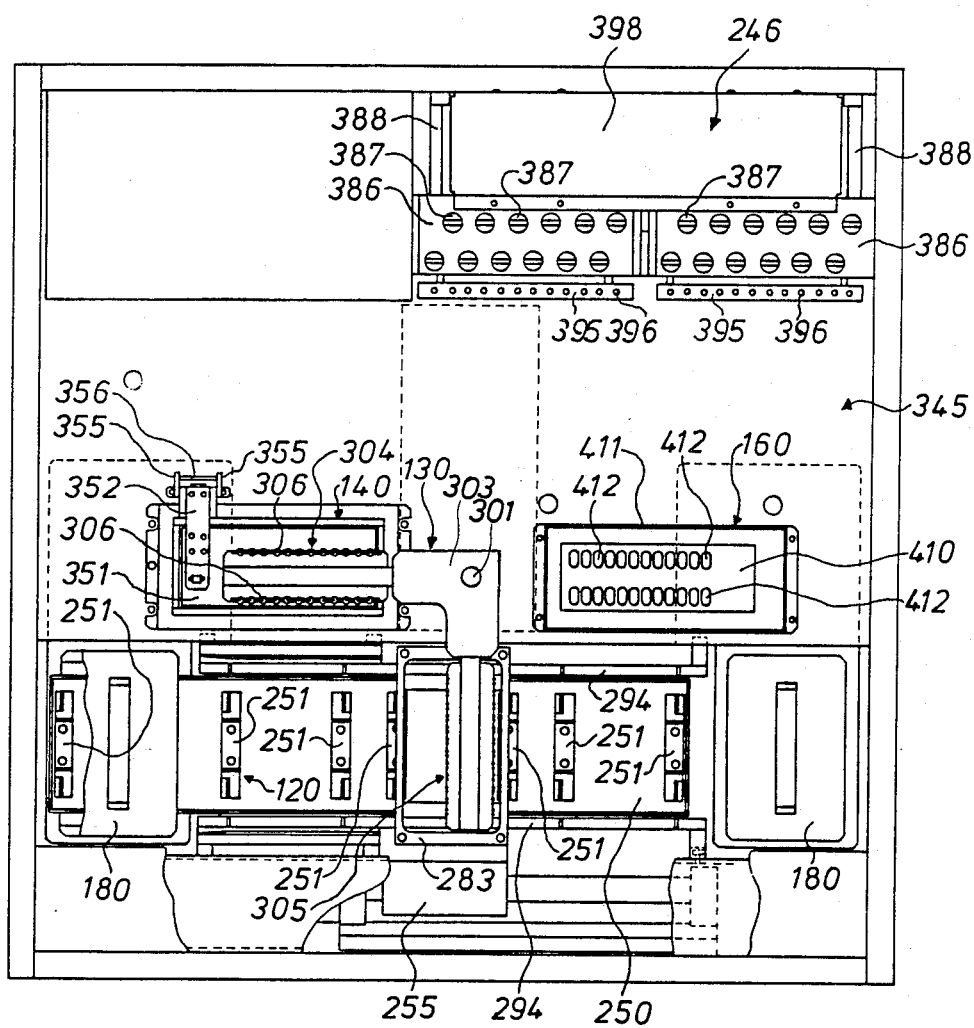
FIGS. 34a to 34c are plan view, front view and side view, respectively of cleaning apparatus, according to one embodiment of the present invention.
Figure 34B:
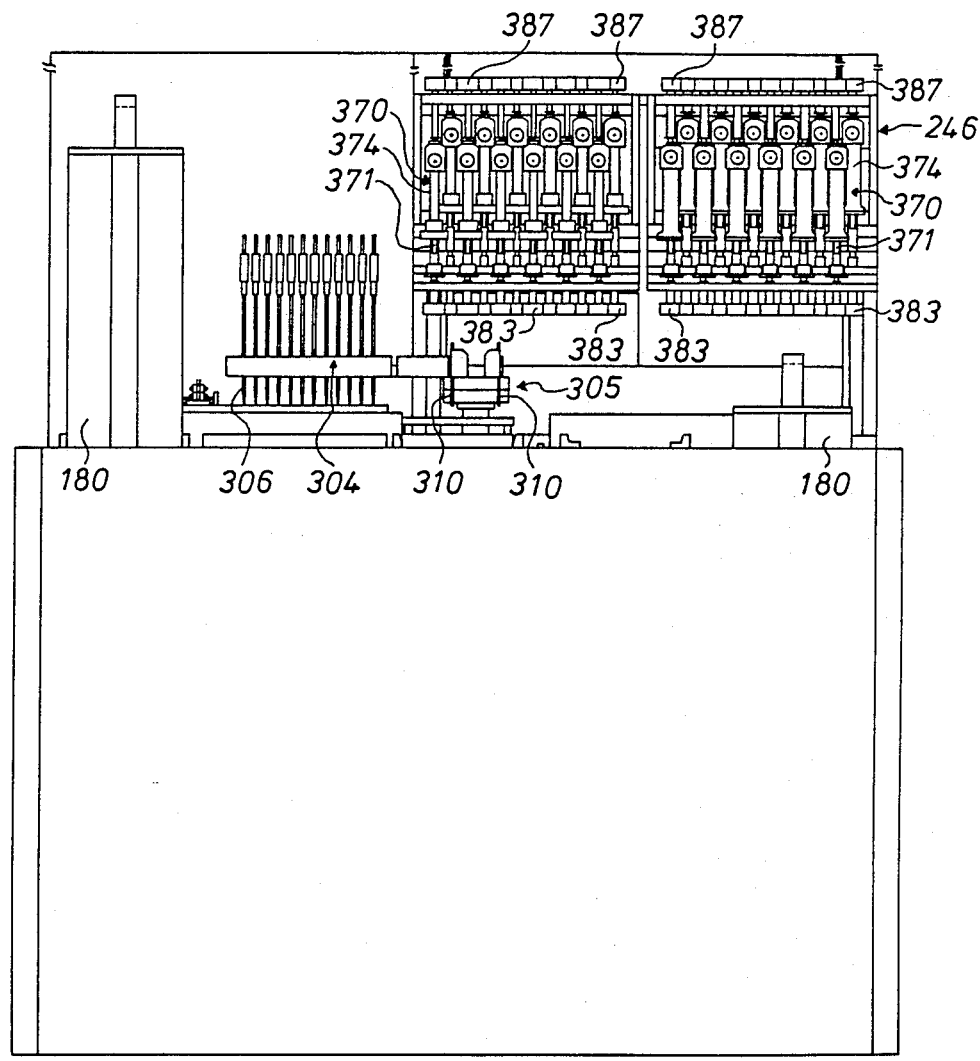
Figure 34:
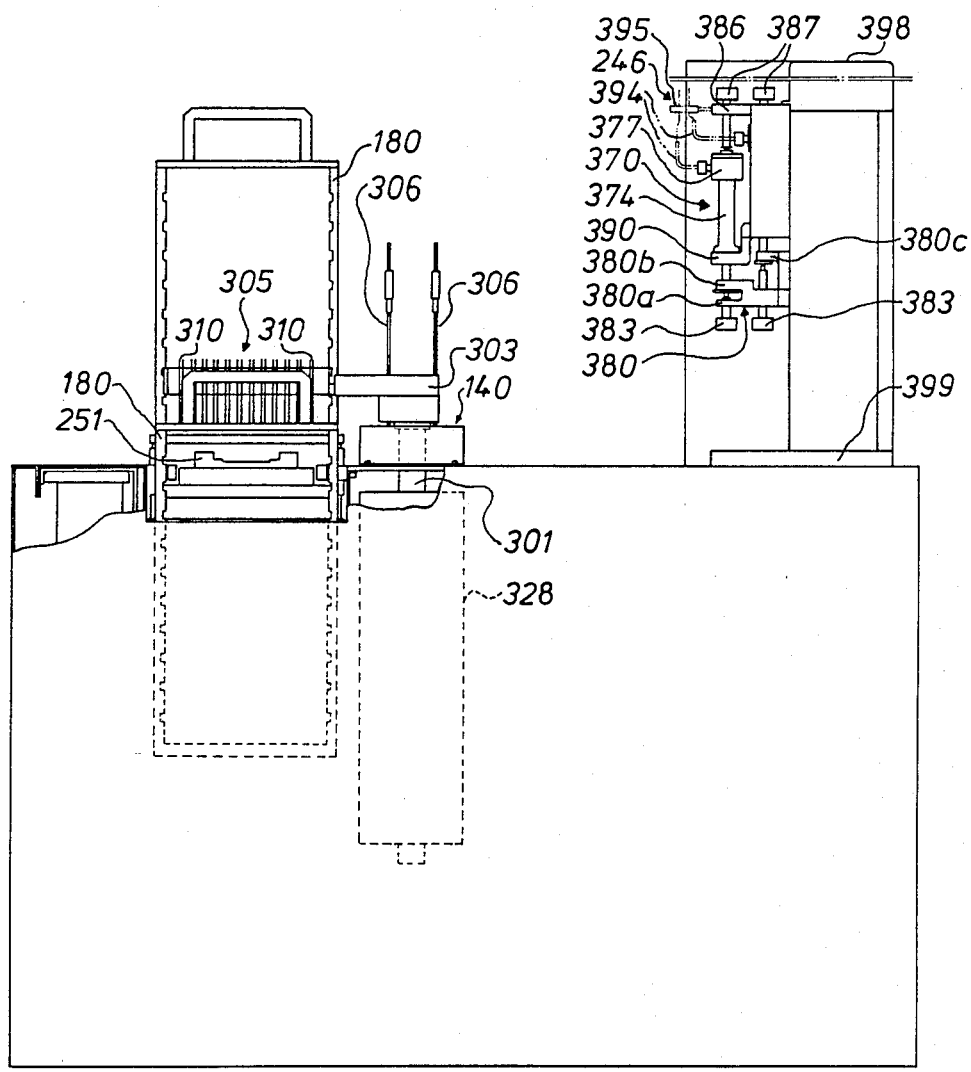

As shown in FIGS. 3 and 34a, the cleaning apparatus includes a supply magazine 180 storing microplates 1 having the wells 2 which had dispensed and coated the reagent solution, a plate transfer mechanism 120 which transfers the microplate 1 at constant pitch, a cleaning fluid nozzle arm unit 130 which dispenses and discharges cleaning fluid to each well 2, a cleaning fluid shelf unit 140 which stores cleaning fluid, an electrodes cleaning shelf unit 160 which cleans the liquid level detecting electrodes at the cleaning fluid nozzle arm unit 130, a cleaning fluid dispense unit 170 which sucks cleaning fluid for three times quantity and dispences cleaning fluid for three times to each well 2, and a discharge magazine 180 storing the microplates 1 having cleaned wells. When the microplates 1 are sequentially transferred to next stage, the discharge magazine 180 can be eliminated.

Figure 35A:
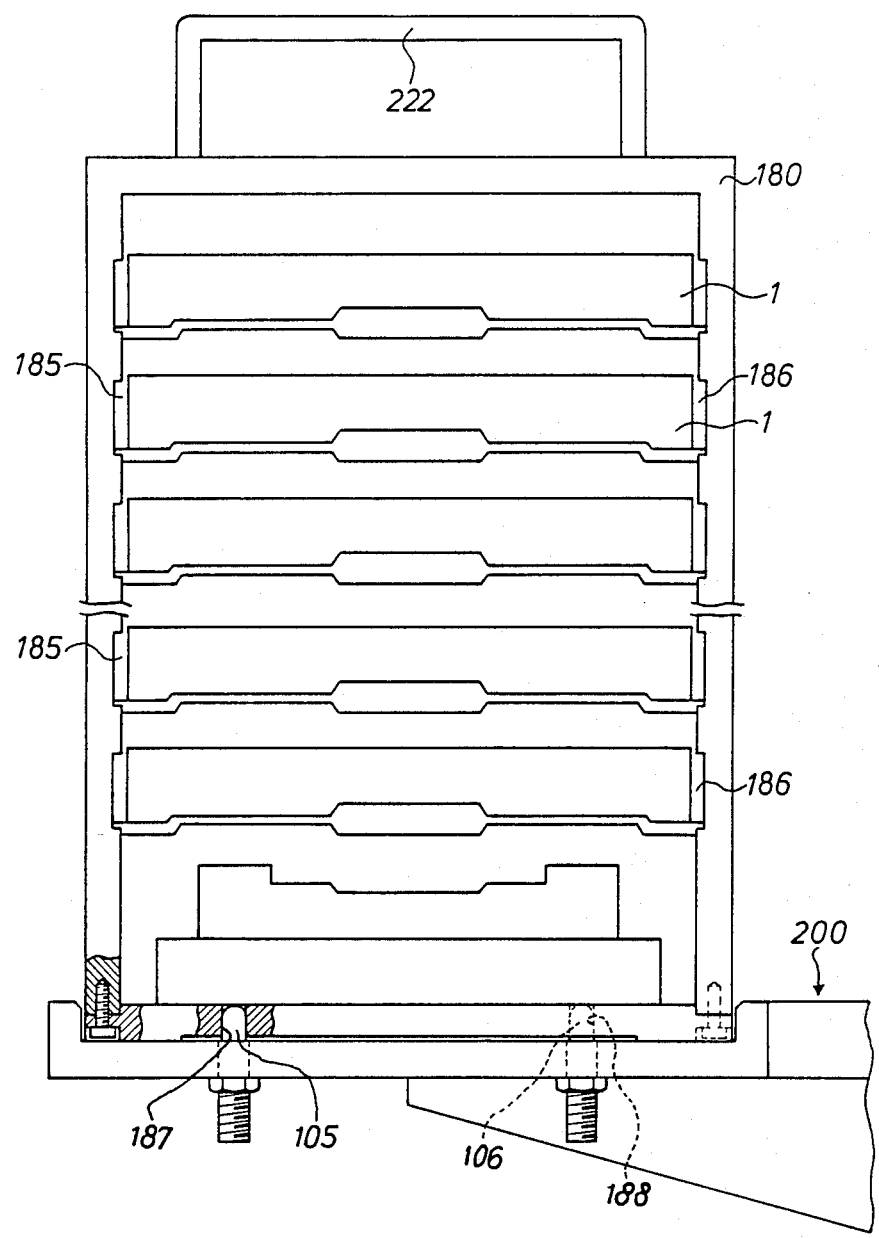
FIGS. 35a to 35e are illustrations of the magazine to store the microplates.
Figure 35:
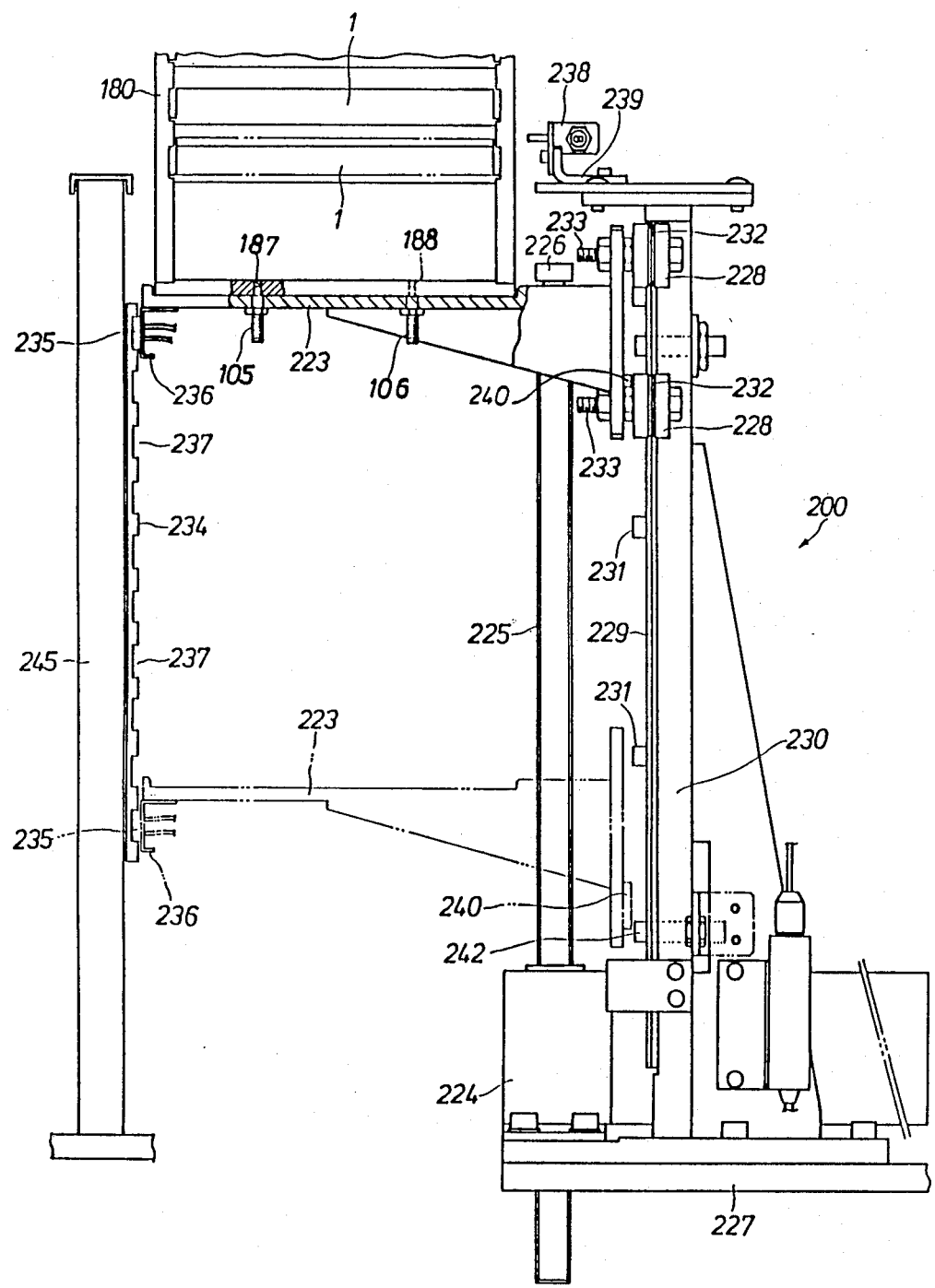
Figure 35C:
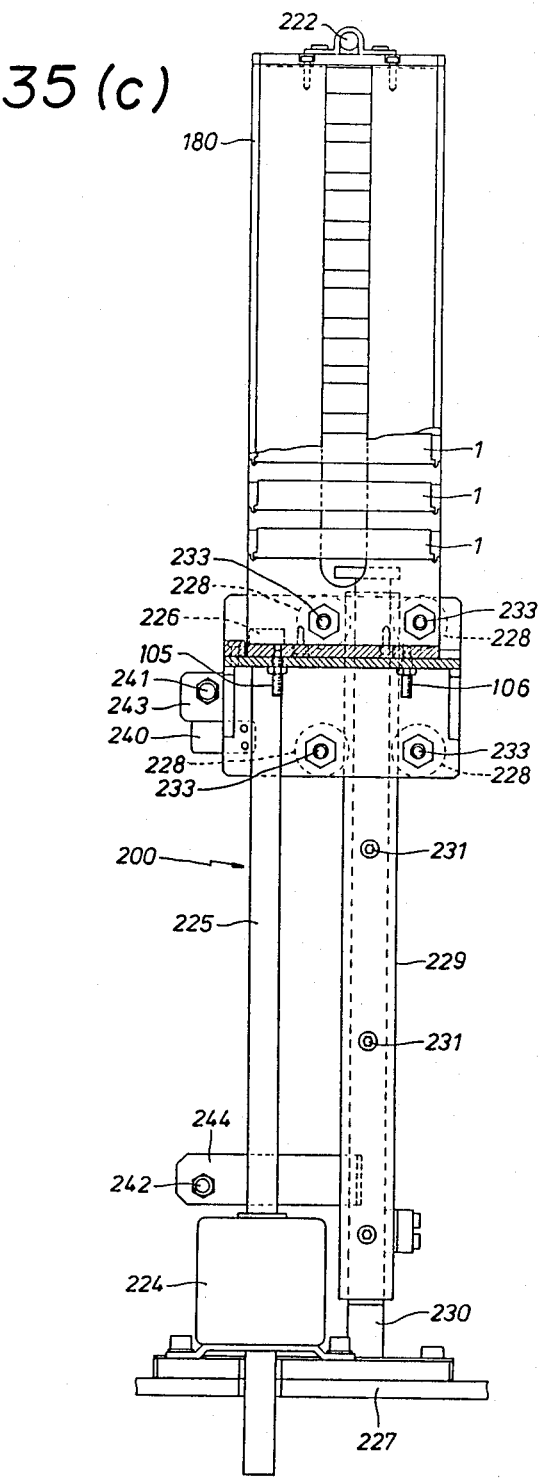
Figure 35D:
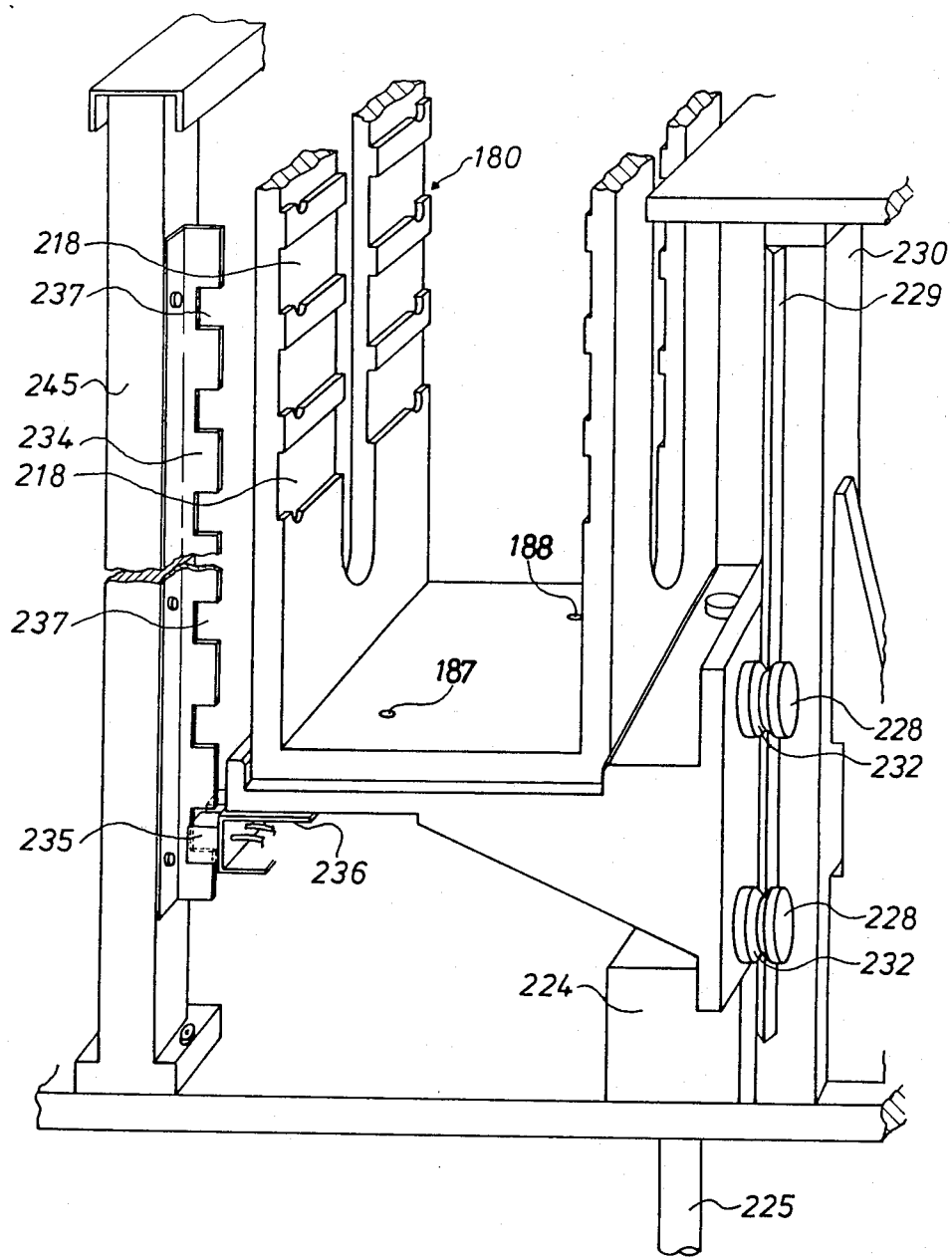

The supply magazine 180 which receives microplates 1 which have passed the coating stage and the incubation stage is adapted to move up and down by a magazine elevator apparatus 200 shown in FIGS. 35b, 35c and 35d. The magazine elevator apparatus 200 comprises a support base 223 which is secured through mounting screws 226 with upper end of an elevator rod 225 which is driven by a motor 224. The motor 224 has means to transfer rotary motion to linear motion. The motor 224 is mounted on an intermediate base 227 about the middle portion of the body of the apparatus 30. On the intermediate base 227, a guide rail plate 229 is secured to guide guide rollers 228 which is rotatably supported on the support base 223. The guide rail plate 229 is secured with the intermediate base 227 through support posts 230, and is secured by screws 231. The guide roller 228 is shown in FIG. 35c. The guide rollers 228 are adapted to support upper and lower guide surfaces of the guide rail plate 229. Two pairs of guide rollers 228 stably support the guide plate 229. Each guide roller 228 forms V-shaped guide groove 232 to engage with corresponding V-shaped edge on the guide plate 229. The guide roller 228 is mounted by a support bolt 233. A sensor plate 234 cooperates with a sensor 235 which is secured with the support base 223 and controls displacement of the support base 223 i.e. elevation of the supply magazine 180, and is parallel with the elevator rod 225. The sensor 235 is a sensor having light transmitter and receiver and is secured with the support base 223 through a support plate 236. The sensor plate 234 forms constant pitch recesses 237 so that when the support base 223 is lowered and the sensor 235 reaches to a position aligning the recess 237, the light receiver of the sensor 235 receives light from the transmitter to stop the lower displacement of the support base 223. The recesses 237 are same as the number of the microplates 1 to be stored, i.e. ten in the embodiment. A sensor 238 detects presence of the microplates 1 stored in the supply magazine 180, and is secured with upper end of the support post 230 through a blacket 239. A sensor plate 240 cooperates with sensors 241 and 242 to control upper and lower limit of the support base 223, and is secured with the support base 223. The sensors 241 and 142 are supported by support plates 243 and 244, and the sensor plate 234 is secured with a support post 245. The supply magazine 180 loaded with ten empty microplates 1 is set to elevated position through the magazine elevator apparatus 200 as shown in FIGS. 34b and 34c.

Figure 35E:
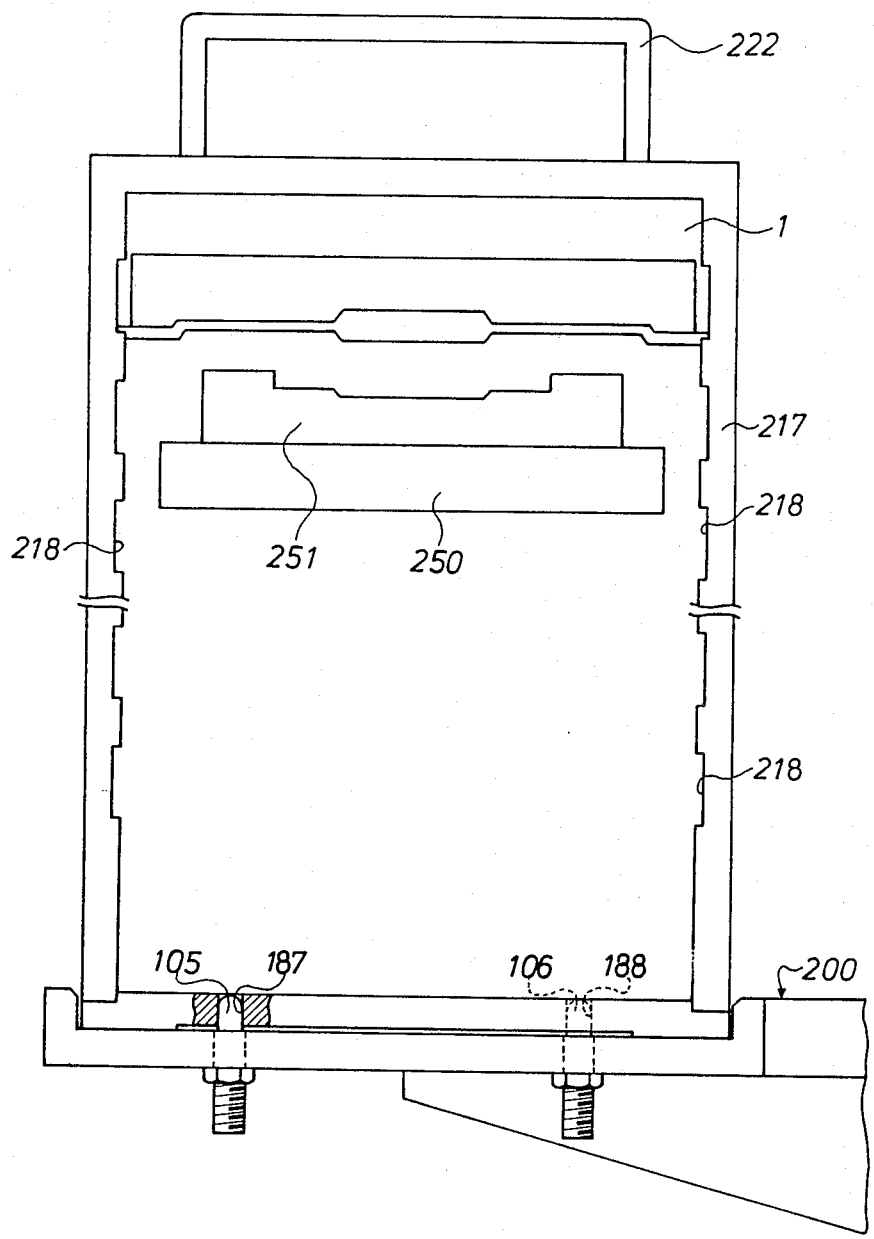

The discharge magazine 180 is same as above mentioned supply magazine 180 and is only difference is initial set position. The empty magazine 180 is set to lowered position by magazine elevator apparatus 200 a shown in FIG. 35e. The microplate 1 completed with coating of solid phase reagent is stored in the magazine 180 which has completed the cleaning stage sequentially from uppermost shelf.

The stage transfer mechanism 120 takes out the microplate 1 one by one from the cleaning fluid nozzle arm unit 180 and transfers the same at constant pitch to the cleaning fluid nozzle arm unit 130, and further stores the microplate 1 which has cleaned into the discharge side magazine 180. The mechanism of the plate transfer mechanism 120 will be described referring to FIGS. 36, 37 and 38.

Figure 37A:
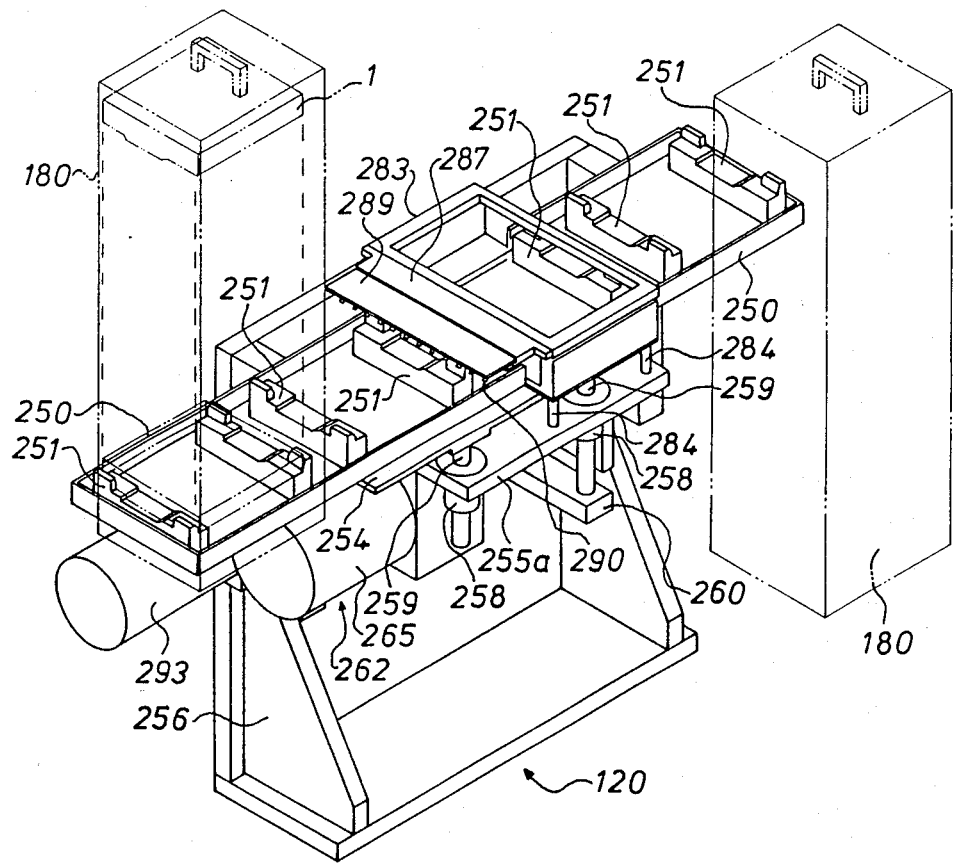
FIGS. 37a to 37c are illustrations of a portion of the cleaning apparatus.
Figure 37B:
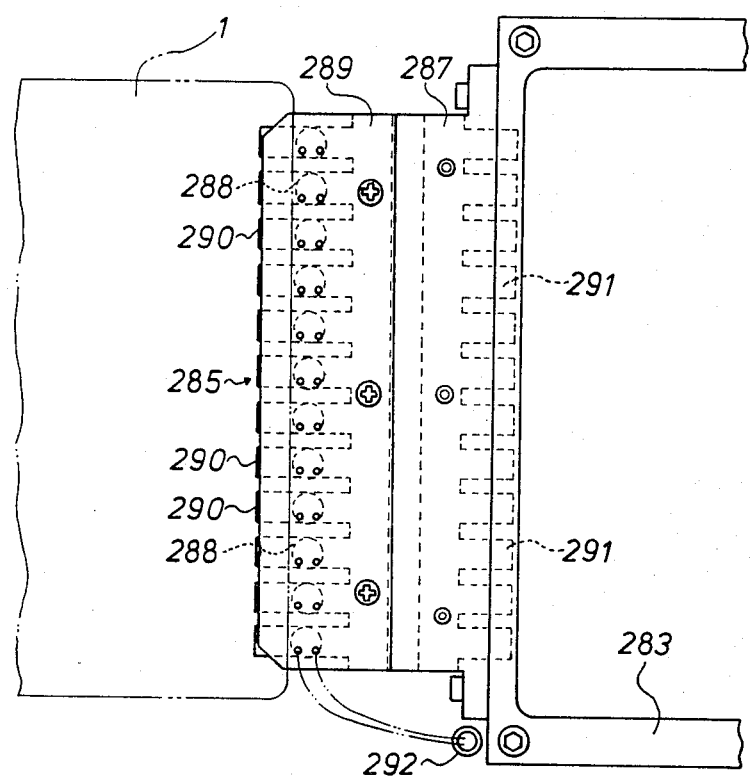
Figure 37C:
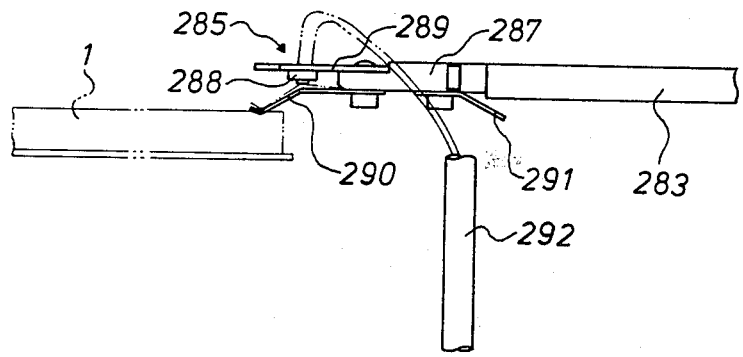
Figure 38A:
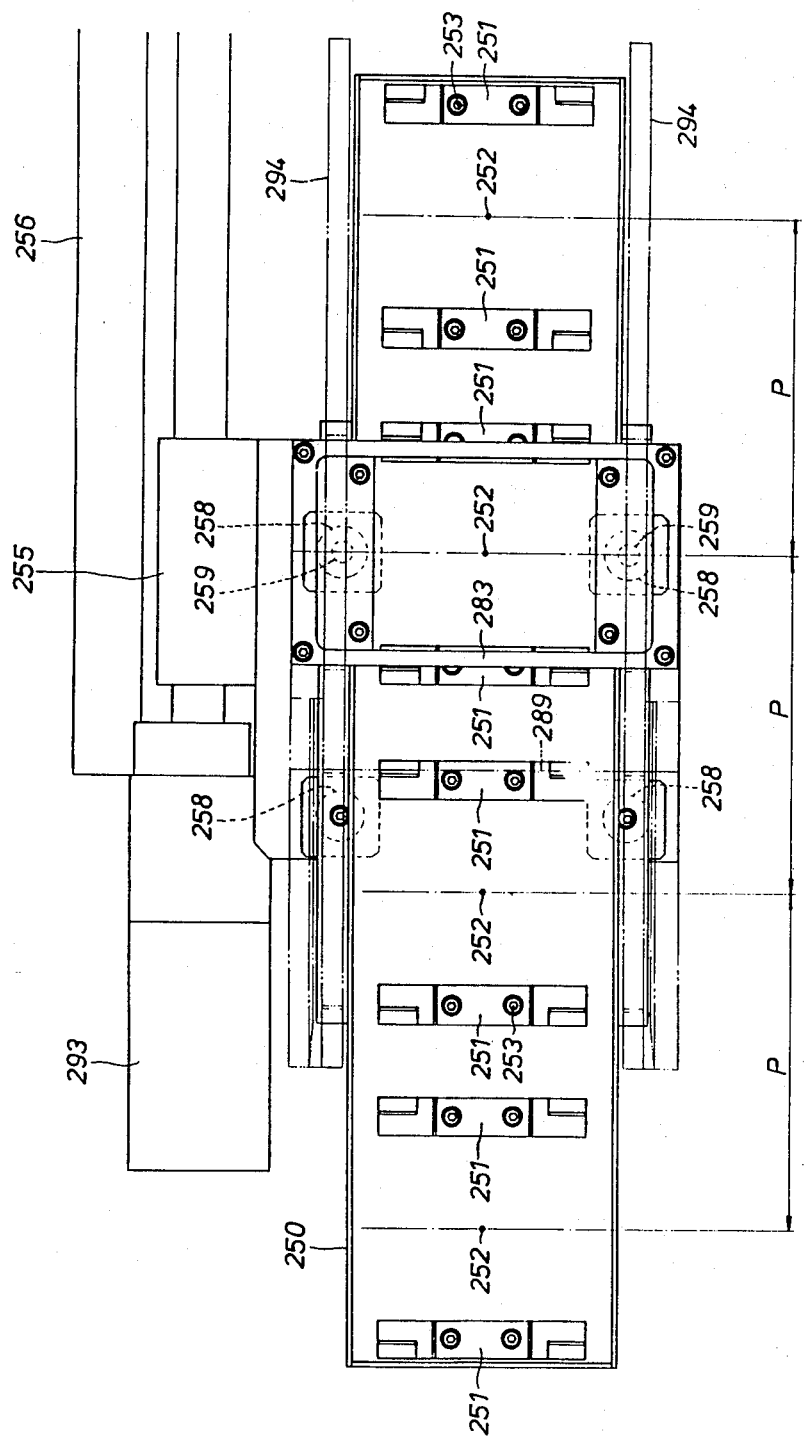
FIGS. 38a to 38c are illustrations of the microplate transfer unit shown in FIG. 36, FIGS. 39a to 39h are illustrations of the nozzle unit and electrode unit of the apparatus shown in FIG. 36, FIGS. 40a and 40b are illustrations of the arm drive unit shown in FIG. 36.
Figure 38B:
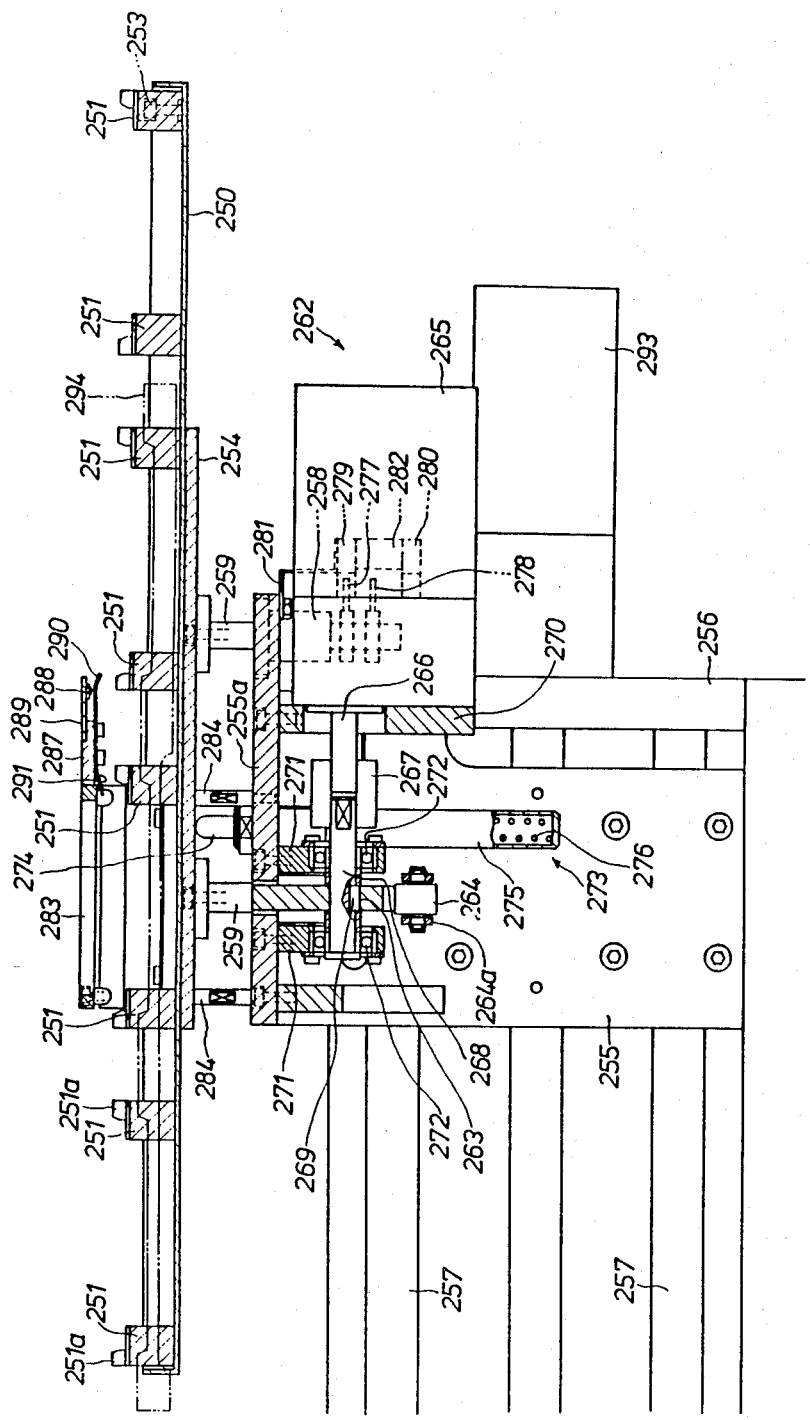
Figure 38C:
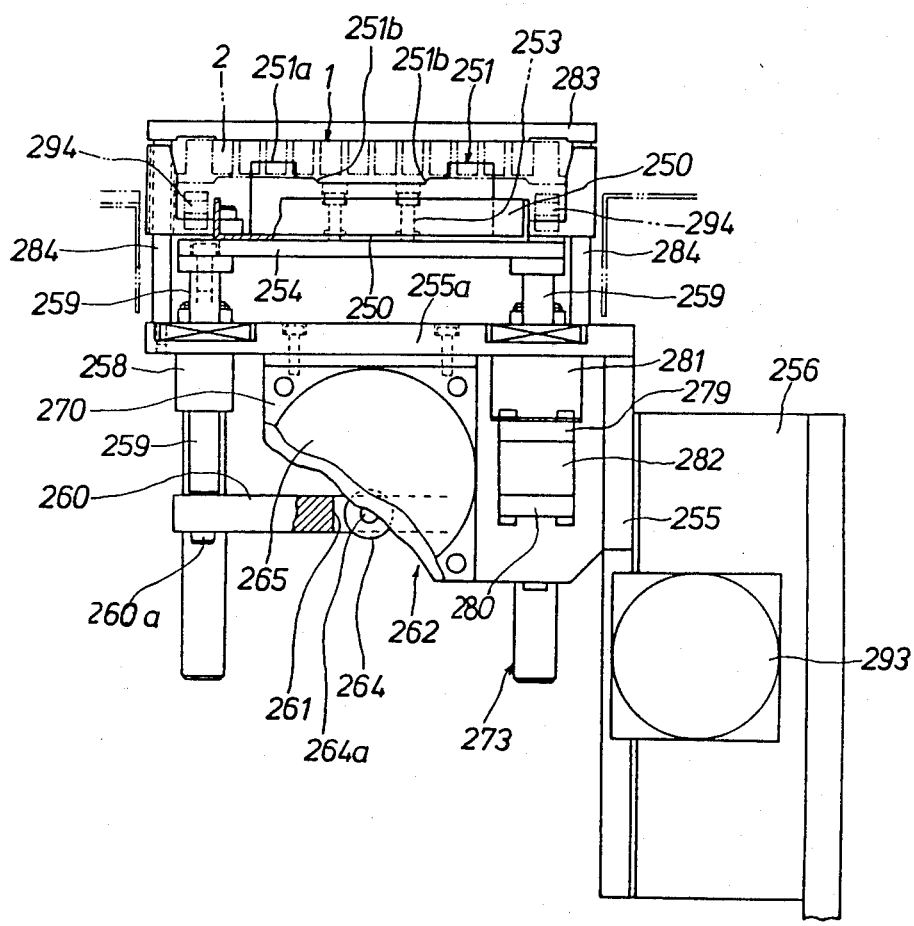

FIG. 36 shows the plate tranfer mechanism 120 and the adjacent apparatus, FIG. 37a shows the plate tranfer mechanism 120. FIGS. 37b and 37c show detail thereof, FIGS. 38a, 38b and 38c are details of FIG. 37a. In the drawing, a receive member support frame 250 secures receive members 251 for the microplate 1 to transfer the microplate 1 at a constant pitch. The receive members 251 are arranged as four pairs of two, and the center distance between the pairs is constant. The members 251 are secured by screws 253. The bottom surface of the frame 250 contacts with a base plate 254 which is secured with the support frame 250 through screws 253. An inverted L-shped slide base 255 is slidably mounted under the plate 254 by a slide rod 257 which is mounted on a fixed frame 256 of the apparatus body, so as to slidable horizontal direction in FIG. 38b. A horizontal part 255a of the slide base 255 mounts four ball bushes 258 on lower surface, and a slide shaft 259 passes through the ball bush 258 vertically slidably. Thus, the plate 254 and the receive member support frame 250 are vertically movable relative to the horizontal part 255a of the slide base 255 through the ball bush 258. Among the four slide shafts 259 which pass through the four ball bushes 258, right side slide shaft 259 in FIG. 38a is connected through connecting plate 260 at lower end by screws 260. Center portion of the connecting plate 260 has an elongated opening 261 in which a cam follower 264 is rotatably supportd by a support shaft 264a to engage with a cam 263 of a cam drive apparatus 262. The cam drive apparatus 262 drives the cam 263 which engages with the cam follower 264, and has a motor 265 having a gear head, a cam shaft 268 connected with an output shaft 266 of the motor 265 through a coupling 267, and a cam 263 secured with the cam shaft 268 through a key 269.

The motor 265 is secured with a motor base 270 which is integrally secured under the horizontal part 255a of the slide base 255. The cam shaft 268 is rotatably supported through bearings 272 which are inserted in cam shaft support plates 271 and 271 depending from the horizontal part 255a of the slide base 255. On the horizontal part 255a of the slide base 255, a support frame upward urging means 273 is mounted to urge upwards the receive member support frame 250 normally. The support frame upward urging means 273 is formed from an urging pin 274 engaging with lower surface of the plate 254, a pin store 275 receiving the urging pin 274, and a coil spring 276 urging the pin 274 upwards, to urge the receive member support table 250 by the urging pin 274 which is urged by the spring 276. The cam 263 is an eccentric cam, and when the cam 263 is driven by the cam drive apparatus 262, the cam 263 cooperates with the cam follower 264 to urge the cam follower 264 downwards to move the receive member support frame 250 downwards against the upwards urging force of the support frame upward urging means 273.

The lower side of the slide shaft 259 mounts vertically spaced two detect members 277 and 278. On the horizontal part 255a of the slide base 255, two sensors 279 and 280 are mounted through a support plate 281 to detect the detect members 277 and 278. By cooperation between the detect members 277 and 278 and the sensors 279 and 280, vertical movement of the receive member support frame 250 is detected. A spacer 282 is shown.

A stopper plate 283 is upward from the horizontal part 255a of the slide base 255 to engage with upper surface of the well 2 on the microplate 1 placed on the receive member 251 when the receive member support frame moves upwards to position the microplate 1. The stopper plate 283 is secured on the horizontal part 255a of the slide base 255 through support posts 284. One side surface of the stopper plate 283 mounts a microwell module detect device 285 to detect module on the microplate 1. On the microplate 1, as described before, a plurality of modules 3 are placed, and the microwell module device 285 detects presence or absence of the module 3. The microwell module detect device 285 is shown in FIGS. 37b and 37c and includes a switch base 287, a switch plate 289 mounting a plurality of detect switches 288, and plate springs 290 to actuate the detect switches 288. The plate springs 290 is adapted to operate the switches 288 individually. The plate spring 290 engages with the edge 3a of the module 3 on the microplate 1. When the microplate 1 moves upwards on the receive member 251, the mounting edge 3a of the module 3 engages with the plate spring 290 to operate the switch 288. Thus, when the all switches 288 are not ON, there is no microplate 1, and when a portion of the switches 288 are not ON, some modules 3 are not placed on the microplate 1. A plate spring 291 to separate the microplate 1, and duct means 292 to pass lead wires of the switches 288 are shown.

A pulse motor 293 is mounted on the fixed frame 256 of the apparatus body to displace and control the slide base 255 along the slide rod 257. The receive member support frame 250 displace a pitch P which is center distance between the center line 252 of the pair of receive members 251 by the pulse motor 293. That is, the microplate 1 placed on the pair of the receive members 251 moves one pitch P through the receive member support frame 250 which is controlled by the pulse motor 293. Also, the microplate 1 on the pair of the receive members 251 is adapted to move constant minor pitch by the pulse motor 293 so that each row of the wells 2 on the microplate 1 can receive and discharge cleaning fluid through the cleaning fluid nozzle arm 130.

A fixed receive member 294 temporary supports the microplate 1 which is transferred from the supply magazine 180. That is, the receive member support frame 250 moves leftward at lowered state through the cam 263 to one pitch P shown in FIG. 38a to penetrate into the supply magazine 180 shown in FIG. 3. In this state, when the cam 263 is rotated releasing the frame 250 to move upwards, one microplate 1 is placed on the left end pair of the receive member 251. In this case, the microplate 1 moves upwards from the fixed receive member 294, and at the upward position, the frame 250 moves to the left by the pulse motor 293 for one pitch P. After the one pitch movement, the receive member support frame 250 moves downwards by the cam 263 lower than the fixed receive member 294 so that the microplate 1 which is on the receive member 251 is temporary received on the fixed receive member 294. In this state, the support frame 250 penetrates into the supply magazine 180, to carry out the microplate 1 in the magazine 180 as before, sequentially one by one.

The receive member 251 forms tapered engage surfaces 251a and 251b to engage with corresponding engage portions of the microplate 1 so that the microplate 1 can be suitably positioned, as shown in FIGS. 38b and 38c.

Figure 39:
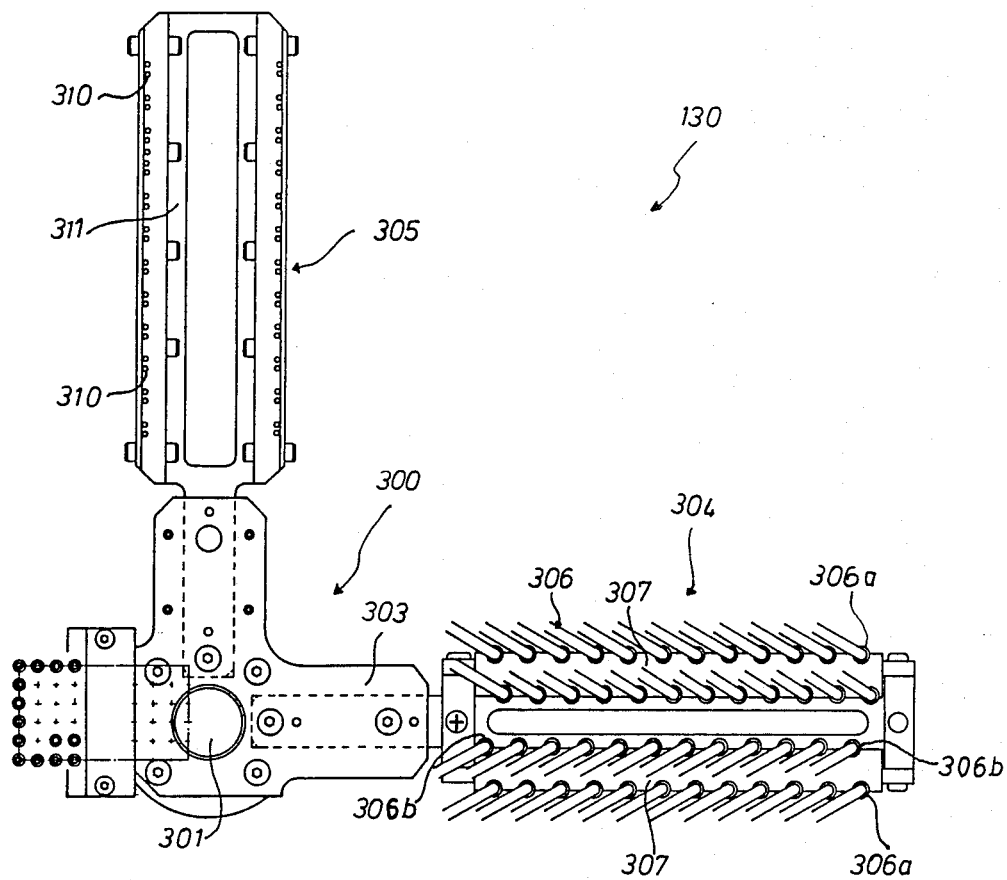
Figure 39B:
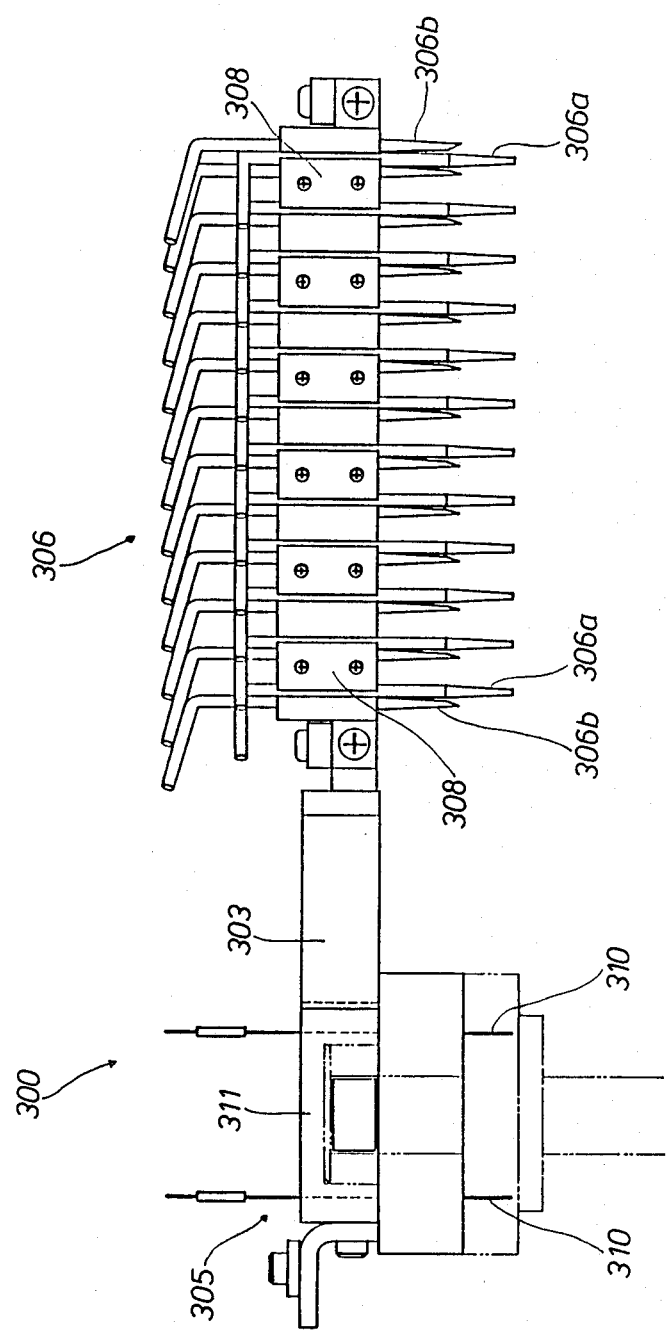

The solution nozzle arm apparatus 130 dispenses cleaning fluid in each well 2 on the microplate 1 and to detect liquid level dispensed in the wells 2, and as shown in FIGS. 39 and 40, includes an arm body unit 300, an arm shaft 301 supporting the arm body unit 300, and an arm drive unit 302 to vertically move and to swirl the arm body unit 300.

The arm body unit 300 is shown in FIG. 39a and comprises an arm base 303 secured with an arm shaft 302 and a cleaning fluid dispense arm 304 and a liquid level detecting arm 305 extending from the arm base 303. The cleaning fluid dispense arm 304 and the liquid level detecting arm 305 are perpendicular each other, and the both arms 304 and 305 are adapted to rotate 90 degree by the arm drive unit 302. The cleaning fluid dispense arm 304 and the liquid level detecting arm are perpendicular each other, and are adapted to rotate 90 degree through an arm drive shaft 302 shown is FIG. 40.

Figure 39D:
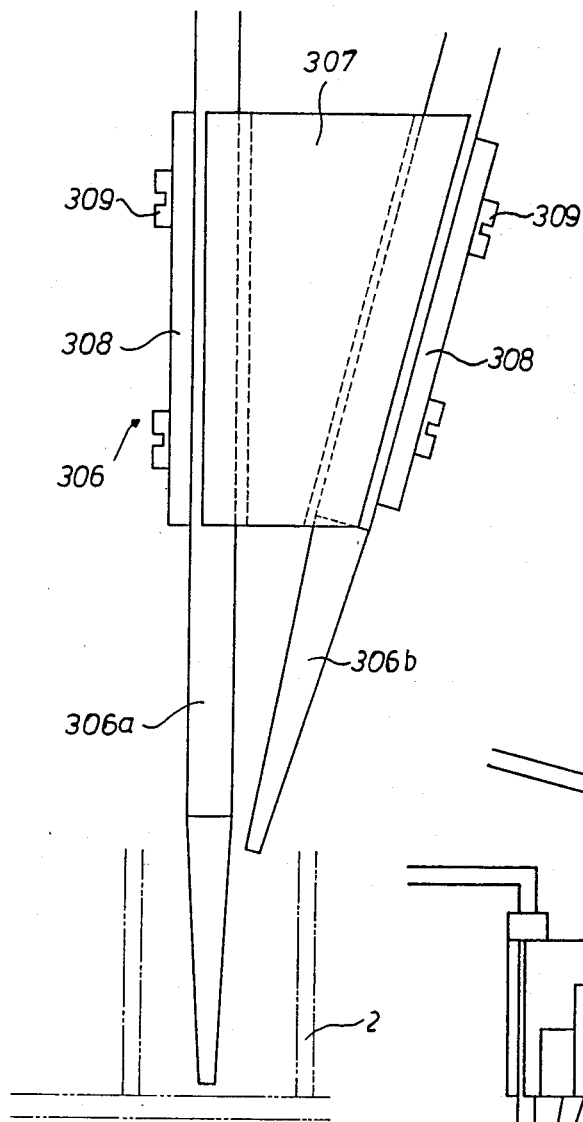
Figure 39C:
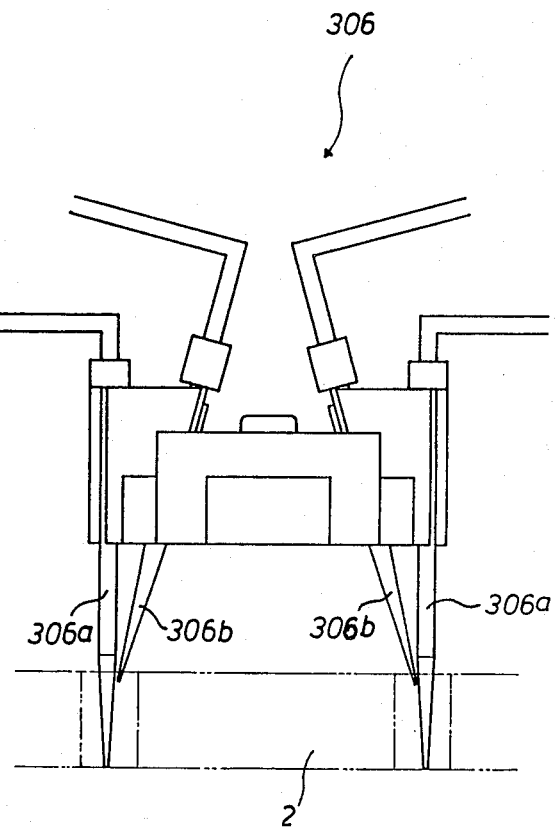
Figure 39E:
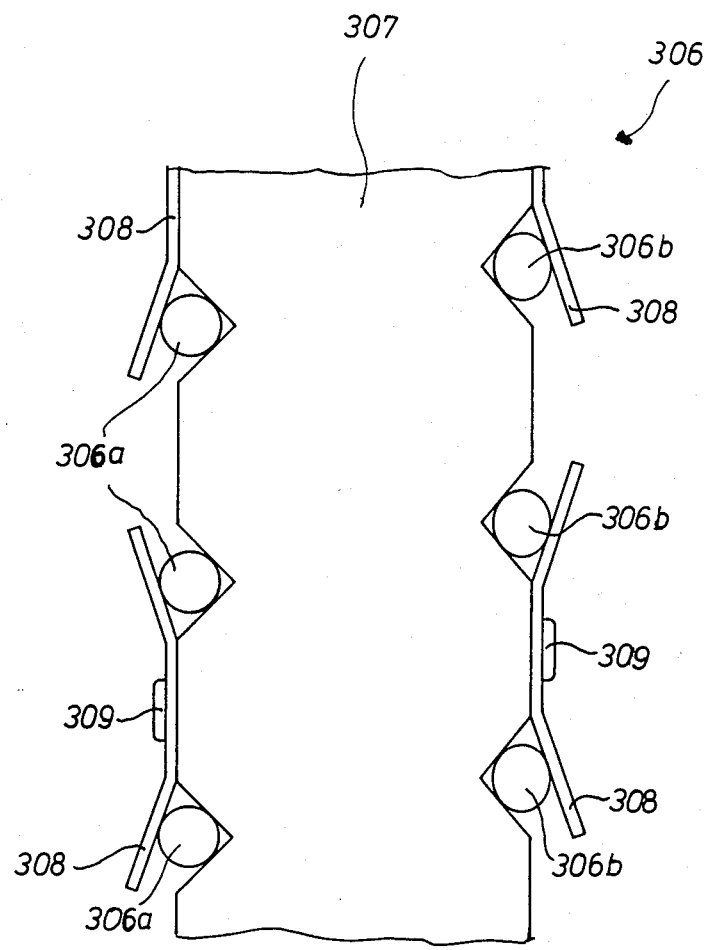
Figure 39:
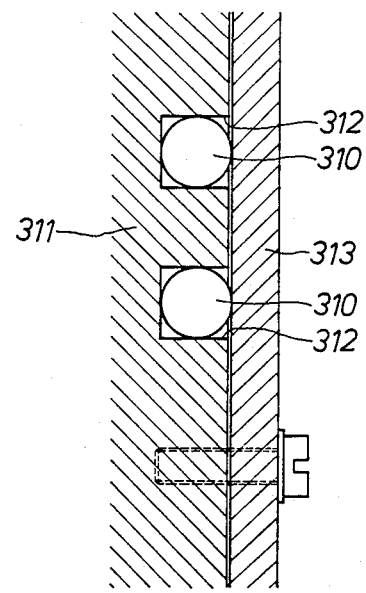
Figure 39:
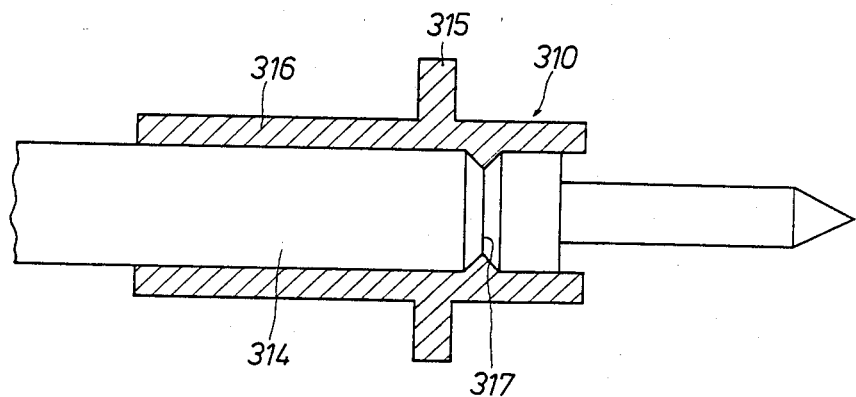

The cleaning fluid dispense arm 304 includes a nozzle unit 306 which sucks cleaning fluid from the cleaning fluid shelf unit 140 a quantity sufficient to dispense three times and to dispense the sucked fluid three times into the wells 2, a nozzle support base 307 to support the nozzle unit 306, and nozzle retainers 308. The nozzle support base 307 is devided in two sheets as shown in FIG. 39a, and is secured with long depending first nozzles 306a as shown in FIG. 39c at outside surface. To inside surface of the nozzle support base 307, second nozzles 306b shorter than the first nozzles 306a are secured. The second nozzles 306b is slanted to the side of the first nozzles 306a as shown in FIG. 39d so that the first nozzles 306a can be cleaned by the cleaning fluid dispensed from the second nozzles 306b. As shown in FIG. 39f the long and short pair of the nozzles 306a and 306b aims in the well 2, and are 24 pairs i.e. two rows of 12 pairs are arranged. Each nozles 306a and 306b are secured in place by nozzle retainers 308 and screws 309.

The liquid level detecting arm 305 includes liquid level detecting electrodes 310 and electrode bases 311 supporting the electrodes 310. The electrodes 310 are received in recesses 312 formed on the electrode base 311 as shown in FIG. 39g and is retained in place by electrode retainers 313. The electrede 310 is shown in FIG. 39h and includes an electrode needle 314 and an outer sleeve 316 having a flange 315. The electrode needle 314 and the sleeve 316 are connected each other by V-shaped clamp portion 317. The electrode needle 314 is adapted to absorb needle tip displacement when the tip is urged. The number of nozzles 306 are 24, i.e. two rows of twelve, and the number of electrodes 310 are 24 sets i.e. 2 rows of 12 sets in the embodiment shown.

Figure 40A:
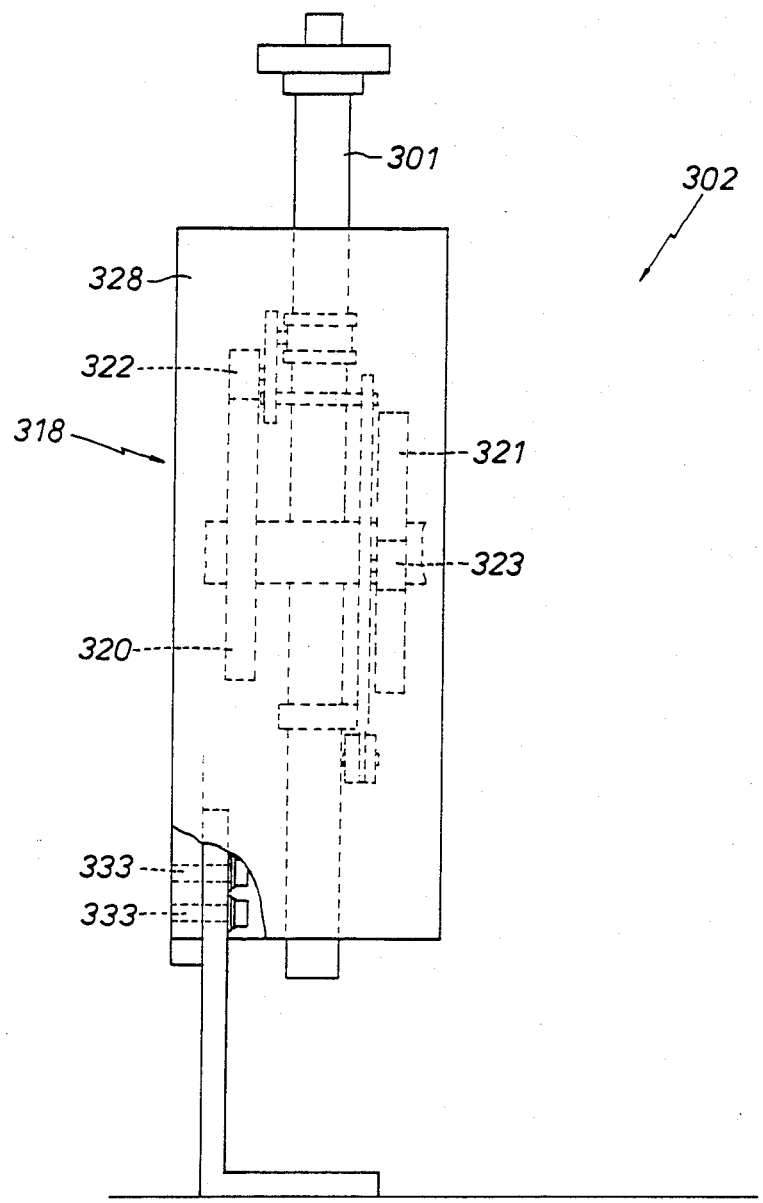
Figure 40B:
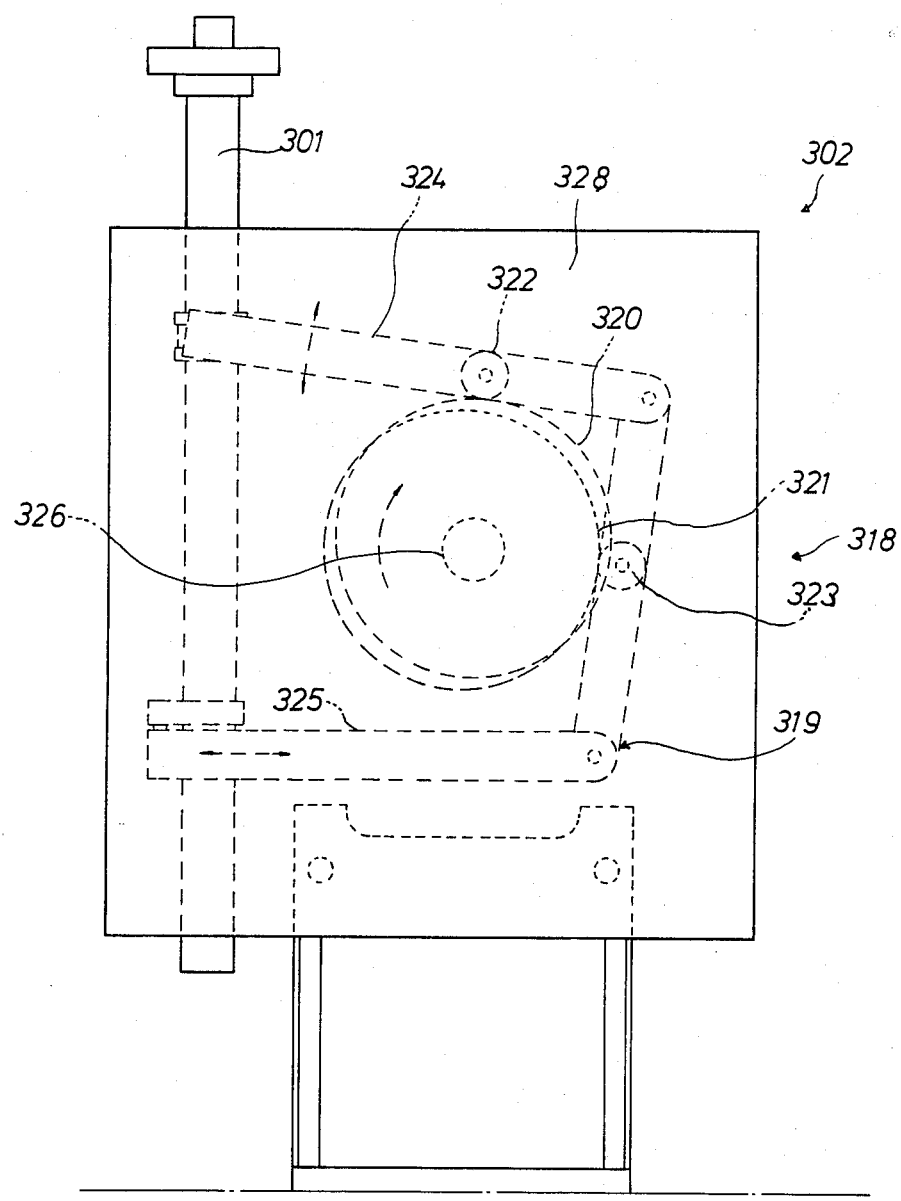

The arm drive unit 302 is shown in FIGS. 40a and 40b, and includes a drive unit 318 to swirl and vertical movement of the arm shaft 301. The drive unit 318 to swirl and vertical movement of the arm shaft 301 is shown in FIGS. 40a and 40b and includes two rotary driven cams 320 and 321, cam followers 322 and 323 engaging the cams 320 and 321, a vertical movement arm 324 and a swirl movement arm 325 operated through the cams 320 and 321 and the cam followers 322 and 323. The cams 320 and 321 are secured with a cam shaft 326, and the cam shaft 326 is rotary driven by a motor, not shown. By rotating the cams 320 and 321, the arm shaft 301 moves vertically or rotates 90 degrees through the vertical movement arn 324 and the swirl movement arm 325. A cover 328 is shown.

Figure 41:
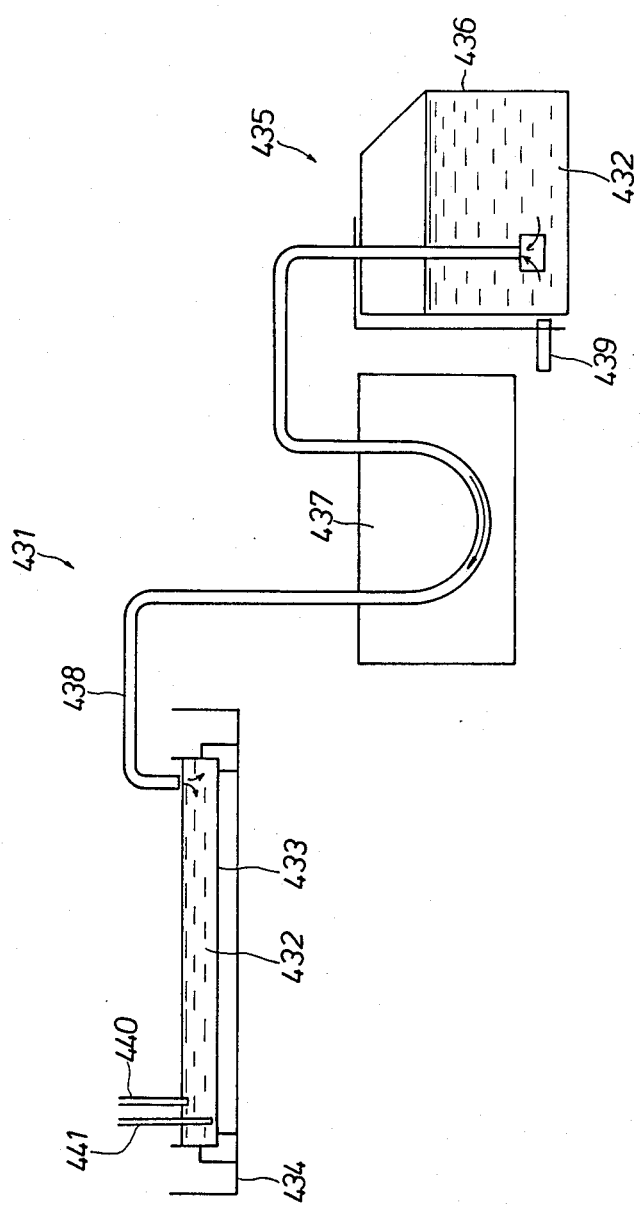
FIG. 41 is an illustration of the cleaning fluid store of the apparatus shown in FIG. 36, FIGS. 42a to 42q are illustrations of the dispense unit shown in FIG. 36.

The cleaning fluid shelf unit 140a which stores cleaning fluid as shown in FIG. 41. As shown, the cleaning fluid shelf unit 431 includes a cleaning fluid container 433 to store cleaning fluid, an overflow receiver 434, and a cleaning fluid supply unit 435. The cleaning fluid supply unit 435 includes a cleaning fluid supply tank 436, a tubing pump 437, and a supply hose 438, and automatically supplies cleaning fluid 432 to the cleaning fluid container 433. The supply tank 436 has a lower limit detect sensor 438, and the container 433 has upper and lower limit detect sensors 440 and 441 for the cleaning fluid 432. When the liquid level is below the lower limits, alarm buzzar operates.

Cleaning fluid 432 in the cleaning fluid container 433 is sucked and supplied through the nozzle unit 306 of the cleaning fluid nozzle arm unit 130 to each well 2 of the microplate 1 which is stopped at predetermined position for three times. The suck and dispense process of the cleaning fluid 432 are performed by a cleaning fluid dispense unit 246.

Figure 42C:
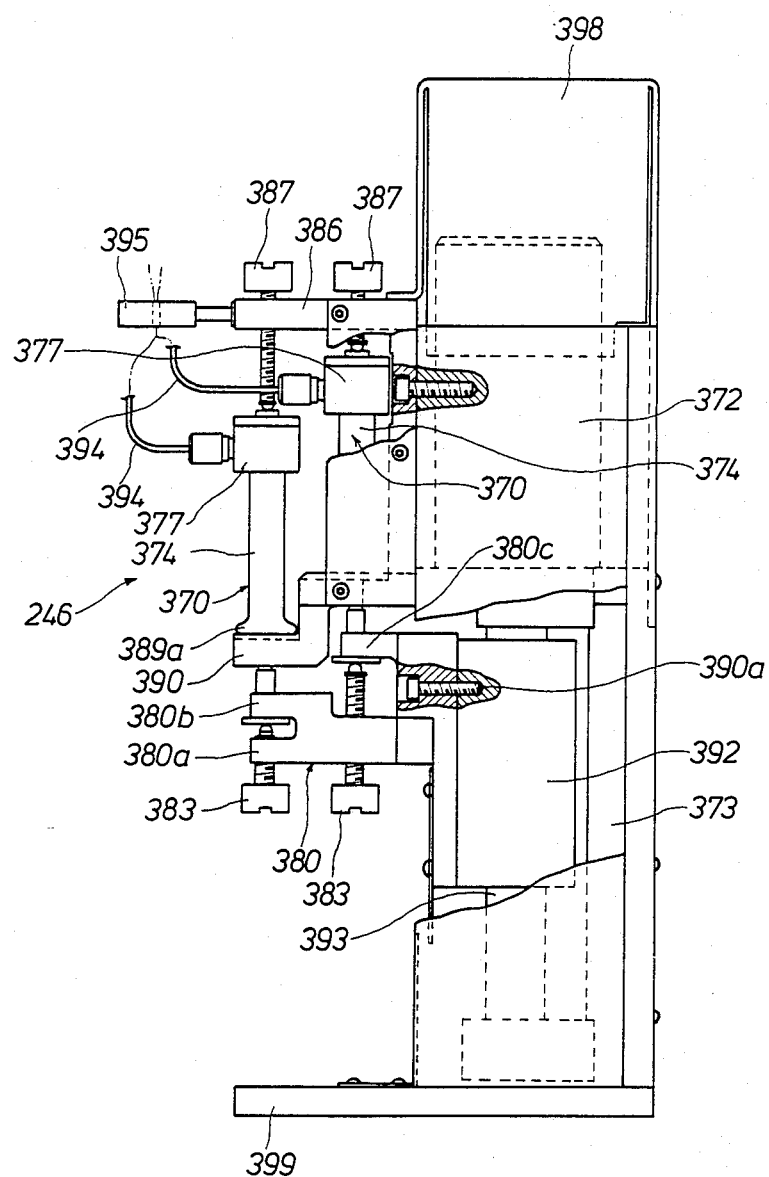

The cleaning fluid dispense unit 246 is shown in FIGS. 42a and 42e and includes a shringe 370 which sucks and dispenses cleaning fluid 432, a pulse motor 372 for vertical drive of a movable shaft 371 of the shringe 370, and a support frame 373 to support the shringe 370 and the pulse motor 372. The shringe 370 is shown in FIG. 42f and includes a cylinder 374, a movable shaft 371 slidable in the cylinder 374, a piston 375 connected to inner end of the shaft 371, a cylinder head 376, and a tube connection 377. The cylinder 370 each corresponds to the nozzle 306 of the solution nozzle arm unit 130. As the number of nozzles 306 are 24, corresponding to the number of the short nozzles 306b shown in FIG. 39d, to suck and discharge cleaning fluid 432, or 2 rows of 12, so that number of the cylinders 370 is also 24. The 24 cylinders 370 are shown in FIGS. 42b and 42d and are arranged on two divided frames 373 as two sets of 12 cylinders 370. The 12 cylinders 370 on each support frame 373 are arranged as shown in FIG. 42b two rows of six, and arranged staggered as to the two rows. The lower end of the movable shaft 371 of each cylinder 370 mounts a boss 379 having a flange 378.

Figure 42G:
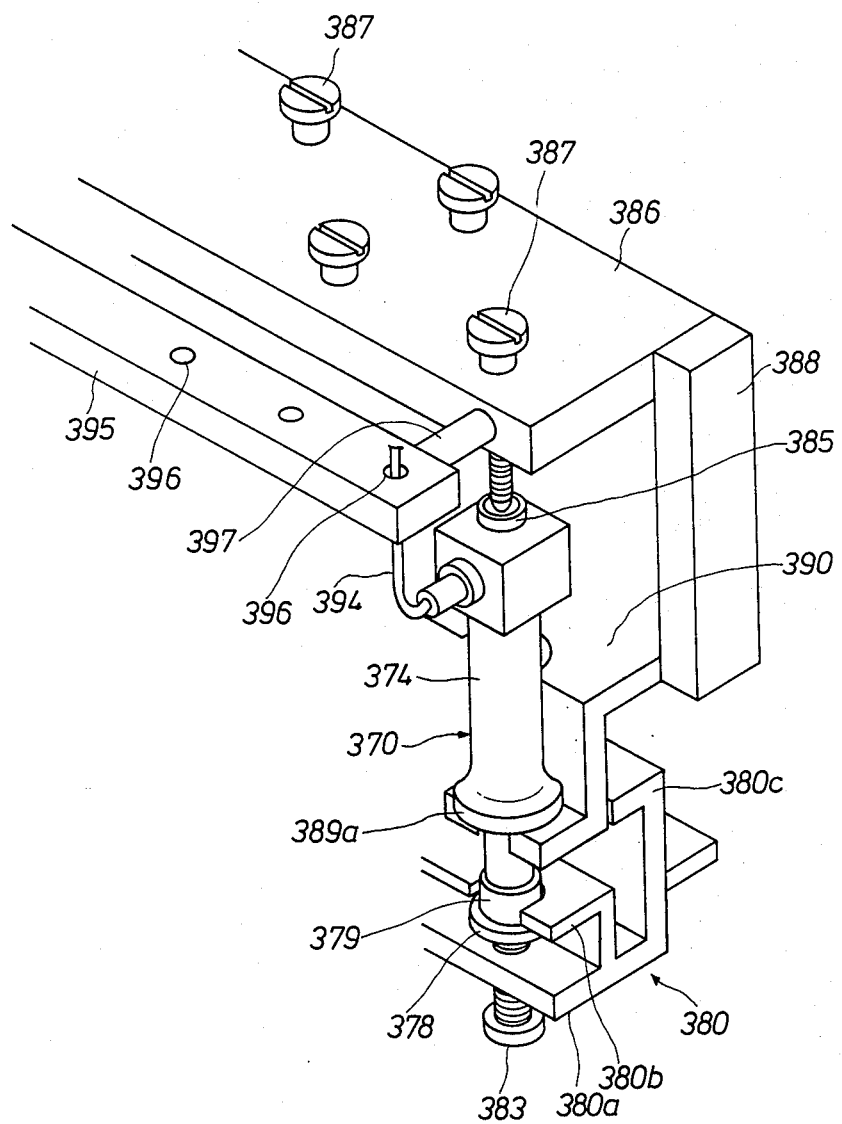
Figure 42:
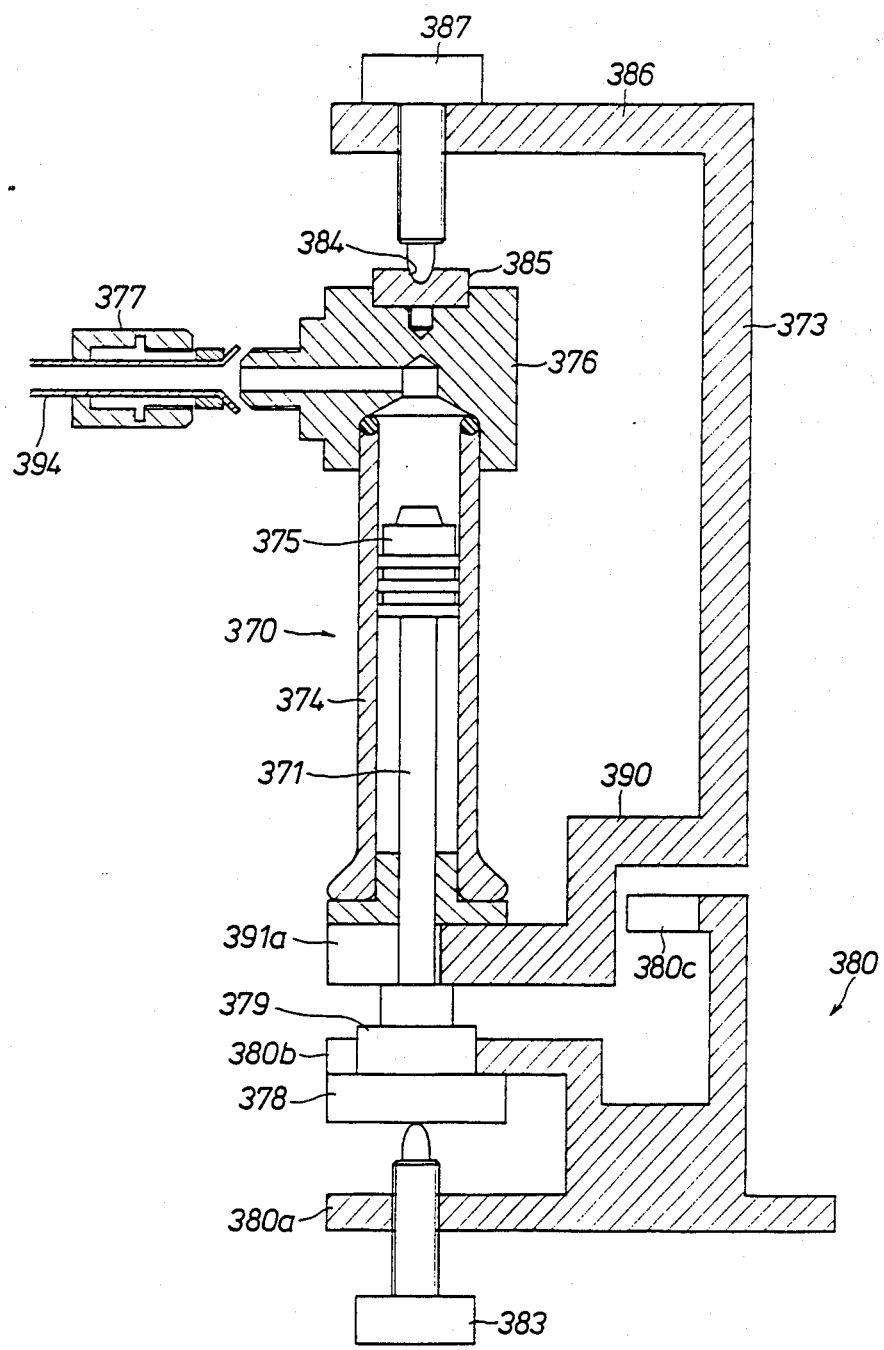
Figure 42I:
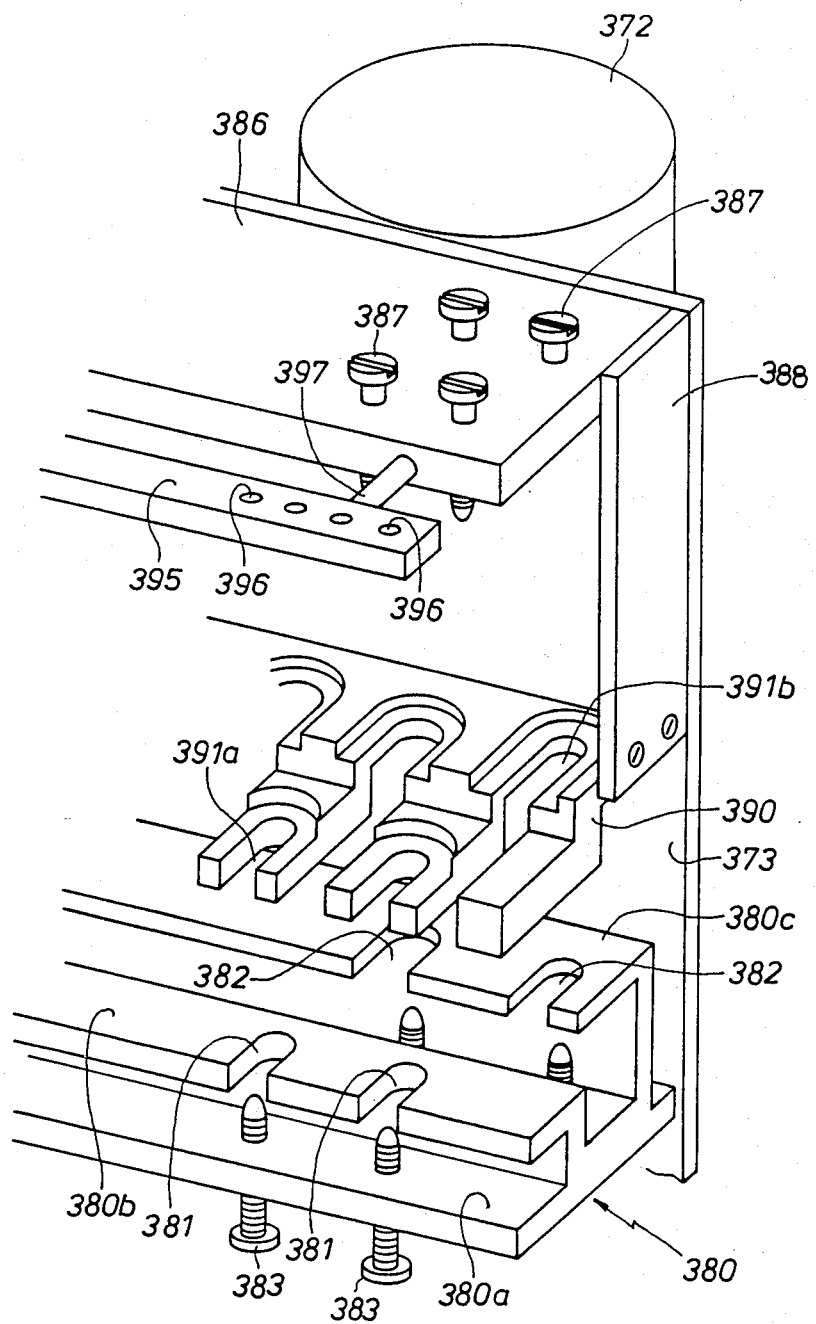
Figure 42:
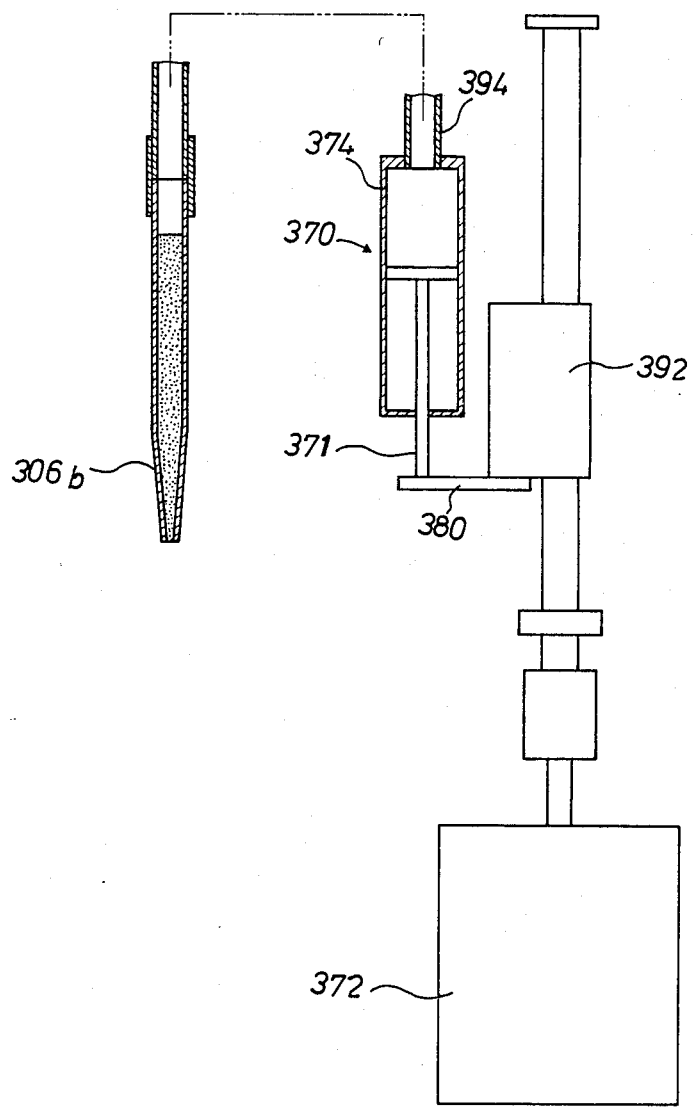
Figure 42:
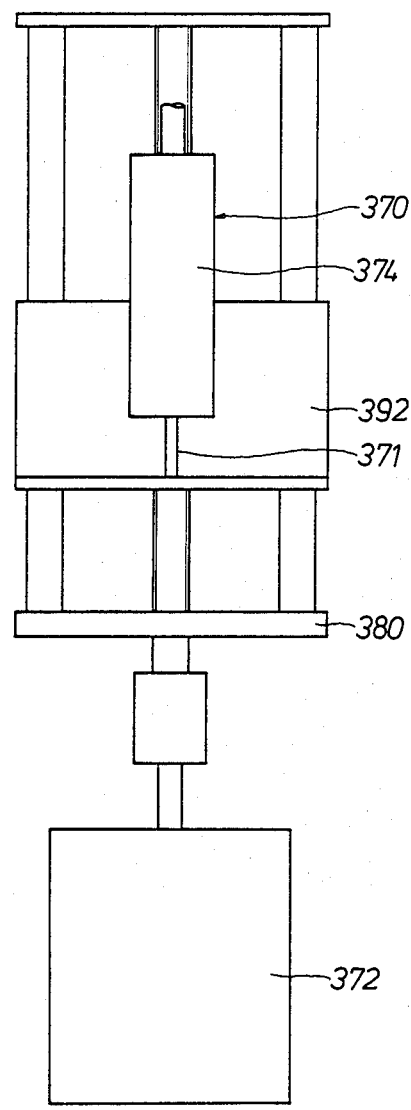
Figure 42:
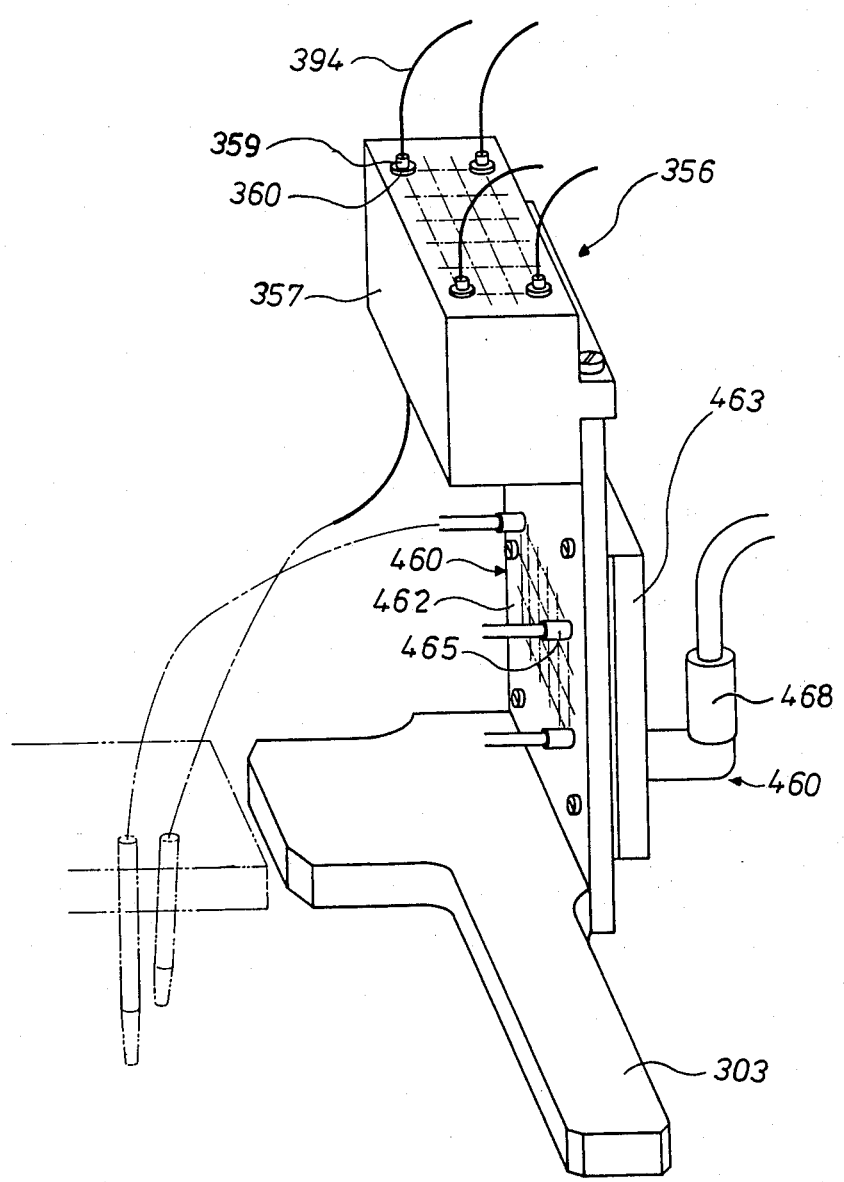

A movable shaft support member 380 is secured with a movable block 392 which moves vertically by the motor 372 and a guide rod 393. The movable shaft support member 380 has a plurality of steps 380a, 380b and 380c as shown in FIGS. 42g and 42i, and the steps 380b and 380c forms a plurality of engage recesses 381 and 382 corresponding to the number of cylinders to be moved. Each boss 379 of the movable shaft 371 of the cylinder 370 engages the recesses 381 and 382 and is retained by a screw 383 which is screwed in the support member 380. The upper portion of the cylinder-head 376 mounts a screw 385 having an engage recess 384, to which lower end of a screw 387 is engaged to retain the cylinder 374. The screw 387 is screwed in an upper base 386. The upper base 386 is secured with the support frame 373 through a connecting member 388. The lower end of the cylinder 374 includes a member 389 having a flange 389a which engages on a crank-like cylinder retainer 390 as shown in FIG. 42i. The retainer 390 forms as many engage recesses 391a and 391b to engage with each flange 389a of the cylinders 374.

Figure 42M:
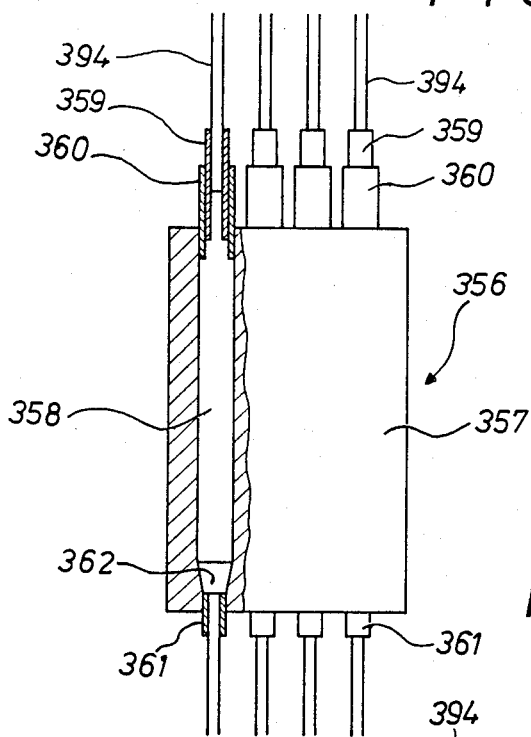
Figure 42N:
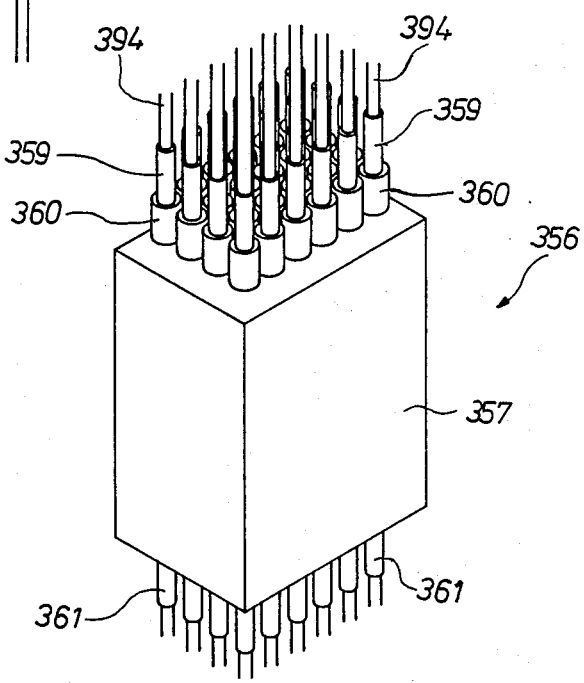

Thus, the movable shaft 371 of the cylinder 370 moves up and down by the pulse motor 372 so that air in the cylinder 374 can be sucked and discharged. To the tube connecting members 377 tubes 394 for suction and exhaust are connected. The tube 374 for each cylinder 370 is connected through a liquid reservoir 356 with each short nozzle 306b, as shown in FIGS. 42m and 42n. The liquid reservoir 356 includes a reservoir body 357, reservoir spaces 358 and connecters 359, 360 and 361 coupled with both ends of the reservoir space 358. The reservoir spaces 358 are same number as the nozzles 306b for suction and discharge of the cleaning fluid so that each shringe 370 is directly connected with each cleaning fluid suction and discharge nozzle 306b. The inside diameter of the reservoir space 358 is selected large enough to absorb space in the tube 394. Further, the connecter 361 side i.e. the cleaning fluid suction and discharge nozzle 306b side forms a taper portion 362 to prevent bubbles from entraining.

As shown in FIG. 42l, the liquid reservoir 356 is secured with a multi-channel coupler 460 which is mounted on the arm base 303. Tubes 394 pass through holes 396 of a tube retain member 395 which is connected with the upper base 386 through support members 397. A cover 398 and a base table 399 is shown.

Figure 42O:
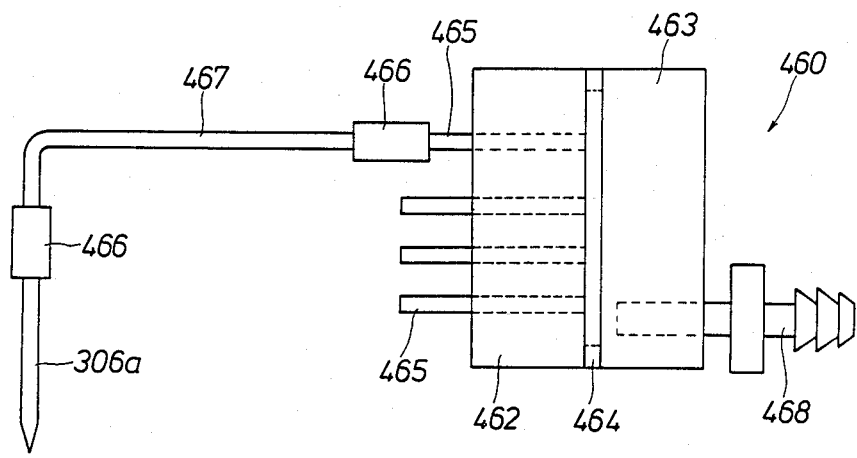
Figure 42P:
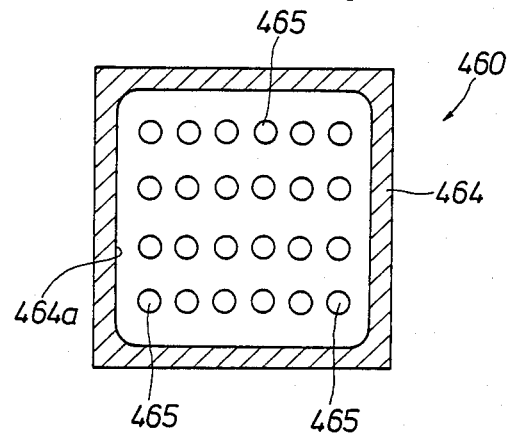
Figure 42:
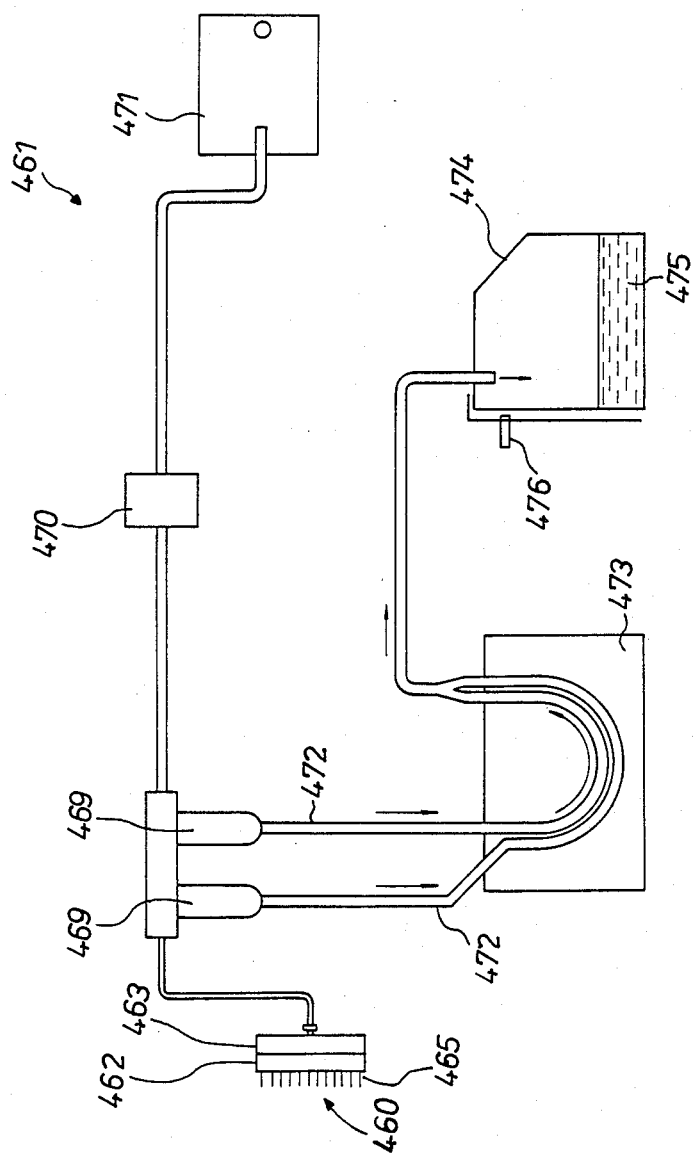

The multi-channel coupler 460 which is mounted on the arm base 303 is adapted to connect the long nozzle 306a i.e. waste fluid discharge nozzle with a waste liquid discharge unit 461 shown in FIG. 42q. As shown in FIGS. 42o and 42p, the coupler 460 includes front and rear transparent acryl resin plates 462 and 463 and a packing 464 of e.g. about 1 m.m. inserted between the plates 462 and 463. Stainless pipes 465 of sane number with the nozzles 306a pass through the front acryl resin plate 462 and are connnected with the nozzles 306a through tube connecters 466 and tubes 467. The packing forms a large space 464a communicating with all stainless pipes 465. The rear acryl resin plate 463 connects with a connecter 468 communicating with the space 464a of the packing 464. The multi-channel coupler 460 is connected through the connecter 468 with a waste liquid discharge unit 461. The waste liquid discharge unit 461 is shown in FIG. 42q and includes a vacuum tank 469, vacuum electro magnetic valve 470, a two head tubing pump 473 and a waste liquid tank 474, and adapted to discharge remaining liquid in the wells 2 to the waste liquid tank 474 as waste. The tank 474 has a sensor 476 to detect upper limit of the waste liquid 475.

Figure 43:
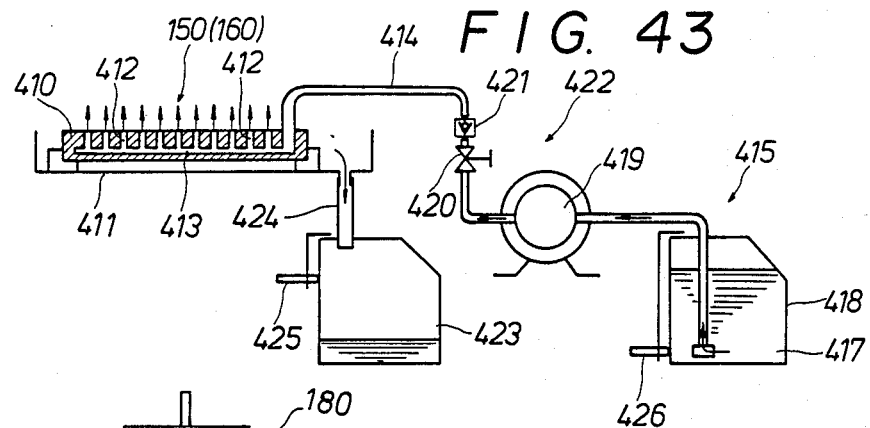
FIG. 43 is an illustration of the cleaning unit shown in FIG. 36, FIGS. 44a to 44f, FIG. 45 and FIGS. 46a and 46b are diagrammatic illustrations of dispense and coating process of blocking solution.
Figure 44A:
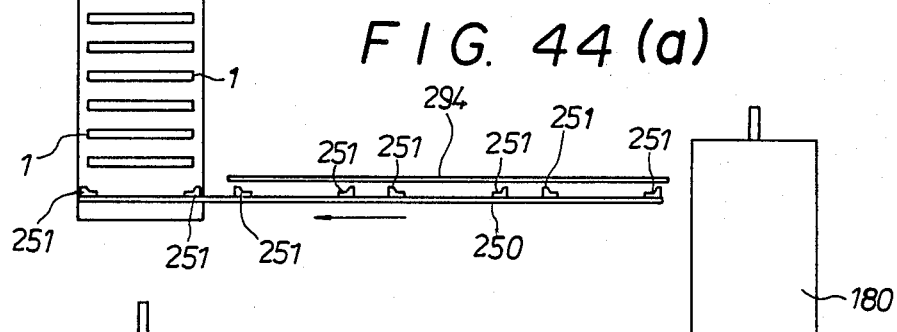
Figure 44B:
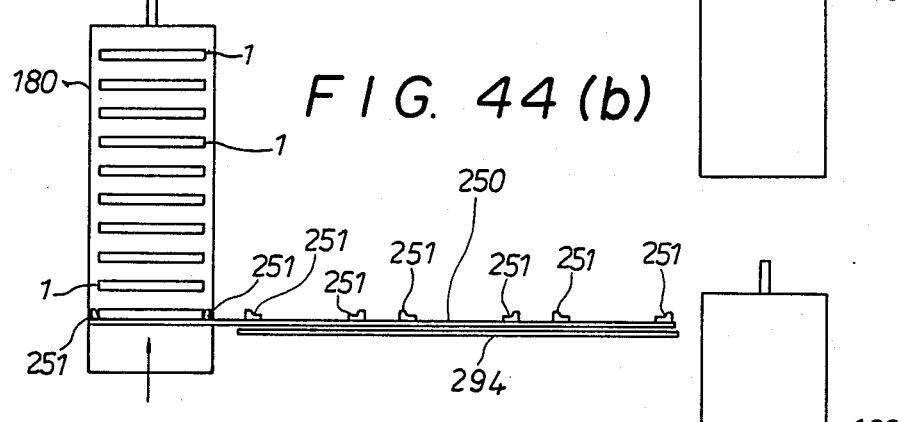
Figure 44C:
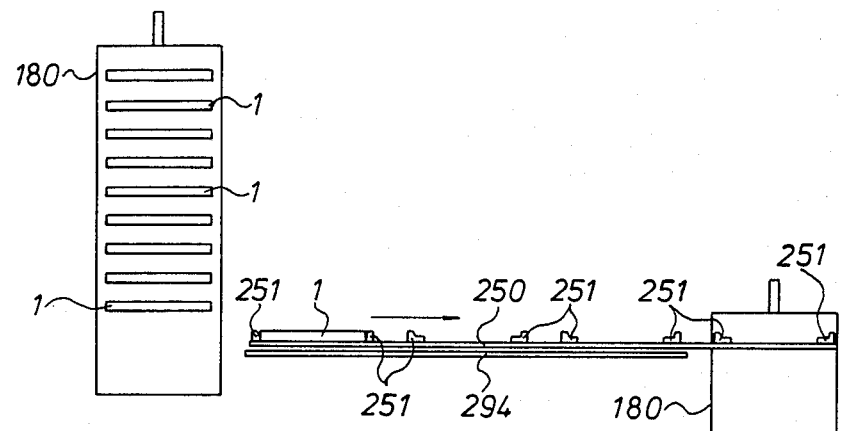
Figure 44D:
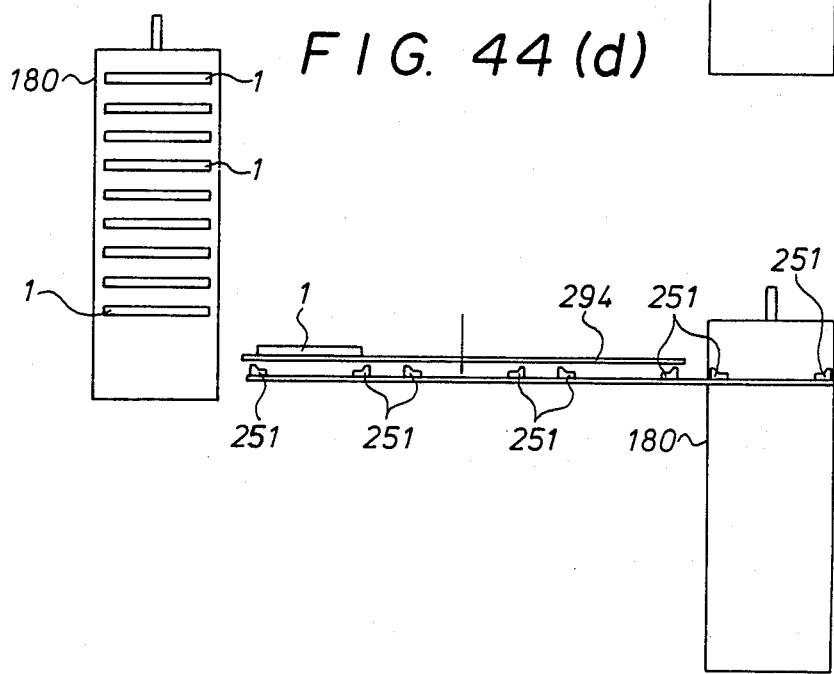
Figure 44E:
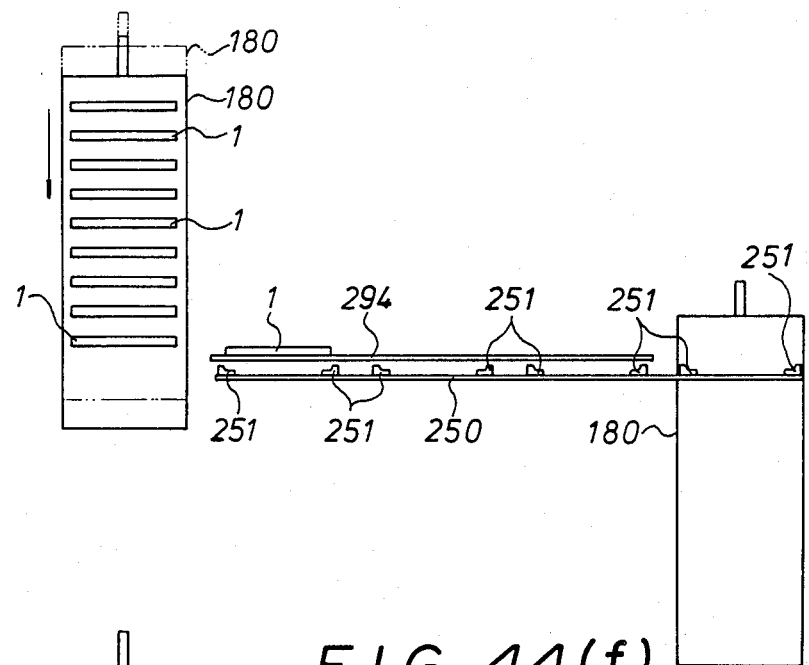
Figure 44F:
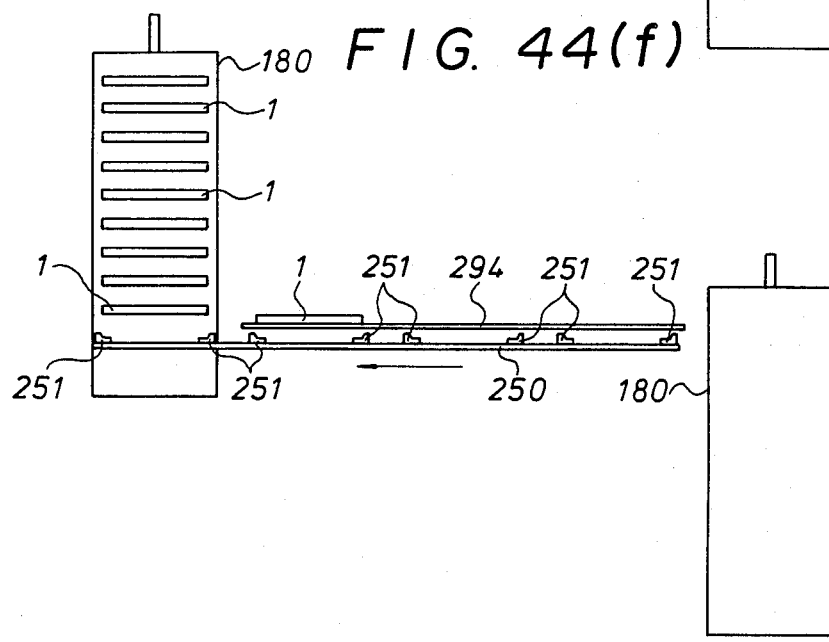
Figure 45:
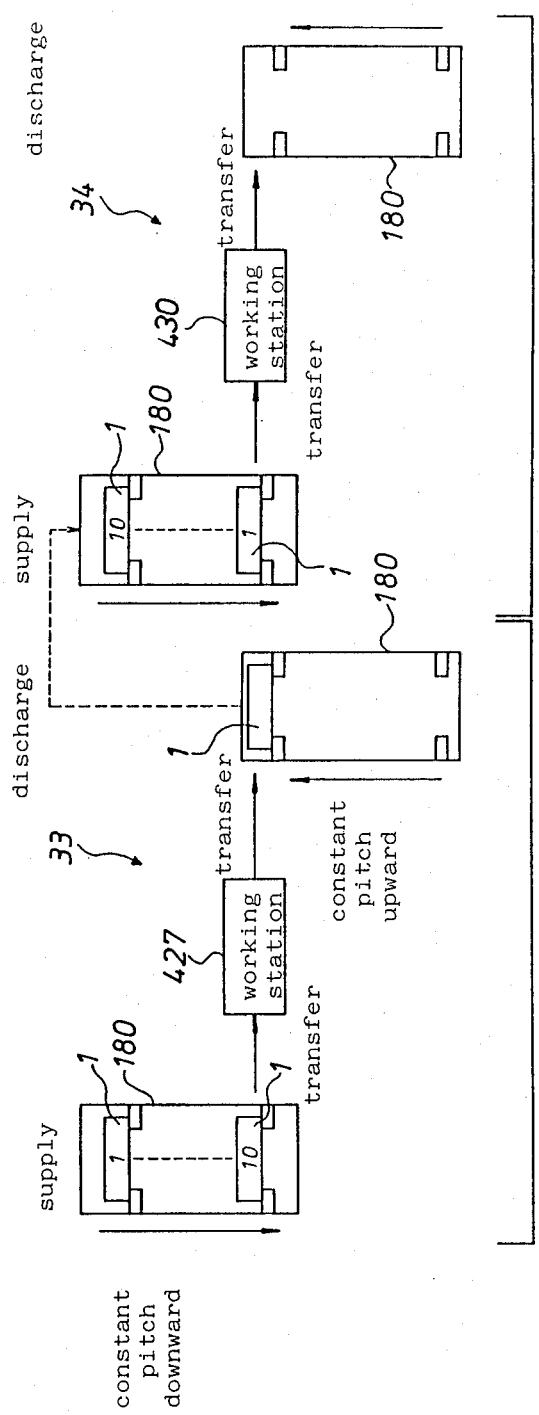
Figure 46A:
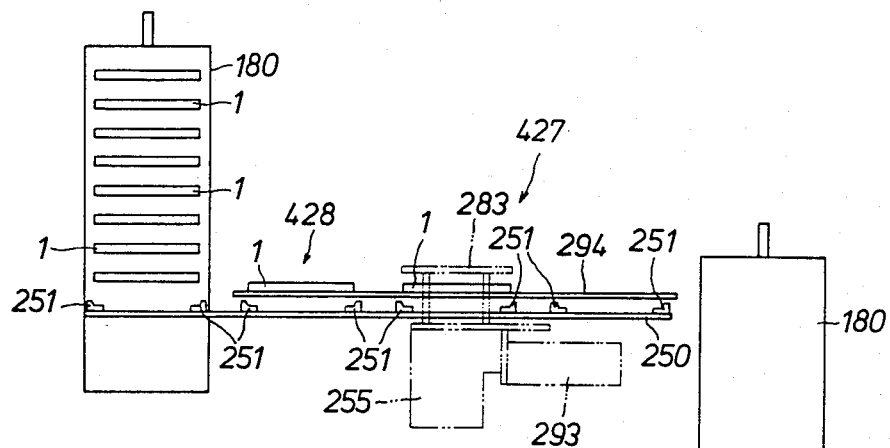
Figure 46B:
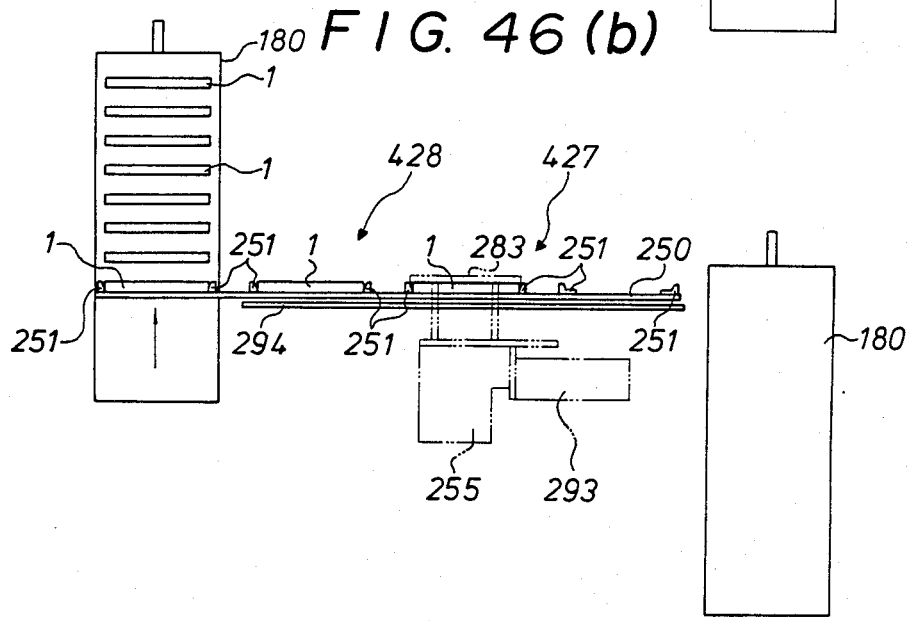
Figure 47:
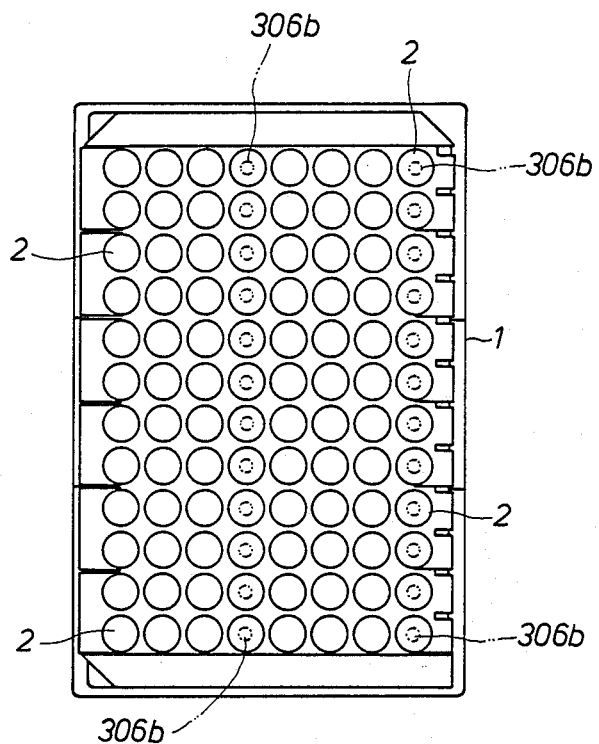
FIG. 47a and 47b are diagramamtic illustrations of blocking solution dispense to the wells in the microplate.
Figure 47:
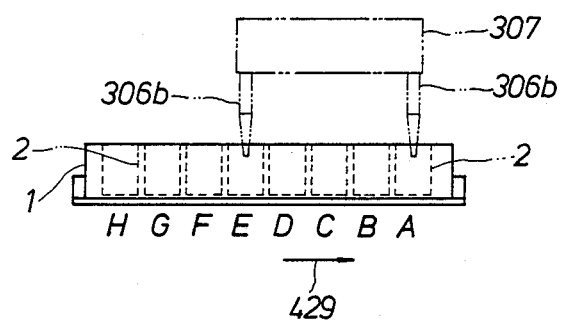

The electrode cleaning shelf unit 160 cleans the liquid level detecting electrodes 310 of the cleaning fluid nozzle arm unit 130. After the liquid level detecting arm 305 of the cleaning fluid nozzle arm unit 130 rotates upwards from the electrode cleaning unit 160, i.e. every time when the liquid level detecting operation to the dispensed cleaning fluid in the wells 2 is completed, the electrodes 310 are cleaned by water flow. The construction will be described in detail referring to FIGS. 36 and 43.

As shown in the drawing, the unit 160 includes a vessel 411 in which a cleaning fluid supply member 410 is mounted. The cleaning fluid supply member 410 includes many cleaning fluid outlets 412 and a cleaning fluid passage 413 connecting with the cleaning fluid outlets 412. The fluid passage 413 is communicated through a supply hose 414 with a cleaning fluid tank 415. The fluid supply member 410 is secured and positioned relative to the vessel 411 to a predetermined position by four screws 416. The fluid outlets 412 are 24 i.e. two rows of 12, corresponding to the number and arrangement of the electrodes 310, to clean each electrode 310 individually. As shown in FIG. 6, each fluid outlet 412 forms two stepped or inside high and outside low construction so that cleaning fluid injected upwards from upper openings 421a backs to thevessel 411 through the lower opening 421b. Thus, washed fluid does not touch or mix with the flesh fluid or the electrodes 310 to keep clean condition.

The cleaning fluid supply unit 415 includes a supply tank 418 to store cleaning fluid 417, a magnet gear pump 419 to suck the fluid from the tank 418 and automatically supply the fluid 417, and a flow rate regulator 422 having a flow rate regulating valve 420 and a check valve 421. The washed fluid passes through, an exhaust pipe 424 under the vessel 411 to a waste tank 423 which has an upper limit detect sensor 425. Also the supply tank 418 has a lower limit detect sensor 426. The cleaning fluid flow simultaneously from the 24 outlets 412 and the flow rate is regulated by the flow rate regulating valve 420. The sensors 425 and 426 are electrostatic capacity sensors and when the lower limit sensor 426 is OFF or the upper limit sensor 425 is ON, warning means, i.e. lamp and buzzar are operated.

As shown in FIG. 36, an indicating panel 450 indicates 96 lamps 451 corresponding to the number of wells 2 in one microplate 1 and is connected with each electrode 310 of the liquid level detecting arm 305 and the micro-well module detecting apparatus 285. The liquid level detection result of the wells 2 by the electrodes 310 is indicated by each lamp 451.

Now, the blocking solution dispense unit 33 is similar with the above described reagent dispense unit 30. When blocking solution is stored in the reagent shelf unit 140, the apparatus 30 is used as apparatus 33. When the blocking solution does not necessiate temperature control, the solution can be supplied automatically.

As to the automatic supply apparatus of the blocking solution, the automatic supply unit of the cleaning fluid can be readily utilized.

The blocking solution incubation apparatus 34 and the blocking solution cleaning apparatus 35 are utterly similar with the reagent incubation apparatus 31 and the reagent cleaning apparatus 32 respectively. Thus, same reference numeral is used in FIG. 3, to shown similar part or portion as to each apparatus, and detailed description is eliminated And further, the drier apparatus 36 may be conventional drying room having suitable control unit to maintain predetermined temperature.

METHOD OF OPERATION

One embodiment of the solid phase forming method, according to the present invention, will be described.

At first, method of coating i.e. forming cleaning fluid resistant reagent film, in each well 2 in the microplate 1 utilizing the above described apparatus will be described.

The supply magazine 180 which houses ten microplates each containing the wells 2 to be coated, is set at predetermined position, i.e. start end side or left side in FIG. 3 of the plate transfer mechanism 120. Also them empty discharge magazine 180 is set at predetermined position, i.e. stroke end side of the plate transfer mechanism 120. The supply magazine 180 is set at most elevated position by the magazine elevator apparatus 200, and the discharge magazine 180 is set at most descended position. When the reagent dispense and coating apparatus 30 and the first incubation apparatus 31 are connected each other and the microplate 1 having reagent coated wells 2 is fed directly to the incubation apparatus 31, the discharge magazine 180 can be eliminated. Each magazine 180 is set at predetermined position by means of the positioning pins 105 and 106.

Next, the plate transfer mechanism 120 transfers the microplate 1 in the supply magazine 180 one by one, and the process will be described referring to FIG. 8a and 8c and FIGS. 14 and 15. At first, the receive member support frame 250 which keeps upward position by the receive frame urging device 273 is lowered by the cam drive unit 262. That is, the motor 265 is operated to rotate the cam 263 which lowers through the cam follower 264 the receive member support frame 250.

Then, the pulse motor 293 is operated to move the the receive member support frame 250 to the direction of the supply magazine 180 for one pitch P. The state is shown in FIG. 14a, and shows that among the four pairs of the receive members 251, the pair of receive member 250 which is most adjacent with the supply magazine 180 is under the lowermost microplate 1 in the supply magazine 180.

Figure 14:
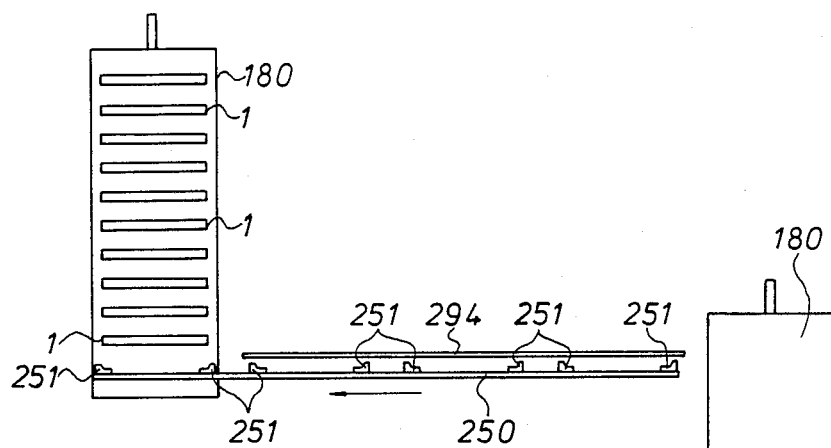
Figure 14:
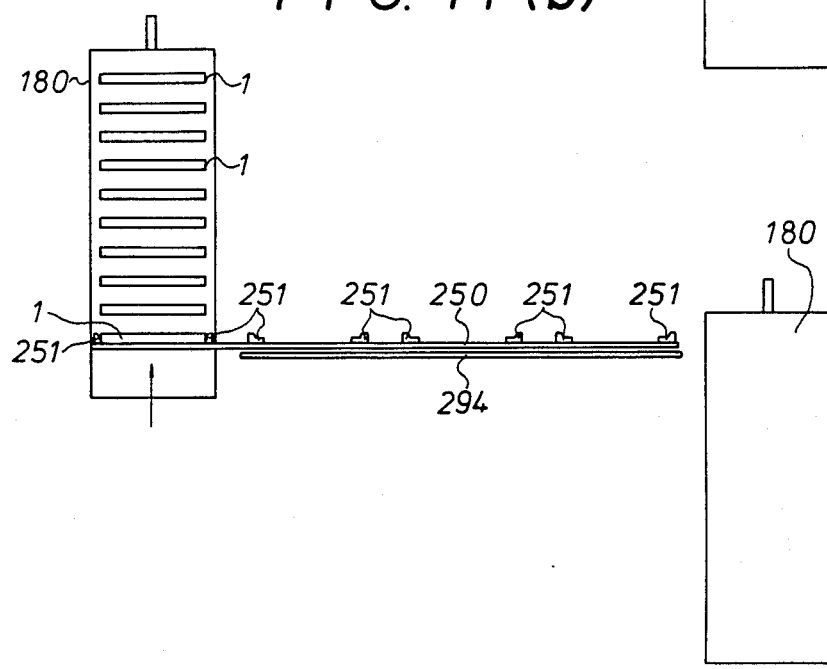
Figure 14:
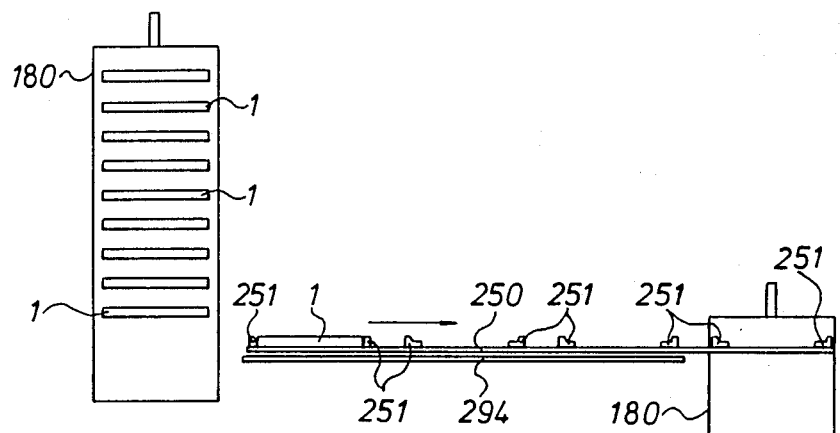
Figure 14:
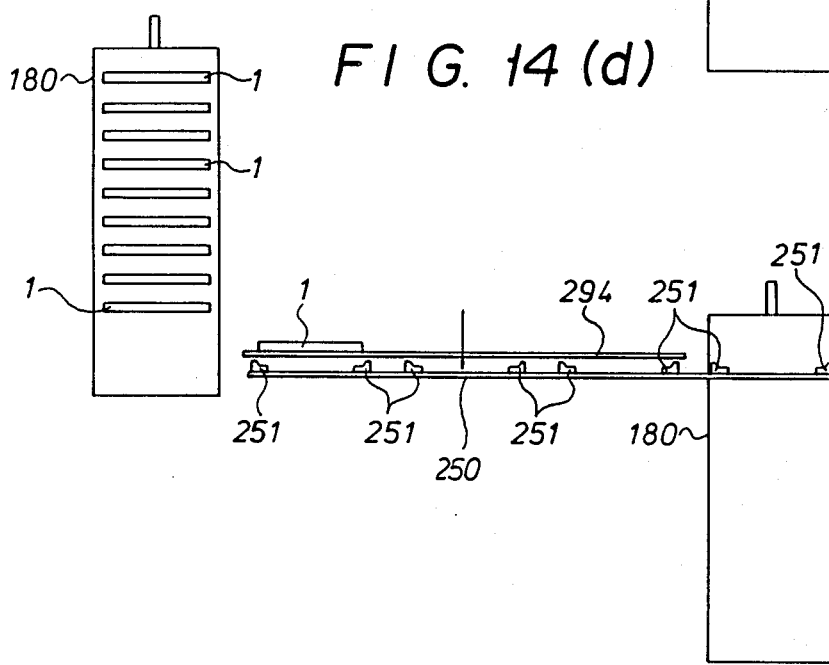
Figure 14E:
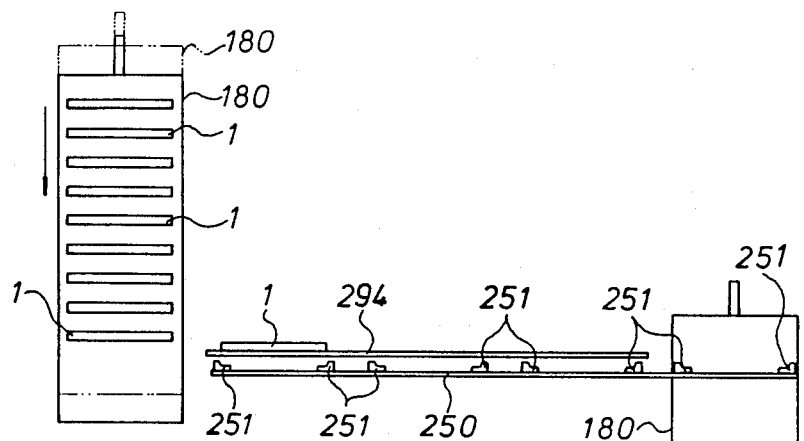

The motor 265 is operated to rotate the cam 263 to release the cam follower 264. Thus, the receive member support frame 250 moves upward by the urging pin 274 of the support frame upwards urging means 273, and the microplate 1 which is stored in the lowermost position of the supply magazine 180 is also moved upward by the receive member 251. This state is shown in FIG. 14e, and as shown, the receive member support frame 250 is upward from the upper surface of the fixed receive member 294.

The pulse motor 293 is operated to transfer the receive member support frame 250 one pitch P to the discharge magazine 180. By the movement, one microplate 1 stored in the lowermost shelf of the supply magazine 180 is transferred out of the supply magazine 180. This state is shown in FIG. 14c.

Then, the motor 265 is operated to rotate the cam 263. The receive member support frame 250 moves downward, and downward from the fixed receive member 294. Thus, the microplate supported by the receive member 251 is placed on the fixed receive member 294. The state is shown in FIG. 14d.

The supply magazine 180 is lowered as constant pitch by cooperation of the sensor plate 234 and the sensor 235, such that the supply magazine 180 is lowered a constant pitch and is stopped at a position that among the ten microplates 1 stored in the magazine 180, the ninth from above takes the original position of the already transferred microplate 1. To perform the downward movement of the supply magazine 180, the motor 224 i.e. a speed control motor with electro-magnetic brake means, is operated to lower the support base 223 through the elevator rod 225. The state is shown in FIG. 14e.

Figure 14F:
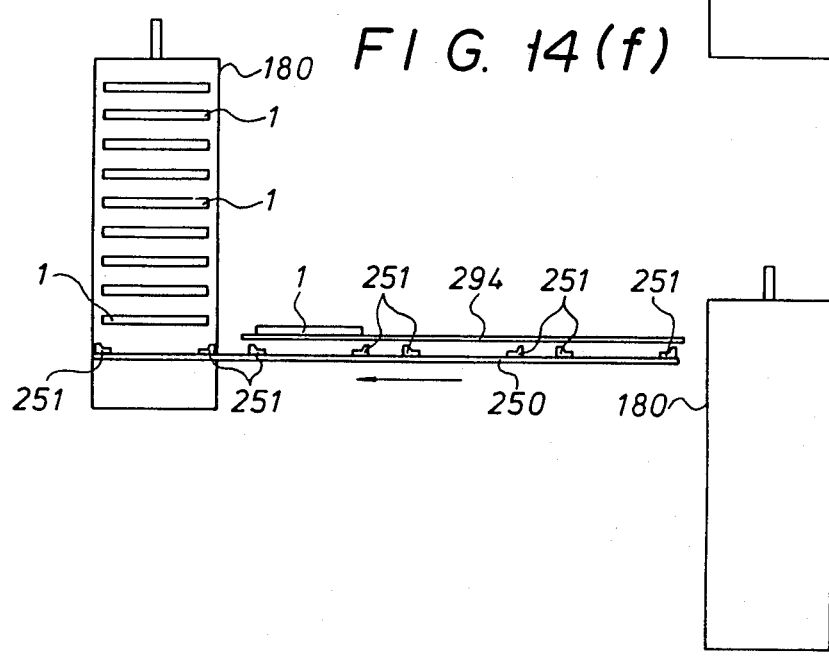
Figure 15:
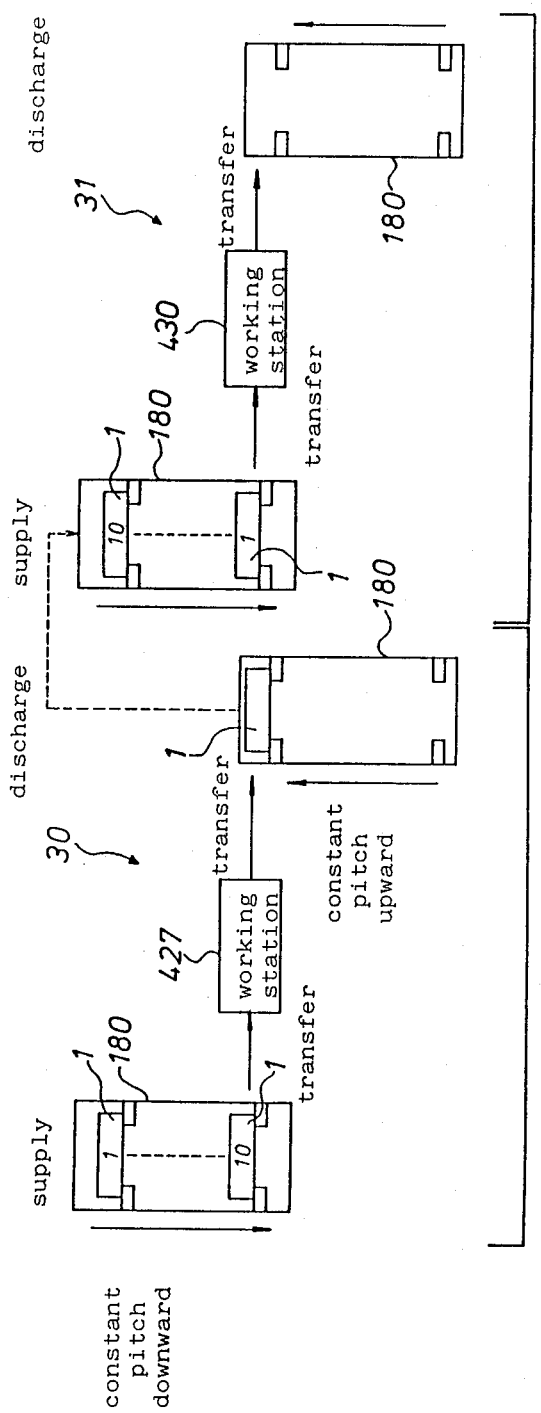
Figure 16:
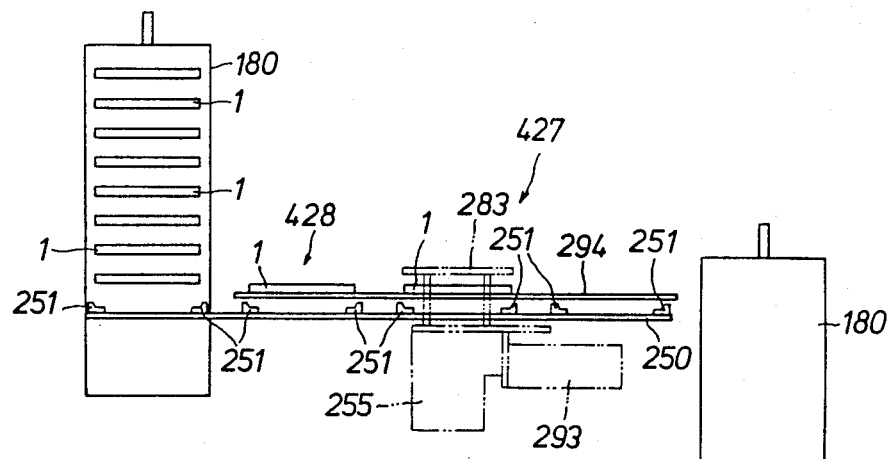
Figure 16:
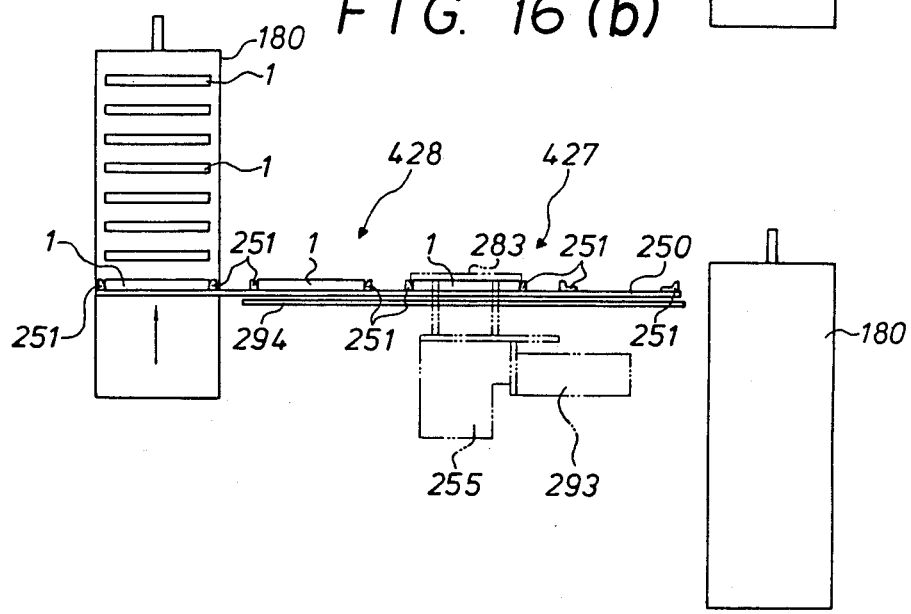
Figure 17:
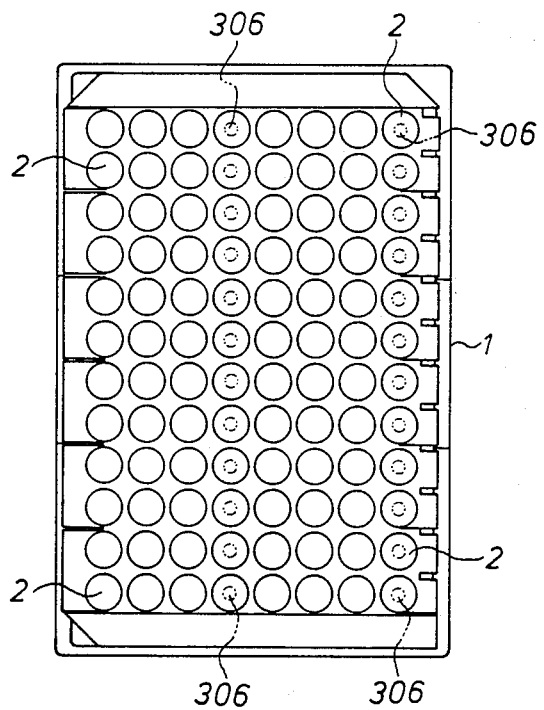
FIGS. 17a and 17b are illustrations of the dispense process to the microplate.
Figure 17:
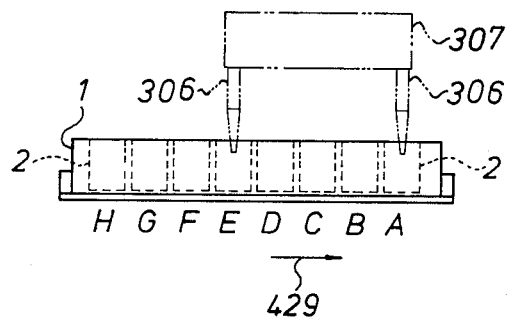

Next, as before, the pulse motor 293 is operated to move the receive member support frame 250 to the direction of the supply magazine 180, to move the receive member 251 which is adjacent to the supply magazine 180 under the lower most microplate 1 i.e. the ninth microplate from above. The state is shown in FIG. 14f which is similar with FIG. 14a. The process is repeated sequentially to transfer the ten microplate 1 in the supply magazine 180. Each well 2 in the microplate 1 is coated with reagent in the working station 427 and the microplate is transferred to the discharge magazine 180. The discharge magazine 180 is controlled to move upward as same pitch with the supply magazine 180 so that empty discharge magazine stores ten microplate which has coated sequentially.

As shown in FIG. 16a, when two microplates 1 are on the fixed receive member 294, the first transferred microplate 1 is reached to the working station 427. Then, when the receiving member support frame 250 is moved upward to receive the third microplate 1, as shown in FIG. 16b, the upper surface of the mounting edge 3a of the module 3 of the microplate 1, shown in FIG. 2a, contacts with the lower surface of the stopper plate 283, and each module 3 of the microplate 1 is held and position between the receiving member 251 and the stopper plate 283. To each well 2 in the micro- plate 1 which is positioned at the working station 427, reagent solution of 100 micro-liter is dispensed. The micro-well module detect unit 285 which is mounted on the stopper plate 283 detects that if the module 3 is on the receive member 251 of the idle station 428 between the stopper plate 283 and the supply magazine 180. When there is no module 3, the machine is stopped and necessary part is supplied.

To perform reagent solution dispense and coating operation the wells 2 in the microplate 1 which is secured at the working station 427, at first, the arm body unit 300 of the solution nozzle arm apparatus 130 is moved upward by the swirl and vertical movement drive unit 318 and then is rotated to position the reagent suction arm 304 just upward from the reagent shelf 140. Next, the arm body unit 300 is lowered to insert the 24 or 2 rows of 12 nozzles 306 of the reagent suction arm 304 into the reagent solution 347 in the reagent shelf 140.

Then, the pulse motor 372 is operated to lower the movable shafts 371 of the shringes 370 which communicate with the nozzles 306, and suction effect of the shringes 370 sucks reagent solution into the nozzles 306 for a predetermined quantity. Next, the arm body unit 300 is moved upwards, and is rotated 90 degree anticlockwise by the swirland vertical drive unit 318. The reagent suction arm 304 is upward from the microplate 1 at the working station 427, and the liquid level detecting arm 305 is upward from the electrode cleaning shelf unit 160. Then, the arm body unit 300 is lowered to insert each nozzle 306 of the arm body unit 300 into each well 2. The pulse motor 327 is operated to move the movable shaft 371 of the shringe 370 upwards to compress air in the shringe 370 so that reagent solution in the nozzle 306 is dispensed for 100 micro-liter into each well 2. The dispense operation is shown in FIGS. 17a and 17b, and is performed as follows: at first, among the eight rows, row A to H, of the wells, rows A and E are dispensed. And the arm body unit 300 is lifted, and the microplate 1 is transferred through the receive member support frame 250 to the direction of arrow 429 one well width. The arm body unit 300 is lowered again and reagent solution is dispensed in the wells 2 of the rows B and F. The operation is repeated until the wells of the rows C and G and rows D and H are all dispensed the reagent solution each 100 micro-liter. Thus the dispense operation is performed.

After the dispense operation of the reagent solution, the arm body unit 300 is lifted and is rotated 90 degree clockwise. Then, the arm body unit 300 is lowered and the 24 nozzles 306 suck reagent solution 347 as before. At the same time, the electrodes 310 of the liquid level detect arm 305 are inserted in the reagent dispensed wells 2 so that impedance change between two electrodes 310 shown in FIG. 9c detects liquid level in each well 2. Thus the liquid level detect operation is performed.

After the reagent suction in the nozzles 306, and the liquid level detection by the electrodes 310, The arm body unit 300 is lifted and is rotated 90 degree again. Next microplate 1 which has empty wells 2 has reached under the arm body unit 300 by the series of movement shown in FIGS. 14a to 14f, and has set there. Then, the arm body unit 300 is lowered and reagent solution is dispensed in the wells 2 as before. At the same time, lower portion of each electrode 310 is upward from the cleaning fluid outlet opening 412 of the electrode cleaning shelf unit 160. Cleaning fluid 417 supplied from the cleaning fluid supply unit 415 is fed from the opening 412 to clean each electrode 310. As the cleaning fluid outlet opening 412 is formed as two steps so that waste fluid after the cleaning is directly discharged to the waste tank 423 without reused to clean the electrode 310.

After the reagent dispense operation into the wells 2 from the nozzles 306 and the cleaning operation of electrodes 310 are fininshed, the arm body unit 300 is lifted and rotated 90 degree anticlockwise. Then the arm body unit 300 is lowered and the nozzles 306 suck reagent solution, and also the electrodes 310 detect liquid level of the reagent dispensed wells 2.

The operations are repeated and all wells 2 in the microplates 1 which are sequentially transferred from the supply magazine 180 are dispensed reagent solution for 100 micro-liter automatically to form cleaning fluid resistant film of the reagent in each well 2 on the inside wall and bottom wall of the well. This is called as coating. The operation is performed continuously until the ten microplates 1 in the supply magazine 180 are all passed through. While the operation, the microwell-module detect device 285 detects the module 3, and if no module condition is detected, the machine is stopped and the module 3 is supplemented. If the microplate 1 is transferred to the working station 427 without one module 3, reagent solution may be dispensed to the empty position to contaminate the machine. The device 285 prevent the machine from such occurence.

The microplate 1 which has the reagent dispensed and coated wells 2 is conveyed into the discharge magazine 180 by the transfer action of the receive member support frame 250. When the receive member support frame 250 is lowered through the cam 263, the microplate 1 conveyed into the uppermost store portion of the discharge magazine 180 shown in FIG. 15c, is stored in place. Then the receive member support frame 250 moves out of the discharge magazine 180 to the supply magazine 180, the discharge magazine is moved upwards constant pitch through the magazine elevator 200 to prepare the next microplate 1 conveyed. The upwards constant pitch movement of the discharge magazine 180 is similar with that to the supply magazine 180.

In the coating apparatus 30 shown in FIG. 3, dispense and coating operation of the reagent solution in the wells 2 in the microplate 1 is completed by the above mentioned operation, and the microplates 1 are stored in the magazine 180. Utilizing the magazine 180, the microplates 1 are conveyed into the incubation apparatus 31, through the supply side elevator 41 of the incubation apparatus 41. The microplate 1 after incubation is stored into the empty magazine 180 which is set at the discharge side elevator 42 and is discharged.

Figure 26:
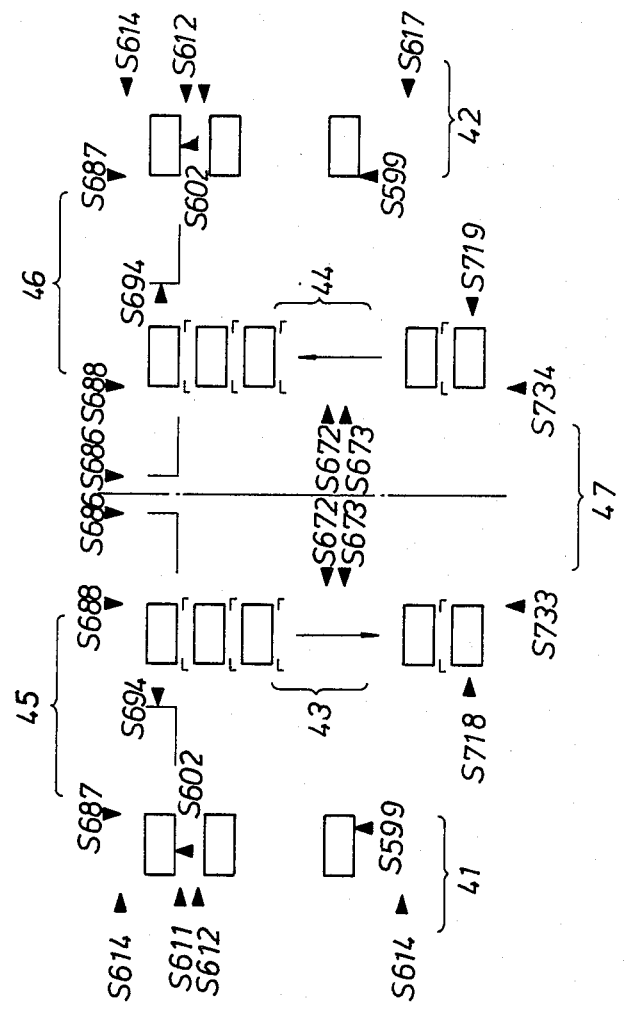
FIG. 26 is an illustration of arrangement of sensors.

As described before, the supply side and discharge side of the incubation apparatus 31 are arranged symmetry about the central heater unit 48, and the sensors of the units are also arranged symmetry as shown in FIG. 26.

Figure 27:
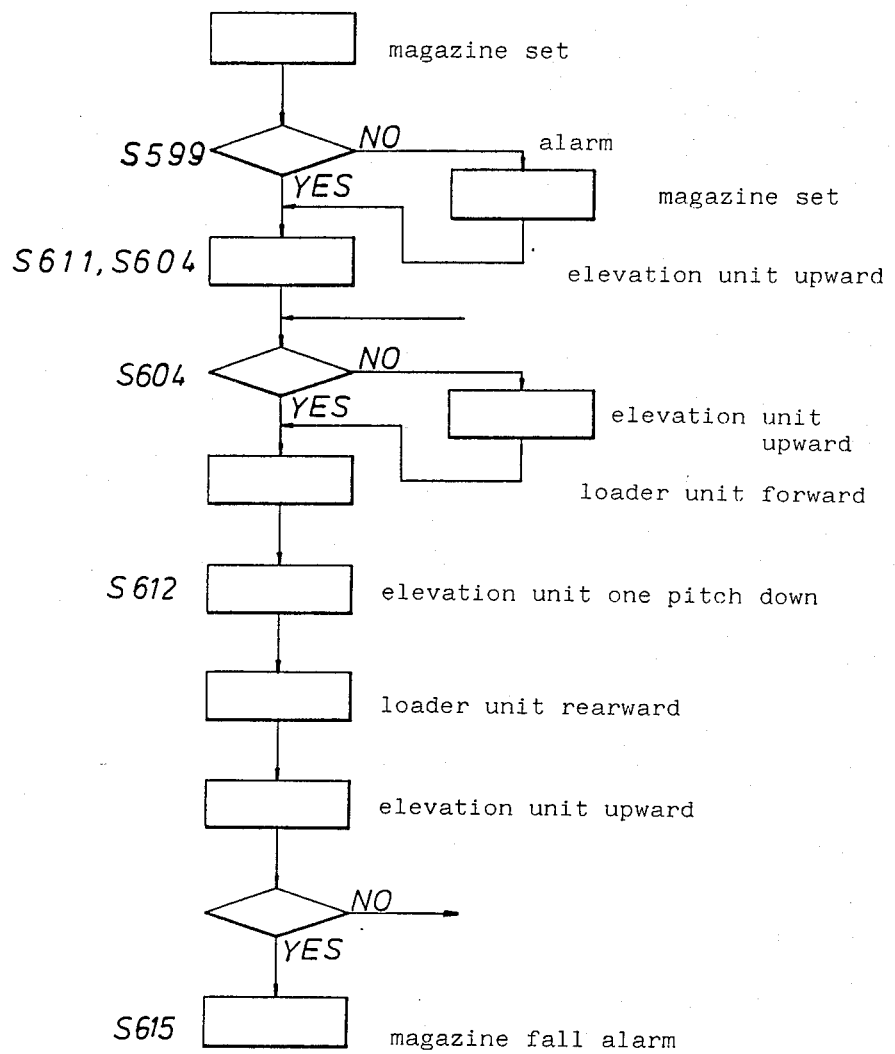
FIG. 27 is a flow chart of the supply side elevation unit.
Figure 28:
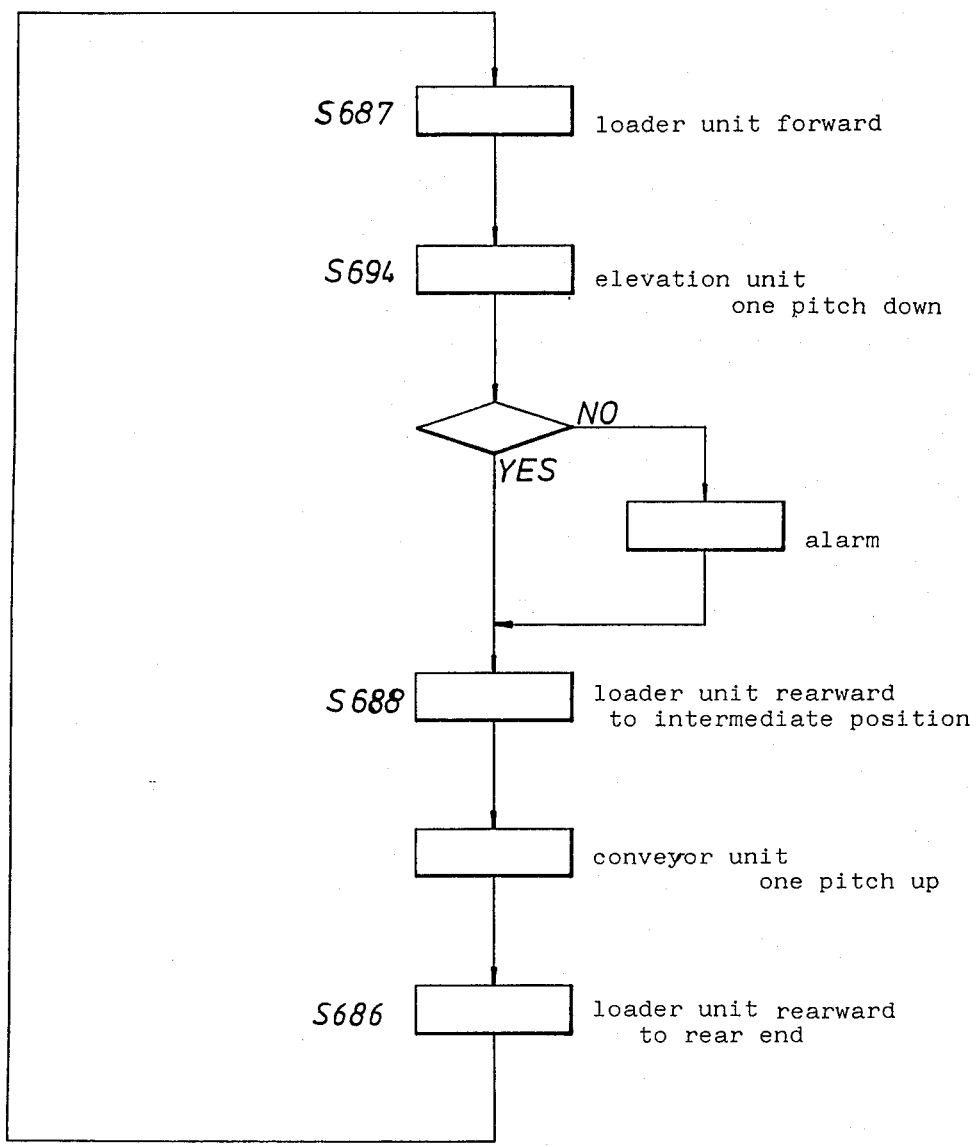
FIG. 28 is a flow chart of the loader unit.
Figure 29:
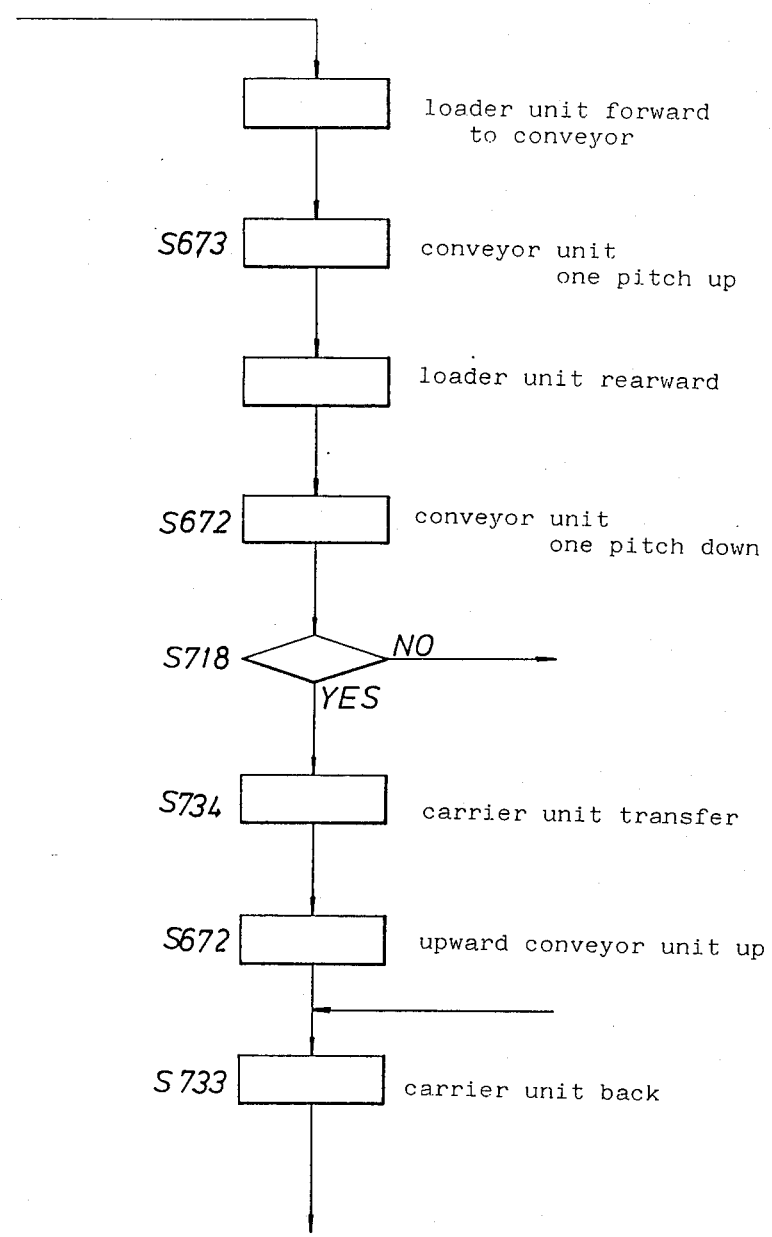
FIG. 29 is a flow chart of the downward conveyor unit.

The microplates 1 are stored in the magazine 180 which is placed on the lift plate 581 of the magazine lift 586 of the supply side elevation unit 41 as shown in FIG. 27.

To place the magazine 180 on the lift plate 581, to the positioning holes 187 and 188 formed in the bottom plate of the magazine 180, the positioning pins 105 and 106 on the lift plate 581 are inserted, and the magazine 180 is guided by the guide plates 582, 583, 584 and 585.

The positioning of the magazine 180 is performed at the lowermost position of the magazine lift 586, and the set position of the magazine 180 at the lowermost position of the magazine lift 586 is attained by operating the motor 587 of the drive unit 593 for the magazine lift 586 to lower the lead screw 590. The shutter 613 attached at the lower end 590b of the screw 590 interrupts the photo-sensor 617, and the detect signal of the sensor 617 is applied to the control portion of the control unit 49, whereby the motor 587 is stopped.

When the magazine 180 is placed on the lift plate 581 of the magazine lift 586, the detect pin 601 on the lift plate 581 energise the micro-switch 599 and the detect signal is applied to the control portion to confirm the normal position setting of the magazine 180 on the magazine lift 586. When the magazine 180 is set abnormal position, alarm signal is produced from the control portion to urge normal positioning, as shown in FIG. 27.

The detect signal of normal position setting of the magazine 180 from the micro-switch 599 is applied to the control portion which operates the motor 587 to rotates the lead screw 590 which lifts the magazine lift 586 for one pitch. By the lift of the magazine lift 586, the shutter 592 also lifts. The slit 607 of the shutter 592 is detected by the sensor 611 which applies detect signal to the control portion. When the detect signal is applied to the control portion, the sensor 604 detects the microplate 1 which is stored in the uppermost shelf of the magazine 180. When the microplate is confirmed, the detect signal is applied to the control portion, and the input signal operates the motor 685 of the loader unit 45 to move forward the arm shaft 682. The transfer plate 681 attached at the end of the arm shaft 682 passes the downward conveyor unit 43, and goes through the feed port 560 opened in the side cover 554 of the frame unit 40, under the microplate 1 which is stored in the upper most shelf of the magazine 180. The arm shaft 682 stops in the forward-most position, and the transfer plate 681 stops under the microplate 1 which is stored in the uppermost shelf of the magazine 180 ready to receive the same, as shown in FIGS. 22a and 22b. As the shutter 689 of the arm shaft 682 interrupts the sensor 687, detect signal from the sensor 687 causes reverse rotation of the motor 587 of the magazine lift 586 to lower the magazine lift 586 for one pitch. By the one pitch downward movement of the magazine lift 586, the microplate 1 which is stored in the uppermost shelf of the magazine 180 is received on the transfer plate 681, as shown in FIG. 22b. Detect signal fom the sensor 612 caused by the one pitch down of the magazine lift 586, and detect signal from the photo-sensor 694 caused by the microplate 1 placed between the guides 691 and 692 of the transfer plate 681, are applied to the control portion which operates the motor 685 of the arm shaft 682 to retract the same. While the retract movement, the shutter 689 interrupts the sensor 688 which applies the detect signal to the control portion which in turn stops themotor 685 to stop the arm shaft 682. The stopped position of the arm shaft 682 is to stop the transfer plate 681 between the engage recesses 636 and 637 of the conveyor belts 634 and 635 of the downward conveyor unit 43, and the opposed edges of the microplate 1 on the transfer plate 681 are engageable with the engage recesses 636 and 637 of the opposed conveyor belts 634 and 635.

The control portion which receives the detect signal from the sensor 688 further causes operation of the motor 650 of the downward conveyor unit 43 to lift the conveyor belts 634 and 635 for one pitch and to receive the microplate 1 which engages at both edges with the engage recesses 636 and 637.

Detail of the one pitch lift movement of the conveyor belt 634 and 635 to receive the microplate 1 from the transfer plate 681 is as follows: By the operation of the motor 650, the rotary shafts 630 and 631 sre driven through the pulleys 652, 653, 654 and 655 to lift the conveyor belts 634 and 635. As the shaft 631 rotates, the shutter 666 secured with the shaft 631 rotates and the slits 665 of the shutter 666 actuates the photo-sensor 672 which produces detect signal to terminate the lift movement.

By the detect signal from the sensor 672, the control portion also operates the motor 685 of the loader unit 45 to retract the arm shaft 682 from the intermediate position. When the detect sensor 686 at rear end of the arm shaft 682 is interrupted by the block member 693 of the transfer plate 681, the detect signal stops the motor 685 to stop the transfer plate 681 ar rear end position. Further, the motor 650 of the downward conveyor unit 43 to lower the conveyor belts 634 and 635 for one pitch, to transfer the microplate 1 which is held between the engage recesses 636 and 637 of the opposed conveyor belts 634 and 635 into the incubation spce.

As the conveyor belts 634 and 635 rotates, the shutter 666 secured with the rotary shaft 631 rotates and the slits 665 of the shutter actuates the sensor 672. By the detect signal of the sensor 672 the one pitch downward movement of the conveyor belts 634 and 635 can be confirmed.

The above mentioned process is repeated, the microplate 1 in the magazine 180 placed in the elevator unit 41 through the loader unit 45 is sequentially conveyd into the downward conveyor unit 43.

As shown in FIG. 27, transfer of the microplates 1 to the downward conveyor unit 43 is continued when the sensor 615 detects presense of the microplate 1 in the magazine 180. As the magazine 180 reaches to upper end, the upper end detect sensor 615 detects the shutter 613 and applies detect signal to the control portion which produces alarm signal to indicate that the magazine 180 is empty, and to replace the magazine 180 to filled magazine.

The microplates 1 are sequentially transferred into the downward conveyor unit 43 and reached to a predetermined number. Among the microplates 1 transferred between the conveyor belts 634 and 635 of the downward conveyor unit 43, from the supply side elevator unit 41 through the loader unit 45, the first transferred microplate 1 reaches to the position to deliver to the carrier unit 47 and is placed between the guide plates 717 on the carrier 716 which are at the deliver position cooperating with the downward movement of the conveyor belts 634 and 635. The deliver position is shown as left end of FIG. 24a.

Figure 32:
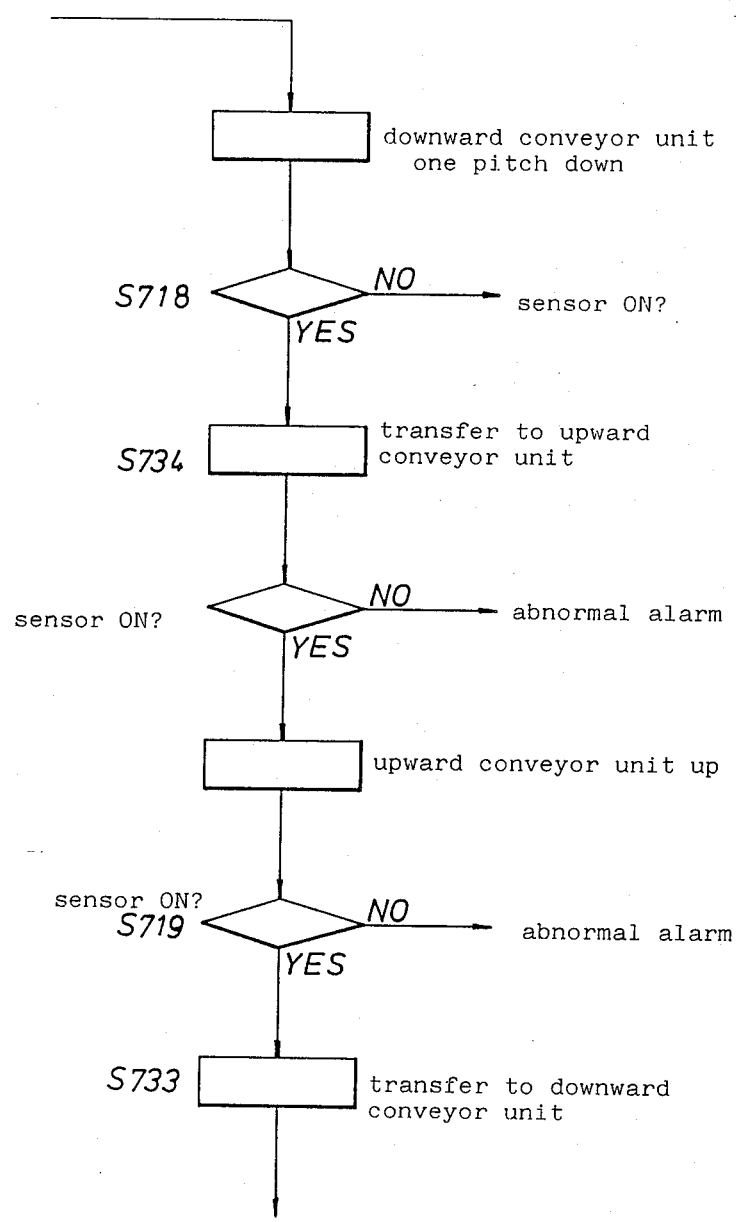
FIG. 32 is a flow chart of the carrier unit.

As to the carrier unit 47, as shown in FIG. 32, by the detect signal of the downward conveyor unit 43 one pitch down detect sensor 672, the fiber sensor 718 of the carrier 716 side detects presense of the microplate 1 placed on the carrier 716, and the detect signal is applied to the control portion which operates the motor 724 of the carrier 716. Thus, the ball screw 711 is rotated through the timing pulleys 723 and 726, to move the carrier 716 to delivery position with the conveyor belts 634 and 635, i.e. to the right of FIG. 24a. As the carrier 716 goes lower end between the conveyor belts 634 and 635 of the upward conveyor unit 44, to deliver the microplate 1 similar with the receive process with the downward conveyor unit 43. The detect sensor 734 of the carrier unit 47 detects presense of the carrier 716 at the delivery position, and the detect signal actuates the fiber sensor 719 to detect presense of the microplate 1 on the carrier 716, and the detect signal is applied to the control portion which actuates the motor 650 of the conveyor unit 44 to lift the conveyor belts 634 and 635 for one pitch. By the upward movement, the microplate 1 transferred by the carrier 716 to delivery position of between the conveyor belts 634 and 635 is held as before, the both edges with the engage recesses 636 and 637 of the conveyor belts 634 and 635 of the upwaard conveyor unit 44, and is moved upwards one pitch with the conveyor belts 634 and 635.

Figure 30:
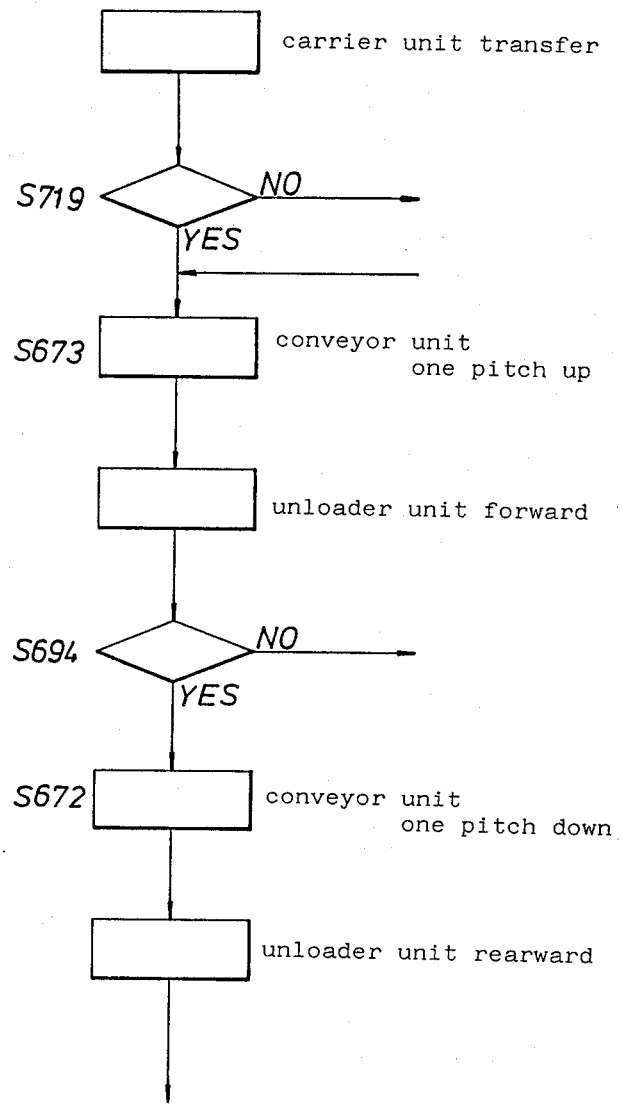
FIG. 30 is a flow chart of the upward conveyor unit.

As shown in FIG. 30, relating to the upward movement of the conveyor belts 634 and 635 of the upward conveyor unit 44, the fiber sensor 719 of the carrier 716 at the side of the upward conveyor unit 44 detects that there is no microplate 1 on the carrier 716 because the transferred microplate 1 has delivered between the conveyor belts 634 and 635 and moved upward. The delivery confirm signal is applied to the control portion which operates the motor 724 to drive the ball screw 711 so that the carrier 716 goes back to the microplate receive position with the downward conveyor unit 43.

Further, as shown in FIG. 30, after the upward movement of the conveyor belts 634 and 635, if the sensor 719 detects the presense of the microplate on the carrier 716, the detect signal is applied to the control portion as abnormal alarm condition.

The return of the carrier is detected by the sensor 733 of the downward conveyor unit 43 side, and the detect signal is applied to the control portion which operates the motor 650 to drive the conveyor belts 634 and 635 of the downward conveyor unit 43 for one pitch downwards. As before, the microplate 1 held between the conveyor belts 634 and 635 is placed on the carrier 716 which moves to the upward conveyor unit 44 between the conveyor belts 634 and 635 thereof, i.e. delivery position. Both edges of the microplate 1 engage with and is held between the engage recesses 636 and 637 of the conveyor belts 634 and 635 of the upward conveyor unit 44, and the microplate 1 moves upward with the conveyor unit 44 to complete the transfer.

Thus, the microplate 1 is sequentially transferred from the downward conveyor unit 43 through the carrier unit 47 to the upward conveyor unit 44, and is held between the conveyor belts 634 and 635 of the upward conveyor unit 44 which moves upwards sequentially one pitch with the microplate 1. Relating to the upward movement of the conveyor unit 44, the microplates 1 held between the conveyor belts 634 and 635 of the upward conveyor unit 44, is stored and discharged one by one through the unloader unit 46 to the steps 185 and 186 of the discharge magazine 180 which is held by the discharge side elevator unit 42.

Figure 31:
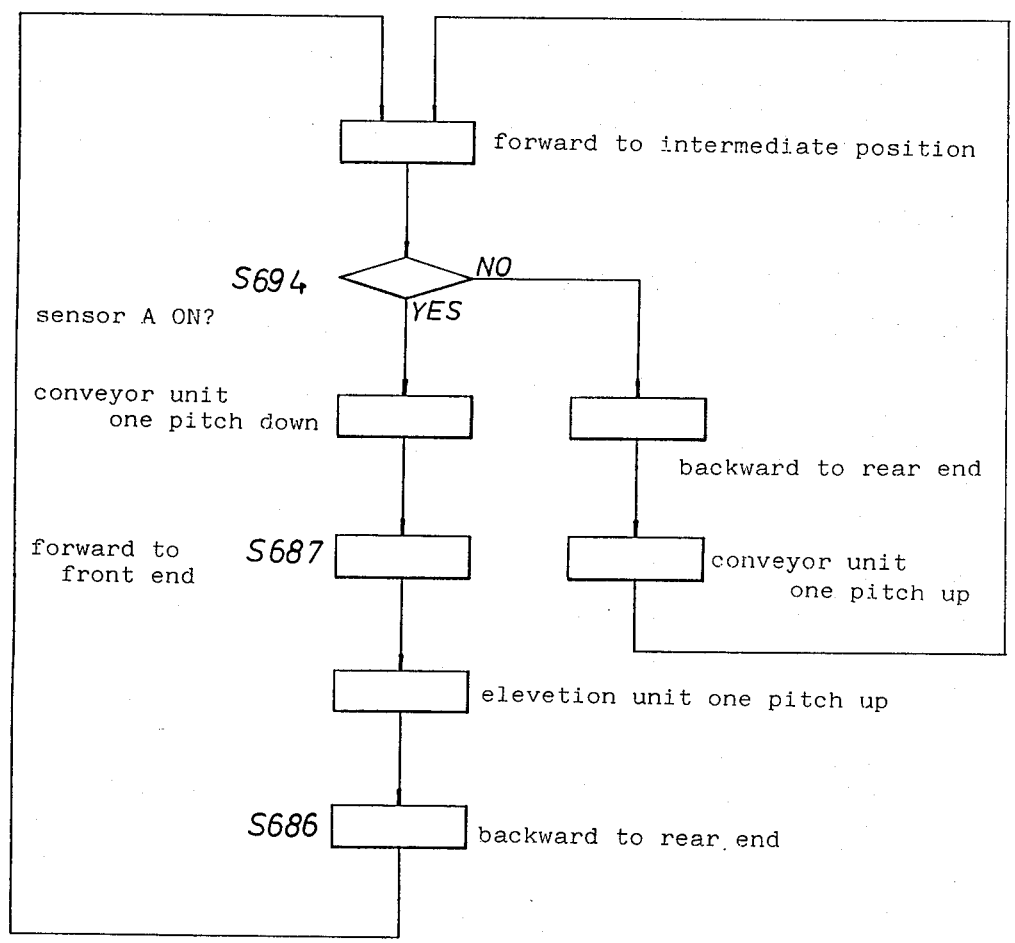
FIG. 31 is a flow chart of the unloader unit.
Figure 33:
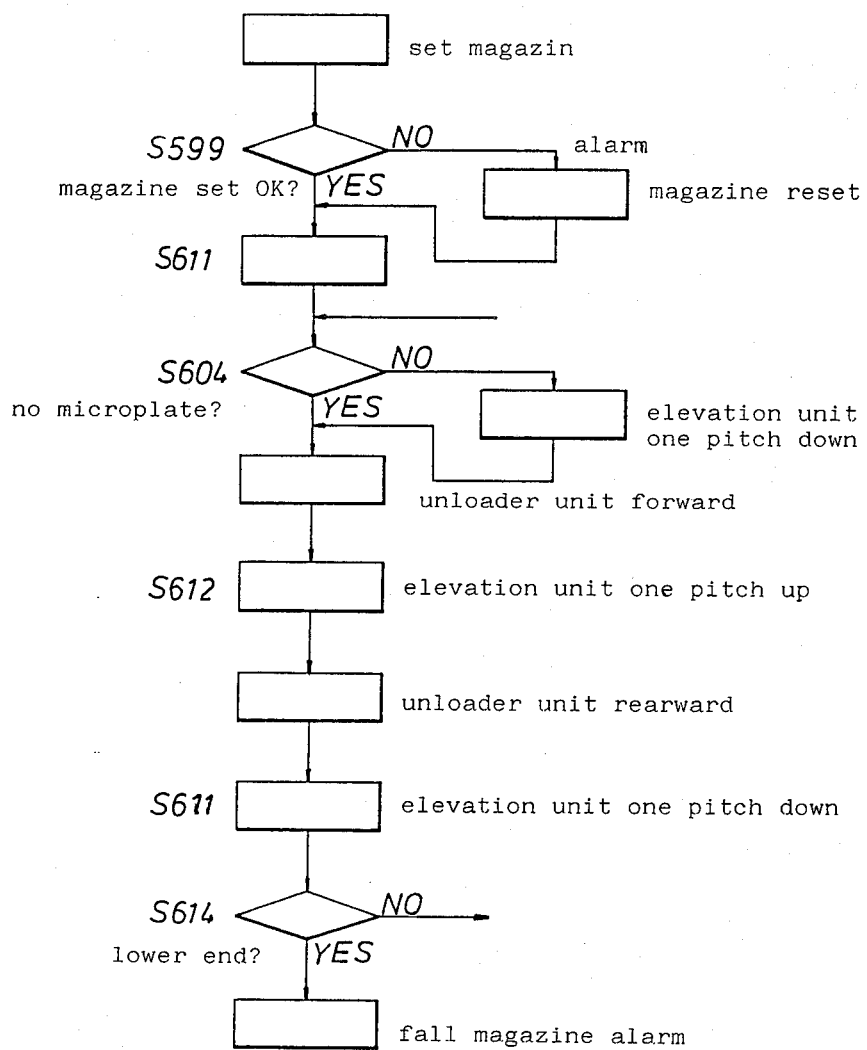
FIG. 33 is a flow chart of the discharge side elevation unit.

Describing in detail, as shown in FIG. 33, the magazine lift 586 of the magazine discharge elevator unit 42 is set at upper end position, and places the empty magazine 180. The micro-switch 599 detects the proper positioning of the microplate 1 of the magazine 180 and operates the motor 587 to lower the magazine lift 586 for one pitch to receive the microplate 1 from the transfer plate 681 of the unloader unit 46. As shown in FIG. 31, the arm shaft 682 of the unloader unit 46 moves forward relating to the one pitch lift of the conveyor belts 634 and 635 of the upward conveyor unit 44, to insert the transfer plate 681 to the intermediate stop position, i.e. under the microplate 1 which is held between the engage recesses 636 and 637 of the conveyor belts 634 and 635 of the upward conveyor unit 44, and to stop at receive position.

By detect signal from the detect sensor 688 at the intermediate stop position, the sensor 694 on the transfer plate 681 actuates to detect presense of the microplate on the transfer plate 681, and the detect signal is applied to the control portion which operates the motor 650 to lower the conveyor belts 634 and 635 of the upward conveyor unit 44 so that the microplate 1 held between the conveyor belts 634 and 635 is transfer onto the transfer plate 681.

Then, the transfer plate 681 returns to rear end position, and is detected by the sensor 686. The detect signal from the sensor 686 is applied to the control portion which stops the motor 683, and also operates the motor 587 of the discharge side elevation unit 42 to lower the magazine lift 586 for one pitch, the movement is confirmed by detect signal from the photo-sensor 611 which actuates by the slit 607 of the shutter 592.

The one pitch descend motion of the magazine lift 586 corresponds to the store pitch of the microplates 1, i.e. pitch of the store shelves in the magazine 180. The motion places the magazine ready to receive next microplate 1 into next store shelf and to allow coming into the transfer plate 681. the process is repeated that the microplate 1 is transferred by the unloader unit 46 from the ascending upward conveyor unit 44 sequentially, and is stored in the magazine 180 of the discharge side elevation unit 42. Also, as shown in FIG. 33, a predetermined number of the microplates 1 are stored in the magazine 180 which is placed on the magazine lift 586, the sensor 586 detecting the lower end of the magazine lift 586, detects the shutter 613 and applies detect signal to the control portion which produces alarm signal to report full condition of the magazine 180.

While the microplate 1 is transferred from the magazine on the supply side elevation unit 41 through the loader unit 45, the downward conveyor unit 43, the carrier unit 47, the upward conveyor unit 44 and the unloader unit 46 to the magazine 180 on the discharge side elevation unit 42, the microplate 1 is heated a predetermined time in the downward and upward conveyor units 43 and 44 and the carrier unit 47 in a temperature atmosphere formed by the heater unit 48 so that in each well 2 in the microplate 1, incubation of coated reagent is completed.

More particularly, each cartridge heater 754 of the heater unit 48 is energized to heat the heater space 767, and fans 768 and 769 are operated to feed the hot air in the heater space 767 to the duct spaces 765 and 766, and also hot air is forced circulated in the transfer spaces of the downward and upward conveyor units 43 and 44 and the carrier unit 47 to heat the spaces to predetermined temperature.

The predetermined temperature to heat the microplate transfer spaces is determined such that the microplates are transferred through the downward and upward conveyor units 43 and 44 and the carrier unit 47, and the wells 2 in the microplates 1 complete the incubation of the reagent coated in the wells. The temperature control in the transfer spaces in the downward and upward conveyor units 43 and 44 and the carrier unit 47 to set temperature is performed by the control sensors 772 mounted in the duct spaces 765 and 766 of the heater unit 48, and the output signal from the sensors 772 is applied to temperature controller, not shown, attached to each cartridge heater 754 to ON-OFF electric source of the heater 754 to maintain the temperature.

When the temperature in any transfer space is abnormal, the sensor 773 detects the condition, and electric sourse of the cartridge heaters 754 is cut off, and lamp and buzzar are operated to indicate the abnormal condition.

Then, the microplates 1 are fed to the blocking solution dispense and coating apparatus 33 to perform dispense and coating of blocking solution, the incubation apparatus 34 to perform incubation and the cleaning apparatus 35 to perform cleaning after the incubation. All these processes and apparatus are similar with the above described reagent dispense and coating, incubation and cleaning process and apparatus so that detailed description will not be necessary. Also as to the drier apparatus 36, conventional means can be used to dry the coating film in the wells by necessary temperature and necessary time to complete solid phase of the film.

As to the method of transfer of the microplates in the dispense and coating of blocking solution process is similar with the dispense and coating process of the reagent solution so that in FIGS. 44 to 47, same reference numeral is used to show similar part or portion, and detailed description is eliminated.

We claim:

1. A method of forming solid phase reagent in micro-module comprising preparing a module plate receiving a plurality of wells to be coated with reagent film, dispensing reagent in each well of the module plate from a plurality of dispensing nozzles corresponding to the number of wells of at least one row on the module plate, incubating the reagent dispensed in the wells to form reagent film in each well while transferring the module plate in predetermined temperature atmosphere, cleaning the wells on the module plate comprising
(a) discharging remaining reagent from the wells by means of discharge nozzles corresponding to the number of the dispensing nozzles,
(b) dispensing cleaning fluid into the wells by means of cleaning nozzles corresponding to the number of the discharge nozzles,
(c) discharging the cleaning fluid from the wells by means of said discharge nozzles, dispensing protect film forming solution into the wells by means of another dispense nozzles corresponding to the number of the first mentioned dispense nozzles, incubating the protect film forming solution in the wells while transferring the module plate in predetermined temperature atmosphere, cleaning the wells on the module plate comprising
(a) discharging remaining protect film forming solution from the wells by means of discharge nozzles corresponding to the number of the dispensing nozzles,
(b) dispensing cleaning fluid into the wells by means of cleaning nozzles corresponding to the number of the discharge nozzles,
(c) discharging the cleaning fluid from the wells by means of said discharge nozzles, and, drying the wells on the module plate in predetermined temperature atmosphere to form coated solid phase reagent film in each well.

2. A reagent coating apparatus in a solid phase reagent producing apparatus comprising magazine means storing a plurality of microplates each having a plurality of micro-wells to be coated, microplate transfer means transferring the microplate one by one from the magazine means to working station and from the working station to next station, and, reagent coating means dispensing reagent in each well on the microplate which is stopped in the working station.

3. A reagent coating apparatus in a solid phase reagent producing apparatus comprising magazine means storing a plurality of microplates each having a plurality of micro-wells to be coated, microplate transfer means transferring the microplate one by one from the magazine means to working station and from the working station to next station, reagent coating means dispensing reagent in each well on the microplate which is stopped in the working station, by means of dispense nozzles, and nozzle cleaning means cleaning said reagent dispense nozzles.

4. A reagent incubation apparatus comprising means to supply microplates each having a plurality of reagent coated wells one by one into incubation atmosphere, supply side transfer means transferring the microplate supplied from the supply means in the incubation atmosphere at predetermined transfer speed, means to deliver the microplate from said supply means to said transfer means, discharge side transfer means transferring the microplate transferred from the supply side transfer means in the incubation atmosphere at predetermined transfer speed, means to transfer the microplate from the supply side transfer means to the discharge side transfer means, means to discharge the microplate from the incubation atmosphere, and, means to deliver the microplate from the discharge side transfer means to the discharge means.

* * * * *